United States Patent [19]

Christianson et al.

[11] Patent Number: 5,340,735

[45] Date of Patent: Aug. 23, 1994

[54] *BACILLUS LENTUS* ALKALINE PROTEASE VARIANTS WITH INCREASED STABILITY

[75] Inventors: Teresa Christianson, Cotati; Dean Goddette, Rohnert Park; Beth F. Ladin, Santa Rosa; Maria R. Lau, Fairfield; Christian Paech, Santa Rosa; Robert B. Reynolds, Santa Rosa; Charles R. Wilson, Santa Rosa; Shiow-Shong Yang, Santa Rosa, all of Calif.

[73] Assignee: COGNIS, Inc., Santa Rosa, Calif.

[21] Appl. No.: 706,691

[22] Filed: May 29, 1991

[51] Int. Cl.$^5$ .............. C12N 9/54; C12N 15/57; C12N 15/75; C12N 15/62
[52] U.S. Cl. ............... 435/221; 435/69.1; 435/69.7; 435/214; 435/220; 435/252.31; 435/320.1; 536/23.2; 536/23.4; 536/23.7; 935/10; 935/14; 935/27; 935/74
[58] Field of Search ............... 435/221, 222, 69.1, 435/252.31, 320.1; 536/23.2

[56] References Cited

U.S. PATENT DOCUMENTS

| | | | |
|---|---|---|---|
| 4,511,490 | 4/1985 | Stanislowski et al. | 252/174.12 |
| 4,760,025 | 7/1988 | Estell et al. | 435/222 |
| 4,914,031 | 4/1990 | Zukowski et al. | 435/222 |
| 4,980,288 | 12/1990 | Bryan et al. | 435/222 |
| 4,990,452 | 2/1991 | Bryan et al. | 435/222 |
| 5,013,657 | 7/1991 | Bryan et al. | 435/172.3 |
| 5,041,378 | 8/1991 | Drummond et al. | 435/234 |
| 5,116,741 | 5/1992 | Bryan et al. | 435/87 |
| 5,118,623 | 6/1992 | Boguslawski et al. | 435/222 |
| 5,155,033 | 10/1992 | Estell et al. | 435/221 |
| 5,185,258 | 2/1993 | Caldwell et al. | 435/220 |

FOREIGN PATENT DOCUMENTS

| | | | |
|---|---|---|---|
| 0251446 | 1/1988 | European Pat. Off. | 435/172.3 |
| 8808164 | 10/1988 | World Int. Prop. O. | 435/172.3 |
| 8902679 | 7/1989 | World Int. Prop. O. | 435/220 |
| 9102792 | 3/1991 | World Int. Prop. O. | 435/221 |

OTHER PUBLICATIONS

Wilson, C., et al., 1991, Journal of Molecular Biology 220(2): 495–506.
Sharp, K. A., et al., 1991, Biochemistry 30(40): 9686–9697.
Bash, P. A., et al., 1987, Science 236(4801): 564–568.
Haner, A. P., et al., 1992, Proteins: Structure, Function, and Genetics, 14(4): 451–464.
Erwin, C. R., et al., 1990, Protein Engineering 4(1): 87–97.
Meloan, B., et al., 1985, FEBS Letters, 183(2): 195–199.
Svendsen, I., et al., 1986, FEBS Letters, 196(2): 228–232.
Wells, J. A., et al, 1987, Proceedings of the National Academy of Sciences, USA 84: 5167–5171.
Russell, A. J., et al., 1987, Journal of Molecular Biology, 193: 803–813.
Betzel, C., et al., 1988, Journal of Molecular Biology, 204: 803–804.

*Primary Examiner*—Robert A. Wax
*Assistant Examiner*—William W. Moore
*Attorney, Agent, or Firm*—Ernest G. Szoke; Wayne C. Jaeschke; John E. Drach

[57] ABSTRACT

Mutant *B. lentus* DSM 5483 proteases are derived by the replacement of at least one amino acid residue of the mature form of the *B. lentus* DSM 5483 alkaline protease. The mutant proteases are expressed by genes which are mutated by site-specific mutagenesis. The amino acid sites selected for replacement are identified by means of a computer based method which compares the three dimensional structure of the wild-type protease and a reference protease.

45 Claims, 18 Drawing Sheets

| | | | | | | | | | | |
|---|---|---|---|---|---|---|---|---|---|---|
| 1 | GLY | C | 27.985 | 27.065 | 7.578 | 8 | ILE | O | 29.238 | 35.790 | 21.181 |
| 1 | GLY | O | 26.834 | 26.692 | 7.822 | 9 | SER | N | 28.255 | 36.591 | 19.284 |
| 1 | GLY | N | 27.785 | 25.660 | 5.657 | 9 | SER | CA | 29.270 | 37.572 | 19.075 |
| 1 | GLY | CA | 28.517 | 26.825 | 6.143 | 9 | SER | CB | 29.158 | 38.161 | 17.652 |
| 2 | GLN | N | 28.745 | 27.585 | 8.522 | 9 | SER | OG | 29.411 | 37.107 | 16.718 |
| 2 | GLN | CA | 28.205 | 27.868 | 9.851 | 9 | SER | C | 29.191 | 38.684 | 20.145 |
| 2 | GLN | CB | 29.179 | 27.265 | 10.835 | 9 | SER | O | 30.236 | 39.113 | 20.660 |
| 2 | GLN | CG | 28.905 | 27.589 | 12.287 | 10 | ARG | N | 27.977 | 39.085 | 20.540 |
| 2 | GLN | CD | 29.834 | 26.805 | 13.151 | 10 | ARG | CA | 27.775 | 40.132 | 21.537 |
| 2 | GLN | OE1 | 29.476 | 25.685 | 13.540 | 10 | ARG | CB | 26.288 | 40.423 | 21.686 |
| 2 | GLN | NE2 | 31.008 | 27.317 | 13.461 | 10 | ARG | CG | 25.946 | 41.656 | 22.562 |
| 2 | GLN | C | 28.045 | 29.384 | 10.049 | 10 | ARG | CD | 26.666 | 42.953 | 22.101 |
| 2 | GLN | O | 28.927 | 30.159 | 9.642 | 10 | ARG | NE | 26.378 | 43.300 | 20.705 |
| 3 | SER | N | 26.940 | 29.781 | 10.693 | 10 | ARG | CZ | 25.394 | 44.138 | 20.338 |
| 3 | SER | CA | 26.568 | 31.160 | 10.999 | 10 | ARG | NH1 | 25.226 | 44.365 | 19.048 |
| 3 | SER | CB | 25.036 | 31.390 | 10.712 | 10 | ARG | NH2 | 24.604 | 44.767 | 21.215 |
| 3 | SER | OG | 24.576 | 30.913 | 9.455 | 10 | ARG | C | 28.351 | 39.782 | 22.893 |
| 3 | SER | C | 26.815 | 31.424 | 12.488 | 10 | ARG | O | 28.942 | 40.673 | 23.476 |
| 3 | SER | O | 26.464 | 30.580 | 13.314 | 11 | VAL | N | 28.222 | 38.532 | 23.377 |
| 4 | VAL | N | 27.371 | 32.570 | 12.897 | 11 | VAL | CA | 28.862 | 38.186 | 24.642 |
| 4 | VAL | CA | 27.534 | 32.913 | 14.309 | 11 | VAL | CB | 28.127 | 37.003 | 25.339 |
| 4 | VAL | CB | 28.860 | 33.625 | 14.552 | 11 | VAL | CG1 | 26.664 | 37.416 | 25.538 |
| 4 | VAL | CG1 | 29.008 | 33.965 | 16.045 | 11 | VAL | CG2 | 28.227 | 35.723 | 24.530 |
| 4 | VAL | CG2 | 30.006 | 32.739 | 14.035 | 11 | VAL | C | 30.343 | 37.832 | 24.471 |
| 4 | VAL | C | 26.397 | 33.869 | 14.655 | 11 | VAL | O | 31.021 | 37.393 | 25.404 |
| 4 | VAL | O | 26.344 | 34.990 | 14.097 | 12 | GLN | N | 30.868 | 37.944 | 23.261 |
| 5 | PRO | N | 25.384 | 33.471 | 15.449 | 12 | GLN | CA | 32.288 | 37.745 | 22.957 |
| 5 | PRO | CD | 25.140 | 32.114 | 15.924 | 12 | GLN | CB | 33.129 | 38.763 | 23.772 |
| 5 | PRO | CA | 24.313 | 34.393 | 15.856 | 12 | GLN | CG | 32.773 | 40.196 | 23.319 |
| 5 | PRO | CB | 23.404 | 33.524 | 16.740 | 12 | GLN | CD | 33.643 | 41.252 | 23.997 |
| 5 | PRO | CG | 23.629 | 32.110 | 16.189 | 12 | GLN | OE1 | 34.842 | 41.403 | 23.753 |
| 5 | PRO | C | 24.823 | 35.677 | 16.538 | 12 | GLN | NE2 | 33.145 | 42.035 | 24.926 |
| 5 | PRO | O | 25.816 | 35.601 | 17.282 | 12 | GLN | C | 32.806 | 36.330 | 23.186 |
| 6 | TRP | N | 24.126 | 36.804 | 16.302 | 12 | GLN | O | 33.978 | 36.104 | 23.557 |
| 6 | TRP | CA | 24.597 | 38.070 | 16.867 | 13 | ALA | N | 31.938 | 35.350 | 22.940 |
| 6 | TRP | CB | 23.589 | 39.231 | 16.567 | 13 | ALA | CA | 32.333 | 33.978 | 23.095 |
| 6 | TRP | CG | 22.313 | 39.360 | 17.414 | 13 | ALA | CB | 31.189 | 33.004 | 22.890 |
| 6 | TRP | CD2 | 22.238 | 40.080 | 18.588 | 13 | ALA | C | 33.418 | 33.589 | 22.084 |
| 6 | TRP | CE2 | 20.905 | 39.872 | 18.955 | 13 | ALA | O | 34.293 | 32.789 | 22.477 |
| 6 | TRP | CE3 | 23.091 | 40.874 | 19.364 | 14 | PRO | N | 33.507 | 34.053 | 20.808 |
| 6 | TRP | CD1 | 21.120 | 38.755 | 17.097 | 14 | PRO | CD | 32.522 | 34.799 | 20.020 |
| 6 | TRP | NE1 | 20.274 | 39.089 | 18.047 | 14 | PRO | CA | 34.622 | 33.646 | 19.943 |
| 6 | TRP | CZ2 | 20.485 | 40.458 | 20.142 | 14 | PRO | CB | 34.311 | 34.283 | 18.601 |
| 6 | TRP | CZ3 | 22.638 | 41.455 | 20.536 | 14 | PRO | CG | 32.806 | 34.270 | 18.606 |
| 6 | TRP | CH2 | 21.339 | 41.249 | 20.918 | 14 | PRO | C | 35.977 | 34.034 | 20.525 |
| 6 | TRP | C | 24.859 | 38.028 | 18.378 | 14 | PRO | O | 36.900 | 33.216 | 20.393 |
| 6 | TRP | O | 25.812 | 38.610 | 18.854 | 15 | ALA | N | 36.096 | 35.170 | 21.257 |
| 7 | GLY | N | 24.056 | 37.299 | 19.142 | 15 | ALA | CA | 37.383 | 35.545 | 21.881 |
| 7 | GLY | CA | 24.171 | 37.250 | 20.597 | 15 | ALA | CB | 37.253 | 36.887 | 22.612 |
| 7 | GLY | C | 25.488 | 36.591 | 21.015 | 15 | ALA | C | 37.837 | 34.470 | 22.892 |
| 7 | GLY | O | 26.135 | 36.993 | 22.000 | 15 | ALA | O | 39.024 | 34.129 | 22.980 |
| 8 | ILE | N | 25.911 | 35.557 | 20.242 | 16 | ALA | N | 36.899 | 33.826 | 23.591 |
| 8 | ILE | CA | 27.125 | 34.811 | 20.543 | 16 | ALA | CA | 37.248 | 32.758 | 24.508 |
| 8 | ILE | CB | 27.250 | 33.554 | 19.559 | 16 | ALA | CB | 36.057 | 32.436 | 25.368 |
| 8 | ILE | CG2 | 28.525 | 32.760 | 19.882 | 16 | ALA | C | 37.632 | 31.505 | 23.705 |
| 8 | ILE | CG1 | 26.016 | 32.625 | 19.654 | 16 | ALA | O | 38.587 | 30.787 | 24.026 |
| 8 | ILE | CD | 25.683 | 32.107 | 21.080 | 17 | HIS | N | 36.927 | 31.180 | 22.610 |
| 8 | ILE | C | 28.303 | 35.772 | 20.363 | 17 | HIS | CA | 37.206 | 29.941 | 21.872 |

FIG.1A

```
17 HIS  CB   36.283 29.667 20.715    27 LYS  N    29.799 19.815 32.589
17 HIS  CG   34.810 29.669 21.066    27 LYS  CA   28.459 19.291 32.434
17 HIS  CD2  33.823 29.867 20.140    27 LYS  CB   28.206 18.148 33.370
17 HIS  ND1  34.240 29.557 22.260    27 LYS  CG   29.146 17.001 33.191
17 HIS  CE1  32.932 29.701 22.082    27 LYS  CD   28.427 15.942 33.969
17 HIS  NE2  32.694 29.881 20.807    27 LYS  CE   29.530 15.137 34.529
17 HIS  C    38.557 30.109 21.246    27 LYS  NZ   29.022 14.047 35.345
17 HIS  O    39.290 29.114 21.115    27 LYS  C    27.394 20.331 32.719
18 ASN  N    38.978 31.354 20.903    27 LYS  O    27.368 20.968 33.797
18 ASN  CA   40.320 31.583 20.379    28 VAL  N    26.512 20.472 31.730
18 ASN  CB   40.420 32.976 19.792    28 VAL  CA   25.435 21.471 31.738
18 ASN  CG   39.771 33.007 18.426    28 VAL  CB   25.628 22.534 30.583
18 ASN  OD1  39.324 34.072 17.991    28 VAL  CG1  24.502 23.560 30.598
18 ASN  ND2  39.604 31.952 17.631    28 VAL  CG2  26.989 23.220 30.749
18 ASN  C    41.377 31.382 21.454    28 VAL  C    24.121 20.739 31.512
18 ASN  O    42.545 31.105 21.147    28 VAL  O    23.947 20.067 30.475
19 ARG  N    41.007 31.481 22.726    29 ALA  N    23.203 20.933 32.446
19 ARG  CA   41.934 31.108 23.756    29 ALA  CA   21.900 20.311 32.385
19 ARG  CB   41.579 31.808 25.055    29 ALA  CB   21.478 19.832 33.763
19 ARG  CG   41.755 33.269 24.901    29 ALA  C    20.906 21.382 31.920
19 ARG  CD   41.327 33.963 26.212    29 ALA  O    20.919 22.490 32.454
19 ARG  NE   41.469 35.388 26.008    30 VAL  N    20.038 21.127 30.938
19 ARG  CZ   40.620 36.280 26.485    30 VAL  CA   19.069 22.069 30.421
19 ARG  NH1  40.880 37.535 26.211    30 VAL  CB   19.123 22.097 28.835
19 ARG  NH2  39.567 35.963 27.217    30 VAL  CG1  18.017 22.967 28.267
19 ARG  C    41.924 29.600 23.992    30 VAL  CG2  20.480 22.654 28.369
19 ARG  O    42.655 29.144 24.864    30 VAL  C    17.731 21.519 30.928
20 GLY  N    41.166 28.766 23.312    30 VAL  O    17.275 20.467 30.425
20 GLY  CA   41.105 27.344 23.620    31 LEU  N    17.155 22.192 31.928
20 GLY  C    40.056 26.959 24.682    31 LEU  CA   15.899 21.751 32.514
20 GLY  O    40.026 25.824 25.187    31 LEU  CB   15.878 22.118 33.997
21 LEU  N    39.130 27.872 25.003    31 LEU  CG   16.523 21.135 34.997
21 LEU  CA   38.098 27.626 26.023    31 LEU  CD1  18.034 21.230 34.828
21 LEU  CB   38.012 28.796 26.984    31 LEU  CD2  16.177 21.487 36.457
21 LEU  CG   39.321 29.049 27.732    31 LEU  C    14.832 22.501 31.724
21 LEU  CD1  39.370 30.463 28.219    31 LEU  O    14.647 23.705 31.887
21 LEU  CD2  39.469 28.017 28.815    32 ASP  N    14.163 21.816 30.801
21 LEU  C    36.767 27.463 25.284    32 ASP  CA   13.254 22.474 29.860
21 LEU  O    36.254 28.371 24.622    32 ASP  CB   14.173 23.197 28.850
22 THR  N    36.294 26.227 25.368    32 ASP  CG   13.567 24.470 28.221
22 THR  CA   35.094 25.767 24.713    32 ASP  OD1  14.128 25.565 28.394
22 THR  CB   35.488 24.785 23.658    32 ASP  OD2  12.549 24.352 27.538
22 THR  OG1  36.139 23.695 24.331    32 ASP  C    12.331 21.405 29.226
22 THR  CG2  36.341 25.467 22.585    32 ASP  O    12.057 20.382 29.870
22 THR  C    34.069 25.126 25.622    33 THR  N    11.874 21.602 27.972
22 THR  O    33.010 24.745 25.146    33 THR  CA   10.956 20.709 27.245
23 GLY  N    34.304 24.953 26.918    33 THR  CB   10.237 21.562 26.131
23 GLY  CA   33.327 24.232 27.761    33 THR  OG1  11.275 22.099 25.255
23 GLY  C    33.680 22.769 27.973    33 THR  CG2   9.394 22.669 26.737
23 GLY  O    32.931 22.033 28.642    33 THR  C    11.600 19.465 26.594
24 SER  N    34.808 22.329 27.403    33 THR  O    10.948 18.766 25.806
24 SER  CA   35.218 20.939 27.546    34 GLY  N    12.919 19.306 26.830
24 SER  CB   36.565 20.776 26.874    34 GLY  CA   13.720 18.216 26.294
24 SER  OG   36.819 19.378 26.828    34 GLY  C    14.758 18.794 25.334
24 SER  C    35.310 20.485 29.016    34 GLY  O    14.875 20.030 25.242
24 SER  O    35.830 21.218 29.880    35 ILE  N    15.492 17.921 24.630
25 GLY  N    34.786 19.290 29.245    35 ILE  CA   16.417 18.299 23.557
25 GLY  CA   34.688 18.702 30.571    35 ILE  CB   17.881 18.366 24.013
25 GLY  C    33.657 19.387 31.517    35 ILE  CG2  18.614 19.017 22.822
25 GLY  O    33.562 19.018 32.697    35 ILE  CG1  18.149 19.249 25.273
26 VAL  N    32.861 20.356 31.079    35 ILE  CD   19.589 19.096 25.859
26 VAL  CA   31.862 20.949 31.956    35 ILE  C    16.257 17.256 22.439
26 VAL  CB   31.863 22.501 31.794    35 ILE  O    16.348 16.042 22.687
26 VAL  CG1  30.812 23.111 32.729    36 SER  N    15.873 17.729 21.243
26 VAL  CG2  33.281 23.055 32.071    36 SER  CA   15.797 16.830 20.099
26 VAL  C    30.488 20.382 31.604    36 SER  CB   14.885 17.400 19.036
26 VAL  O    30.089 20.375 30.446    36 SER  OG   13.589 17.293 19.580
```

FIG. 1B

| | | | | | | | | | | |
|---|---|---|---|---|---|---|---|---|---|---|
| 36 | SER | C | 17.166 | 16.572 | 19.462 | 44 | ARG | C | 24.399 | 12.088 | 27.123 |
| 36 | SER | O | 18.018 | 17.473 | 19.331 | 44 | ARG | O | 24.863 | 11.030 | 27.534 |
| 37 | THR | N | 17.380 | 15.298 | 19.076 | 45 | GLY | N | 23.168 | 12.489 | 27.392 |
| 37 | THR | CA | 18.541 | 14.930 | 18.274 | 45 | GLY | CA | 22.286 | 11.766 | 28.306 |
| 37 | THR | CB | 18.300 | 13.522 | 17.755 | 45 | GLY | C | 21.220 | 12.697 | 28.867 |
| 37 | THR | OG1 | 18.169 | 12.722 | 18.926 | 45 | GLY | O | 21.009 | 13.824 | 28.377 |
| 37 | THR | CG2 | 19.401 | 13.039 | 16.808 | 46 | GLY | N | 20.524 | 12.208 | 29.871 |
| 37 | THR | C | 18.675 | 15.912 | 17.089 | 46 | GLY | CA | 19.453 | 12.976 | 30.489 |
| 37 | THR | O | 17.670 | 16.153 | 16.374 | 46 | GLY | C | 18.430 | 12.113 | 31.221 |
| 38 | HIS | N | 19.880 | 16.435 | 16.837 | 46 | GLY | O | 18.632 | 10.912 | 31.445 |
| 38 | HIS | CA | 20.021 | 17.474 | 15.806 | 47 | ALA | N | 17.313 | 12.744 | 31.558 |
| 38 | HIS | CB | 19.786 | 18.868 | 16.461 | 47 | ALA | CA | 16.222 | 12.120 | 32.291 |
| 38 | HIS | CG | 19.722 | 20.046 | 15.486 | 47 | ALA | CB | 16.461 | 12.192 | 33.779 |
| 38 | HIS | CD2 | 20.803 | 20.545 | 14.801 | 47 | ALA | C | 14.953 | 12.896 | 31.997 |
| 38 | HIS | ND1 | 18.655 | 20.775 | 15.114 | 47 | ALA | O | 15.007 | 14.081 | 31.604 |
| 38 | HIS | CE1 | 19.051 | 21.670 | 14.239 | 48 | SER | N | 13.817 | 12.215 | 32.075 |
| 38 | HIS | NE2 | 20.348 | 21.530 | 14.048 | 48 | SER | CA | 12.537 | 12.888 | 31.947 |
| 38 | HIS | C | 21.432 | 17.344 | 15.305 | 48 | SER | CB | 11.680 | 12.343 | 30.801 |
| 38 | HIS | O | 22.341 | 17.174 | 16.118 | 48 | SER | OG | 10.390 | 12.945 | 30.842 |
| 39 | PRO | N | 21.740 | 17.555 | 14.025 | 48 | SER | C | 11.760 | 12.680 | 33.243 |
| 39 | PRO | CD | 20.795 | 17.752 | 12.918 | 48 | SER | O | 11.740 | 11.558 | 33.791 |
| 39 | PRO | CA | 23.135 | 17.467 | 13.571 | 49 | PHE | N | 11.224 | 13.808 | 33.696 |
| 39 | PRO | CB | 23.084 | 17.619 | 12.070 | 49 | PHE | CA | 10.358 | 13.821 | 34.885 |
| 39 | PRO | CG | 21.744 | 18.261 | 11.799 | 49 | PHE | CB | 10.967 | 14.782 | 35.924 |
| 39 | PRO | C | 24.112 | 18.457 | 14.195 | 49 | PHE | CG | 12.302 | 14.253 | 36.403 |
| 39 | PRO | O | 25.318 | 18.260 | 14.162 | 49 | PHE | CD1 | 13.454 | 14.844 | 35.923 |
| 40 | ASP | N | 23.645 | 19.520 | 14.832 | 49 | PHE | CD2 | 12.383 | 13.128 | 37.204 |
| 40 | ASP | CA | 24.583 | 20.488 | 15.375 | 49 | PHE | CE1 | 14.676 | 14.300 | 36.225 |
| 40 | ASP | CB | 24.218 | 21.897 | 14.900 | 49 | PHE | CE2 | 13.616 | 12.590 | 37.509 |
| 40 | ASP | CG | 25.453 | 22.801 | 14.740 | 49 | PHE | CZ | 14.760 | 13.176 | 37.008 |
| 40 | ASP | OD1 | 26.526 | 22.264 | 14.551 | 49 | PHE | C | 8.915 | 14.206 | 34.546 |
| 40 | ASP | OD2 | 25.389 | 24.037 | 14.740 | 49 | PHE | O | 8.115 | 14.601 | 35.418 |
| 40 | ASP | C | 24.561 | 20.439 | 16.874 | 50 | VAL | N | 8.571 | 14.104 | 33.248 |
| 40 | ASP | O | 24.918 | 21.450 | 17.480 | 50 | VAL | CA | 7.230 | 14.424 | 32.796 |
| 41 | LEU | N | 24.080 | 19.327 | 17.430 | 50 | VAL | CB | 7.264 | 15.245 | 31.450 |
| 41 | LEU | CA | 24.102 | 19.142 | 18.883 | 50 | VAL | CG1 | 5.869 | 15.427 | 30.821 |
| 41 | LEU | CB | 22.713 | 19.260 | 19.513 | 50 | VAL | CG2 | 7.766 | 16.635 | 31.755 |
| 41 | LEU | CG | 21.938 | 20.541 | 19.465 | 50 | VAL | C | 6.512 | 13.085 | 32.594 |
| 41 | LEU | CD1 | 20.485 | 20.249 | 19.882 | 50 | VAL | O | 6.894 | 12.336 | 31.695 |
| 41 | LEU | CD2 | 22.642 | 21.595 | 20.331 | 51 | PRO | N | 5.443 | 12.724 | 33.315 |
| 41 | LEU | C | 24.635 | 17.780 | 19.265 | 51 | PRO | CD | 4.826 | 13.553 | 34.344 |
| 41 | LEU | O | 24.417 | 16.802 | 18.530 | 51 | PRO | CA | 4.805 | 11.411 | 33.232 |
| 42 | ASN | N | 25.298 | 17.707 | 20.415 | 51 | PRO | CB | 3.632 | 11.476 | 34.218 |
| 42 | ASN | CA | 25.792 | 16.443 | 20.953 | 51 | PRO | CG | 4.118 | 12.525 | 35.235 |
| 42 | ASN | CB | 27.341 | 16.452 | 21.066 | 51 | PRO | C | 4.358 | 10.971 | 31.854 |
| 42 | ASN | CG | 27.960 | 15.195 | 21.667 | 51 | PRO | O | 4.621 | 9.848 | 31.454 |
| 42 | ASN | OD1 | 29.168 | 15.169 | 21.967 | 52 | GLY | N | 3.693 | 11.820 | 31.082 |
| 42 | ASN | ND2 | 27.260 | 14.090 | 21.803 | 52 | GLY | CA | 3.269 | 11.377 | 29.746 |
| 42 | ASN | C | 25.176 | 16.272 | 22.354 | 52 | GLY | C | 4.368 | 11.323 | 28.690 |
| 42 | ASN | O | 25.590 | 16.890 | 22.332 | 52 | GLY | O | 4.117 | 10.848 | 27.575 |
| 43 | ILE | N | 24.152 | 15.442 | 22.457 | 53 | GLU | N | 5.606 | 11.757 | 28.996 |
| 43 | ILE | CA | 23.458 | 15.252 | 23.736 | 53 | GLU | CA | 6.645 | 11.848 | 28.005 |
| 43 | ILE | CB | 21.958 | 15.077 | 23.423 | 53 | GLU | CB | 6.909 | 13.311 | 27.676 |
| 43 | ILE | CG2 | 21.208 | 14.865 | 24.766 | 53 | GLU | CG | 5.740 | 13.985 | 27.008 |
| 43 | ILE | CG1 | 21.451 | 16.284 | 22.605 | 53 | GLU | CD | 5.991 | 15.433 | 26.597 |
| 43 | ILE | CD | 20.150 | 16.044 | 21.857 | 53 | GLU | OE1 | 7.145 | 15.826 | 26.393 |
| 43 | ILE | C | 24.075 | 14.023 | 24.422 | 53 | GLU | OE2 | 5.012 | 16.167 | 26.462 |
| 43 | ILE | O | 24.160 | 12.963 | 23.781 | 53 | GLU | C | 7.901 | 11.202 | 28.519 |
| 44 | ARG | N | 24.520 | 14.131 | 25.675 | 53 | GLU | O | 8.803 | 11.919 | 28.919 |
| 44 | ARG | CA | 25.246 | 13.030 | 26.309 | 54 | PRO | N | 8.059 | 9.880 | 28.483 |
| 44 | ARG | CB | 26.332 | 13.557 | 27.250 | 54 | PRO | CD | 7.103 | 8.945 | 27.908 |
| 44 | ARG | CG | 27.060 | 14.753 | 26.730 | 54 | PRO | CA | 9.245 | 9.200 | 29.004 |
| 44 | ARG | CD | 27.731 | 14.330 | 25.467 | 54 | PRO | CB | 8.817 | 7.745 | 28.993 |
| 44 | ARG | NE | 29.007 | 13.812 | 25.844 | 54 | PRO | CG | 7.964 | 7.702 | 27.752 |
| 44 | ARG | CZ | 30.106 | 14.554 | 25.653 | 54 | PRO | C | 10.548 | 9.487 | 28.240 |
| 44 | ARG | NH1 | 31.274 | 14.034 | 26.023 | 54 | PRO | O | 11.625 | 9.172 | 28.750 |
| 44 | ARG | NH2 | 30.099 | 15.758 | 25.065 | 55 | SER | N | 10.497 | 10.048 | 27.015 |

FIG.1C

```
55 SER  CA   11.678 10.360 26.197    65 HIS  CA   16.749 26.168 20.989
55 SER  CB   11.310 10.444 24.730    65 HIS  CB   15.534 27.012 20.769
55 SER  OG   12.390 10.759 23.870    65 HIS  CG   15.850 28.409 28.237
55 SER  C    12.250 11.702 26.559    65 HIS  CD2  15.686 28.794 18.918
55 SER  O    11.469 12.540 27.001    65 HIS  ND1  16.319 29.457 20.941
56 THR  N    13.533 11.968 26.265    65 HIS  CE1  16.438 30.455 20.096
56 THR  CA   14.084 13.315 26.487    65 HIS  NE2  16.056 30.048 18.887
56 THR  CB   15.596 13.250 26.945    65 HIS  C    17.672 26.657 22.118
56 THR  OG1  16.283 12.433 25.998    65 HIS  O    18.820 27.073 21.904
56 THR  CG2  15.743 12.741 28.390    66 VAL  N    17.220 26.535 23.376
56 THR  C    13.978 14.192 25.225    66 VAL  CA   18.084 26.803 24.544
56 THR  O    14.370 15.358 25.250    66 VAL  CB   17.351 26.378 25.832
57 GLN  N    13.331 13.623 24.170    66 VAL  CG1  18.194 26.482 27.092
57 GLN  CA   13.252 14.317 22.886    66 VAL  CG2  16.264 27.335 25.994
57 GLN  CB   12.743 13.375 21.797    66 VAL  C    19.427 26.062 24.466
57 GLN  CG   13.825 12.370 21.360    66 VAL  O    20.494 26.687 24.586
57 GLN  CD   15.108 13.013 20.762    67 ALA  N    19.347 24.730 24.292
57 GLN  OE1  15.091 13.752 19.766    67 ALA  CA   20.534 23.878 24.204
57 GLN  NE2  16.267 12.793 21.390    67 ALA  CB   20.081 22.462 23.828
57 GLN  C    12.314 15.495 23.027    67 ALA  C    21.526 24.393 23.140
57 GLN  O    11.395 15.425 23.858    67 ALA  O    22.732 24.464 23.385
58 ASP  N    12.508 16.545 22.256    68 GLY  N    21.028 24.843 21.978
58 ASP  CA   11.724 17.738 22.451    68 GLY  CA   21.890 25.373 20.923
58 ASP  CB   12.619 18.910 22.214    68 GLY  C    22.602 26.682 21.221
58 ASP  CG   12.036 20.302 22.427    68 GLY  O    23.730 26.888 20.726
58 ASP  OD1  10.950 20.447 23.006    69 THR  N    22.009 27.580 22.020
58 ASP  OD2  12.737 21.245 22.032    69 THR  CA   22.727 28.785 22.414
58 ASP  C    10.499 17.854 21.573    69 THR  CB   21.703 29.733 23.084
58 ASP  O    10.627 18.076 20.358    69 THR  OG1  20.690 29.972 22.076
59 GLY  N     9.311 17.809 22.191    69 THR  CG2  22.339 31.046 23.576
59 GLY  CA    8.021 17.992 21.500    69 THR  C    23.902 28.431 23.353
59 GLY  C     7.601 19.445 21.318    69 THR  O    24.986 29.042 23.288
59 GLY  O     6.527 19.731 20.754    70 ILE  N    23.686 27.426 24.235
60 ASN  N     8.431 20.374 21.802    70 ILE  CA   24.771 26.952 25.107
60 ASN  CA    8.085 21.787 21.793    70 ILE  CB   24.305 25.947 26.219
60 ASN  CB    8.166 22.340 23.222    70 ILE  CG2  25.501 25.525 27.092
60 ASN  CG    7.768 23.804 23.268    70 ILE  CG1  23.197 26.607 27.065
60 ASN  OD1   8.585 24.702 23.090    70 ILE  CD   22.458 25.687 28.103
60 ASN  ND2   6.503 24.085 23.545    70 ILE  C    25.820 26.222 24.285
60 ASN  C     8.971 22.642 20.883    70 ILE  O    27.014 26.530 24.398
60 ASN  O     8.525 23.378 20.022    71 ALA  N    25.447 25.251 23.451
61 GLY  N    10.269 22.585 21.093    71 ALA  CA   26.467 24.349 22.986
61 GLY  CA   11.202 23.372 20.337    71 ALA  CB   26.523 23.129 23.948
61 GLY  C    12.035 24.187 21.318    71 ALA  C    26.352 23.895 21.578
61 GLY  O    13.231 24.429 21.115    71 ALA  O    26.869 22.805 21.295
62 HIS  N    11.417 24.583 22.439    72 ALA  N    25.785 24.709 20.671
62 HIS  CA   12.068 25.515 23.336    72 ALA  CA   25.772 24.252 19.280
62 HIS  CB   11.034 25.886 24.385    72 ALA  CB   25.105 25.252 18.367
62 HIS  CG   11.450 27.020 25.268    72 ALA  C    27.223 24.056 18.832
62 HIS  CD2  11.218 28.363 25.048    72 ALA  O    28.112 24.803 19.205
62 HIS  ND1  11.969 26.858 26.498    73 LEU  N    27.412 22.934 18.090
62 HIS  CE1  12.011 28.039 27.067    73 LEU  CA   28.744 22.458 17.726
62 HIS  NE2  11.572 28.932 26.189    73 LEU  CB   28.630 21.030 17.087
62 HIS  C    13.371 24.957 23.944    73 LEU  CG   27.913 19.969 17.918
62 HIS  O    14.409 25.642 23.918    73 LEU  CD1  27.805 18.638 17.193
63 GLY  N    13.351 23.723 24.453    73 LEU  CD2  28.650 19.898 19.221
63 GLY  CA   14.577 23.186 25.039    73 LEU  C    29.465 23.384 16.782
63 GLY  C    15.709 23.028 24.021    73 LEU  O    28.857 23.968 15.858
63 GLY  O    16.870 23.232 24.356    74 ASN  N    30.768 23.410 17.002
64 THR  N    15.375 22.712 22.746    74 ASN  CA   31.650 24.268 16.196
64 THR  CA   16.392 22.485 21.700    74 ASN  CB   32.829 24.736 17.002
64 THR  CB   15.729 21.894 20.395    74 ASN  CG   33.638 25.786 16.240
64 THR  OG1  15.057 20.682 20.709    74 ASN  OD1  33.278 26.358 15.207
64 THR  CG2  16.823 21.570 19.338    74 ASN  ND2  34.798 26.098 16.774
64 THR  C    17.078 23.790 21.373    74 ASN  C    32.170 23.435 15.022
64 THR  O    18.287 23.840 21.192    74 ASN  O    33.097 22.639 15.197
65 HIS  N    16.252 24.838 21.308    75 ASN  N    31.602 23.663 13.836
```

FIG.1D

| | | | | | | | | | | |
|---|---|---|---|---|---|---|---|---|---|---|
| 75 | ASN | CA | 31.833 | 22.805 | 12.665 | 85 | SER | C | 31.718 | 21.142 | 25.147 |
| 75 | ASN | CB | 30.957 | 21.533 | 12.702 | 85 | SER | O | 32.117 | 20.128 | 25.689 |
| 75 | ASN | CG | 29.491 | 21.798 | 13.007 | 86 | ALA | N | 30.806 | 21.904 | 25.738 |
| 75 | ASN | OD1 | 28.914 | 22.891 | 12.815 | 86 | ALA | CA | 30.151 | 21.459 | 26.967 |
| 75 | ASN | ND2 | 28.869 | 20.780 | 13.605 | 86 | ALA | CB | 29.153 | 22.489 | 27.391 |
| 75 | ASN | C | 31.502 | 23.581 | 11.415 | 86 | ALA | C | 29.408 | 20.122 | 26.787 |
| 75 | ASN | O | 31.582 | 24.793 | 11.490 | 86 | ALA | O | 28.914 | 19.771 | 25.689 |
| 76 | SER | N | 31.121 | 22.947 | 10.298 | 87 | GLU | N | 29.338 | 19.367 | 27.882 |
| 76 | SER | CA | 30.794 | 23.635 | 9.055 | 87 | GLU | CA | 28.637 | 18.102 | 27.917 |
| 76 | SER | CB | 31.452 | 22.852 | 7.920 | 87 | GLU | CB | 29.274 | 17.235 | 28.985 |
| 76 | SER | OG | 32.867 | 22.956 | 8.023 | 87 | GLU | CG | 30.727 | 16.977 | 28.652 |
| 76 | SER | C | 29.308 | 23.826 | 8.771 | 87 | GLU | CD | 31.359 | 15.911 | 29.523 |
| 76 | SER | O | 28.913 | 24.172 | 7.628 | 87 | GLU | OE1 | 30.638 | 15.142 | 30.165 |
| 77 | ILE | N | 28.486 | 23.612 | 9.815 | 87 | GLU | OE2 | 32.580 | 15.850 | 29.550 |
| 77 | ILE | CA | 27.049 | 23.710 | 9.658 | 87 | GLU | C | 27.172 | 18.407 | 28.237 |
| 77 | ILE | CB | 26.315 | 22.283 | 9.597 | 87 | GLU | O | 26.787 | 18.788 | 29.353 |
| 77 | ILE | CG2 | 26.735 | 21.594 | 8.269 | 88 | LEU | N | 26.340 | 18.241 | 27.230 |
| 77 | ILE | CG1 | 26.604 | 21.393 | 10.803 | 88 | LEU | CA | 24.949 | 18.654 | 27.326 |
| 77 | ILE | CD | 25.657 | 20.178 | 10.887 | 88 | LEU | CB | 24.566 | 19.080 | 25.910 |
| 77 | ILE | C | 26.407 | 24.494 | 10.799 | 88 | LEU | CG | 23.561 | 20.137 | 25.626 |
| 77 | ILE | O | 26.960 | 24.700 | 11.891 | 88 | LEU | CD1 | 23.929 | 21.475 | 26.321 |
| 78 | GLY | N | 25.199 | 24.925 | 10.501 | 88 | LEU | CD2 | 23.521 | 20.293 | 24.093 |
| 78 | GLY | CA | 24.338 | 25.534 | 11.486 | 88 | LEU | C | 24.042 | 17.570 | 27.876 |
| 78 | GLY | C | 24.874 | 26.773 | 12.159 | 88 | LEU | O | 24.093 | 16.491 | 27.282 |
| 78 | GLY | O | 25.345 | 27.713 | 11.542 | 89 | TYR | N | 23.223 | 17.777 | 28.919 |
| 79 | VAL | N | 24.781 | 26.721 | 13.475 | 89 | TYR | CA | 22.249 | 16.807 | 29.449 |
| 79 | VAL | CA | 25.226 | 27.840 | 14.293 | 89 | TYR | CB | 22.538 | 16.474 | 30.942 |
| 79 | VAL | CB | 23.977 | 28.470 | 15.058 | 89 | TYR | CG | 23.828 | 15.673 | 31.047 |
| 79 | VAL | CG1 | 23.105 | 29.130 | 14.034 | 89 | TYR | CD1 | 25.048 | 16.317 | 30.920 |
| 79 | VAL | CG2 | 23.172 | 27.468 | 15.841 | 89 | TYR | CE1 | 26.230 | 15.627 | 30.860 |
| 79 | VAL | C | 26.342 | 27.460 | 15.258 | 89 | TYR | CD2 | 23.797 | 14.292 | 31.142 |
| 79 | VAL | O | 27.035 | 26.445 | 15.015 | 89 | TYR | CE2 | 24.979 | 13.578 | 31.070 |
| 80 | LEU | N | 26.574 | 28.266 | 16.310 | 89 | TYR | CZ | 26.175 | 14.250 | 30.937 |
| 80 | LEU | CA | 27.681 | 28.023 | 17.216 | 89 | TYR | OH | 27.340 | 13.513 | 30.872 |
| 80 | LEU | CB | 28.856 | 28.882 | 16.777 | 89 | TYR | C | 20.847 | 17.347 | 29.318 |
| 80 | LEU | CG | 30.090 | 28.886 | 17.612 | 89 | TYR | O | 20.561 | 18.513 | 29.646 |
| 80 | LEU | CD1 | 30.630 | 27.510 | 17.592 | 90 | ALA | N | 20.000 | 16.511 | 28.733 |
| 80 | LEU | CD2 | 31.076 | 29.900 | 17.113 | 90 | ALA | CA | 18.613 | 16.880 | 28.538 |
| 80 | LEU | C | 27.210 | 28.436 | 18.614 | 90 | ALA | CB | 17.991 | 16.206 | 27.306 |
| 80 | LEU | O | 26.667 | 29.536 | 18.725 | 90 | ALA | C | 17.794 | 16.453 | 29.749 |
| 81 | GLY | N | 27.333 | 27.597 | 19.625 | 90 | ALA | O | 17.565 | 15.260 | 29.984 |
| 81 | GLY | CA | 26.928 | 28.085 | 20.924 | 91 | VAL | N | 17.307 | 17.405 | 30.542 |
| 81 | GLY | C | 28.076 | 28.805 | 21.662 | 91 | VAL | CA | 16.489 | 17.070 | 31.706 |
| 81 | GLY | O | 29.253 | 28.863 | 21.248 | 91 | VAL | CB | 17.050 | 17.737 | 32.979 |
| 82 | VAL | N | 27.794 | 29.222 | 22.883 | 91 | VAL | CG1 | 16.278 | 17.172 | 34.186 |
| 82 | VAL | CA | 28.824 | 29.876 | 23.663 | 91 | VAL | CG2 | 18.529 | 17.434 | 33.152 |
| 82 | VAL | CB | 28.207 | 30.550 | 24.929 | 91 | VAL | C | 15.086 | 17.576 | 31.413 |
| 82 | VAL | CG1 | 29.266 | 31.108 | 25.913 | 91 | VAL | O | 14.803 | 18.789 | 31.545 |
| 82 | VAL | CG2 | 27.250 | 31.691 | 24.395 | 92 | LYS | N | 14.186 | 16.716 | 30.935 |
| 82 | VAL | C | 29.915 | 28.926 | 24.085 | 92 | LYS | CA | 12.860 | 17.211 | 30.608 |
| 82 | VAL | O | 31.102 | 29.295 | 24.118 | 92 | LYS | CB | 12.271 | 16.257 | 29.604 |
| 83 | ALA | N | 29.504 | 27.716 | 24.494 | 92 | LYS | CG | 10.802 | 16.621 | 29.273 |
| 83 | ALA | CA | 30.437 | 26.706 | 24.970 | 92 | LYS | CD | 10.070 | 15.579 | 28.398 |
| 83 | ALA | CB | 30.194 | 26.444 | 26.456 | 92 | LYS | CE | 10.580 | 15.652 | 26.970 |
| 83 | ALA | C | 30.270 | 25.404 | 24.181 | 92 | LYS | NZ | 9.873 | 14.730 | 26.095 |
| 83 | ALA | O | 29.605 | 24.459 | 24.615 | 92 | LYS | C | 12.009 | 17.347 | 31.892 |
| 84 | PRO | N | 30.827 | 25.356 | 22.956 | 92 | LYS | O | 11.719 | 16.396 | 32.624 |
| 84 | PRO | CD | 31.627 | 26.423 | 22.334 | 93 | VAL | N | 11.659 | 18.596 | 32.162 |
| 84 | PRO | CA | 30.449 | 24.325 | 21.985 | 93 | VAL | CA | 10.834 | 18.966 | 33.299 |
| 84 | PRO | CB | 30.988 | 24.826 | 20.658 | 93 | VAL | CB | 11.520 | 19.956 | 34.315 |
| 84 | PRO | CG | 31.954 | 25.925 | 20.928 | 93 | VAL | CG1 | 12.719 | 19.267 | 34.948 |
| 84 | PRO | C | 30.900 | 22.929 | 22.328 | 93 | VAL | CG2 | 11.808 | 21.301 | 33.634 |
| 84 | PRO | O | 30.460 | 21.987 | 21.673 | 93 | VAL | C | 9.545 | 19.632 | 32.844 |
| 85 | SER | N | 31.795 | 22.800 | 23.311 | 93 | VAL | O | 8.636 | 19.907 | 33.627 |
| 85 | SER | CA | 32.303 | 21.525 | 23.810 | 94 | LEU | N | 9.434 | 19.988 | 31.564 |
| 85 | SER | CB | 33.826 | 21.574 | 23.944 | 94 | LEU | CA | 8.253 | 20.628 | 31.023 |
| 85 | SER | OG | 34.358 | 21.691 | 22.630 | 94 | LEU | CB | 8.576 | 22.025 | 30.524 |

FIG. 1E

| | | | | | | | | | | |
|---|---|---|---|---|---|---|---|---|---|---|
| 94 | LEU | CG | 9.291 | 22.983 | 31.432 | 105 | ILE | CA | 11.308 | 20.992 | 38.055 |
| 94 | LEU | CD1 | 9.772 | 24.188 | 30.604 | 105 | ILE | CB | 10.782 | 22.425 | 38.033 |
| 94 | LEU | CD2 | 8.380 | 23.374 | 32.555 | 105 | ILE | CG2 | 12.002 | 23.365 | 38.118 |
| 94 | LEU | C | 7.783 | 19.781 | 29.830 | 105 | ILE | CG1 | 9.919 | 22.652 | 36.794 |
| 94 | LEU | O | 8.605 | 19.154 | 29.150 | 105 | ILE | CD | 9.191 | 24.036 | 36.796 |
| 95 | GLY | N | 6.479 | 19.754 | 29.581 | 105 | ILE | C | 12.186 | 20.703 | 39.293 |
| 95 | GLY | CA | 5.913 | 18.985 | 28.494 | 105 | ILE | O | 13.406 | 20.539 | 39.166 |
| 95 | GLY | C | 5.987 | 19.713 | 27.150 | 106 | ALA | N | 11.585 | 20.494 | 40.484 |
| 95 | GLY | O | 6.394 | 20.881 | 27.052 | 106 | ALA | CA | 12.324 | 20.165 | 41.677 |
| 96 | ALA | N | 5.518 | 18.995 | 26.112 | 106 | ALA | CB | 11.347 | 20.164 | 42.870 |
| 96 | ALA | CA | 5.460 | 19.485 | 24.733 | 106 | ALA | C | 13.009 | 18.797 | 41.505 |
| 96 | ALA | CB | 4.826 | 18.408 | 23.824 | 106 | ALA | O | 14.185 | 18.706 | 41.872 |
| 96 | ALA | C | 4.659 | 20.791 | 24.611 | 107 | GLN | N | 12.452 | 17.715 | 40.904 |
| 96 | ALA | O | 4.945 | 21.657 | 23.772 | 107 | GLN | CA | 13.267 | 16.487 | 40.797 |
| 97 | ASP | N | 3.680 | 20.986 | 25.508 | 107 | GLN | CB | 12.484 | 15.170 | 40.501 |
| 97 | ASP | CA | 2.957 | 22.248 | 25.636 | 107 | GLN | CG | 11.380 | 14.761 | 41.453 |
| 97 | ASP | CB | 1.637 | 22.010 | 26.330 | 107 | GLN | CD | 10.582 | 13.516 | 41.085 |
| 97 | ASP | CG | 1.665 | 21.267 | 27.665 | 107 | GLN | OE1 | 9.435 | 13.412 | 41.526 |
| 97 | ASP | OD1 | 2.704 | 20.782 | 28.130 | 107 | GLN | NE2 | 11.040 | 12.542 | 40.292 |
| 97 | ASP | OD2 | 0.596 | 21.183 | 28.270 | 107 | GLN | C | 14.299 | 16.625 | 39.702 |
| 97 | ASP | C | 3.645 | 23.410 | 26.351 | 107 | GLN | O | 15.333 | 15.973 | 39.804 |
| 97 | ASP | O | 3.058 | 24.477 | 26.509 | 108 | GLY | N | 14.058 | 17.494 | 38.722 |
| 98 | GLY | N | 4.885 | 23.232 | 26.820 | 108 | GLY | CA | 15.068 | 17.832 | 37.732 |
| 98 | GLY | CA | 5.597 | 24.264 | 27.561 | 108 | GLY | C | 16.281 | 18.376 | 38.456 |
| 98 | GLY | C | 5.223 | 24.311 | 29.038 | 108 | GLY | O | 17.409 | 17.922 | 38.169 |
| 98 | GLY | O | 5.866 | 24.997 | 29.828 | 109 | LEU | N | 16.086 | 19.337 | 39.380 |
| 99 | ARG | N | 4.228 | 23.548 | 29.442 | 109 | LEU | CA | 17.203 | 19.921 | 40.151 |
| 99 | ARG | CA | 3.746 | 23.492 | 30.813 | 109 | LEU | CB | 16.703 | 21.098 | 40.941 |
| 99 | ARG | CB | 2.274 | 23.049 | 30.885 | 109 | LEU | CG | 16.358 | 22.306 | 40.103 |
| 99 | ARG | CG | 1.275 | 23.728 | 29.965 | 109 | LEU | CD1 | 15.553 | 23.267 | 40.958 |
| 99 | ARG | CD | 1.373 | 25.198 | 30.169 | 109 | LEU | CD2 | 17.613 | 22.976 | 39.579 |
| 99 | ARG | NE | 0.065 | 25.771 | 29.978 | 109 | LEU | C | 17.899 | 18.952 | 41.088 |
| 99 | ARG | CZ | -0.085 | 27.070 | 29.703 | 109 | LEU | O | 19.137 | 18.923 | 41.163 |
| 99 | ARG | NH1 | -1.339 | 27.516 | 29.555 | 110 | GLU | N | 17.146 | 18.078 | 41.739 |
| 99 | ARG | NH2 | 0.956 | 27.923 | 29.560 | 110 | GLU | CA | 17.767 | 16.997 | 42.502 |
| 99 | ARG | C | 4.518 | 22.498 | 31.672 | 110 | GLU | CB | 16.706 | 16.208 | 43.295 |
| 99 | ARG | O | 4.851 | 21.418 | 31.175 | 110 | GLU | CG | 16.044 | 17.043 | 44.443 |
| 100 | GLY | N | 4.746 | 22.767 | 32.962 | 110 | GLU | CD | 16.869 | 17.518 | 45.693 |
| 100 | GLY | CA | 5.370 | 21.790 | 33.846 | 110 | GLU | OE1 | 16.284 | 18.250 | 46.507 |
| 100 | GLY | C | 5.043 | 22.002 | 35.327 | 110 | GLU | OE2 | 18.058 | 17.205 | 45.884 |
| 100 | GLY | O | 4.933 | 23.136 | 35.803 | 110 | GLU | C | 18.562 | 16.049 | 41.616 |
| 101 | ALA | N | 4.881 | 20.881 | 36.029 | 110 | GLU | O | 19.674 | 15.702 | 42.025 |
| 101 | ALA | CA | 4.592 | 20.897 | 37.462 | 111 | TRP | N | 18.111 | 15.691 | 40.389 |
| 101 | ALA | CB | 4.090 | 19.544 | 37.966 | 111 | TRP | CA | 18.867 | 14.850 | 39.469 |
| 101 | ALA | C | 5.844 | 21.210 | 38.278 | 111 | TRP | CB | 18.049 | 14.586 | 38.169 |
| 101 | ALA | O | 6.945 | 20.745 | 37.930 | 111 | TRP | CG | 18.743 | 13.709 | 37.091 |
| 102 | ILE | N | 5.672 | 21.920 | 39.412 | 111 | TRP | CD2 | 19.617 | 14.121 | 36.111 |
| 102 | ILE | CA | 6.812 | 22.262 | 40.268 | 111 | TRP | CE2 | 19.919 | 12.914 | 35.467 |
| 102 | ILE | CB | 6.297 | 23.134 | 41.461 | 111 | TRP | CE3 | 20.195 | 15.302 | 35.658 |
| 102 | ILE | CG2 | 7.414 | 23.536 | 42.429 | 111 | TRP | CD1 | 18.535 | 12.343 | 37.029 |
| 102 | ILE | CG1 | 5.672 | 24.383 | 40.856 | 111 | TRP | NE1 | 19.264 | 11.895 | 36.042 |
| 102 | ILE | CD | 6.675 | 25.257 | 40.045 | 111 | TRP | CZ2 | 20.803 | 12.903 | 34.389 |
| 102 | ILE | C | 7.555 | 21.016 | 40.763 | 111 | TRP | CZ3 | 21.073 | 15.292 | 34.585 |
| 102 | ILE | O | 8.790 | 21.014 | 40.848 | 111 | TRP | CH2 | 21.370 | 14.099 | 33.959 |
| 103 | SER | N | 6.839 | 19.922 | 41.067 | 111 | TRP | C | 20.160 | 15.563 | 39.124 |
| 103 | SER | CA | 7.477 | 18.691 | 41.459 | 111 | TRP | O | 21.198 | 14.910 | 39.072 |
| 103 | SER | CB | 6.399 | 17.659 | 41.711 | 112 | ALA | N | 20.134 | 16.881 | 38.876 |
| 103 | SER | OG | 5.570 | 17.479 | 40.562 | 112 | ALA | CA | 21.331 | 17.620 | 38.528 |
| 103 | SER | C | 8.451 | 18.211 | 40.361 | 112 | ALA | CB | 21.029 | 19.102 | 38.310 |
| 103 | SER | O | 9.575 | 17.820 | 40.676 | 112 | ALA | C | 22.411 | 17.530 | 39.612 |
| 104 | SER | N | 8.068 | 18.299 | 39.085 | 112 | ALA | O | 23.578 | 17.183 | 39.356 |
| 104 | SER | CA | 8.950 | 17.948 | 37.972 | 113 | GLY | N | 22.019 | 17.742 | 40.859 |
| 104 | SER | CB | 8.185 | 18.077 | 36.660 | 113 | GLY | CA | 22.962 | 17.686 | 41.947 |
| 104 | SER | OG | 7.214 | 17.048 | 36.535 | 113 | GLY | C | 23.404 | 16.258 | 42.205 |
| 104 | SER | C | 10.230 | 18.802 | 37.897 | 113 | GLY | O | 24.567 | 16.052 | 42.565 |
| 104 | SER | O | 11.330 | 18.272 | 37.756 | 114 | ASN | N | 22.524 | 15.285 | 42.009 |
| 105 | ILE | N | 10.136 | 20.124 | 38.041 | 114 | ASN | CA | 22.901 | 13.872 | 42.191 |

FIG.1F

| | | | | | | | | | | |
|---|---|---|---|---|---|---|---|---|---|---|
| 114 | ASN | CB | 21.735 | 12.858 | 42.176 | 123 | SER | OG | 16.514 | 29.408 | 29.479 |
| 114 | ASN | CG | 20.764 | 12.994 | 43.318 | 123 | SER | C | 13.240 | 29.029 | 31.383 |
| 114 | ASN | OD1 | 21.095 | 13.531 | 44.373 | 123 | SER | O | 12.521 | 28.751 | 30.400 |
| 114 | ASN | ND2 | 19.511 | 12.575 | 43.163 | 124 | LEU | N | 12.818 | 29.236 | 32.647 |
| 114 | ASN | C | 23.820 | 13.339 | 41.111 | 124 | LEU | CA | 11.426 | 29.119 | 33.059 |
| 114 | ASN | O | 24.532 | 12.346 | 41.311 | 124 | LEU | CB | 11.093 | 27.646 | 33.233 |
| 115 | ASN | N | 23.767 | 13.953 | 39.923 | 124 | LEU | CG | 12.008 | 26.810 | 34.115 |
| 115 | ASN | CA | 24.558 | 13.494 | 38.817 | 124 | LEU | CD1 | 11.540 | 26.904 | 35.610 |
| 115 | ASN | CB | 23.678 | 13.382 | 37.576 | 124 | LEU | CD2 | 11.993 | 25.356 | 33.606 |
| 115 | ASN | CG | 22.871 | 12.090 | 37.637 | 124 | LEU | C | 11.200 | 29.897 | 34.347 |
| 115 | ASN | OD1 | 23.296 | 11.044 | 37.144 | 124 | LEU | O | 12.165 | 30.261 | 35.045 |
| 115 | ASN | ND2 | 21.716 | 12.088 | 38.291 | 125 | GLY | N | 9.951 | 30.177 | 34.709 |
| 115 | ASN | C | 25.761 | 14.354 | 38.510 | 125 | GLY | CA | 9.733 | 31.019 | 35.884 |
| 115 | ASN | O | 26.352 | 14.277 | 37.428 | 125 | GLY | C | 8.243 | 31.204 | 36.140 |
| 116 | GLY | N | 26.126 | 15.225 | 39.431 | 125 | GLY | O | 7.396 | 31.003 | 35.252 |
| 116 | GLY | CA | 27.354 | 15.971 | 39.331 | 126 | SER | N | 7.991 | 31.643 | 37.370 |
| 116 | GLY | C | 27.372 | 16.991 | 38.204 | 126 | SER | CA | 6.640 | 31.772 | 37.888 |
| 116 | GLY | O | 28.450 | 17.247 | 37.614 | 126 | SER | CB | 6.331 | 30.503 | 38.752 |
| 117 | MET | N | 26.235 | 17.614 | 37.909 | 126 | SER | OG | 5.242 | 30.673 | 39.682 |
| 117 | MET | CA | 26.210 | 18.667 | 36.878 | 126 | SER | C | 6.623 | 33.055 | 38.707 |
| 117 | MET | CB | 24.807 | 19.105 | 36.509 | 126 | SER | O | 7.650 | 33.353 | 39.302 |
| 117 | MET | CG | 23.929 | 18.029 | 35.895 | 127 | PRO | N | 5.544 | 33.844 | 38.839 |
| 117 | MET | SD | 24.529 | 17.426 | 34.290 | 127 | PRO | CD | 4.300 | 33.663 | 38.088 |
| 117 | MET | CE | 24.874 | 15.741 | 34.705 | 127 | PRO | CA | 5.458 | 35.005 | 39.740 |
| 117 | MET | C | 26.888 | 19.893 | 37.466 | 127 | PRO | CB | 4.310 | 35.813 | 39.157 |
| 117 | MET | O | 26.805 | 20.170 | 38.688 | 127 | PRO | CG | 3.377 | 34.706 | 38.715 |
| 118 | HIS | N | 27.549 | 20.672 | 36.615 | 127 | PRO | C | 5.258 | 34.663 | 41.234 |
| 118 | HIS | CA | 28.186 | 21.879 | 37.094 | 127 | PRO | O | 5.342 | 35.518 | 42.119 |
| 118 | HIS | CB | 29.481 | 22.174 | 36.318 | 128 | SER | N | 4.904 | 33.408 | 41.511 |
| 118 | HIS | CG | 30.504 | 21.026 | 36.418 | 128 | SER | CA | 4.673 | 32.939 | 42.860 |
| 118 | HIS | CD2 | 30.795 | 20.176 | 35.397 | 128 | SER | CB | 3.340 | 32.142 | 42.821 |
| 118 | HIS | ND1 | 31.283 | 20.653 | 37.437 | 128 | SER | OG | 2.292 | 33.013 | 42.389 |
| 118 | HIS | CE1 | 32.020 | 19.622 | 37.044 | 128 | SER | C | 5.845 | 32.100 | 43.399 |
| 118 | HIS | NE2 | 31.715 | 19.339 | 35.797 | 128 | SER | O | 6.430 | 31.293 | 42.646 |
| 118 | HIS | C | 27.256 | 23.067 | 36.967 | 129 | PRO | N | 6.223 | 32.275 | 44.678 |
| 118 | HIS | O | 27.293 | 23.989 | 37.781 | 129 | PRO | CD | 5.713 | 33.322 | 45.595 |
| 119 | VAL | N | 26.349 | 23.070 | 35.989 | 129 | PRO | CA | 7.185 | 31.419 | 45.363 |
| 119 | VAL | CA | 25.540 | 24.246 | 35.723 | 129 | PRO | CB | 7.492 | 32.187 | 46.641 |
| 119 | VAL | CB | 26.124 | 25.082 | 34.533 | 129 | PRO | CG | 6.138 | 32.757 | 46.937 |
| 199 | VAL | CG1 | 25.194 | 26.267 | 34.244 | 129 | PRO | C | 6.639 | 29.999 | 45.605 |
| 119 | VAL | CG2 | 27.537 | 25.612 | 34.864 | 129 | PRO | O | 5.416 | 29.779 | 45.693 |
| 119 | VAL | C | 24.194 | 23.670 | 35.344 | 130 | SER | N | 7.567 | 29.069 | 45.789 |
| 119 | VAL | O | 24.123 | 22.627 | 34.674 | 130 | SER | CA | 7.242 | 27.724 | 46.139 |
| 120 | ALA | N | 23.150 | 24.305 | 35.817 | 130 | SER | CB | 7.197 | 26.894 | 44.888 |
| 120 | ALA | CA | 21.801 | 23.917 | 35.457 | 130 | SER | OG | 7.387 | 25.528 | 45.215 |
| 120 | ALA | CB | 21.074 | 23.434 | 36.689 | 130 | SER | C | 8.260 | 27.146 | 47.092 |
| 120 | ALA | C | 21.128 | 25.170 | 34.893 | 130 | SER | O | 9.462 | 27.127 | 46.751 |
| 120 | ALA | O | 21.156 | 26.255 | 35.503 | 131 | ALA | N | 7.759 | 26.596 | 48.220 |
| 121 | ASN | N | 20.621 | 25.061 | 33.673 | 131 | ALA | CA | 8.619 | 25.896 | 49.154 |
| 121 | ASN | CA | 19.917 | 26.133 | 32.994 | 131 | ALA | CB | 7.818 | 25.334 | 50.312 |
| 121 | ASN | CB | 20.330 | 26.144 | 31.516 | 131 | ALA | C | 9.445 | 24.755 | 48.557 |
| 121 | ASN | CG | 19.771 | 27.348 | 30.778 | 131 | ALA | O | 10.670 | 24.654 | 48.755 |
| 121 | ASN | OD1 | 20.464 | 28.304 | 30.514 | 132 | THR | N | 8.761 | 23.973 | 47.716 |
| 121 | ASN | ND2 | 18.511 | 27.315 | 30.418 | 132 | THR | CA | 9.373 | 22.810 | 47.044 |
| 121 | ASN | C | 18.399 | 25.942 | 33.133 | 132 | THR | CB | 8.274 | 22.155 | 46.232 |
| 121 | ASN | O | 17.793 | 24.936 | 32.715 | 132 | THR | OG1 | 7.351 | 21.804 | 47.256 |
| 122 | LEU | N | 17.740 | 26.917 | 33.768 | 132 | THR | CG2 | 8.667 | 20.937 | 45.371 |
| 122 | LEU | CA | 16.277 | 26.942 | 33.962 | 132 | THR | C | 10.547 | 23.223 | 46.156 |
| 122 | LEU | CB | 15.895 | 27.041 | 35.454 | 132 | THR | O | 11.674 | 22.711 | 46.213 |
| 122 | LEU | CG | 16.010 | 25.856 | 36.340 | 133 | LEU | N | 10.257 | 24.266 | 45.394 |
| 122 | LEU | CD1 | 15.879 | 26.350 | 37.770 | 133 | LEU | CA | 11.185 | 24.742 | 44.396 |
| 122 | LEU | CD2 | 14.914 | 24.875 | 36.068 | 133 | LEU | CB | 10.467 | 25.753 | 43.511 |
| 122 | LEU | C | 15.706 | 28.182 | 33.264 | 133 | LEU | CG | 11.231 | 26.287 | 42.326 |
| 122 | LEU | O | 15.618 | 29.298 | 33.808 | 133 | LEU | CD1 | 11.504 | 25.174 | 41.324 |
| 123 | SER | N | 15.297 | 28.013 | 32.012 | 133 | LEU | CD2 | 10.395 | 27.377 | 41.663 |
| 123 | SER | CA | 14.756 | 29.116 | 31.232 | 133 | LEU | C | 12.393 | 25.365 | 45.081 |
| 123 | SER | CB | 15.184 | 28.969 | 29.748 | 133 | LEU | O | 13.539 | 25.053 | 44.693 |

FIG.1G

| | | | | | | | | | | |
|---|---|---|---|---|---|---|---|---|---|---|
| 134 | GLU | N | 12.164 | 26.195 | 46.111 | 143 | ARG | NE | 22.030 | 17.901 | 45.589 |
| 134 | GLU | CA | 13.276 | 26.827 | 46.768 | 143 | ARG | CZ | 21.037 | 17.422 | 44.816 |
| 134 | GLU | CB | 12.749 | 27.786 | 47.793 | 143 | ARG | NH1 | 20.140 | 18.281 | 44.355 |
| 134 | GLU | CG | 13.795 | 28.476 | 48.645 | 143 | ARG | NH2 | 20.887 | 16.134 | 44.524 |
| 134 | GLU | CD | 13.249 | 29.330 | 49.814 | 143 | ARG | C | 26.745 | 20.456 | 44.602 |
| 134 | GLU | OE1 | 14.013 | 30.014 | 50.482 | 143 | ARG | O | 27.216 | 19.708 | 43.740 |
| 134 | GLU | OE2 | 12.046 | 29.337 | 50.036 | 144 | GLY | N | 27.007 | 21.760 | 44.635 |
| 134 | GLU | C | 14.181 | 25.795 | 47.420 | 144 | GLY | CA | 27.925 | 22.456 | 43.737 |
| 134 | GLU | O | 15.396 | 25.915 | 47.353 | 144 | GLY | C | 27.365 | 22.887 | 42.396 |
| 135 | GLN | N | 13.598 | 24.770 | 48.060 | 144 | GLY | O | 28.139 | 23.324 | 41.539 |
| 135 | GLN | CA | 14.373 | 23.701 | 48.651 | 145 | VAL | N | 26.048 | 22.782 | 42.186 |
| 135 | GLN | CB | 13.350 | 22.830 | 49.331 | 145 | VAL | CA | 25.465 | 22.150 | 40.874 |
| 135 | GLN | CG | 13.897 | 21.596 | 59.006 | 145 | VAL | CB | 24.118 | 22.435 | 40.672 |
| 135 | GLN | CD | 12.823 | 20.790 | 50.764 | 145 | VAL | CG1 | 23.521 | 22.778 | 39.291 |
| 135 | GLN | OE1 | 11.779 | 20.305 | 50.258 | 145 | VAL | CG2 | 24.324 | 20.921 | 40.792 |
| 135 | GLN | NE2 | 13.143 | 20.692 | 52.060 | 145 | VAL | C | 25.262 | 24.680 | 40.827 |
| 135 | GLN | C | 15.248 | 22.952 | 47.620 | 145 | VAL | O | 24.836 | 25.282 | 41.840 |
| 135 | GLN | O | 16.434 | 22.651 | 47.868 | 146 | LEU | N | 25.677 | 25.350 | 39.742 |
| 136 | ALA | N | 14.690 | 22.749 | 46.420 | 146 | LEU | CA | 25.317 | 26.759 | 39.578 |
| 136 | ALA | CA | 15.406 | 22.071 | 45.337 | 146 | LEU | CB | 26.351 | 27.518 | 38.740 |
| 136 | ALA | CB | 14.430 | 21.762 | 44.225 | 146 | LEU | CG | 26.005 | 28.987 | 38.374 |
| 136 | ALA | C | 16.556 | 22.950 | 44.802 | 146 | LEU | CD1 | 25.819 | 29.816 | 39.604 |
| 136 | ALA | O | 17.676 | 22.465 | 44.513 | 146 | LEU | CD2 | 27.114 | 29.556 | 37.506 |
| 137 | VAL | N | 16.313 | 24.272 | 44.677 | 146 | LEU | C | 23.979 | 26.800 | 38.875 |
| 137 | VAL | CA | 17.375 | 25.224 | 44.305 | 146 | LEU | O | 23.873 | 26.371 | 37.710 |
| 137 | VAL | CB | 16.834 | 26.694 | 44.238 | 147 | VAL | N | 22.940 | 27.297 | 39.523 |
| 137 | VAL | CG1 | 17.988 | 27.738 | 44.134 | 147 | VAL | CA | 21.611 | 27.371 | 38.926 |
| 137 | VAL | CG2 | 15.876 | 26.776 | 43.047 | 147 | VAL | CB | 20.552 | 27.093 | 40.011 |
| 137 | VAL | C | 18.531 | 25.152 | 45.317 | 147 | VAL | CG1 | 19.153 | 27.272 | 39.387 |
| 137 | VAL | O | 19.711 | 24.982 | 44.974 | 147 | VAL | CG2 | 20.649 | 25.642 | 40.526 |
| 138 | ASN | N | 18.136 | 25.179 | 46.588 | 147 | VAL | C | 21.405 | 28.740 | 38.305 |
| 138 | ASN | CA | 19.136 | 25.146 | 47.616 | 147 | VAL | O | 21.480 | 29.768 | 38.965 |
| 138 | ASN | CB | 18.498 | 25.457 | 48.973 | 148 | VAL | N | 21.138 | 28.776 | 37.003 |
| 138 | ASN | CG | 18.125 | 26.934 | 49.063 | 148 | VAL | CA | 21.007 | 30.019 | 36.251 |
| 138 | ASN | OD1 | 18.598 | 27.789 | 48.320 | 148 | VAL | CB | 21.982 | 30.003 | 35.055 |
| 138 | ASN | ND2 | 17.258 | 27.299 | 49.985 | 148 | VAL | CG1 | 21.916 | 31.349 | 34.328 |
| 138 | ASN | C | 19.869 | 23.832 | 47.685 | 148 | VAL | CG2 | 23.403 | 29.791 | 35.562 |
| 138 | ASN | O | 21.103 | 23.849 | 47.846 | 148 | VAL | C | 19.557 | 30.040 | 35.781 |
| 139 | SER | N | 19.209 | 22.709 | 47.506 | 148 | VAL | O | 19.127 | 29.064 | 35.128 |
| 139 | SER | CA | 19.937 | 21.466 | 47.610 | 149 | ALA | N | 18.826 | 31.120 | 36.019 |
| 139 | SER | CB | 19.001 | 20.303 | 47.649 | 149 | ALA | CA | 17.387 | 31.187 | 35.758 |
| 139 | SER | OG | 18.203 | 20.407 | 46.479 | 149 | ALA | CB | 16.610 | 31.028 | 37.063 |
| 139 | SER | C | 20.860 | 21.316 | 46.403 | 149 | ALA | C | 16.952 | 32.515 | 35.111 |
| 139 | SER | O | 22.027 | 20.902 | 46.586 | 149 | ALA | O | 17.539 | 33.555 | 35.396 |
| 140 | ALA | N | 20.431 | 21.663 | 45.160 | 150 | ALA | N | 15.931 | 32.454 | 34.249 |
| 140 | ALA | CA | 21.392 | 21.545 | 44.053 | 150 | ALA | CA | 15.375 | 33.605 | 33.549 |
| 140 | ALA | CB | 20.755 | 21.895 | 42.723 | 150 | ALA | CB | 14.427 | 33.109 | 32.448 |
| 140 | ALA | C | 22.593 | 22.460 | 44.264 | 150 | ALA | C | 14.588 | 34.558 | 34.469 |
| 140 | ALA | O | 23.740 | 22.070 | 44.057 | 150 | ALA | O | 13.789 | 34.092 | 35.290 |
| 141 | THR | N | 22.377 | 23.682 | 44.756 | 151 | SER | N | 14.717 | 35.878 | 34.313 |
| 141 | THR | CA | 23.473 | 24.599 | 45.081 | 151 | SER | CA | 13.991 | 36.841 | 35.145 |
| 141 | THR | CB | 22.851 | 25.918 | 45.587 | 151 | SER | CB | 14.526 | 38.284 | 34.979 |
| 141 | THR | OG1 | 22.034 | 26.472 | 44.549 | 151 | SER | OG | 14.430 | 38.730 | 33.630 |
| 141 | THR | CG2 | 23.908 | 26.914 | 45.924 | 151 | SER | C | 12.485 | 36.873 | 34.867 |
| 141 | THR | C | 24.419 | 23.994 | 46.121 | 151 | SER | O | 11.692 | 37.218 | 35.761 |
| 141 | THR | O | 25.644 | 24.024 | 45.907 | 152 | GLY | N | 12.062 | 36.534 | 33.633 |
| 142 | SER | N | 23.975 | 23.363 | 47.202 | 152 | GLY | CA | 10.646 | 36.425 | 33.269 |
| 142 | SER | CA | 24.937 | 22.839 | 48.134 | 152 | GLY | C | 10.382 | 37.457 | 32.193 |
| 142 | SER | CB | 24.216 | 22.599 | 49.442 | 152 | GLY | O | 11.117 | 38.447 | 32.024 |
| 142 | SER | OG | 23.086 | 21.786 | 49.207 | 153 | ASN | N | 9.271 | 37.263 | 31.499 |
| 142 | SER | C | 25.620 | 21.592 | 47.583 | 153 | ASN | CA | 8.969 | 38.082 | 30.352 |
| 142 | SER | O | 26.616 | 21.131 | 48.150 | 153 | ASN | CB | 8.689 | 37.237 | 29.116 |
| 143 | ARG | N | 25.155 | 21.025 | 46.447 | 153 | ASN | CG | 9.865 | 36.443 | 28.658 |
| 143 | ARG | CA | 25.865 | 19.945 | 45.761 | 153 | ASN | OD1 | 11.041 | 36.707 | 28.880 |
| 143 | ARG | CB | 24.848 | 18.907 | 45.261 | 153 | ASN | ND2 | 9.501 | 35.396 | 27.943 |
| 143 | ARG | CG | 24.269 | 18.107 | 46.467 | 153 | ASN | C | 7.759 | 38.990 | 30.526 |
| 143 | ARG | CD | 23.132 | 17.127 | 46.152 | 153 | ASN | O | 7.190 | 39.421 | 29.524 |

FIG.1H

| | | | | | | | | | | | |
|---|---|---|---|---|---|---|---|---|---|---|---|
| 154 | SER | N | 7.390 | 39.398 | 31.739 | 164 | ARG | CB | 12.939 | 36.127 | 43.071 |
| 154 | SER | CA | 6.193 | 40.206 | 31.915 | 164 | ARG | CG | 12.741 | 37.084 | 44.237 |
| 154 | SER | CB | 5.577 | 39.973 | 33.284 | 164 | ARG | CD | 13.377 | 38.408 | 43.906 |
| 154 | SER | OG | 6.365 | 40.558 | 34.319 | 164 | ARG | NE | 13.251 | 39.367 | 44.988 |
| 154 | SER | C | 6.534 | 41.682 | 31.798 | 164 | ARG | CZ | 14.206 | 39.530 | 45.901 |
| 154 | SER | O | 5.599 | 42.468 | 31.793 | 164 | ARG | NH1 | 14.020 | 40.475 | 46.838 |
| 155 | GLY | N | 7.805 | 42.092 | 31.773 | 164 | ARG | NH2 | 15.289 | 38.737 | 45.965 |
| 155 | GLY | CA | 8.154 | 43.499 | 31.759 | 164 | ARG | C | 15.032 | 35.123 | 43.973 |
| 155 | GLY | C | 8.028 | 44.150 | 33.143 | 164 | ARG | O | 15.559 | 35.875 | 44.807 |
| 155 | GLY | O | 8.292 | 45.349 | 33.278 | 165 | TYR | N | 15.147 | 33.808 | 44.046 |
| 156 | ALA | N | 7.640 | 43.439 | 34.195 | 165 | TYR | CA | 15.787 | 33.157 | 45.176 |
| 156 | ALA | CA | 7.476 | 44.065 | 35.498 | 165 | TYR | CB | 15.503 | 31.609 | 45.150 |
| 156 | ALA | CB | 6.649 | 43.170 | 36.405 | 165 | TYR | CG | 14.046 | 31.230 | 45.501 |
| 156 | ALA | C | 8.814 | 44.359 | 36.187 | 165 | TYR | CD1 | 13.399 | 31.807 | 46.600 |
| 156 | ALA | O | 9.864 | 43.754 | 35.891 | 165 | TYR | CE1 | 12.084 | 31.484 | 46.885 |
| 157 | SER | N | 8.746 | 45.315 | 37.132 | 165 | TYR | CD2 | 13.379 | 30.328 | 44.696 |
| 157 | SER | CA | 9.857 | 45.747 | 37.932 | 165 | TYR | CE2 | 12.067 | 30.003 | 44.992 |
| 157 | SER | CB | 9.592 | 47.150 | 38.402 | 165 | TYR | CZ | 11.444 | 30.587 | 46.078 |
| 157 | SER | OG | 8.442 | 47.158 | 39.213 | 165 | TYR | OH | 10.133 | 30.227 | 46.357 |
| 157 | SER | C | 10.085 | 44.828 | 39.123 | 165 | TYR | C | 17.293 | 33.408 | 45.179 |
| 157 | SER | O | 10.623 | 45.251 | 40.147 | 165 | TYR | O | 17.996 | 33.477 | 44.141 |
| 158 | SER | N | 9.695 | 43.568 | 39.049 | 166 | ALA | N | 17.829 | 33.600 | 46.368 |
| 158 | SER | CA | 10.126 | 42.600 | 40.061 | 166 | ALA | CA | 19.222 | 33.986 | 46.544 |
| 158 | SER | CB | 9.046 | 42.518 | 41.150 | 166 | ALA | CB | 19.552 | 34.070 | 48.042 |
| 158 | SER | OG | 7.823 | 41.997 | 40.640 | 166 | ALA | C | 20.231 | 33.070 | 45.878 |
| 158 | SER | C | 10.335 | 41.293 | 39.275 | 166 | ALA | O | 21.192 | 33.553 | 45.278 |
| 158 | SER | O | 9.682 | 41.091 | 38.225 | 167 | ASN | N | 19.920 | 31.767 | 45.871 |
| 159 | ILE | N | 11.265 | 40.413 | 39.718 | 167 | ASN | CA | 20.860 | 30.806 | 45.280 |
| 159 | ILE | CA | 11.600 | 39.245 | 38.894 | 167 | ASN | CB | 20.778 | 29.446 | 46.048 |
| 159 | ILE | CB | 13.164 | 39.024 | 38.847 | 167 | ASN | CG | 21.566 | 29.545 | 47.374 |
| 159 | ILE | CG2 | 13.801 | 40.300 | 38.272 | 167 | ASN | OD1 | 22.592 | 30.238 | 47.502 |
| 159 | ILE | CG1 | 13.729 | 38.612 | 40.201 | 167 | ASN | ND2 | 21.130 | 28.931 | 48.461 |
| 159 | ILE | CD | 15.208 | 38.246 | 40.013 | 167 | ASN | C | 20.712 | 30.572 | 43.776 |
| 159 | ILE | C | 10.906 | 37.978 | 39.381 | 167 | ASN | O | 21.411 | 29.727 | 43.205 |
| 159 | ILE | O | 10.454 | 37.888 | 40.528 | 168 | ALA | N | 19.760 | 31.248 | 43.121 |
| 160 | SER | N | 10.806 | 36.974 | 38.510 | 168 | ALA | CA | 19.673 | 31.167 | 41.683 |
| 160 | SER | CA | 10.114 | 35.754 | 38.841 | 168 | ALA | CB | 18.206 | 31.007 | 41.284 |
| 160 | SER | CB | 9.658 | 35.097 | 37.513 | 168 | ALA | C | 20.259 | 32.481 | 41.121 |
| 160 | SER | OG | 10.700 | 34.817 | 36.581 | 168 | ALA | O | 19.961 | 33.600 | 41.595 |
| 160 | SER | C | 10.947 | 34.777 | 39.691 | 169 | MET | N | 21.005 | 32.366 | 40.015 |
| 160 | SER | O | 12.152 | 34.921 | 39.958 | 169 | MET | CA | 21.563 | 33.497 | 39.321 |
| 161 | TYR | N | 10.265 | 33.738 | 40.148 | 169 | MET | CB | 22.854 | 33.069 | 38.636 |
| 161 | TYR | CA | 10.867 | 32.645 | 40.876 | 169 | MET | CG | 23.476 | 34.273 | 37.972 |
| 161 | TYR | CB | 9.887 | 32.231 | 41.988 | 169 | MET | SD | 25.057 | 33.851 | 37.212 |
| 161 | TYR | CG | 9.698 | 33.315 | 43.030 | 169 | MET | CE | 25.641 | 35.532 | 37.199 |
| 161 | TYR | CD1 | 10.614 | 33.397 | 44.072 | 169 | MET | C | 20.493 | 33.939 | 38.305 |
| 161 | TYR | CE1 | 10.459 | 34.368 | 45.057 | 169 | MET | O | 19.998 | 33.150 | 37.484 |
| 161 | TYR | CD2 | 8.619 | 34.189 | 42.939 | 170 | ALA | N | 20.047 | 35.196 | 38.436 |
| 161 | TYR | CE2 | 8.459 | 35.175 | 43.906 | 170 | ALA | CA | 18.956 | 35.777 | 37.681 |
| 161 | TYR | CZ | 9.384 | 35.241 | 44.953 | 170 | ALA | CB | 18.208 | 36.758 | 38.591 |
| 161 | TYR | OH | 9.270 | 36.241 | 45.896 | 170 | ALA | C | 19.430 | 36.504 | 36.432 |
| 161 | TYR | C | 11.101 | 31.499 | 39.865 | 170 | ALA | O | 20.278 | 37.405 | 36.596 |
| 161 | TYR | O | 10.257 | 31.307 | 38.975 | 171 | VAL | N | 18.927 | 36.158 | 35.241 |
| 162 | PRO | N | 12.153 | 30.681 | 39.954 | 171 | VAL | CA | 19.332 | 36.739 | 33.966 |
| 162 | PRO | CD | 12.388 | 29.536 | 39.042 | 171 | VAL | CB | 19.862 | 35.590 | 33.075 |
| 162 | PRO | CA | 13.162 | 30.687 | 41.003 | 171 | VAL | CG1 | 20.380 | 36.267 | 31.766 |
| 162 | PRO | CB | 13.715 | 29.232 | 40.966 | 171 | VAL | CG2 | 20.946 | 34.749 | 33.786 |
| 162 | PRO | CG | 13.726 | 28.915 | 39.470 | 171 | VAL | C | 18.192 | 37.445 | 33.235 |
| 162 | PRO | C | 14.243 | 31.756 | 40.879 | 171 | VAL | O | 17.145 | 36.824 | 32.979 |
| 162 | PRO | O | 15.044 | 31.845 | 41.789 | 172 | GLY | N | 18.474 | 38.712 | 32.887 |
| 163 | ALA | N | 14.352 | 32.580 | 39.814 | 172 | GLY | CA | 17.594 | 39.568 | 32.123 |
| 163 | ALA | CA | 15.393 | 33.575 | 39.716 | 172 | GLY | C | 18.038 | 39.553 | 30.640 |
| 163 | ALA | CB | 15.165 | 34.416 | 38.441 | 172 | GLY | O | 19.106 | 39.023 | 30.302 |
| 163 | ALA | C | 15.538 | 34.529 | 40.935 | 173 | ALA | N | 17.231 | 40.184 | 29.781 |
| 163 | ALA | O | 16.640 | 34.874 | 41.399 | 173 | ALA | CA | 17.461 | 40.220 | 28.347 |
| 164 | ARG | N | 14.417 | 34.878 | 41.559 | 173 | ALA | CB | 16.278 | 39.626 | 27.617 |
| 164 | ARG | CA | 14.385 | 35.740 | 42.745 | 173 | ALA | C | 17.667 | 41.631 | 27.812 |

FIG.1I

| | | | | | | | | | | | |
|---|---|---|---|---|---|---|---|---|---|---|---|
| 173 | ALA | O | 16.987 | 42.599 | 28.169 | 182 | SER | CB | 9.735 | 46.338 | 25.967 |
| 174 | THR | N | 18.639 | 41.714 | 26.910 | 182 | SER | OG | 9.316 | 45.472 | 24.927 |
| 174 | THR | CA | 18.993 | 42.944 | 26.178 | 182 | SER | C | 10.061 | 44.602 | 27.814 |
| 174 | THR | CB | 20.504 | 43.281 | 26.349 | 182 | SER | O | 9.557 | 44.957 | 28.879 |
| 174 | THR | OG1 | 21.329 | 42.130 | 26.074 | 183 | PHE | N | 10.058 | 43.321 | 27.403 |
| 174 | THR | CG2 | 20.733 | 43.727 | 27.767 | 183 | PHE | CA | 9.501 | 42.231 | 28.191 |
| 174 | THR | C | 18.715 | 42.787 | 24.688 | 183 | PHE | CB | 9.261 | 40.999 | 27.282 |
| 174 | THR | O | 18.622 | 41.662 | 24.148 | 183 | PHE | CG | 10.501 | 40.486 | 26.518 |
| 175 | ASP | N | 18.674 | 43.934 | 24.029 | 183 | PHE | CD1 | 11.508 | 39.734 | 27.142 |
| 175 | ASP | CA | 18.518 | 43.907 | 22.588 | 183 | PHE | CD2 | 10.653 | 40.840 | 25.173 |
| 175 | ASP | CB | 17.388 | 44.840 | 22.148 | 183 | PHE | CE1 | 12.617 | 39.325 | 26.421 |
| 175 | ASP | CG | 17.584 | 46.353 | 22.386 | 183 | PHE | CE2 | 11.782 | 40.415 | 24.478 |
| 175 | ASP | OD1 | 18.675 | 46.844 | 22.682 | 183 | PHE | CZ | 12.774 | 39.665 | 25.095 |
| 175 | ASP | OD2 | 16.579 | 47.047 | 22.291 | 183 | PHE | C | 10.359 | 41.795 | 29.380 |
| 174 | ASP | C | 19.794 | 44.258 | 21.834 | 183 | PHE | O | 9.889 | 41.025 | 30.246 |
| 175 | ASP | O | 20.844 | 44.480 | 22.440 | 184 | SER | N | 11.615 | 42.247 | 29.427 |
| 176 | GLN | N | 19.724 | 44.498 | 20.516 | 184 | SER | CA | 12.551 | 41.670 | 30.410 |
| 176 | GLN | CA | 20.938 | 44.742 | 19.737 | 184 | SER | CB | 13.998 | 42.030 | 30.045 |
| 176 | GLN | CB | 20.702 | 44.722 | 18.237 | 184 | SER | OG | 14.926 | 41.420 | 30.947 |
| 176 | GLN | CG | 20.123 | 43.400 | 17.797 | 184 | SER | C | 12.281 | 42.125 | 31.843 |
| 176 | GLN | CD | 18.592 | 43.272 | 17.887 | 184 | SER | O | 12.450 | 43.331 | 32.137 |
| 176 | GLN | OE1 | 17.837 | 44.022 | 18.543 | 185 | GLN | N | 11.911 | 41.197 | 32.727 |
| 176 | GLN | NE2 | 18.083 | 42.254 | 17.196 | 185 | GLN | CA | 11.652 | 41.622 | 34.089 |
| 176 | GLN | C | 21.534 | 46.084 | 20.056 | 185 | GLN | CB | 11.034 | 40.489 | 34.904 |
| 176 | GLN | O | 22.690 | 46.302 | 19.783 | 185 | GLN | CG | 9.595 | 40.335 | 34.482 |
| 177 | ASN | N | 20.836 | 46.989 | 20.719 | 185 | GLN | CD | 8.912 | 39.174 | 35.165 |
| 177 | ASN | CA | 21.382 | 48.288 | 21.098 | 185 | GLN | OE1 | 8.817 | 39.005 | 36.377 |
| 177 | ASN | CB | 20.321 | 49.300 | 20.975 | 185 | GLN | NE2 | 8.397 | 38.320 | 34.331 |
| 177 | ASN | CG | 19.832 | 49.550 | 19.587 | 185 | GLN | C | 12.960 | 42.075 | 34.773 |
| 177 | ASN | OD1 | 20.577 | 49.605 | 18.631 | 185 | GLN | O | 14.066 | 41.606 | 34.458 |
| 177 | ASN | ND2 | 18.526 | 49.678 | 19.484 | 186 | TYR | N | 12.871 | 43.046 | 35.676 |
| 177 | ASN | C | 21.895 | 48.299 | 22.521 | 186 | TYR | CA | 14.048 | 43.618 | 36.349 |
| 177 | ASN | O | 22.380 | 49.322 | 23.026 | 186 | TYR | CB | 14.488 | 44.924 | 35.634 |
| 178 | ASN | N | 21.875 | 47.139 | 23.202 | 186 | TYR | CG | 13.385 | 45.992 | 35.576 |
| 178 | ASN | CA | 22.256 | 47.033 | 24.623 | 186 | TYR | CD1 | 12.362 | 45.872 | 34.635 |
| 178 | ASN | CB | 23.735 | 47.479 | 24.896 | 186 | TYR | CE1 | 11.347 | 46.805 | 34.553 |
| 178 | ASN | CG | 24.734 | 46.515 | 24.314 | 186 | TYR | CD2 | 13.385 | 47.049 | 36.468 |
| 178 | ASN | OD1 | 24.433 | 45.324 | 24.210 | 186 | TYR | CE2 | 12.386 | 47.988 | 36.396 |
| 178 | ASN | ND2 | 25.920 | 46.928 | 23.917 | 186 | TYR | CZ | 11.376 | 47.855 | 35.450 |
| 178 | ASN | C | 21.345 | 47.835 | 25.547 | 186 | TYR | OH | 10.418 | 48.846 | 35.328 |
| 178 | ASN | O | 21.747 | 48.392 | 26.576 | 186 | TYR | C | 13.735 | 43.925 | 37.819 |
| 179 | ASN | N | 20.081 | 47.806 | 25.174 | 186 | TYR | O | 12.616 | 43.620 | 38.262 |
| 179 | ASN | CA | 19.000 | 48.319 | 26.009 | 186 | GLY | N | 14.620 | 44.547 | 38.575 |
| 179 | ASN | CB | 18.044 | 49.165 | 25.243 | 187 | GLY | CA | 14.330 | 44.849 | 39.958 |
| 179 | ASN | CG | 18.566 | 50.593 | 25.088 | 187 | GLY | C | 15.232 | 44.062 | 40.892 |
| 179 | ASN | OD1 | 19.289 | 51.155 | 25.949 | 187 | GLY | O | 16.318 | 43.548 | 40.541 |
| 179 | ASN | ND2 | 18.250 | 51.181 | 23.925 | 188 | ALA | N | 14.782 | 43.915 | 42.140 |
| 179 | ASN | C | 18.230 | 47.101 | 26.490 | 188 | ALA | CA | 15.616 | 43.340 | 43.172 |
| 179 | ASN | O | 18.246 | 46.016 | 25.872 | 188 | ALA | CB | 14.891 | 43.435 | 44.515 |
| 180 | ARG | N | 17.579 | 47.276 | 27.645 | 188 | ALA | C | 15.973 | 41.884 | 42.894 |
| 180 | ARG | CA | 16.734 | 46.241 | 28.230 | 188 | ALA | O | 15.134 | 41.065 | 42.549 |
| 180 | ARG | CB | 16.050 | 46.746 | 29.525 | 189 | GLY | N | 17.263 | 41.594 | 42.986 |
| 180 | ARG | CG | 15.269 | 45.653 | 30.233 | 189 | GLY | CA | 17.747 | 40.223 | 42.778 |
| 180 | ARG | CD | 14.562 | 46.201 | 31.492 | 189 | GLY | C | 18.299 | 39.938 | 41.358 |
| 180 | ARG | NE | 13.537 | 47.146 | 31.076 | 189 | GLY | O | 18.911 | 38.873 | 41.139 |
| 180 | ARG | CZ | 12.271 | 46.850 | 30.720 | 190 | LEU | N | 18.128 | 40.857 | 40.397 |
| 180 | ARG | NH1 | 11.476 | 47.846 | 30.339 | 190 | LEU | CA | 18.646 | 40.601 | 39.064 |
| 180 | ARG | NH2 | 11.709 | 45.650 | 30.752 | 190 | LEU | CB | 18.023 | 41.621 | 38.094 |
| 180 | ARG | C | 15.639 | 45.909 | 27.213 | 190 | LEU | CG | 18.302 | 41.454 | 36.607 |
| 180 | ARG | O | 14.991 | 46.855 | 26.715 | 190 | LEU | CD1 | 17.688 | 40.163 | 36.140 |
| 181 | ALA | N | 15.377 | 44.644 | 26.848 | 190 | LEU | CD2 | 17.844 | 42.716 | 35.848 |
| 181 | ALA | CA | 14.225 | 44.338 | 26.002 | 190 | LEU | C | 20.169 | 40.671 | 39.079 |
| 181 | ALA | CB | 14.266 | 42.883 | 25.663 | 190 | LEU | O | 20.776 | 41.624 | 39.589 |
| 181 | ALA | C | 12.942 | 44.677 | 26.771 | 191 | ASP | N | 20.847 | 39.677 | 38.505 |
| 181 | ALA | O | 12.873 | 44.495 | 28.009 | 191 | ASP | CA | 22.285 | 39.597 | 38.558 |
| 182 | SER | N | 11.894 | 45.172 | 26.133 | 191 | ASP | CB | 22.732 | 38.168 | 38.777 |
| 182 | SER | CA | 10.757 | 45.650 | 26.927 | 191 | ASP | CG | 22.428 | 37.668 | 40.182 |

FIG.1J

| | | | | | | | | | | |
|---|---|---|---|---|---|---|---|---|---|---|
|191|ASP|OD1|22.903|38.250|41.148|201|SER|CA|19.476|28.584|17.356|
|191|ASP|OD2|21.685|36.717|40.309|201|SER|CB|19.283|28.528|18.891|
|191|ASP|C|23.037|40.095|37.355|201|SER|OG|20.089|27.563|19.530|
|191|ASP|O|24.122|40.674|37.449|201|SER|C|18.875|27.346|16.701|
|192|ILE|N|22.464|39.842|36.171|201|SER|O|18.062|27.448|15.779|
|192|ILE|CA|23.192|40.070|34.908|202|THR|N|19.318|26.189|17.171|
|192|ILE|CB|24.291|38.919|34.852|202|THR|CA|18.879|24.880|16.747|
|192|ILE|CG2|23.628|37.619|34.325|202|THR|CB|19.769|23.760|17.461|
|192|ILE|CG1|25.513|39.314|34.012|202|THR|OG1|19.869|24.043|18.866|
|192|ILE|CD|26.686|38.323|34.226|202|THR|CG2|21.204|23.712|16.888|
|192|ILE|C|22.176|40.008|33.774|202|THR|C|17.412|24.706|17.082|
|192|ILE|O|21.020|39.545|33.967|202|THR|O|16.901|25.159|18.115|
|193|VAL|N|22.644|40.477|32.608|203|TYR|N|16.712|23.986|16.227|
|193|VAL|CA|21.847|40.379|31.392|203|TYR|CA|15.286|23.728|16.398|
|193|VAL|CB|21.246|41.745|30.945|203|TYR|CB|14.508|24.820|15.615|
|193|VAL|CG1|20.189|42.187|31.967|203|TYR|CG|13.165|25.140|16.239|
|193|VAL|CG2|22.326|42.772|30.755|203|TYR|CD1|13.129|25.884|17.421|
|193|VAL|C|22.653|39.820|30.203|203|TYR|CE1|11.918|26.223|17.992|
|193|VAL|O|23.885|39.799|30.174|203|TYR|CD2|11.996|24.708|15.619|
|194|ALA|N|21.891|39.376|29.204|203|TYR|CE2|10.770|25.044|16.193|
|194|ALA|CA|22.453|38.810|28.000|203|TYR|CZ|10.757|25.798|17.369|
|194|ALA|CB|22.770|37.303|28.253|203|TYR|OH|9.560|26.166|17.949|
|194|ALA|C|21.446|38.965|26.837|203|TYR|C|14.941|22.322|15.901|
|194|ALA|O|20.264|39.273|27.044|203|TYR|O|15.658|21.779|15.040|
|195|PRO|N|21.872|38.794|25.576|204|PRO|N|13.905|21.662|16.450|
|195|PRO|CD|23.294|38.583|25.188|204|PRO|CD|13.057|22.111|17.596|
|195|PRO|CA|21.018|38.880|24.377|204|PRO|CA|13.468|20.319|15.980|
|195|PRO|CB|21.899|38.465|23.180|204|PRO|CB|12.178|20.026|16.797|
|195|PRO|CG|23.321|38.854|23.643|204|PRO|CG|12.414|20.819|18.098|
|195|PRO|C|19.802|38.002|24.479|204|PRO|C|13.249|20.306|14.463|
|195|PRO|O|19.931|36.816|24.761|204|PRO|O|12.965|21.337|13.825|
|196|GLY|N|18.648|38.574|24.192|205|GLY|N|13.473|19.119|13.895|
|196|GLY|CA|17.403|37.833|24.257|205|GLY|CA|13.358|18.927|12.435|
|196|GLY|C|16.401|38.217|23.175|205|GLY|C|14.643|19.310|11.724|
|196|GLY|O|15.214|37.925|23.303|205|GLY|O|14.632|19.630|10.535|
|197|VAL|N|16.829|38.890|22.088|206|SER|N|15.770|19.252|12.442|
|197|VAL|CA|15.888|39.285|21.035|206|SER|CA|17.067|19.586|11.924|
|197|VAL|CB|15.690|40.877|21.010|206|SER|CB|17.523|18.417|11.036|
|197|VAL|CG1|14.919|41.323|19.738|206|SER|OG|17.461|17.216|11.797|
|197|VAL|CG2|15.038|41.327|22.327|206|SER|C|17.098|20.931|11.175|
|197|VAL|C|16.483|38.785|19.727|206|SER|O|17.591|21.045|10.047|
|197|VAL|O|17.672|38.897|19.432|207|THR|N|16.566|21.968|11.842|
|198|ASN|N|15.627|38.173|18.937|207|THR|CA|16.518|23.294|11.258|
|198|ASN|CA|15.957|37.626|17.630|207|THR|CB|15.070|23.518|10.667|
|198|ASN|CB|16.220|38.703|16.520|207|THR|OG1|15.190|24.695|9.866|
|198|ASN|CG|15.814|38.095|15.160|207|THR|CG2|13.924|23.606|11.700|
|198|ASN|OD1|15.010|37.149|15.093|207|THR|C|16.928|24.275|12.354|
|198|ASN|ND2|16.255|38.621|14.013|207|THR|O|17.600|23.908|13.342|
|198|ASN|C|17.160|36.718|17.695|208|TYR|N|16.632|25.546|12.113|
|198|ASN|O|18.147|36.910|16.978|208|TYR|CA|17.071|26.693|12.914|
|199|VAL|N|17.039|35.746|18.605|208|TYR|CB|18.333|27.321|12.307|
|199|VAL|CA|18.096|34.791|18.849|208|TYR|CG|19.364|26.245|12.061|
|199|VAL|CB|18.135|34.490|20.377|208|TYR|CD1|19.428|25.565|10.842|
|199|VAL|CG1|19.303|33.623|20.702|208|TYR|CE1|20.274|24.513|10.648|
|199|VAL|CG2|18.493|35.732|21.205|208|TYR|CD2|20.152|25.869|13.110|
|199|VAL|C|17.872|33.522|18.017|208|TYR|CE2|20.978|24.825|12.917|
|199|VAL|O|16.912|32.776|18.194|208|TYR|CZ|21.039|24.151|11.713|
|200|GLN|N|18.706|33.324|17.005|208|TYR|OH|21.935|23.103|11.601|
|200|GLN|CA|18.771|32.144|16.138|208|TYR|C|15.936|27.689|12.911|
|200|GLN|CB|19.584|32.515|14.908|208|TYR|O|15.224|27.863|11.906|
|200|GLN|CG|19.819|31.348|13.964|209|ALA|N|15.728|28.316|14.076|
|200|GLN|CD|20.240|31.677|12.544|209|ALA|CA|14.653|29.234|14.266|
|200|GLN|OE1|21.324|32.176|12.338|209|ALA|CB|13.489|28.384|14.707|
|200|GLN|NE2|19.592|31.494|11.476|209|ALA|C|15.041|30.312|15.266|
|200|GLN|C|19.433|30.946|16.796|209|ALA|O|16.021|30.178|16.019|
|200|GLN|O|20.567|31.114|17.277|210|SER|N|14.378|31.450|15.089|
|201|SER|N|18.810|29.768|16.799|210|SER|CA|14.567|32.642|15.914|

FIG.1K

| | | | | | | | | | | |
|---|---|---|---|---|---|---|---|---|---|---|
| 210 | SER | CB | 14.614 | 33.893 | 15.065 | 220 | HIS | CG | 23.307 | 34.345 | 25.237 |
| 210 | SER | OG | 15.788 | 33.756 | 14.342 | 220 | HIS | CD2 | 24.010 | 34.501 | 24.048 |
| 210 | SER | C | 13.456 | 32.819 | 16.920 | 220 | HIS | ND1 | 21.999 | 34.359 | 24.936 |
| 210 | SER | O | 12.255 | 32.689 | 16.610 | 220 | HIS | CE1 | 21.849 | 34.518 | 23.642 |
| 211 | SER | N | 13.895 | 33.079 | 18.152 | 220 | HIS | NE2 | 23.064 | 34.607 | 23.115 |
| 211 | LEU | CA | 12.990 | 33.304 | 19.244 | 220 | HIS | C | 25.048 | 32.824 | 28.410 |
| 211 | LEU | CB | 12.963 | 32.089 | 20.118 | 220 | HIS | O | 26.276 | 32.626 | 28.383 |
| 211 | LEU | CG | 12.368 | 30.848 | 19.535 | 221 | VAL | N | 24.370 | 32.933 | 29.566 |
| 211 | LEU | CD1 | 12.346 | 29.857 | 20.657 | 221 | VAL | CA | 25.084 | 32.989 | 30.830 |
| 211 | LEU | CD2 | 10.940 | 31.056 | 19.033 | 221 | VAL | CB | 24.180 | 33.727 | 31.843 |
| 211 | LEU | C | 13.372 | 34.503 | 20.110 | 221 | VAL | CG1 | 24.746 | 33.674 | 33.267 |
| 211 | LEU | O | 14.547 | 34.927 | 20.110 | 221 | VAL | CG2 | 24.119 | 35.194 | 31.366 |
| 212 | ASN | N | 12.439 | 35.024 | 20.912 | 221 | VAL | C | 25.477 | 31.606 | 31.299 |
| 212 | ASN | CA | 12.734 | 36.191 | 21.741 | 221 | VAL | O | 26.612 | 31.424 | 31.734 |
| 212 | ASN | CB | 11.883 | 37.403 | 21.413 | 222 | ALA | N | 24.617 | 30.614 | 31.120 |
| 212 | ASN | CG | 11.961 | 37.853 | 19.972 | 222 | ALA | CA | 24.981 | 29.223 | 31.421 |
| 212 | ASN | OD1 | 12.979 | 38.246 | 19.415 | 222 | ALA | CB | 23.871 | 28.283 | 31.032 |
| 212 | ASN | ND2 | 10.841 | 37.797 | 19.283 | 222 | ALA | C | 26.229 | 28.786 | 30.670 |
| 212 | ASN | C | 12.354 | 35.787 | 23.156 | 222 | ALA | O | 27.129 | 28.121 | 31.204 |
| 212 | ASN | O | 11.336 | 35.119 | 23.350 | 223 | GLY | N | 26.258 | 29.180 | 29.388 |
| 213 | GLY | N | 13.070 | 36.197 | 24.217 | 223 | GLY | CA | 27.463 | 28.928 | 28.649 |
| 213 | GLY | CA | 12.648 | 35.928 | 25.599 | 223 | GLY | C | 28.715 | 29.661 | 29.070 |
| 213 | GLY | C | 13.834 | 35.974 | 26.520 | 223 | GLY | O | 29.806 | 29.064 | 29.098 |
| 213 | GLY | O | 14.990 | 35.843 | 26.099 | 224 | ALA | N | 28.557 | 30.955 | 29.357 |
| 214 | THR | N | 13.583 | 36.141 | 27.832 | 224 | ALA | CA | 29.708 | 31.677 | 29.842 |
| 214 | THR | CA | 14.658 | 36.016 | 28.829 | 224 | ALA | CB | 29.313 | 33.106 | 30.058 |
| 214 | THR | CB | 14.204 | 36.523 | 30.242 | 224 | ALA | C | 30.261 | 31.051 | 31.147 |
| 214 | THR | OG1 | 12.998 | 35.812 | 30.594 | 224 | ALA | O | 31.463 | 30.894 | 31.314 |
| 214 | THR | CG2 | 14.014 | 38.055 | 30.271 | 225 | ALA | N | 29.387 | 30.580 | 32.016 |
| 214 | THR | C | 15.128 | 34.527 | 28.894 | 225 | ALA | CA | 29.771 | 29.836 | 33.221 |
| 214 | THR | O | 16.253 | 34.214 | 29.302 | 225 | ALA | CB | 28.560 | 29.321 | 34.020 |
| 215 | SER | N | 14.304 | 33.607 | 28.380 | 225 | ALA | C | 30.593 | 28.603 | 32.864 |
| 215 | SER | CA | 14.663 | 32.187 | 28.217 | 225 | ALA | O | 31.630 | 28.374 | 33.487 |
| 215 | SER | CB | 13.425 | 31.449 | 27.696 | 226 | ALA | N | 30.248 | 27.816 | 31.843 |
| 215 | SER | OG | 12.324 | 31.235 | 28.564 | 226 | ALA | CA | 31.033 | 26.664 | 31.490 |
| 215 | SER | C | 15.860 | 31.981 | 27.237 | 226 | ALA | CB | 30.292 | 25.958 | 30.380 |
| 215 | SER | O | 16.588 | 30.993 | 27.305 | 226 | ALA | C | 32.446 | 27.078 | 31.054 |
| 216 | MET | N | 16.039 | 32.907 | 26.272 | 226 | ALA | O | 33.421 | 26.381 | 31.370 |
| 216 | MET | CA | 17.165 | 32.901 | 25.324 | 227 | LEU | N | 32.587 | 28.209 | 30.328 |
| 216 | MET | CB | 16.776 | 33.575 | 24.055 | 227 | LEU | CA | 33.888 | 28.734 | 29.901 |
| 216 | MET | CG | 15.843 | 32.791 | 23.121 | 227 | LEU | CB | 33.691 | 29.983 | 28.955 |
| 216 | MET | SD | 14.133 | 32.519 | 23.660 | 227 | LEU | CG | 32.901 | 29.762 | 27.666 |
| 216 | MET | CE | 14.311 | 30.783 | 23.925 | 227 | LEU | CD1 | 32.816 | 31.015 | 26.813 |
| 216 | MET | C | 18.372 | 33.638 | 25.885 | 227 | LEU | CD2 | 33.598 | 28.704 | 26.902 |
| 216 | MET | O | 19.506 | 33.386 | 25.460 | 227 | LEU | C | 34.782 | 29.060 | 31.088 |
| 217 | ALA | N | 18.136 | 34.558 | 26.845 | 227 | LEU | O | 35.954 | 28.623 | 31.131 |
| 217 | ALA | CA | 19.249 | 35.257 | 27.465 | 228 | VAL | N | 34.176 | 29.711 | 32.105 |
| 217 | ALA | CB | 18.739 | 36.485 | 28.240 | 228 | VAL | CA | 34.951 | 30.076 | 33.286 |
| 217 | ALA | C | 19.991 | 34.343 | 28.432 | 228 | VAL | CB | 34.114 | 31.094 | 34.168 |
| 217 | ALA | O | 21.223 | 34.249 | 28.386 | 228 | VAL | CG1 | 34.822 | 31.451 | 35.502 |
| 218 | THR | N | 19.211 | 33.574 | 29.199 | 228 | VAL | CG2 | 33.950 | 32.402 | 33.362 |
| 218 | THR | CA | 19.756 | 32.657 | 30.231 | 228 | VAL | C | 35.340 | 28.814 | 34.074 |
| 218 | THR | CB | 18.587 | 31.860 | 30.888 | 228 | VAL | O | 36.468 | 28.777 | 34.573 |
| 218 | THR | OG1 | 17.719 | 32.837 | 31.429 | 229 | LYS | N | 34.502 | 27.781 | 34.115 |
| 218 | THR | CG2 | 19.040 | 30.887 | 31.979 | 229 | LYS | CA | 34.817 | 26.566 | 34.865 |
| 218 | THR | C | 20.824 | 31.704 | 29.700 | 229 | LYS | CB | 33.575 | 25.679 | 34.978 |
| 218 | THR | O | 21.912 | 31.648 | 30.275 | 229 | LYS | CG | 33.758 | 24.324 | 35.713 |
| 219 | PRO | N | 20.683 | 31.008 | 28.586 | 229 | LYS | CD | 34.180 | 24.479 | 37.170 |
| 219 | PRO | CD | 19.479 | 30.843 | 27.793 | 229 | LYS | CE | 34.230 | 23.097 | 37.844 |
| 219 | PRO | CA | 21.708 | 30.099 | 28.089 | 229 | LYS | NZ | 34.394 | 23.211 | 39.298 |
| 219 | PRO | CB | 21.074 | 29.384 | 26.909 | 229 | LYS | C | 35.919 | 25.792 | 34.170 |
| 219 | PRO | CG | 19.943 | 30.268 | 26.471 | 229 | LYS | O | 36.804 | 25.233 | 34.841 |
| 219 | PRO | C | 23.027 | 30.765 | 27.704 | 230 | GLN | N | 35.915 | 25.679 | 32.835 |
| 219 | PRO | O | 24.060 | 30.108 | 27.745 | 230 | GLN | CA | 37.001 | 24.957 | 32.188 |
| 220 | HIS | N | 22.994 | 32.051 | 27.346 | 230 | GLN | CB | 36.692 | 24.852 | 30.683 |
| 220 | HIS | CA | 24.239 | 32.770 | 27.094 | 230 | GLN | CG | 37.819 | 24.181 | 29.916 |
| 220 | HIS | CB | 23.997 | 34.219 | 26.600 | 230 | GLN | CD | 37.806 | 24.343 | 28.410 |

FIG.1L

| | | | | | | | | | | | |
|---|---|---|---|---|---|---|---|---|---|---|---|
| 230 | GLN | OE1 | 36.941 | 24.907 | 27.731 | 238 | VAL | C | 30.741 | 31.770 | 43.322 |
| 230 | GLN | NE2 | 38.866 | 23.779 | 27.864 | 238 | VAL | O | 30.584 | 32.955 | 42.971 |
| 230 | GLN | C | 38.324 | 25.710 | 32.453 | 239 | GLN | N | 31.903 | 31.146 | 43.181 |
| 230 | GLN | O | 39.365 | 25.106 | 32.722 | 239 | GLN | CA | 33.058 | 31.865 | 42.654 |
| 231 | LYS | N | 38.320 | 27.043 | 32.369 | 239 | GLN | CB | 34.348 | 31.007 | 42.712 |
| 231 | LYS | CA | 39.482 | 27.877 | 32.678 | 239 | GLN | CG | 34.787 | 30.771 | 44.165 |
| 231 | LYS | CB | 39.085 | 29.347 | 32.389 | 239 | GLN | CD | 36.001 | 29.847 | 44.293 |
| 231 | LYS | CG | 40.041 | 30.518 | 32.637 | 239 | GLN | OE1 | 35.946 | 28.629 | 44.354 |
| 231 | LYS | CD | 41.380 | 30.478 | 31.945 | 239 | GLN | NE2 | 37.174 | 30.441 | 44.326 |
| 231 | LYS | CE | 42.078 | 31.872 | 31.997 | 239 | GLN | C | 32.811 | 32.264 | 41.203 |
| 231 | LYS | NZ | 42.377 | 32.352 | 33.343 | 239 | GLN | O | 33.124 | 33.398 | 40.784 |
| 231 | LYS | C | 39.970 | 27.715 | 34.142 | 240 | ILE | N | 32.261 | 31.291 | 40.463 |
| 231 | LYS | O | 41.173 | 27.658 | 34.409 | 240 | ILE | CA | 31.950 | 31.500 | 39.047 |
| 232 | ASN | N | 39.023 | 27.635 | 35.097 | 240 | ILE | CB | 31.410 | 30.186 | 38.368 |
| 232 | ASN | CA | 39.292 | 27.588 | 36.520 | 240 | ILE | CG2 | 31.025 | 30.399 | 36.876 |
| 232 | ASN | CB | 38.801 | 28.848 | 37.227 | 240 | ILE | CG1 | 32.503 | 29.161 | 38.463 |
| 232 | ASN | CG | 39.339 | 30.115 | 36.617 | 240 | ILE | CD | 32.041 | 27.775 | 37.973 |
| 232 | ASN | OD1 | 40.486 | 30.464 | 36.859 | 240 | ILE | C | 30.902 | 32.584 | 38.896 |
| 232 | ASN | ND2 | 38.537 | 30.834 | 35.845 | 240 | ILE | O | 31.087 | 33.511 | 38.104 |
| 232 | ASN | C | 38.595 | 26.402 | 37.158 | 241 | ARG | N | 29.819 | 32.484 | 39.667 |
| 232 | ASN | O | 37.635 | 26.555 | 37.907 | 241 | ARG | CA | 28.769 | 33.495 | 39.638 |
| 233 | PRO | N | 39.057 | 25.173 | 36.945 | 241 | ARG | CB | 27.701 | 33.092 | 40.655 |
| 233 | PRO | CD | 40.245 | 24.847 | 36.150 | 241 | ARG | CG | 26.634 | 34.192 | 40.895 |
| 233 | PRO | CA | 38.320 | 23.978 | 37.376 | 241 | ARG | CD | 25.462 | 33.692 | 41.771 |
| 233 | PRO | CB | 39.053 | 22.819 | 36.729 | 241 | ARG | NE | 24.364 | 34.639 | 41.945 |
| 233 | PRO | CG | 40.441 | 23.367 | 36.519 | 241 | ARG | CZ | 23.323 | 34.340 | 42.749 |
| 233 | PRO | C | 38.155 | 23.820 | 38.863 | 241 | ARG | NH1 | 22.325 | 35.215 | 42.920 |
| 233 | PRO | O | 37.266 | 23.094 | 39.274 | 241 | ARG | NH2 | 23.252 | 33.149 | 43.371 |
| 234 | SER | N | 38.962 | 24.489 | 39.675 | 241 | ARG | C | 29.313 | 34.923 | 39.937 |
| 234 | SER | CA | 38.725 | 24.374 | 41.124 | 241 | ARG | O | 29.037 | 35.874 | 39.200 |
| 234 | SER | CB | 40.005 | 24.643 | 41.961 | 242 | ASN | N | 30.153 | 35.073 | 40.959 |
| 234 | SER | OG | 40.378 | 26.007 | 41.847 | 242 | ASN | CA | 30.649 | 36.413 | 41.277 |
| 234 | SER | C | 37.635 | 25.309 | 41.680 | 242 | ASN | CB | 31.391 | 36.455 | 42.609 |
| 234 | SER | O | 37.203 | 25.124 | 42.824 | 242 | ASN | CG | 30.386 | 36.371 | 43.746 |
| 235 | TRP | N | 37.151 | 26.270 | 40.878 | 242 | ASN | OD1 | 29.177 | 36.652 | 43.659 |
| 235 | TRP | CA | 36.213 | 27.246 | 41.393 | 242 | ASN | ND2 | 30.877 | 35.881 | 44.877 |
| 235 | TRP | CB | 36.022 | 28.366 | 40.435 | 242 | ASN | C | 31.591 | 36.931 | 40.225 |
| 235 | TRP | CG | 37.165 | 29.323 | 40.391 | 242 | ASN | O | 31.631 | 38.152 | 39.938 |
| 235 | TRP | CD2 | 37.103 | 30.539 | 39.761 | 243 | HIS | N | 32.330 | 36.012 | 39.584 |
| 235 | TRP | CE2 | 38.384 | 31.011 | 39.929 | 243 | HIS | CA | 33.284 | 36.451 | 38.593 |
| 235 | TRP | CE3 | 36.167 | 31.261 | 39.083 | 243 | HIS | CB | 34.183 | 35.327 | 38.178 |
| 235 | TRP | CD1 | 38.405 | 29.059 | 40.930 | 243 | HIS | CG | 35.409 | 35.790 | 37.413 |
| 235 | TRP | NE1 | 39.136 | 30.109 | 40.623 | 243 | HIS | CD2 | 36.367 | 36.638 | 37.902 |
| 235 | TRP | CZ2 | 38.726 | 32.237 | 39.404 | 243 | HIS | ND1 | 35.770 | 35.447 | 36.181 |
| 235 | TRP | CZ3 | 36.502 | 32.474 | 38.559 | 243 | HIS | CE1 | 36.908 | 36.044 | 35.892 |
| 235 | TRP | CH2 | 37.775 | 32.956 | 38.720 | 243 | HIS | NE2 | 37.250 | 36.757 | 36.945 |
| 235 | TRP | C | 34.862 | 26.643 | 41.637 | 243 | HIS | C | 32.559 | 36.966 | 37.370 |
| 235 | TRP | O | 34.427 | 25.726 | 40.941 | 243 | HIS | O | 32.988 | 37.984 | 36.820 |
| 236 | SER | N | 34.206 | 27.137 | 42.669 | 244 | LEU | N | 31.473 | 36.265 | 36.963 |
| 236 | SER | CA | 32.884 | 26.712 | 43.011 | 244 | LEU | CA | 30.709 | 36.649 | 35.801 |
| 236 | SER | CB | 32.771 | 26.915 | 44.541 | 244 | LEU | CB | 29.576 | 35.636 | 35.501 |
| 236 | SER | OG | 32.691 | 28.301 | 44.902 | 244 | LEU | CG | 29.971 | 34.234 | 34.958 |
| 236 | SER | C | 31.891 | 27.549 | 42.200 | 244 | LEU | CD1 | 28.719 | 33.367 | 34.841 |
| 236 | SER | O | 32.195 | 28.606 | 41.637 | 244 | LEU | CD2 | 30.649 | 34.360 | 33.602 |
| 237 | ASN | N | 30.645 | 27.084 | 42.278 | 244 | LEU | C | 30.147 | 38.007 | 36.104 |
| 237 | ASN | CA | 29.495 | 27.743 | 41.705 | 244 | LEU | O | 30.189 | 38.853 | 35.217 |
| 237 | ASN | CB | 28.255 | 26.923 | 42.112 | 245 | LYS | N | 29.690 | 38.289 | 37.328 |
| 237 | ASN | CG | 27.966 | 26.679 | 43.605 | 245 | LYS | CA | 29.178 | 39.632 | 37.654 |
| 237 | ASN | OD1 | 28.706 | 27.112 | 44.495 | 245 | LYS | CB | 28.452 | 39.593 | 38.993 |
| 237 | ASN | ND2 | 26.851 | 26.017 | 43.928 | 245 | LYS | CG | 27.193 | 38.687 | 38.928 |
| 237 | ASN | C | 29.388 | 29.219 | 42.117 | 245 | LYS | CD | 26.536 | 38.412 | 40.289 |
| 237 | ASN | O | 29.255 | 30.109 | 41.266 | 245 | LYS | CE | 25.811 | 39.677 | 40.573 |
| 238 | VAL | N | 29.592 | 29.555 | 43.414 | 245 | LYS | NZ | 25.221 | 39.607 | 41.886 |
| 238 | VAL | CA | 29.576 | 30.945 | 43.876 | 245 | LYS | C | 30.300 | 40.665 | 37.714 |
| 238 | VAL | CB | 29.553 | 30.919 | 45.442 | 245 | LYS | O | 30.125 | 41.805 | 37.257 |
| 238 | VAL | CG1 | 29.767 | 32.294 | 46.097 | 246 | ASN | N | 31.462 | 40.279 | 38.199 |
| 238 | VAL | CG2 | 28.199 | 30.344 | 45.805 | 246 | ASN | CA | 32.579 | 41.194 | 38.352 |

FIG. 1M

```
246 ASN  CB   33.697 40.568 39.196    256 LEU  CG   16.565 49.634 34.134
246 ASN  CG   33.286 40.502 40.651    256 LEU  CD1  16.919 50.482 32.887
246 ASN  OD1  32.445 41.245 41.165    256 LEU  CD2  15.095 49.321 34.182
246 ASN  ND2  33.814 39.538 41.375    256 LEU  C    18.284 46.162 34.546
246 ASN  C    33.188 41.620 37.046    256 LEU  O    17.798 45.300 33.803
246 ASN  O    33.819 42.686 36.960    257 TYR  N    19.566 46.246 34.888
247 THR  N    33.020 40.781 36.033    257 TYR  CA   20.590 45.390 34.268
247 THR  CA   33.574 41.115 34.734    257 TYR  CB   21.608 46.225 33.447
247 THR  CB   34.386 39.916 34.179    257 TYR  CG   20.957 47.106 32.389
247 THR  OG1  33.492 38.818 34.055    257 TYR  CD1  20.349 46.459 31.337
247 THR  CG2  35.608 39.565 35.059    257 TYR  CE1  19.733 47.179 30.384
247 THR  C    32.516 41.547 33.737    257 TYR  CD2  20.951 48.503 32.449
247 THR  O    32.865 41.792 32.575    257 TYR  CE2  20.330 49.219 31.446
248 ALA  N    31.252 41.714 34.123    257 TYR  CZ   19.731 48.536 30.426
248 ALA  CA   30.213 42.085 33.162    257 TYR  OH   19.142 49.131 29.335
248 ALA  CB   28.829 41.914 33.800    257 TYR  C    21.424 44.557 35.226
248 ALA  C    30.385 43.558 32.731    257 TYR  O    22.226 43.739 34.776
248 ALA  O    30.961 44.395 33.440    258 GLY  N    21.305 44.756 36.542
249 THR  N    29.950 43.949 31.551    258 GLY  CA   22.222 44.130 37.496
249 THR  CA   30.001 45.323 31.096    258 GLY  C    23.630 44.552 37.201
249 THR  CB   29.955 45.301 29.552    258 GLY  O    23.896 45.710 36.877
249 THR  OG1  31.151 44.706 29.080    259 SER  N    24.511 43.586 37.273
249 THR  CG2  29.830 46.690 28.965    259 SER  CA   25.897 43.856 36.955
249 THR  C    28.830 46.105 31.676    259 SER  CB   26.747 42.633 37.239
249 THR  O    27.664 45.760 31.425    259 SER  OG   26.779 42.518 38.660
250 SER  N    29.067 47.214 32.412    259 SER  C    26.153 44.278 35.527
250 SER  CA   27.941 47.994 32.947    259 SER  O    27.225 44.856 35.285
250 SER  CB   28.405 49.102 33.875    260 GLY  N    25.225 44.013 34.600
250 SER  OG   27.267 49.862 34.279    260 GLY  CA   25.413 44.431 33.222
250 SER  C    27.136 48.631 31.822    260 GLY  C    25.476 43.210 32.331
250 SER  O    27.687 49.164 30.857    260 GLY  O    24.999 42.106 32.672
251 LEU  N    25.824 48.523 31.929    261 LEU  N    26.036 43.461 31.151
251 LEU  CA   24.949 49.115 30.934    261 LEU  CA   26.105 42.461 30.087
251 LEU  CB   24.067 48.019 30.342    261 LEU  CB   26.274 43.195 28.721
251 LEU  CG   24.737 46.908 29.627    261 LEU  CG   26.349 42.381 27.424
251 LEU  CD1  23.663 46.020 29.043    261 LEU  CD1  25.064 41.598 27.191
251 LEU  CD2  25.595 47.430 28.481    261 LEU  CD2  26.675 43.372 26.282
251 LEU  C    24.069 50.231 31.462    261 LEU  C    27.234 41.470 30.309
251 LEU  O    23.214 50.787 30.769    261 LEU  O    28.410 41.842 30.426
252 GLY  N    24.239 50.606 32.703    262 VAL  N    26.851 40.192 30.263
252 GLY  CA   23.317 51.538 33.279    262 VAL  CA   27.872 39.161 30.432
252 GLY  C    22.880 50.976 34.613    262 VAL  CB   27.227 37.754 30.407
252 GLY  O    23.651 50.372 35.376    262 VAL  CG1  26.633 37.448 29.036
253 SER  N    21.614 51.241 34.872    262 VAL  CG2  28.305 36.734 30.824
253 SER  CA   20.958 50.918 36.106    262 VAL  C    28.935 39.300 29.331
253 SER  CB   19.470 51.165 35.891    262 VAL  O    28.661 39.699 28.193
253 SER  OG   18.813 51.273 37.150    263 ASN  N    30.181 39.070 29.700
253 SER  C    21.195 49.492 36.567    263 ASN  CA   31.271 39.216 28.755
253 SER  O    20.900 48.587 35.786    263 ASN  CB   31.866 40.599 28.993
254 THR  N    21.694 49.321 37.796    263 ASN  CG   33.072 40.880 28.136
254 THR  CA   21.773 48.021 38.431    263 ASN  OD1  33.666 40.009 27.502
254 THR  CB   22.417 48.071 39.869    263 ASN  ND2  33.498 42.124 28.143
254 THR  OG1  23.694 48.691 39.803    263 ASN  C    32.250 38.068 28.945
254 THR  CG2  22.671 46.670 40.414    263 ASN  O    33.119 37.994 29.826
254 THR  C    20.311 47.594 38.557    264 ALA  N    32.136 37.126 28.030
254 THR  O    20.041 46.419 38.445    264 ALA  CA   32.947 35.931 28.088
255 ASN  N    19.316 48.480 38.694    264 ALA  CB   32.528 34.857 27.080
255 ASN  CA   17.930 48.038 38.783    264 ALA  C    34.404 36.250 27.801
255 ASN  CB   17.061 49.253 39.031    264 ALA  O    35.259 35.517 28.331
255 ASN  CG   15.600 48.927 39.271    265 GLU  N    34.752 37.304 27.054
255 ASN  OD1  15.191 48.158 40.157    265 GLU  CA   36.169 37.625 26.884
255 ASN  ND2  14.771 49.580 38.459    265 GLU  CB   36.346 38.768 25.842
255 ASN  C    17.441 47.296 37.526    265 GLU  CG   37.790 39.302 25.597
255 ASN  O    16.752 46.279 37.550    265 GLU  CD   38.470 40.138 26.723
256 LEU  N    17.889 47.805 36.389    265 GLU  OE1  39.623 39.854 27.100
256 LEU  CA   17.437 47.297 35.108    265 GLU  OE2  37.835 41.060 27.255
256 LEU  CB   17.435 48.386 34.041    265 GLU  C    36.745 38.057 28.227
```

FIG.1N

```
265 GLU  O    37.766  37.524  28.689   307 H2O OH2  26.065  37.253  43.741
266 ALA  N    36.098  39.020  28.897   308 H2O OH2  11.945  45.684  23.380
266 ALA  CA   36.698  39.536  30.109   309 H2O OH2  19.643  10.507  40.112
266 ALA  CB   35.959  40.800  30.534   310 H2O OH2  38.430  41.954  36.077
266 ALA  C    36.677  38.485  31.228   311 H2O OH2  13.501  39.873  16.866
266 ALA  O    37.562  38.418  32.099   312 H2O OH2  16.785  49.578  21.745
267 ALA  N    35.677  37.593  31.161   313 H2O OH2  28.911  19.876  22.976
267 ALA  CA   35.566  36.560  32.179   314 H2O OH2  29.797  51.940  35.038
267 ALA  CB   34.165  35.963  32.078   315 H2O OH2   8.968  16.983  43.770
267 ALA  C    36.616  35.454  32.087   316 H2O OH2  21.830  26.021  49.724
267 ALA  O    36.811  34.737  33.081   317 H2O OH2  18.231  35.980  44.119
268 THR  N    37.257  35.279  30.927   318 H2O OH2  17.725  35.088  15.203
268 THR  CA   38.227  34.187  30.751   319 H2O OH2  34.481  23.007  20.146
268 THR  CB   37.888  33.276  29.515   320 H2O OH2  19.764  37.086  46.005
268 THR  OG1  37.799  34.092  28.362   321 H2O OH2  13.211  26.583  10.242
268 THR  CG2  36.575  32.530  29.710   322 H2O OH2  10.729  31.502  26.207
268 THR  C    39.617  34.741  30.576   323 H2O OH2  22.023  36.663  14.105
268 THR  O    40.534  33.996  30.218   324 H2O OH2  26.324  19.922  21.851
269 THR  N    39.728  36.045  30.801   325 H2O OH2  30.661  17.697  22.182
269 ARG  CA   41.008  36.690  30.810   326 H2O OH2   8.433  17.883  24.882
269 ARG  CB   40.656  38.156  30.839   327 H2O OH2  32.021  21.783  19.092
269 ARG  CG   41.824  39.000  30.472   328 H2O OH2  32.606  20.038  14.623
269 ARG  CD   41.544  40.401  29.949   329 H2O OH2  27.918  17.370  24.830
269 ARG  NE   42.811  40.930  29.432   330 H2O OH2  17.445  14.094  24.149
269 ARG  CZ   43.324  42.136  29.787   331 H2O OH2  16.527  18.554  15.250
269 ARG  NH1  44.518  43.533  29.265   332 H2O OH2  15.380  14.546  15.873
269 ARG  NH2  42.681  42.951  30.667   333 H2O OH2  12.129  16.040  17.903
269 ARG  C    41.844  36.161  32.014   334 H2O OH2  13.873  16.685  15.209
269 ARG  OT1  41.328  35.597  32.990   335 H2O OH2   6.048  18.751  34.243
269 ARG  OT2  43.070  36.206  31.952   336 H2O OH2   4.411  16.951  35.536
270  CM  CM   27.629  24.423  14.043   337 H2O OH2   6.528  15.046  39.508
271  CM  CM   18.482  35.001  42.551   338 H2O OH2   4.188  15.102  37.754
272 H2O OH2   35.625  16.277  36.682   339 H2O OH2   7.267  13.144  37.517
273 H2O OH2   19.773  36.339  42.049   340 H2O OH2   7.231  10.169  35.676
274 H2O OH2   28.438  25.352  47.303   341 H2O OH2   9.229  11.210  38.524
275 H2O OH2   25.023  30.639  43.381   342 H2O OH2  13.492   9.745  35.358
276 H2O OH2   23.352  28.163  42.310   343 H2O OH2  12.026  44.524  42.622
277 H2O OH2   21.594  35.893  18.729   344 H2O OH2  11.004  41.120  45.663
278 H2O OH2   22.058  31.111  19.688   345 H2O OH2  10.220  39.693  42.722
279 H2O OH2   18.752  45.063  40.645   346 H2O OH2  12.059  47.753  40.959
280 H2O OH2   18.039  30.216  23.124   347 H2O OH2   9.164  48.300  42.769
281 H2O OH2   14.078   9.380  32.356   348 H2O OH2  11.958  43.338  44.851
282 H2O OH2   15.449  19.938  28.355   349 H2O OH2  11.239  46.641  44.371
283 H2O OH2   15.927  25.605  30.476   350 H2O OH2   4.931  44.533  41.923
284 H2O OH2   12.858  32.346  37.185   351 H2O OH2   6.403  36.291  34.865
285 H2O OH2   11.544  33.624  27.713   352 H2O OH2   5.564  39.764  36.611
286 H2O OH2   11.580   8.103  31.642   353 H2O OH2   8.066  29.304  32.467
287 H2O OH2   42.076  35.854  14.697   401 H2O OH2  23.985  29.300  19.050
288 H2O OH2    8.591  11.660  25.062   402 H2O OH2  22.840  42.988  23.949
289 H2O OH2   34.301  29.140  15.200   403 H2O OH2  24.648  47.653  34.651
290 H2O OH2   30.440  24.492  43.369   404 H2O OH2  22.155  15.174  18.497
291 H2O OH2   35.793  42.916  26.272   405 H2O OH2  22.394  50.724  27.973
292 H2O OH2   30.881  38.720  32.534   406 H2O OH2  25.205  15.404  16.200
293 H2O OH2   29.323  24.894  39.464   407 H2O OH2  16.769  30.931  11.057
294 H2O OH2   30.053  41.242  26.124   408 H2O OH2   6.421  46.954  36.986
295 H2O OH2   26.029  30.946  34.554   409 H2O OH2  39.155  36.951  34.253
296 H2O OH2   23.950  42.830  40.424   410 H2O OH2  30.425  43.985  26.477
297 H2O OH2   22.857  33.906  20.288   411 H2O OH2  15.991  34.160  48.706
298 H2O OH2   29.750  12.657  20.465   412 H2O OH2  33.843  20.940   9.231
299 H2O OH2   16.182  42.867  32.920   413 H2O OH2  16.995  50.196  28.127
300 H2O OH2   20.509  35.549  16.195   415 H2O OH2  38.899  33.531  34.689
301 H2O OH2   21.065  41.688  15.225   416 H2O OH2  17.892  19.864  44.040
302 H2O OH2   12.353  41.495  42.254   417 H2O OH2  34.568  30.498  17.440
303 H2O OH2   11.733  34.741  14.055   419 H2O OH2  35.622  20.284  42.959
304 H2O OH2    7.156  35.456  31.880   420 H2O OH2   0.206  12.428  34.387
305 H2O OH2    7.914  47.871  34.970   421 H2O OH2  38.833  23.281  24.721
306 H2O OH2    5.154  42.915  39.674   422 H2O OH2  27.524  37.611  14.941
```

FIG.10

| | | | | | | | | | | |
|---|---|---|---|---|---|---|---|---|---|---|
|423|H2O|OH2|33.375|39.759|31.397|474|H2O|OH2|33.485|27.966|24.079|
|425|H2O|OH2|10.662|51.211|37.076|475|H2O|OH2|16.400|18.715|49.507|
|426|H2O|OH2|28.400|26.227|22.233|476|H2O|OH2|34.584|26.355|28.896|
|427|H2O|OH2|37.069|31.271|18.172|477|H2O|OH2|18.844|26.392|36.213|
|428|H2O|OH2|35.149|22.967|42.892|478|H2O|OH2|17.595|33.022|12.700|
|429|H2O|OH2|14.410|35.423|17.549|479|H2O|OH2|19.970|49.821|15.851|
|430|H2O|OH2|34.593|37.589|20.470|480|H2O|OH2|29.931|22.624|47.074|
|431|H2O|OH2|33.293|43.729|30.636|481|H2O|OH2|28.764|29.952|13.997|
|432|H2O|OH2|18.935|12.276|22.731|482|H2O|OH2|24.923|29.997|46.055|
|433|H2O|OH2|36.502|38.642|39.753|483|H2O|OH2|4.494|34.569|48.325|
|434|H2O|OH2|30.888|44.367|36.634|484|H2O|OH2|25.927|28.389|42.632|
|435|H2O|OH2|6.433|14.502|42.412|485|H2O|OH2|19.179|31.050|19.865|
|436|H2O|OH2|23.735|32.721|13.204|486|H2O|OH2|33.544|35.859|34.951|
|437|H2O|OH2|30.269|39.336|42.632|489|H2O|OH2|7.275|28.059|36.209|
|438|H2O|OH2|6.916|37.376|38.041|490|H2O|OH2|18.187|52.286|20.471|
|439|H2O|OH2|31.535|45.230|24.294|491|H2O|OH2|14.703|47.608|24.076|
|440|H2O|OH2|21.133|38.497|43.405|492|H2O|OH2|14.414|29.083|26.931|
|441|H2O|OH2|26.156|30.548|26.735|493|H2O|OH2|20.741|38.573|12.784|
|442|H2O|OH2|20.961|41.888|36.136|494|H2O|OH2|32.484|22.352|42.540|
|443|H2O|OH2|10.366|9.353|42.909|495|H2O|OH2|11.669|32.823|30.485|
|444|H2O|OH2|15.664|13.252|41.086|496|H2O|OH2|25.506|21.376|19.908|
|445|H2O|OH2|15.488|35.603|22.544|498|H2O|OH2|14.394|49.504|27.686|
|446|H2O|OH2|8.523|29.548|42.831|499|H2O|OH2|39.498|21.926|32.920|
|448|H2O|OH2|6.347|42.537|28.354|500|H2O|OH2|20.574|46.516|27.909|
|449|H2O|OH2|20.408|28.429|14.479|501|H2O|OH2|41.254|36.175|22.038|
|451|H2O|OH2|9.986|37.579|24.768|502|H2O|OH2|18.615|23.589|42.251|
|452|H2O|OH2|34.820|21.034|34.828|503|H2O|OH2|23.238|48.249|18.498|
|453|H2O|OH2|17.186|30.632|13.537|504|H2O|OH2|11.027|27.025|49.749|
|454|H2O|OH2|12.491|19.964|46.613|505|H2O|OH2|6.051|28.870|41.533|
|455|H2O|OH2|31.523|29.927|11.890|506|H2O|OH2|20.329|51.097|40.041|
|456|H2O|OH2|12.628|27.138|21.026|507|H2O|OH2|34.042|46.991|33.740|
|457|H2O|OH2|33.466|44.288|34.479|508|H2O|OH2|18.800|14.484|12.899|
|458|H2O|OH2|19.599|43.860|38.560|509|H2O|OH2|23.984|14.515|28.480|
|459|H2O|OH2|16.152|29.460|52.727|510|H2O|OH2|14.955|20.395|22.995|
|460|H2O|OH2|12.458|29.430|17.126|511|H2O|OH2|31.742|13.971|22.917|
|461|H2O|OH2|37.639|14.784|37.217|512|H2O|OH2|13.014|49.698|46.176|
|462|H2O|OH2|9.851|34.465|20.032|513|H2O|OH2|3.857|17.317|43.260|
|463|H2O|OH2|33.545|17.795|26.313|514|H2O|OH2|8.348|35.692|23.895|
|464|H2O|OH2|9.256|16.911|34.260|515|H2O|OH2|9.871|28.970|29.151|
|465|H2O|OH2|35.476|39.839|21.547|516|H2O|OH2|18.301|41.737|20.959|
|467|H2O|OH2|23.365|24.048|13.490|517|H2O|OH2|10.419|21.355|11.387|
|468|H2O|OH2|11.732|35.837|17.577|518|H2O|OH2|11.150|32.989|33.268|
|469|H2O|OH2|30.073|50.380|31.035|519|H2O|OH2|43.085|38.642|27.705|
|471|H2O|OH2|16.204|22.887|7.809|520|H2O|OH2|20.416|57.764|27.758|
|472|H2O|OH2|27.601|27.623|26.352|521|H2O|OH2|40.300|29.469|52.597|
|473|H2O|OH2|2.443|14.804|32.338| | | | | | |

FIG.1P

BACILLUS LENTUS ALKALINE PROTEASE VARIANTS WITH INCREASED STABILITY

BACKGROUND OF THE INVENTION

1. Field of the Invention

This invention relates to mutant proteolytic enzymes having improved properties relative to the wild-type enzyme, to genetic constructs which code for the mutant proteolytic enzymes, to methods of predicting mutations which enhance the stability of the enzyme, and to methods of producing the mutant proteolytic enzymes.

2. Description of the Related Art

Subtilisins are a family of extracellular proteins having molecular weights in the range of 25,000–35,000 daltons and are produced by various Bacillus species. These proteins function as peptide hydrolases in that they catalyze the hydrolysis of peptide linkages in protein substrates at neutral and alkaline pH values. Subtilisins are termed serine proteases because they contain a specific serine residue which participates in the catalytic hydrolysis of peptide substrates. A subtilisin enzyme isolated from soil samples and produced by *Bacillus lentus* for use in detergent formulations having increased protease and oxidative stability over commercially available enzymes under conditions of pH 7 to 10 and at temperature of 10 to 60° C. in aqueous solutions has been disclosed in copending patent application Ser. No. 07/398,854, filed on Aug. 25, 1989. This *B. lentus* alkaline protease enzyme (BLAP, vide infra) is obtained in commercial quantities by cultivating a *Bacillus licheniformis* ATCC 53926 strain which had been transformed by an expression plasmid which contained the wild type BLAP gene and the *B. licheniformis* ATCC 53926 alkaline protease gene promoter.

Industrial processes generally are performed under physical conditions which require highly stable enzymes. Enzymes may be inactivated by high temperatures, pH extremes, oxidation, and surfactants. Even though Bacillus subtilisin proteases are currently used in many industrial applications, including detergent formulations, stability improvements are still needed. Market trends are toward more concentrated detergent powders, and an increase in liquid formulations. Increased shelf stability and oxidative stability, with retention of catalytic efficiency are needed. It is therefore desirable to isolate novel enzymes with increased stability, or to improve the stability of existing enzymes, including subtilisin proteases such as BLAP.

The stability of a protein is a function of its three dimensional structure. A protein folds into a three dimensional conformation based upon the primary amino acid sequence, and upon its surrounding environment. The function and stability of a protein are a direct result of its three dimensional structure.

A large body of information has been published which describes changes in enzyme properties as a result of alterations in the primary amino acid sequence of the enzyme. These alterations can result from random or site specific alterations of the gene which expresses the enzyme using genetic engineering techniques. Random approaches mutagenize total cellular DNA, followed by selection for the synthesis of an enzyme with improved properties. This approach requires neither knowledge of the three dimensional structure of the enzyme, nor any predictive capability on the part of the researcher. Site directed mutagenesis, on the other hand, requires a rational approach for the introduction of amino acid changes. In this approach one or more amino acids may be replaced by other residues by altering the DNA sequence which encodes the protein. This can be accomplished using oligonucleotide directed in vitro mutagenesis. The following references teach site-directed mutagenesis procedures used to generate specific amino acid substitution(s): Hines, J.C., and Ray, D.S. (1980) Gene 11:207–218; Zoller, M.J., and Smith, M. (1982) Nucleic Acids Res. 10:6487–6500; Norrander, J., et al. (1983) Gene 26:101–106; Morinaga, Y., et al. (1984) Bio/Technology 2:636–639; Kramer, W., et al. (1984) Nucleic Acids Res. 12:9441–9456; Carter, P., et al. (1985) Nucleic Acids Res. 13:4431–4443; Kunkel, T.A. (1985) Proc. Natl. Acad. Scio USA 82:488–492; Bryan, P., et al. (1986) Proc. Natl. Acad. Sci. USA 83:3743–3745.

A rational approach may or may not require knowledge of a protein's structure. For example, patent application WO 89/06279 describes the comparison of the primary amino acid sequence of different subtilisins while contrasting differences in physical and chemical properties. The primary amino acid sequences of the different subtilisins are aligned for the greatest homology, while taking into account amino acid insertions, deletions, and total number of amino acids.

Currently, the amino acid sequences of at least 10 subtilisin proteases have been published. Eight of these subtilisins were isolated from species of Bacilli, and include subtilisin 168 (Stahl, M.L., and Ferrari, E. (1984) J. Bacteriol. 158:411–418), subtilisin BPN' (Vasantha, N., et al., (1984) J. Bacteriol. 159:811–819), subtilisin Carlsberg (Jacobs, M., et al. (1985) Nucleic Acids Res. 13:8913–8926), subtilisin DY (Nedkov, P., et al. (1985) Biol. Chem. Hoppe-Seyler 366:421–430), subtilisin amylosacchariticus (Kurihara, M., et al. (1972) J. Biol. Chem. 247:5619–5631), subtilisin mesenticopeptidase (Svendsen, I., et al. (1986) FEBS Lett. 196:228–232), subtilisin 147 and subtilisin 309 (Hastrup et al. (1989) WO 9/06279), subtilisin PB92 (Van Eekelen et al. (1989) EP 328229), and subtilisin BLAP (Ladin, B., et al. (1990) Society for Industrial Microbiology Annual Meeting, Abstract P60). The remaining two subtilisin sequences are thermitase from the fungus *Thermoactinomyces vulgaris* (Meloun, B., et al. (1985) FEBS Lett. 183:195–200), and proteinase K from the fungus *Tritirachium album limber* (Jany, K.-D., and Mayer, B. (1985) Biol. Chem. Hoppe-Seyler 366:485–492).

Methods for obtaining optimum alignment of homologous proteins are described in Atlas of Protein Sequence and Structure, Vol. 5, Supplement 2 (1976) (Dayhoff, M.O., ed., Natl. Biomed. Res. Found., Silver Springs, Md.). This comparison is then used to identify specific amino acid alterations which might produce desirable improvements in the target enzyme. Wells, J.A., et al. (1987) Proc. Natl. Acad. Sci. USA 84:1219–1223, used primary sequence alignment to predict site directed mutations which affect the substrate specificity of a subtilisin. Using the alignment approach WO 89/06279 teaches the construction of mutant subtilisins having improved properties including an increased resistance to oxidation, increased proteolytic activity, and improved washing performance for laundry detergent applications. Patent applications WO 89/09819, and WO 89/09830 teach improvement in the thermal stability of subtilisin BPN' by the introduction of one or more amino acid changes based on the alignment of the primary amino acid sequences of subtilisin BPN' with the more thermal stable subtilisin Carlsberg. From hereon, amino acids will be referred to by the one or three letter code as defined in Table 1.

TABLE 1

One and Three Letter Code for Amino Acids

A=Ala=Alanine
C=Cys=Cysteine
D=Asp=Aspartic acid or aspartate
E=Glu=Glutamic acid or glutamate
F=Phe=Phenylalanine
G=Gly=Glycine
H=His=Histidine
I=Ile=Isoleucine
K=Lys=Lysine
L=Leu=Leucine
M=Met=Methionine
N=Asn=Asparagine
P=Pro=Proline
Q=Gln=Glutamine
R=Arg=Arginine
S=Ser=Serine
T=Thr=Threonine
V=Val=Valine
W=Trp=Tryptophan
Y=Tyr=Tyrosine Rational mutational approaches may also predict mutations which improve an enzyme property based upon the three dimensional structure of an enzyme, in addition to the alignment of primary amino acid sequences described above. One method for determining the three dimensional structure of a protein involves the growing of crystals of the protein, followed by X-ray crystallographic analysis. This technique has been successfully used to determine several high resolution subtilisin structures such as thermitase (Teplyakov, A.V., et al. (1990) 214:261-279), subtilisin BPN' (Bott, R., et al. (1988) J. Biol. Chem. 263:7895-7906) and subtilisin Carlsberg (Bode, W., et al. (1986) EMBO J. 5:813-818), for example.

EP 0251446 teaches the construction of mutant carbonyl hydrolases (proteases) which have at least one property different from the parental carbonyl hydrolase. It describes mutations which effect (either improve or decrease) oxidative stability, substrate specificity, catalytic activity, thermal stability, alkaline stability, pH activity profile, and resistance to autoproteolysis. These mutations were selected for introduction into *Bacillus amyloliquefaciens* subtilisin BPN' after alignment of the primary sequences of BPN' and proteases from *B. subtilis, B. licheniformis,* and thermitase. Such alignment can then be used to select amino acids in these other proteases which differ, as substitutes for the equivalent amino acid in the *B. amyloliquefaciens* carbonyl hydrolase. This application also describes alignment on the basis of a 1.8 Å X-ray crystal structure of the *B. amyloliquefaciens* protease. Amino acids in the carbonyl hydrolase of *B. amyloliquefaciens* which when altered can affect stability, substrate specificity, or catalytic efficiency include: Met50, Met124, and Met222 for oxidative stability; Tyr104, Ala152, Glu156, Gly166, Gly169, Phe189, and Tyr217 for substrate specificity; N155 alterations were found to decrease turnover, and lower Km; Asp36, Ile107, Lys170, Asp197, Ser204, Lys213, and Met222 for alkaline stability; and Met199, and Tyr21 for thermal stability. Alteration of other amino acids was found to affect multiple properties of the protease. Included in this category are Ser24, Met50, Asp156, Gly166, Gly169, and Tyr217. Substitution at residues Ser24, Met50, Ile107, Glu156, Gly166, Gly169, Ser204, Lys213, Gly215, and Tyr217 was predicted to increase thermal and alkaline stability. An important point about this patent application is that with the exception of those mutations effecting substrate specificity, no rational mutational approach for improving the alkaline or temperature stability of a protease based upon computer simulations of an X-ray crystal structure is described.

WO 88/08028 teaches a method for redesigning proteins to increase stability by altering amino acid residues that are in close proximity to the protein's metal ion binding site. This application describes the alteration of a calcium ion binding site present within subtilisin BPN' through the substitution, insertion, or deletion of amino acid residue(s) in close proximity to that site so that the electrostatic attraction between the amino acids and the calcium ion is increased. The characterization of the calcium ion binding site is accomplished through the analysis of a 1.3 Å three dimensional structure of subtilisin BPN' using a high resolution computer graphics system. This approach allows the selection of amino acids acceptable for replacing the native amino acids in the protease by first simulating the change using the computer model. This allows for the identification of any problems including steric hindrance prior to the actual construction and testing of the mutant proteases.

U.S. Pat. Nos. 4908773 and 4853871 teach a computer based method for evaluating the three dimensional structure of a protein to select amino acid residues where the introduction of a novel disulfide bond will potentially stabilize the protein. Potentially acceptable amino acid residues can then be ranked, and replaced using computer simulation, prior to the actual construction of the mutant protein using site directed mutagenesis protocols.

Several patent applications combine published data on biochemical stability with computer analysis of three dimensional protease structures in order to predict mutations which stabilize the enzyme. U.S. Pat. No. 4,914,031 and WO 88/08033 and WO 87/04461 teach a method for improving the pH and thermal stability of subtilisin aprA by replacing asparagine residues present in asparagine/glycine pairs. Asparagine/glycine pairs in proteins have been shown to undergo cyclization to form cyclic imide anhydroaspartylglycine (Bornstein, P., and Balian, G. (1977) Methods Enzymol. 47:132-145). This cyclic imide is susceptible to base hydrolyzed cleavage leading to inactivation of the enzyme. Computer analysis of the three dimensional structure of the aprA protease also predicted that formation of the cyclic imide could lead to protease inactivation resulting from a shift of the side chain of the active site serine. The decision to replace the asparagine residue and not the glycine residue was based upon alignment of the aprA sequence with other subtilisin-like enzymes, cucumisin and proteinase K.

Sensitivity to oxidation is an important deficiency of serine proteases used in detergent applications (Stauffer, C.E., and Etson, D. (1969) J. Biol. Chemo 244:5333-5338). EP 0130756, EP 0247647, and U.S. Pat. No. 4,760,025 teach a saturation mutation method where one or multiple mutations are introduced into the subtilisin BPN' at amino acid residues Asp32, Asn155, Tyr104, Met222, Gly166, His64, Ser221, Gly169, Glu156, Ser33, Phe189, Tyr217, and/or Ala152. Using this approach mutant proteases exhibiting improved oxidative stability, altered substrate specificity, and/or altered pH activity profiles are obtained. A method is taught in which improved oxidative stability is achieved by substitution of methionine, cysteine, tryptophan, and lysine residues. These publications also teach that mutations within the active site region of the protease are also most likely to influence activity. Random or selected mutations can be introduced into a target gene using the experimental approach but neither EP 0130756, EP 0247647, nor U.S. Pat. No. 4,760,025 teach a method for predicting amino acid alterations which will improve the thermal or surfactant stability of the protease.

WO 8705050 teaches a random mutagenesis approach for construction of subtilisin mutants exhibiting enhanced thermal stability. One or more random mutations are introduced into single stranded target DNA using the chemical mutagens sodium bisulfite, nitrous acid, and formic acid. Subsequently, the mutated DNA is transformed into a Bacillus host and at least 50,000 colonies are screened by a filter assay to identify proteases with improved properties. Site directed mutagenesis can then be used to introduce all possible mutations into a site identified through the random mutagenesis screen. No method for pre selection of amino acids to be altered is taught.

EP 0328229 teaches the isolation and characterization of PB92 subtilisin mutants with improved properties for laundry detergent applications based upon wash test results. It teaches that biochemical properties are not reliable parameters for predicting enzyme performance in the wash. Methods for selection of mutations involve the substitution of amino acids by other amino acids in the same category (polar, nonpolar, aromatic, charged, aliphatic, and neutral), the substitution of polar amino acids asparagine and glutamine by charged amino acids, and increasing the anionic character of the protease at sites not involved with the active site. No method for identifying which specific amino acids should be altered is taught, and no rational mutational approach is taught which is based on alignment of X-ray structures of homologous proteases with different properties.

EP 0260105 teaches the construction of subtilisin BPN' mutants with altered transesterification rate/hydrolysis rate ratios and nucleophile specificities by changing specific amino acid residues within 15 Å of the catalytic triad. Russell, A.J., and Fersht, A.R. (1987) Nature 328:496–500, and Russell, A.J., et al. (1987) J. Mol. Biol. 193:803–813, teach the isolation of a subtilisin BPN' mutant (D099S) that had a change in the surface charge 1415 Å from the active site. This substitution causes an effect on the pH dependence of the subtilisin's catalytic reaction.

There are a number of different strategies for increasing protein stability. Many of these methods suggest types of substitutions to improve the stability of a protein but do not teach a method for identifying amino acid residues within a protein which should be substituted. From entropic arguments, many types of substitutions have been suggested such as Gly to Ala and any amino acid to Pro (Matthews, B.W., et al. (1987) Proc. Natl. Acad. Sci. 84:6663–6667). Likewise, while it is clear that increasing the apolar size of an amino acid in the core will add to stability, adverse packing effects may more than compensate for the hydrophobic effect, resulting in a decrease in protein stability (Sandberg, W.S., and Terwilliger, T.C. (1989) Science 245:54–57). Menéndez-Arias, L., and Argos, P. (1990) J. Mol. Biol. 206:397–406, performed a statistical evaluation of amino acid substitutions of thermophilic and mesophilic molecules and proposed that decreased flexibility and increased hydrophobicity in the e-helical regions contributes most towards increasing protein stability. From their data, they formulated a set of empirical rules to improve stability.

Increasing the hydrophobicity of certain side chains has long been suggested as a means to improve protein stability. The hydrophobic exclusion of nonpolar amino acids is the largest force driving protein folding. This has been studied by examining the partitioning of amino acids or amino acid analogs from water to a hydrophobic medium. While the numbers vary depending on the work, these studies generally agree that burying a hydrophobic side chain increases protein stability. For example, Kellis, J.T., Jr., et al. (1988) Nature 333:784–786, estimated that the removal of a methyl group destabilizes the enzyme by 1.1 kcal/mole assuming no other structural perturbations occur. Conversely, this predicts that the addition of a methylene group should add 1.1 kcal/mol if no unfavorable contacts occur. Similarly, Sandberg, W.S., and Terwilliger, T.C. (1989) Science 245:54–57, showed that the effect of removing or adding methylene groups is the sum of the hydrophobic effect and structural distortions. Simply adding buried hydrophobic groups may not increase protein stability because the total effect of adding or deleting a methyl group on the local packing structure must be considered. As the protein interior has a paracrystalline structure (Chothia, C. (1975) Nature 254:304–308), small distortions in the remainder of the structure resulting from the addition methyl group may exact a high cost and reduce rather than increase stability.

Along the same lines, the core of λ repressor has been shown to be amazingly tolerant to apolar amino acid substitutions in a functional assay (Bowie, J.U., et al. (1990) Science 247:1306–1310). It is not clear that this is true for larger proteins. The constraints on the hydrophobic core of a small protein may be less stringent than a larger protein simply due to the volume of the core relative to the number of amino acids which need to pack into the region. As the volume of the hydrophobic core increases, the number of amino acids which must pack together correctly increases, requiring more specific nonlocal interactions.

It has been recognized that increasing the interior hydrophobicity of a protein as a means of increasing the stability is hampered by the difficulty of determining which positions in the protein will lead to stabilization when substituted (Sandberg, W.S., and Terwilliger, T.C. (1991) Trends Biotechnol. 9:59–63). The methods discussed above provide a means of determining what substitutions to make to improve stability but do not identify which sites in the protein are most important. The present invention provides a method of determining which positions in the protein will lead to stabilization when substituted.

SUMMARY OF THE INVENTION

Other than in the operating examples, or where otherwise indicated, all numbers expressing quantities of ingredients or reaction conditions used herein are to be understood as modified in all instances by the term "about".

The native or wild-type protease from which the mutant proteases according to the invention are derived is a *B. lentus* alkaline protease (BLAP) obtained from *B. lentus* DSM 5483 having 269 amino acid residues, a molecular mass of 26,823 daltons, and a calculated isoelectric point of 9.7 based on standard pK values. The BLAP gene is obtained by isolating the chromosomal DNA from the *B. lentus* strain DSM 5483, constructing DNA probes having homology to putative DNA sequences encoding regions of the *B. lentus* protease, preparing genomic libraries from the isolated chromosomal DNA, and screening the libraries for the gene of interest by hybridization to the probes.

Mutant *B. lentus* DSM 5483 proteases have been made which are derived by the replacement of at least one amino acid residue of the mature form of the *B. lentus* DSM 5483 alkaline protease. The sites for replacement are selected from the group consisting of Ser3, Val4, Ser36, Asn42, Ala47, Thr56, Thr69, Glu87, Ala96, Ala101, Ile102, Ser104, Asn114, His118, Ala120, Ser130, Ser139, Thr141, Ser142, Ser157, Ala188, Val193, Val199, Gly205, Ala224, Lys229, Ser236, Asn237, Asn242, His243, Asn255, Thr268. The replacement amino acid residues are listed in Table 2. The numbering of the mutant proteases is based on the *B. lentus* DSM 5483 wild-type protease as given in the SEQ ID NO:52.

Genes which express the mutant *B. lentus* DSM 5483 proteases according to the invention are made by altering one or more codons of the wild-type *B. lentus* DSM 5483 alkaline protease gene which encode for a protease derived by accomplishing at least one of the amino acid substitutions listed in Table 2.

The protease sites listed in Table 2 are sites predicted to affect thermal and surfactant stability relative to the wild-type protease. These sites are identified by means of a computer based method which compares the three dimensional structure of the wild-type protease (henceforth, the target protein) and a homologous protease (henceforth, the reference protein). The three dimensional coordinates of the wild-type protease are probed with an uncharged probe molecule to produce a probe-accessible surface which has an external surface the interior of which contains one or more probe-accessible internal cavities. The amino acids of the reference protein having side chains lying outside the solvent-accessible surface or inside the internal cavities of the target protein are identified by aligning the three dimensional coordinates of the target protein and the reference protein.

Proteins having greater thermal and surfactant stability are produced by replacing the amino acid in the target protein if the amino acid in the target protein can be changed without creating unacceptable steric effects. The amino acid in the target protein is altered by site directed mutagenesis of the gene which expresses the target protein.

Genetic constructs are made which contain in the direction of transcription a promoter, ribosomal binding site, initiation codon and the major portion of the pre region of the *Bacillus licheniformis* ATCC 53926 alkaline protease gene operably linked to a portion of the pre region and all of the pro and mature regions of the *Bacillus lentus* DSM 5483 alkaline protease gene followed by a 164 bp DNA fragment containing the transcription terminator from the ATCC 53926 alkaline protease gene. The *Bacillus lentus* DSM 5483 alkaline protease gene is altered to produce a mutant gene which encodes for a protease derived by accomplishing at least one of the amino acid substitutions listed in Table 2. Mutant protease is made by fermenting a Bacillus strain transformed with a genetic construct containing a mutated *Bacillus lentus* DSM 5483 alkaline protease gene.

BRIEF DESCRIPTION OF THE FIGURES

FIG. 1A through 1P collectively depict the atomic coordinates for *Bacillus lentus* alkaline protease (BLAP) to 1.4 Å resolution.

DESCRIPTION OF THE PREFERRED EMBODIMENTS

Figure 2:
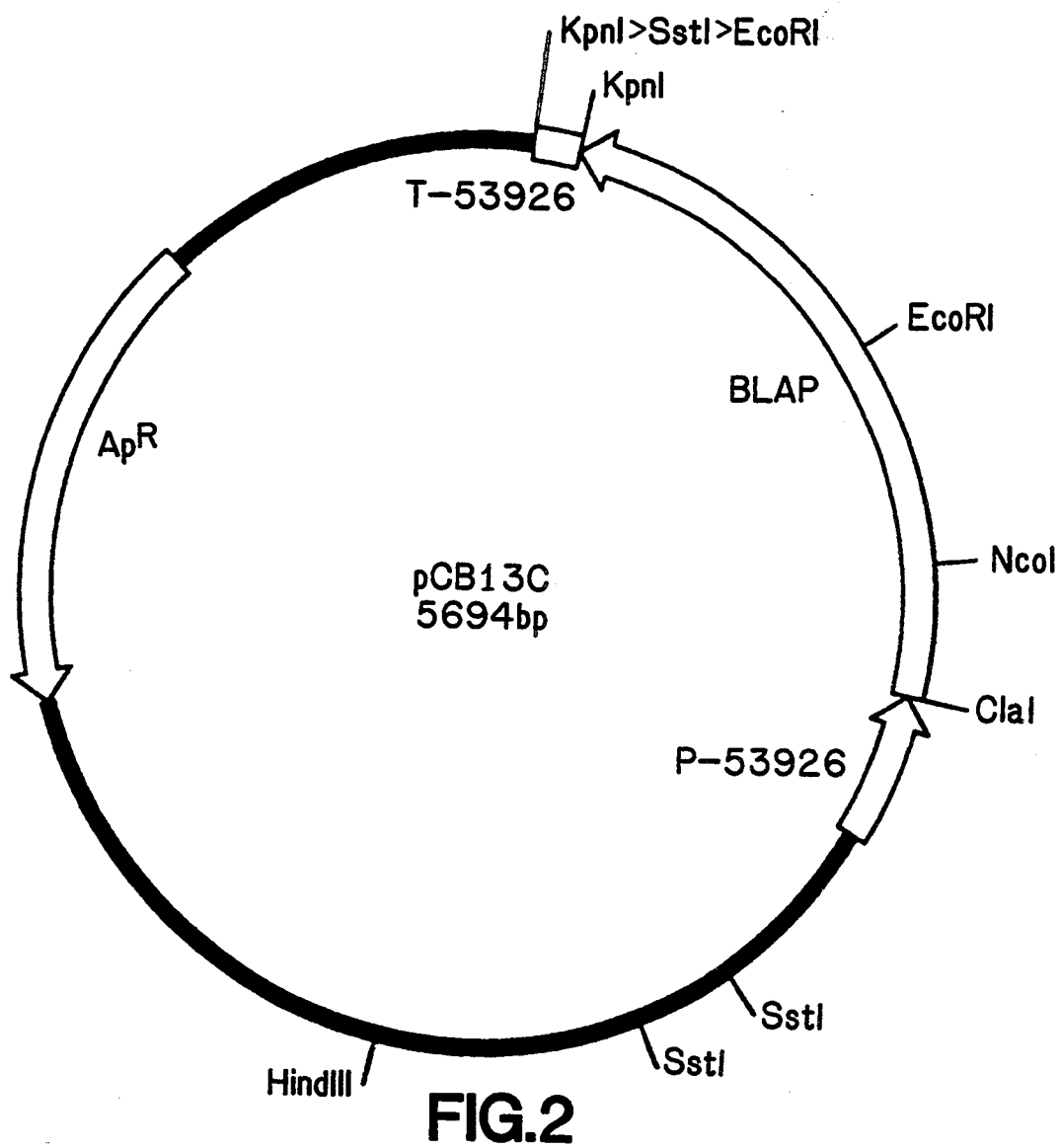
FIG. 2 shows the restriction map for plasmid pCB13C which contains a hybrid gene fusion between the *Bacillus licheniformis* ATCC 53926 protease gene and the *Bacillus lentus* DSM 5483 BLAP gene. The promoter, ribosomal binding site and presequence (P-53926) from ATCC 53926 were fused to the pro- and mature sequence of the SLAP gene. The transcription terminator of ATCC 53926 (T-53926) was appended to the SLAP coding region.

One aspect of the invention relates to mutant proteolytic enzymes which have superior thermal stability and surfactant stability relative to the wild-type protease as determined by laboratory tests. The mutant proteases according to the invention are those derived by the replacement of at least one amino acid residue of the mature *Bacillus lentus* DSM 5483 alkaline protease wherein said one amino acid residue which is selected from the group consisting of Ser3, Val4, Ser36, Asn42, Ala47, Thr56, Thr69, Glu87, Ala96, Ala101, Ile102, Ser104, Asn114, His118, Ala120, Ser130, Ser139, Thr141, Ser142, Ser157, Ala188, Val193, Val199, Gly205, Ala224, Lys229, Ser236, Asn237, Asn242, His243, Asn255, Thr268 is replaced with the amino acid residues listed in Table 2. Table 2 shows the identity and position of the wild-type amino acid and the amino acid residue(s) which replace it in the mutant protein. For example, the first entry in Table 2 shows Ser3, a serine residue at position 3 which can be replaced by threonine (abbreviated as T using the one letter code for amino acids) or any small amino acid. A small amino acid is defined as glycine, alanine, valine, serine, threonine or cysteine. A small hydrophobic amino acid is defined as glycine, alanine, threonine, valine or isoleucine. A charged amino acid is defined as lysine, arginine, histidine, glutamate or aspartate. The abbreviation a.a. stands for "amino acid" residue.

TABLE 2

| Residue | Replacement Amino Acid |
|---|---|
| Ser3 | T or any small, hydrophobic a.a. |
| Val4 | I, S or any small a.a. |
| Ser36 | A, T or any small a.a. |
| Ser42 | F, A, T, V, I, Y |
| Ala47 | W or any small a.a. except A |
| Thr56 | V, S or any small, hydrophobic a.a. |
| Thr69 | R, A or any charged a.a. |
| Glu87 | R, M or any charged a.a. |
| Ala96 | I, N, S or any small, hydrophobic a.a. |
| Ala101 | T, S or any small, hydrophobic a.a. |
| Ile102 | W or any small a.a. except P |
| Ser104 | T or any small, hydrophobic a.a. |

TABLE 2-continued

| Residue | Replacement Amino Acid |
|---|---|
| Asn114 | S, Q or any small, hydrophobic a.a. |
| His118 | F or any a.a. except P and W |
| Ala120 | V or any small, hydrophobic a.a. |
| Ser130 | A, T or any small, hydrophobic a.a. |
| Ser139 | A, T, Y or any a.a. except P and W |
| Thr141 | W or any a.a. except P |
| Ser142 | A, T or any small, hydrophobic a.a. |
| Ser157 | T or any small, hydrophobic a.a. |
| Ala188 | P or any small, hydrophobic a.a. |
| Val193 | M or any small, hydrophobic a.a. |
| Val199 | I or any small, hydrophobic a.a. |
| Gly205 | V or any small, hydrophobic a.a. |
| Ala224 | V or any small, hydrophobic a.a. |
| Lys229 | W or any a.a. except P |
| Ser236 | A, T or any small, hydrophobic a.a. |
| Asn237 | A, N, Q, M or any small, hydrophobic a.a. |
| Asn242 | A, N, Q, M or any small, hydrophobic a.a. |
| His243 | A, N, Q, M or any small, hydrophobic a.a. |
| Asn255 | P or any small, hydrophobic a.a. |
| Thr268 | V or any small, hydrophobic a.a. |

The amino acid sequences of the preferred proteolytic enzymes are given in SEQ ID NO:1 to SEQ ID NO:51. The preferred mutated *B. lentus* DSM 5483 proteases which are encoded for by genes according to the invention as disclosed above are given in SEQ ID NO: 53 to 105. These proteases are produced by bacterial strains which have been transformed with plasmids containing a native or hybrid gene, mutated at one or more nucleotide base pairs by known mutagenesis methods. These mutant genes encode for proteases in which selected amino acid residues have been substituted for by other amino acids.

The mutant proteases according to the invention are listed in Table 3.

TABLE 3

| | Temperature Stability | | SDS Stability | |
|---|---|---|---|---|
| | 50° C., pH 11.0 | 60° C., pH 10.0 | pH 10.5, 50° C. | pH 8.6, 50° C. |
| Mutation | t½ (min) | t½ (min) | t½ (min) | t½ (min) |
| S3T, V4I, A188P, V193M, V199I | 120 | 67 | 3.2 | 12 |
| S3T, A188P, V193M, V199I | 95 | 60 | 3.75 | 18.5 |
| V4I, A188P, V193M, V199I | 72 | 39 | 1.75 | 3.75 |
| S139Y, A188P, V193M, V199I | 69 | 33 | 1.4 | 4.6 |
| S130T, S139Y, A188P, V193M, V199I | 64 | 22 | 2 | 6.3 |
| A188P, V193M, V199I | 55 | 23.5 | 3.0 | 12.5 |
| S3T, A188P, V193M | 54 | 21 | 1.5 | 3.4 |
| S157T | 52 | 17.5 | 1.2 | 0.95 |
| A188P, V193M | 50 | 27 | 2.5 | 7.25 |
| A188P | 48 | 19 | 1.4 | 2.8 |
| S3T, V4I, A188P, V193M | 43 | 21 | 1.4 | 3.7 |
| V193M | 42 | 16.6 | 1.2 | 3.0 |
| S104T | 42 | 8 | 1.0 | 1.8 |
| T69V | 41 | 12.3 | 0.8 | 1.8 |
| V4I, A188P, V193M | 40 | 19 | 1.25 | 2.7 |
| A224V | 39 | 15 | 0.9 | 1.1 |
| V199I | 38.5 | 11.6 | 1.0 | 2.0 |
| V4I | 32.5 | 10 | 0.75 | 1.0 |
| S3T | 32 | 6.6 | 1.2 | 2.8 |
| S139Y | 26 | 8.8 | 1.0 | 2.0 |
| N242A | 26 | 7.4 | 0.9 | 1.9 |
| S236T | 25.5 | 8.4 | 1.0 | 2.0 |
| S36A | 23.8 | 8.6 | 0.9 | 1.8 |
| H243A | 23 | 5.9 | 0.8 | 1.7 |
| A101T | 23 | 4.7 | 0.5 | 2.75 |
| S236A | 23 | 5.1 | 0.8 | 1.3 |
| E87R | 22.5 | 9.0 | 0.4 | 1.2 |
| N114S | 22 | 7.9 | 1.1 | 1.3 |
| A47W | 21 | 7.2 | 0.9 | 1.05 |
| A120S | 20.5 | 8.4 | 0.9 | 1.4 |
| T56V | 20 | 8.5 | 0.8 | 0.7 |
| A120V | 20 | 11.8 | 0.65 | 1.9 |
| G205V | 20 | 6.8 | 1.1 | 2.8 |
| S130A | 20 | 8.8 | 0.4 | 1.0 |
| S130T | 20 | 7.2 | 0.4 | 1.1 |
| A96I | 19 | 12 | 1.0 | 1.4 |
| S104T, S139Y, A224V | 18 | 9.5 | 1.0 | 1.8 |
| S139A | 18.5 | 7.8 | 0.5 | 0.8 |
| S142T | 17.5 | 11.5 | 0.9 | 1.7 |
| S139T | 16.5 | 4.3 | 0.5 | 0.8 |
| I102W | 16.5 | 7.2 | 0.7 | 1.6 |
| A96N | 16 | 6 | 0.9 | 0.95 |
| N42F | 16 | 5.9 | 1.0 | 1.4 |
| S142A | 16 | 9 | 1.0 | 1.7 |
| H118F | 15.8 | 5.1 | 1.0 | 1.3 |
| N237A | 15 | 7.8 | 0.67 | 1.3 |
| N255P | 15.0 | 5.3 | 1.2 | 1.25 |
| T141W, N237A | 14 | 5.4 | 0.33 | 1.1 |
| T268V | 14 | 3.8 | 0.75 | 1.1 |
| K229W | 13.4 | 4.6 | 1.0 | 1.4 |
| T141W | 12 | 6.5 | 0.6 | 1.4 |
| wildtype | 12.0 | 3.0 | 0.8 | 1.6 |

Any of the proteases listed in Table 3 will exhibit greater stability in some manner than the wild-type protease BLAP. The entries under the "Mutation" heading of Table 3 shows the identity of the wild-type amino acid (using the one letter code), its position, and the amino acid which replaces it in the mutant protease. For example, S3T signifies that the serine at position 3 of the mature protease is replaced with a threonine. Some of the preferred mutant proteases are single replacements at specific locations such as a protease wherein valine at position 4 is replaced by isoleucine to specific combinations of replacements such as a protease wherein threonine at position 141 is replaced by tryptophan and asparagine at position 237 is replaced by alanine. The latter protease containing two replacements is one of only a number of possibilities.

The preferred mutant proteases according to the invention are identified as: (S3T, V4I, A188P, V193M, V199I); E87R; (S3T, A188P, V193M, V199I); N114S; (V4I, A188P, V193M, V199I); A47W; (S139Y, A188P, V193M, V199I); A120S; (S130T, S139Y, A188P, V193M, V199I); T56V; A120V;(A188P, V193M, V199I); G205V; (S3T, A188P, V193M); S130A; S130T; S157T; A96I; (S104T, S139Y, A224V); S139A; S142T; S139T; I102W; V193M; A96N; N42F; S142A; H118F; N237A; N255P; (T141W, N237A); T268V; K229W; T141W; (A188P, V193M); V4I; S3T; S139Y; N242A; S236T; S36A; H243A; A101T; S236A; A188P; (S3T, V4I, A188P, V193M); V193M; S104T; T69V; (V4I, A188P, V193M); A224V; V199I. The system used to designate the above preferred proteases first lists the amino acid residue in the mature form of the B. lentus DSM 5483 alkaline protease at the numbered position followed by the replacement amino acid residue using the one letter codes for amino acids. For example, V193M is a protease in which valine has been replaced by methionine at position 193 of the mature B. lentus DSM 5483 alkaline protease. A mutant protease identified by more than one such designation is a mutant protease which contains all of the indicated substitutions. For example, (A188P, V193M) is a protease in which valine has been replaced by methionine at position 193 of the mature B. lentus DSM 5483 protease and alanine at position 188 has been replaced by proline.

Mutant forms of the B. lentus DSM 5483 alkaline protease are prepared by site-specific mutagenesis of DNA encoding the mature form of either wild-type BLAP, or a mutant BLAP. The DNA fragment encoding the mature form of wild type BLAP was prepared using plasmid pCB13C. Plasmid pCB13C contains a hybrid fusion between the B. licheniformis ATCC 53926 protease gene and the B. lentus DSM 5483 BLAP gene, shown in FIG. 2. Specifically, this hybrid fusion contains DNA encoding the promoter, ribosomal binding site, and 21 residues of the pre sequence from the ATCC 53926 protease gene fused to a DNA sequence encoding the last five residues of the BLAP pre sequence and all of the pro and mature residues of BLAP. This fusion is referred to as the ClaI fusion because this restriction site is located at the juncture between the ATCC 53926 and DSM 5483 DNA's. A new ClaI restriction site had to be introduced into the ATCC 53926 alkaline protease gene near to the junction of the pre and pro sequences. The ClaI site was introduced into the ATCC 53926 alkaline protease gene by using a polymerase chain reaction (PCR) to amplify a DNA fragment containing sequence information from the N-terminal part of the ATCC 53926 alkaline protease gene. The amplified fragment included the ATCC 53926 alkaline protease promoter, ribosomal binding site, initiation codon, and most of the pre sequence. This 292 bp DNA fragment was flanked by AvaI and ClaI restriction sites at its 5' and 3' ends, respectively. The BLAP gene already contained a naturally occurring ClaI site at the corresponding position. Analysis of the DNA sequence across the fusion of the ATCC 53926 and BLAP genes confirmed the expected DNA and amino acid sequences.

Figure 3:
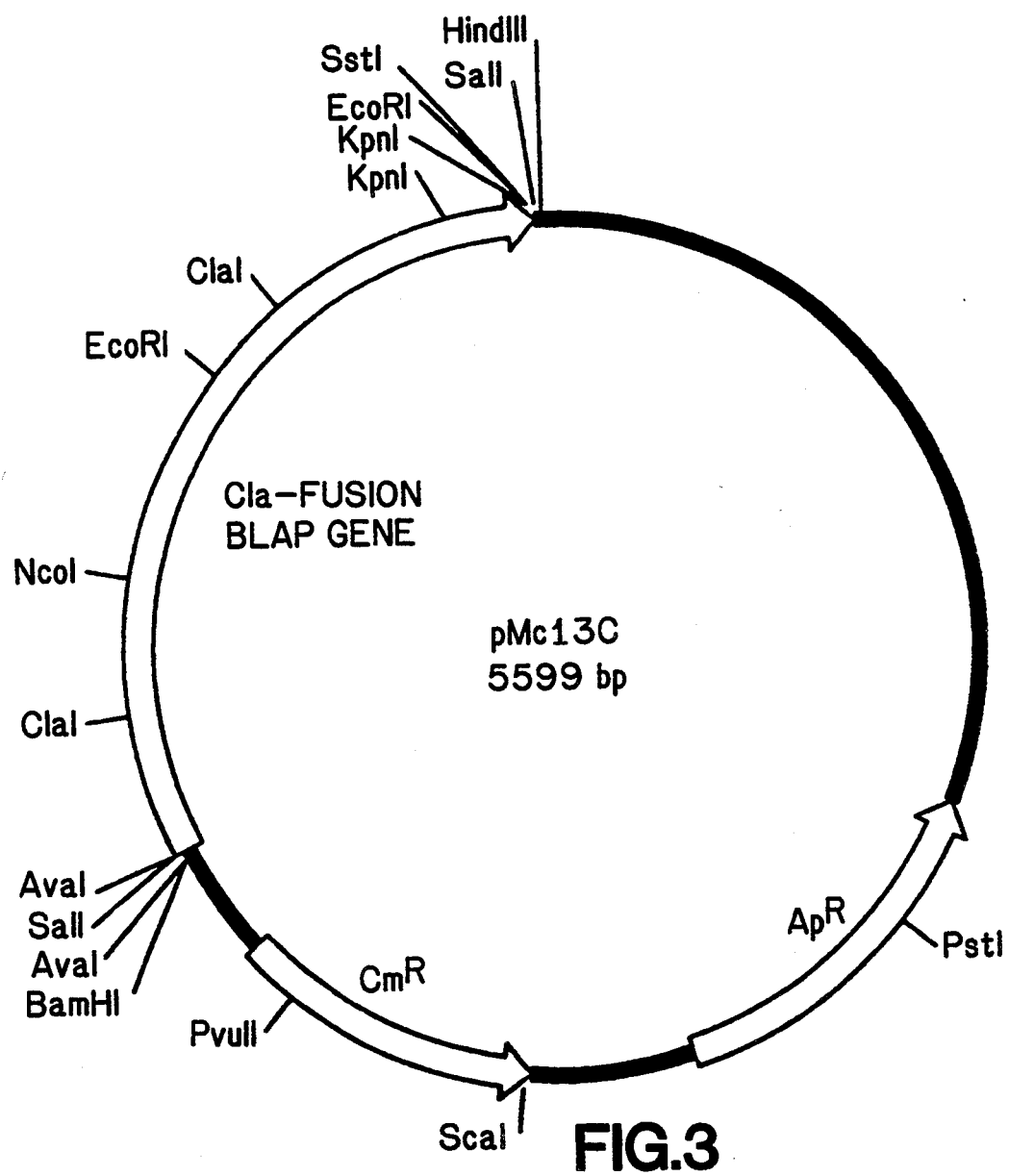
FIG. 3 shows the restriction map for plasmid pMc13C which is derived from pMac5-8 and contains the SLAP gene and carries an amber mutation in the $Ap^R$ gene which renders it inactive.

Before any mutagenesis can be carried out, the gene is subcloned into the mutagenesis vector pMa5-8. This is accomplished by synthesizing a DNA fragment containing the ClaI fusion gene and the ATCC 53926 transcription terminator as a SalI cassette using the PCR. The PCR was carried out using conditions as described by the manufacturer (Perkin Elmer Cetus, Norwalk, CT.). In the PCR, two synthetic oligonucleotides bearing SalI sites are used as primers and Escherichia coli vector pCB13C DNA as a template. After cutting the PCR product with SalI, this fragment is cloned into the mutagenic plasmid pMc5-8 which has previously been cut with SalI and dephosphorylated with bacterial alkaline phosphatase. Plasmids pMc5-8, and pMa5-8 described below were obtained from H.-J. Fritz and are described by Stanssens, P., et al. (1989) Nucleic Acids Res. 17:4441-4454. SalI sites are chosen to allow the PCR fragment to be cloned into pMc5-8 in both orientations. The ligation mix is transformed into E. coli WK6. Chloramphenicol resistant (Cm$^R$) transformants are screened for the presence of an insert and a correct plasmid construct pMc13C is identified as shown in FIG. 3. Once the gene is cloned into the pMc vector and desirable sites for mutation are identified, the mutation(s) is introduced using synthetic DNA oligonucleotides according to a modification of a published protocol (Stanssens, P., et al. (1989) Nucleic Acids Res. 17:4441-4454). The oligonucleotide containing the mutation(s) to be introduced is annealed to a gapped duplex (gd) structure which carries the BLAP gene on a segment of single stranded (ss) DNA. The gapped duplex can be formed by annealing linear ss DNA from pMc13C with denatured and restricted pMa5-8 DNA. Plasmid pMa5-8 contains an active ampicillin resistance gene but has an inactivating point mutation in the chloramphenicol resistance gene, whereas plasmid pMc13C contains, in addition to an intact BLAP gene, an active chloramphenicol resistance gene, but has an inactivating point mutation in the ampicillin resistance gene. The annealed product is the gd DNA which is a double stranded heteroduplex with ass DNA gap spanning the entire cloned BLAP gene. The mutant oligonucleotide is able to anneal to homologous ss BLAP DNA within the gap and the remaining gap is filled in by DNA polymerase I (Klenow fragment) and ligated using T4 DNA ligase, purchased from New England Biolabs Inc., Beverly, Ma. The mutagenic efficiency of such a system can be improved by the use of Exonuclease III (Exo III) purchased from New England Biolabs Inc., Beverly, MA. Exo III is an exodeoxyribonuclease that digests double stranded DNA from the 3' end. As a free 3' end is required, closed circular ss DNA or ds DNA is unaffected by this enzyme. A subsequent treatment of the product of the fill-in reaction with Exo III removes any species with only partially filled gaps. This significantly improves the mutagenic efficiency and is the preferred mutagenesis method. The product of the fill-in reaction is then transformed into a repair deficient E. coli strain such as WK6mutS and ampicillin resistant transformants (Ap$^R$) are selected. Replication of the transformed heteroduplex phasmid results in two different progenies. One progeny contains the wild type BLAP gene and the intact chloramphenicol resistance gene, but an inactive ampicillin resistance gene. The other progeny contains a BLAP gene carrying the mutation of interest and is resistant to ampicillin but not to chloramphenicol.

Selection of Ap$^R$, Cm$^s$ mutant transformants with ampicillin is not sufficient to stop some background growth of the Ap$^s$, Cm$^R$ progeny carrying the wild type BLAP gene. Therefore, it is necessary to perform a second transformation into *E. coli* using plasmid DNA prepared from the Ap$^R$ transformants of the WK6mutS strain. This second transformation uses a low plasmid concentration with a large number of recipient cells of a suppressor deficient strain of *E. coli* such as WK6. This approach decreases the likelihood of a recipient cell receiving plasmid DNA from both progeny. Ap$^R$ transformants are selected and plasmid DNA from several transformants is isolated and screened for the presence of the mutation. The pMa mutant derivative of the first mutagenesis round can be used for a second round of mutagenesis by preparing ss DNA of that species and annealing it to XbaI/HindIII restricted and denatured DNA of pMc5-8. Plasmid pMc5-8 is identical to pMa-5-8 except that it contains an active chloramphenicol resistance gene and an inactive ampicillin resistance gene. The general procedure is the same as that described above.

The mutant BLAP proteases can be produced by transferring the mutant BLAP genes from their particular *E. coli* pMa13C derivative vector into a plasmid vector which can replicate in Bacillus. To accomplish this, the mutant BLAP genes are separated from their pMa13C plasmids by digestion with the restriction endonucleases AvaI and SstI, followed by ligation to the larger AvaI/SstI fragment from either plasmid pH70 or pC51. These AvaI/SstI fragments from pH70 and pC51 include the DNA sequences necessary for replication in Bacillus and encode either kanamycin resistance (Km$^R$) or tetracycline resistance (TC$^R$), respectively. Plasmid pH70 is constructed by cloning the ATCC 53926 alkaline protease gene carried on a EcoRI/BamHI DNA fragment into the Km$^R$ plasmid pUB110 between the EcoRI and BamHI sites. Plasmid pC51 is constructed by cloning the ATCC 53926 protease gene carried on a EcoRI-BamHI fragment into the Tc$^R$ plasmid pBC16 between the EcoRI and BamHI sites. The larger AvaI-SstI fragment from either pH70 or pC51 used for cloning the mutant BLAP genes is first purified from other DNA fragments by high pressure liquid chromatography (HPLC) on a Gen-Pak FAX column (Waters, Milford, MA). The column is 4.6 mm by 100 mm in size and contains a polymer-based high performance anion-exchange resin. Conditions for elution of the DNA are a flow rate of 0.75 ml/min with a gradient of Buffer A (25 mMtris(hydroxymethyl)aminomethane (Tris) pH 8.0 containing 1 mMdisodium ethylenediamine tetraacetic acid (EDTA)) and Buffer B (25 mM Tris pH 8.0, 1 mM EDTA, 1 M NaCl) starting at 50% each and reaching a final concentration of 30% Buffer A and 70% Buffer B.

After ligation the mutant BLAP plasmids are transformed into *B. subtilis* DB104. The genes encoding the major alkaline and neutral proteases present in this strain have been inactivated (Kawamura, F., and Doi, R.A. (1984) J. Bacteriol. 160:442-444). Cells of *B. subtilis* DB104 transformed by these plasmids grow on a nutrient-skim milk agar in the presence of either kanamycin or tetracycline. Transformants of DB104 that manufacture mutant protease are identified by the formation of clear zones of hydrolysis in the skim milk. Confirmation that the protease-producing transformants carry a plasmid-borne BLAP gene with the desired mutation(s) is accomplished by purifying plasmid DNA from a culture of each transformant. The plasmid DNA is purified away from cell protein and chromosomal DNA by SDS-salt precipitation followed by chromatography over a Qiagen ion-exchange column (Qiagen corporation, Studio City, CA). AvaI-SstI digested plasmid DNAs from different transformants are compared with AvaI/SstI-digested derivatives of plasmid pH70 or pC51 known to carry an intact BLAP gene. Restriction digests of these plasmids are compared by agarose gel electrophoresis to identify plasmids that have the proper-sized AvaI/SstI DNA fragments. Selected plasmid DNAs are then sequenced across the region of the expected BLAP mutation(s) to confirm that the desired mutation(s) are present. One or more clones of each BLAP mutation are stored frozen in 15% glycerol at −70° C. and also cultivated in shake flasks (Example 4, Production of Proteases) to produce mutant protease for characterization.

Another aspect of the invention provides a computer based method for identifying the sites which affect the storage, thermal, SDS and pH stability of a protein. This method is based on the hypothesis that protein stability may be enhanced by decreasing the volume of internal cavities and improving surface packing of amino acid side chains. The interior of a protein contains many apolar amino acids which are tightly packed into a nearly crystalline state. One way in which these interior amino acids affect protein stability is through packing effects. These include van der Waal interactions, distortion of the remainder of the protein and electrostatic effects. Packing effects have been studied by measuring the contribution of methyl groups in the interior of a protein to the overall stability of the protein. It has been estimated that the removal of a methyl group from the interior of a protein destabilizes it by about 1.1 kcal/mol assuming no other perturbations occur (Kellis, J.T., Jr., et al. (1988) Nature 333:784-786). However, the inverse may not be true. Simply adding buried hydrophobic groups may not increase protein stability because the total effect of adding or deleting a methyl group on the local packing structure must be considered. As the protein interior has a para-crystalline structure (Chothia, C. (1975) Nature 254:304-308), small distortions in the remainder of the structure resulting from the addition methyl group may exact a high cost and reduce rather than increase stability.

While it is known in the art to make certain substitutions which may affect protein stability, there is no known way of identifying which sites in the protein will lead to stabilization when substituted. For example, it has been suggested that protein stability would be increased if alanine were substituted for glycine or serine; or if threonine were substituted for serine (Matthews, B.W., et al. (1987) Proc. Natl. Acad. Sci. 84:6663-6667); or if proline were substituted for glycine. However, the sites in which one or more of these substitutions should be made has been so far unpredictable. Other methods depend on comparisons of the amino acid sequences of different but related proteins. However, this does not show which sites are important to stability, only which positions are different.

There are two computer based methods for identifying the sites which affect the stability of a protein according to the invention.

In the first method for identifying sites which affect the stability of protein, the first step comprises generating a probe-accessible surface by analyzing the target protein coordinates with an uncharged probe molecule having a radius of about 0.9 to about 2.0 Å. It is important that no water molecules be included in the protein structure during this analysis. The second step of this method is the identification of the amino acids which form the boundaries of the internal cavities. These amino acids comprise a set of positions which, if mutated, may increase the stability of the protein. An increase in stability can be achieved by amino acid substitutions which decrease the volume of the internal cavities.

The molecular modeling program QUANTA (trademark of Polygen Corporation, 200 Fifth Ave., Waltham, MA 02254) was used to calculate probe-accessible surfaces as well as perform the alignment of the three dimensional coordinates of the proteins. These functions can be carried out equally well by other molecular modeling programs which are also commercially available. The following is a list of commercially available programs which can also be used to calculate probe-accessible surfaces: Insight or InsightII (trademark of Biosym Technologies, Inc., 10065 Barnes Canyon Road—Suite A, San Diego, Calif. 92121), BIOGRAF (trademark of Biodesign, Inc., 199 S. Los Robles Ave., #270, Pasadena, Calif. 91101) or Sybyl (trademark of Tripos Associates, 1699 S. Hanley Road, St. Louis, MO 63144)

The probe-accessible surface referred to in step 1 of the first method can be generated in several ways (Richards, F.M. (1977) Annu. Rev. Biophys. Bioeng. 6:151-176): A spherical probe of radius R (0.9 to 2.0 Å) is allowed to roll on the outside of a molecule while maintaining contact with the van der Waal surface. The surface defined by the center of the probe is defined as the probe-accessible surface. Alternatively, a similar surface can be generated by increasing the van der Waal radii of all the atoms in a protein by the radius of the probe. Overlapping surfaces are eliminated and the remaining surface represents the probe-accessible surface. In the preferred embodiment, a three-dimensional box of dimensions 50×50×50 Å with a 1 Å grid size in all three dimensions (x, y, and z) is centered on the center of mass of the target protein coordinates. Most preferably, the dimensions of the probe map are adjusted such that all of the protein atoms fall within the probe map's bounds. The grid size of 1 Å provides a sufficiently high resolution to clearly define the probe-accessible surface although another grid size could be used, ranging from 0.5 to 3.0 Å. An uncharged probe molecule is positioned at each grid point and the energy of interaction between the probe and the target protein atoms is determined. The energy of nonbonded interaction ($E_{nb}$) contains only the van der Waal component such that $$E_{nb} = \sum_{\substack{\text{nonbonded} \\ i,j \text{ pairs}}} 4\epsilon_{ij}\left[\left(\frac{\sigma_{ij}}{r}\right)^{12} - \left(\frac{\sigma_{ij}}{r}\right)^{6}\right]$$

EQUATION (1)

where r is the nonbonded distance, $\epsilon_{ij}$ is the dispersion well depth and $\sigma_{ij}$ is the Lennard-Jones diameter. The result is a map consisting of a box with energy values at each grid point. This map can be contoured at a particular energy value to generate surfaces which correspond to the solvent accessible surface and internal cavities (Goodford, P.J. (1985) J. Med. Chem. 28:849-857). The value at which to contour the maps can vary depending on the particular radius used and the parameters used to define the probe molecule and the particular method used to generate the probe. The preferred embodiment is to used a probe radius of 0.9 Å and contour the surface at 10 kcal/mol.

The external surface of the probe-accessible surface is also known as the solvent-accessible surface. Probe-accessible surfaces inside of the solvent accessible surface are defined as internal cavities and represent cavities large enough to accommodate a molecule with a radius equal to the probe radius. The presence of such a cavity on the inside of a protein does not imply that the cavity will in fact be filled by one or more solvent molecules.

The second step of the method for identifying sites which affect the stability of a protein is the identification of the amino acids which form the internal cavities. The internal cavities are defined by the amino acids which make up its boundaries. These amino acids comprise a set of positions which, if mutated, may increase the stability of the protein.

In a second method for identifying sites which affect the stability of a protein, the first step comprises generating a probe-accessible surface by analyzing the target protein coordinates with an uncharged probe molecule having a radius of about 0.9 to about 2.0 Å. It is important that no water molecules be included in the protein structure during this analysis. This step is the same as the first step of the method set forth above.

The second step involves aligning the three dimensional structure of the target protein and a reference protein by moving the three dimensional coordinates of the reference protein into the coordinate frame of the target protein. The reference protein is usually chosen so that a high degree of similarity exists between it and the target protein so that packing differences between the target and reference protein which potentially affect the stability of the target protein can be identified. The reference protein can be any protein for which a three dimensional structure is available which is homologous to the target protein. Examples of such proteins include but are not limited to subtilisin Carlsberg, subtilisin BPN', proteinase K, and Thermitase. When the target protein is BLAP, one preferred reference protein is Thermitase. Thermitase is an extra-cellular subtilisin-like serine protease isolated from *Thermoactinomyces vulgaris* (Fr/ mmel, C., et al. (1978) Acta Biol. Med. Ger. 37:1193-1204). The protein amino acid sequence of thermitase is 42% identical to BLAP. The high degree of similarity between these two proteins provides an ideal system with which to examine packing differences that affect BLAP stability. In this second step the three 5 dimensional structures of Thermitase and BLAP are aligned using the computer program QUANTA ™. The three dimensional alignment is carried out by first aligning the primary sequences of the two proteins to determine which amino acids are equivalent. This is accomplished using FASTA (Myers, E.W., and Miller, W. (1988) Comput. Applic. Biosci. 4:11-17; Pearson, W.R., and Lipman, D.J. (1988) Proc. Natl. Acad. Sci. USA 85:2444-2448). Based on this alignment of the primary sequence, residues are matched for subsequent alignment of the three dimensional structures using MULTLSQ (Sutcliffe, M.J., et al. (1987) Protein Eng. 1:377-384; Kabsch, W. (1976) Acta Cryst. A32:9-22-923). This program uses one structure as fixed coordinates (the target protein coordinates) and then rotates and translates a second structure (the reference protein coordinates) so as to give the smallest root mean squared (r.m.s.) deviation between the two sets of three dimensional coordinates. For example, the alignment of the BLAP and thermitase three dimensional coordinates results in an r.m.s. deviation between equivalent $\alpha$-carbons of 0.8 Å. This demonstrates that the amino acid sequences of BLAP and thermitase fold into three dimensional structures which are extremely similar.

In the third step, the alignment of the three dimensional structures is used to identify sites which affect the stability of the target protein. This can be accomplished by a variety of methods. Using a computer program designed to display protein structures and surfaces such as QUANTA ™, the structure of the reference protein can be displayed with the probe-accessible surface. The combined display of the reference protein and probe-accessible surface can then be visually examined to determine which amino acids in the reference protein fall outside of the solvent-accessible surface or inside internal cavities. An alternative method which can be used comprises coloring the atoms of the reference protein by determining whether amino acids in the reference protein fall outside of the solvent-accessible surface or inside internal cavities. The probe-accessible surface map (probe map) was used to color the atoms in the transformed subtilisin BPN' structure. In order to color each atom, an energy value needs to be interpolated from the probe map at each atomic coordinate.

The probe map consists of three dimensional grid with an energy value (E) at each grid point. In the preferred embodiment, the probe map is a 50×50×50 Å box centered on the center of mass of the protein with a 1 Å grid unit in all three dimensions (x, y, and z). In its optimal conception, the size of the probe map is adjusted such that all of the protein atoms fall within the probe map's bounds. The energy value at each protein atom position was approximated by interpolating from the energy values from the surrounded eight grid points in the probe map. Given the energy value at each point from the probe map, the grid spacing, and the atomic coordinate, it is a simple matter for any one skilled in the art to interpolate an energy value at each atomic coordinate.

In one such method, an energy value of zero is assigned arbitrarily if an atom falls outside the bounds of the map. From a given atomic coordinate (x,y,z), the eight closest grid points from the probe map which surround (x,y,z) are identified such that ($x_1 < x < x_2$), ($y_1 < y < y_2$), and ($z_1 < z < z_2$). The eight grid points are then A ($x_1$, $y_1$, $z_1$), B ($x_1$, $y_1$, $z_2$), C ($x_1$, $y_2$, $z_2$), D ($x_1$, $Y_2$, $z_1$), E ($x_2$, $y_1$, $z_1$), F ($x_2$, $y_1$, $z_2$), G ($x_2$, $y_2$, $z_2$), and H ($x_2$, $y_2$, $z_1$). The energy value (E) at a given grid point such as ($x_1$, $y_1$, $z_1$) is then E ($x_1$, $y_1$, $z_1$) or equivalently $E_A$. The energy at a specific atomic coordinate E (x,y,z) can be interpolated from the probe map given the eight nearest surrounding grid points (A through H, as described above) and the value at each grid point ($E_A$ through $E_H$). The equation which was used for calculating the energy at specific atomic coordinates, E (x,y,z), is shown in Equation (2). The energy value at each coordinate can then be stored and used to display the molecule.

EQUATION (2)

$$E_{(x,y,z)} = \left( \frac{x - x_1}{x_2 - x_1} \right)(E_o - E_k) + E_k$$

where $$E_o = \left( \frac{y - y_1}{y_2 - y_1} \right)(E_m - E_l) + E_l;$$

and $$E_k = \left( \frac{y - y_1}{y_2 - y_1} \right)(E_j - E_i) + E_i;$$

and where $$E_i = \left( \frac{z - z_1}{z_2 - z_1} \right)(E_F - E_E) + E_E;$$

$$E_j = \left( \frac{z - z_1}{z_2 - z_1} \right)(E_G - E_H) + E_H;$$

$$E_l = \left( \frac{z - z_1}{z_2 - z_1} \right)(E_B - E_A) + E_A;$$

$$E_m = \left( \frac{z - z_1}{z_2 - z_1} \right)(E_C - E_D) + E_D;$$

The protein atoms were colored on the basis of this interpolated energy value. The protein was displayed using QUANTA ™ and atoms with interpolated energies below 10 kcal/mol were colored as red. Atoms with interpolated energies above 10 kcal/mol were colored green. Visual inspection allowed identification of side chains which penetrated the solvent accessible surface or penetrated internal cavities.

There are also two computer based methods for increasing the stability of a protein. The first method comprises the steps of: (1) generating a probe-accessible surface of said target protein by probing the coordinates of said protein with an uncharged probe molecule having a radius of about 0.9 to about 2.0 Å, wherein said probe-accessible surface has an external surface the interior of which contains one or more probe-accessible internal cavities; (2) identifying the amino acids which make up the boundaries of the internal cavities, wherein said amino acids comprise a set of sites which when mutated increase the stability of the protein; (3) identifying an amino acid mutation which would decrease the volume of said internal cavities; (4) determining if said amino acid in said target protein can be changed without creating unacceptable steric interactions; (5) replacing the amino acid in said target protein by site-directed mutagenesis of the gene which expresses said target protein.

The first two steps of the above first method for improving the stability of a protein are the same as those disclosed above for the first computer based method for identifying the sites which affect the stability of a protein.

In step (3) an amino acid identified in step (2) is examined with the goal of identifying a mutation which would decrease the volume of said internal cavity. The size, shape and position of said internal cavity often defines and limits what mutations are acceptable and allowable given the distinct shape and size of each individual amino acid side chain. However, as a particular site in the protein has been identified for mutation, appropriate mutations can be also be determined by applying any of the various heuristics which define generally acceptable mutations (Matthews, B.W., et al. (1987) Proc. Natl. Acad. Sci. 84:6663–6667; Menéndez-Arias, L., and Argos, P. (1990) J. Mol. Biol. 206:397–406; Sandberg, W.S., and Terwilliger, T.C. (1991) Trends Biotechnol. 9:59–63; Bordo, D., and Argos, P. (1991) J. Mol. Biol. 217:721–729).

In step (4) a determination is then made if the amino acid identified for change in the target protein can be mutated or changed without creating a conformation of the target protein having unacceptable steric interactions. The separation distance between two atoms considered unacceptably short is some percentage of the sum of the van der Waal radii of the two atoms in question. Values of 90–95% of the sum of the van der Waal radii are common though others could be used. Common atoms between the original and replacement amino acid side chain are located and fixed in the same position. The new amino acid is rotated to find the position with the least number of close contacts or unacceptable steric interactions (distances shorter than physically reasonable). The separation distance at which two atoms are considered unreasonably short is some percentage of the sum of the van der Waal radii of the two atoms in question. Values of 90–95% of the sum of the van der Waal radii are common though others could be used. If all conformations of the new amino acid have close contacts, the amino acid substitution is rejected. A conformation with no close contacts which can be matched to a preferred amino acid conformation as defined by Ponder, J.W., and Richards, F.M. (1987) J. Mol. Biol. 193:775–791, is most highly desirable. In step (6) the amino acid identified for change to the corresponding amino acid in the same position in the reference protein is changed by site-directed mutagenesis of the gene which expresses the target protein by the methods disclosed above.

The second method comprises the steps of: (1) generating a probe-accessible surface of said target protein by probing the three dimensional coordinates of said protein with an uncharged probe molecule having a radius of about 0.9 to about 2.0 Å, wherein said probe-accessible surface has an external surface the interior of which contains one or more probe-accessible internal cavities; (2) aligning said three dimensional coordinates of said target protein and a reference protein by moving the three dimensional coordinates of said reference protein into the coordinate frame of said target protein; (3) identifying an amino acid in said reference protein whose side chain lies outside said solvent-accessible surface of said protein or inside said internal cavities of said target protein; (4) identifying the amino acid in said target protein which occupies the equivalent position as said amino acid in said reference protein; (5) determining if said amino acid in said target protein can be changed without creating unacceptable steric effects; (6) replacing the amino acid in said target protein with the corresponding amino acid in the equivalent position in said reference protein by site-directed mutagenesis of the gene which expresses said target protein.

The first three steps of this method are the same as steps (1), (2), and (3) of the second method for the second computer based method for identifying the sites which affect the stability of a protein.

In step (4) the amino acid in the target protein which occupies the equivalent position as the amino acid in the reference protein is identified. Equivalency is determined from the primary sequence alignment and three dimensional structure alignment described above. Given two protein structures, a target and a reference structure, which have been aligned, equivalent amino acids are defined as pairs of amino acids, one from the target and one from the reference protein, which may differ in identity but occupy close to the same position in the secondary and tertiary structure of the two proteins.

The following examples are meant to illustrate but not to limit the invention.

EXAMPLE 1

Identification of Sites in BLAP for mutagenesis

The structure of BLAP was obtained by X-ray crystallography and solved to 1.4 Å. The atomic coordinates are shown in FIG. 1. Water molecules were removed from the structure and the protein coordinates were used to generate a probe-accessible surface using a computer program QUANTA TM (version 3.0). This program can be used to calculate a probe-interaction map. The coordinates of BLAP were read into the computer and the following parameters were set in order to perform the probe interaction grid calculation. A Van der Waal calculation was requested with a "proton" probe (radius of 0.9 Å) with a charge of 0.0. The box dimensions were set to 50 Å with a grid size of 1 Å centered on the e-carbon of residue 219. The maximum energy was set to 500 and the minimum to $-100$. This means that energy values which exceed 500 will be set to 500. An energy value will exceed 500 when the probe is very close to an atom in the protein. The calculations were performed on a Silicon Graphics Inc. (2105 Landings Drive, Suite 2105, Mountain View, Calif. 94043) 4D/220 PowerIris TM workstation. QUANTA TM was used to visualize the probe-accessible surface. The map was contoured at 50 kcal/mol but this value depends on the particular constants in use and the method used to generate the probe accessible surface. The map was displayed simultaneously with the structure of BLAP and amino acid side chains which defined the boundaries of the internal cavities were identified visually.

One such amino acid was threonine-69. This side chain is completely buried with only 2% of its surface being solvent accessible. The hydroxyl group of the side chain defined part of the border of two internal cavities. These particular cavities are occupied by water molecules 278 on one side, and 280 on the other. Mutating this amino acid to valine represents a conservative change which increases the hydrophobicity of the side chain while having little effect on size and shape. Using computer modeling, it was determined that mutating threonine-69 to valine would not create any close contacts with other protein atoms or significantly perturb the structure if the valine occupies the same position as the hydroxyl of threonine-69 in the wild type protein. An oligonucleotide was synthesized which carried a mutation of the codon for threonine-69 to valine (T69V). This oligonucleotide was used to create a site directed mutation in the BLAP gene which was subcloned into a Bacillus vector and expressed in *B. subtilis* DB104 (See Examples 4 and 5). Strains were identified which were expressing the mutant protease and several shake flasks were prepared to produce the mutant protein (See Example 5). The mutant protease was purified from the shake flask media and characterized for surfactant and temperature stability (See Examples 7, 10, and 11).

The mutation T69V resulted in a 340% increase in the half-life of the protease at 50° C., from 12 minutes to 41 minutes (See Table 3).

EXAMPLE 2 energy values of the surrounding eight nearest grid points in the probe map. The protein atoms were colored on the basis of this interpolated energy value. The protein was displayed using QUANTA ™ and atoms were displayed in different colors depending on their interpolated energy value. For example, if the energy were greater than 400 the atoms were dark blue; between 300 and 400, light blue; 200 and 300, green; 200 to 100 yellow; and between −100 and 100, red. Visual inspection of such a display allowed identification of side chains which penetrated the solvent accessible surface or internal cavities.

One such amino acid was methionine-199 (1CSE numbering) in subtilisin Carlsberg. The amino acid was identified by visual inspection of the transformed 1CSE structure (as described above). Below, the coordinates of residue 199 from the transformed 1CSE structure are shown in the Brookhaven Protein Data Bank file format along with the interpolated energy values.

| | | | | | | | | | |
|---|---|---|---|---|---|---|---|---|---|
| Coordinates of Methionine-199 from the 1.2 Å structure of subtilisin Carlsberg. | | | | | | | | | |
| ATOM | 1364 | N | MET | 199 | 22.392 | 40.705 | 32.311 | 1.0 | 500.00 |
| ATOM | 1365 | CA | MET | 199 | 21.675 | 40.581 | 31.054 | 1.0 | 500.00 |
| ATOM | 1366 | C | MET | 199 | 22.438 | 39.677 | 30.103 | 1.0 | 500.00 |
| ATOM | 1367 | O | MET | 199 | 23.689 | 39.601 | 30.254 | 1.0 | 500.00 |
| ATOM | 1368 | CB | MET | 199 | 21.621 | 41.991 | 30.511 | 1.0 | 500.00 |
| ATOM | 1369 | CG | MET | 199 | 20.868 | 42.994 | 31.426 | 1.0 | 500.00 |
| ATOM | 1370 | SD | MET | 199 | 19.150 | 42.631 | 31.891 | 1.0 | 211.58 |
| ATOM | 1371 | CE | MET | 199 | 18.273 | 43.395 | 30.493 | 1.0 | 41.68 |

Identification of Sites in BLAP for Mutagenesis Based on Other Proteases (A) Comparison to subtilisin Carlsberg The three dimensional coordinates of subtilisin Carlsberg (1CSE) were obtained from the Brookhaven Protein Database (Bernstein, F.C., et al. (1977) J. Mol. Biol. 112:535-542). The protease structures were aligned using the molecular modeling program QUANTA ™. The BLAP coordinates were held fixed. The α-carbons of residues 1 to 32 of BLAP were matched to residues 1 to 32 of 1CSE, respectively; residues 40 to 60 of BLAP to residues 41 to 61 of 1CSE; residues 80 to 155 of BLAP to residues 82 to 157 of 1CSE; residues 170 to 269 of BLAP to residues 176 to 275 of 1CSE. The BLAP structure was held fixed, and the 1CSE structure was rotated and translated such that the r.m.s. deviation between the α-carbons of matched residues was minimized. The translation vector (−10.68738, 31.28904, −5.32134) and the rotation matrix

| | | |
|---|---|---|
| (0.17406 | −0.65535 | 0.73500 |
| −0.42119 | −0.72422 | −0.54599 |
| 0.89011 | −0.21454 | −0.40209) | were applied to the coordinates of 1CSE and the transformed coordinates were saved (henceforth, the transformed 1CSE structure). The final r.m.s. deviation between the matched 229 α-carbon pairs was 0.872 Å.

The probe-accessible surface map calculated in Example 1 was used to color the atoms in the transformed 1CSE structure. The entire map, which consists of three dimensional grid of (x, y, z) coordinates in space and an energy value at each position, was read into computer memory along with the protein coordinates (the transformed 1CSE structure). The energy value at each atom position was approximated by interpolating from the Column 1 is the record type; column 2 is the atom number; column 3 is the atom name; column 4 is the residue name; column 5 is the residue number; columns 6, 7 & 8 are the x, y, z coordinates of the atom, respectively; column 9 is the occupancy; column 10 is normally the temperature factor but this has been replaced with the interpolated energy value. Note that a value of 500 in this column means that the atom in nearly completely within the van der Waal surface of the BLAP molecule. When the probe map was calculated (see Example 1), energy values greater than 500 were set to 500. As can be seen, atoms 1370 and 1371 have significantly lower energy values (column 10). The end of this methionine residue extends into an internal cavity in the BLAP molecule.

This residue is equivalent in secondary and tertiary structure to valine-193 in BLAP. Using computer modeling, valine-193 in BLAP was changed to methionine. The χ values for the new methionine side chain in BLAP were taken from the subtilisin BPN' structure. In this conformation, the new side chain had no close contacts except for the ε-carbon of the methionine which contacted a crystallographic water in the BLAP structure.

An oligonucleotide was synthesized which mutated the codon for valine-193 to methionine (V193M) in the BLAP gene. This oligonucleotide was used to create a site directed mutation in the BLAP gene which was subcloned into a Bacillus vector and expressed in *B. subtilis* DB104 (See Examples 3, 4, and 5). Strains were identified which were expressing the mutant protease and several shake flasks were prepared to produce the mutant protein (See Example 5). The mutant protease was purified from the shake flask media and characterized for temperature and surfactant stability (See Examples 6, 7, 10, and 11).

The mutation V193M resulted in a 350% increase in the half-life of the protease at 50° C. from 12 minutes to 42 minutes (See Table 3).

(B) Comparison to Thermitase

The three-dimensional coordinates of thermitase (1TEC) were obtained from the Brookhaven Protein Database (Bernstein, F.C., et al. (1977) J. Mol. Biol. 112:535–542). The structures of BLAP and 1TEC were aligned using the molecular modeling program QUANTA ™ by matching equivalent α-carbons as listed below.

| Matched α-carbons between BLAP and Thermitase (1TEC) | |
|---|---|
| BLAP | 1TEC |
| 5–20 | 12–27 |
| 23–34 | 29–41 |
| 43–72 | 52–81 |
| 75–227 | 85–237 |
| 232–256 | 240–264 |

The BLAP structure was held fixed and the 1TEC structure was rotated and translated such that the r.m.s. deviation between the α-carbons of matched residues was minimized. The translation vector (14.92521, 33.43270, 40.92134) and the rotation matrix

| (0.79048 | −0.20395 | −0.57753 |
|---|---|---|
| −0.01688 | 0.93532 | −0.35340 |
| 0.61225 | 0.28911 | 0.73591) | were applied to the coordinates of 1TEC and the transformed coordinates were saved (henceforth, the transformed 1TEC structure). The final r.m.s. deviation between the matched 236 α-carbon pairs was 1.384 Å.

The probe-accessible surface map was used to color the atoms in the transformed 1TEC structure. The entire probe map was read into computer memory along with the coordinates of the transformed 1TEC structure. The energy value at each atomic position was interpolated from the energy values of the eight surrounding grid points in the probe map. The protein was displayed using QUANTA ™ and atoms were displayed in different colors as a function of their interpolated energy value. For example, if the energy were greater than 400 the atoms were dark blue; between 300 and 400, light blue; 200 and 300, green; 200 to 100 yellow; and between −100 and 100, red. Visual inspection of such a display allowed identification of side chains which penetrated the solvent accessible surface or internal cavities.

One such amino acid was tyrosine-149 (1TEC numbering) in thermitase. The amino acid was identified by visual inspection of the transformed 1TEC structure. Below, the coordinates of residue 149 from the transformed 1TEC structure are shown in the Brookhaven Protein Data Bank file format along with the interpolated energy values.

| Coordinates of Tyrosine-149 from the 2.0 Å structure of Thermitase | | | | | | | | | |
|---|---|---|---|---|---|---|---|---|---|
| ATOM | 1052 | N | TYR | 149 | 19.783 | 23.026 | 47.326 | 1.0 | 500.00 |
| ATOM | 1053 | CA | TYR | 149 | 20.372 | 21.668 | 47.275 | 1.0 | 500.00 |
| ATOM | 1054 | C | TYR | 149 | 21.456 | 21.557 | 46.165 | 1.0 | 500.00 |
| ATOM | 1055 | O | TYR | 149 | 22.619 | 21.330 | 46.486 | 1.0 | 500.00 |
| ATOM | 1056 | CB | TYR | 149 | 19.282 | 20.595 | 47.169 | 1.0 | 500.00 |
| ATOM | 1057 | CG | TYR | 149 | 19.859 | 19.183 | 46.935 | 1.0 | 227.30 |
| ATOM | 1058 | CD1 | TYR | 149 | 20.262 | 18.427 | 48.038 | 1.0 | 79.13 |
| ATOM | 1059 | CD2 | TYR | 149 | 20.014 | 18.722 | 45.608 | 1.0 | 275.01 |
| ATOM | 1060 | CE1 | TYR | 149 | 20.762 | 17.146 | 47.807 | 1.0 | 10.99 |
| ATOM | 1061 | CE2 | TYR | 149 | 20.531 | 17.425 | 45.371 | 1.0 | 500.00 |
| ATOM | 1062 | CZ | TYR | 149 | 20.860 | 16.649 | 46.488 | 1.0 | 131.28 |
| ATOM | 1063 | OH | TYR | 149 | 21.165 | 15.337 | 46.282 | 1.0 | 147.29 |

Column 10 is normally the temperature factor but this has been replaced with the interpolated energy value. As can be seen, the phenyl ring of the tyrosine side chain has significantly lower energy values (column 10 of atoms CG, CD1, CD2, CE1, CE2 and CZ).

This residue is equivalent in secondary and tertiary structure to serine-139 in BLAP. Using computer modeling, serine-139 in BLAP was changed to tyrosine. The χ values for the new tyrosine side chain in BLAP were taken from the thermitase structure. In this conformation, the new side chain had no close contacts that could not be alleviated by small changes (less than 5°) of the χ values. The modeled tyrosine side chain in BLAP fits neatly into a crevice on the surface of the BLAP protein between two surface helices.

An oligonucleotide was synthesized which mutated the codon for serine-139 to tyrosine (S139Y) in the BLAP gene. This oligonucleotide was used to create a site directed mutation in the BLAP gene which was subcloned into a Bacillus vector and expressed in *B. subtilis* DB104 (See Examples 3, 4, and 5). Strains were identified which expressed the mutant protease and several shake flasks were prepared to produce the mutant protein (See Example 5). The mutant protease was purified from the shake flask culture and characterized for temperature and surfactant stability (See Examples 6, 7, 10, and 11).

The mutation S139Y resulted in a 216% increase in the half-life of the protease at 50° C., from 12 minutes to 26 minutes (See Table 3).

EXAMPLE 3

Site Directed Mutagenesis of the BLAP gene

This mutagenesis procedure was first described by Stanssens, P., et al. (1989) Nucleic Acids Res. 17:4441–4454. While this is the preferred method, many other methods could be used to introduce oligonucleotide site-directed mutations, particularly those which use single stranded DNA. For example, the method of Kunkel (Kunkel, T.A. (1985) Proc. Natl. Acad. Sci. USA 82:488–492) has also been used.

A synthetic oligonucleotide was synthesized which mutates the codon of threonine-69 to the codon for valine. The mutagenic oligonucleotide was annealed to a gapped duplex DNA which carries the BLAP gene on a segment of single stranded (ss) DNA. The gapped duplex (gd) was formed by denaturing linear DNA's from pMc13C and pMa5-8 followed by re-annealing. The mutagenic oligonucleotide annealed to homologous ss BLAP DNA within the gap and the remaining gap was filled in by a DNA polymerase and ligated using T4 DNA ligase. Subsequent treatment of the product of the fill-in reaction with ExoIII removed any species with only partially filled gaps.

The product of the fill-in reaction was then transformed into a repair deficient E. coli strain such as WK6mutS. Plasmid DNA from the recombinant E. coli WK6mutS was prepared and transformed in a low plasmid/recipient ratio into a suppressor deficient strain of E. coli such as WK6. Ampicillin resistant transformants were selected and plasmid DNA of several candidates was purified and checked for the presence of the mutation.

The mutant BLAP protease was expressed by transferring the mutant BLAP genes from their particular E. coli pMa13C derivative vector into a plasmid vector which can replicate in Bacillus such as pH70 or pC51. In the following example, the plasmids pC51 and pH70 can be used interchangeably with the exception that plasmid pH70 encodes resistance to kanamycin while plasmid pC51 encodes resistance to tetracycline. The mutant BLAP gene was separated from the pMa13C plasmids by digestion with the restriction endonucleases AvaI and SstI and then ligated with an AvaI-SstI cut fragment of plasmid pH70 that includes the regions necessary for kanamycin resistance and for replication in Bacillus. The pH70 AvaI-SstI fragment was purified by high pressure liquid chromatography (HPLC). After ligation the mutant BLAP plasmids were transformed into B. subtilis DB104, a strain that has been engineered to inactivate its own genes encoding the major alkaline and neutral proteases. B. subtilis DB104 transformed by these plasmids were grown on a nutrient-skim milk agar in the presence of the antibiotic kanamycin. Clones that manufactured mutant protease were identified by the formation of clear zones of hydrolysis in the skim milk. Plasmid DNA was purified from these clones to verify that the protease-producing clones carried the a plasmid-borne BLAP gene with the desired mutation. The plasmid DNA was purified away from cell protein and chromosomal DNA by SDS-salt precipitation followed by chromatography over a Qiagen ion-exchange column (Qiagen Corporation). AvaI-SstI digested plasmid DNAs from different clones were compared with AvaI/SstI-digested derivatives of plasmid pH70 known to carry an intact BLAP gene. Plasmid digests were compared by agarose gel electrophoresis to identify plasmids that have the proper-sized AvaI/SstI DNA fragments. Selected plasmid DNAs were then sequenced across the region of the particular BLAP mutation to confirm that the mutation was present. One or more clones of each BLAP mutation were stored frozen in 15% glycerol at −70° C. and also cultivated in shake flasks (Examples 4 and 5) to manufacture mutant protease for characterization.

EXAMPLE 4

Production of Proteases

Each strain of B. subtilis DB104 that carried a plasmid with one of the mutant BLAP genes was cultivated in shake flasks to make the mutant protease. Strains were grown in 50 ml precultures of (Difco) Luria Broth (LB) with the antibiotic kanamycin for pH70 derived clones or tetracycline for pC51 derived clones at 37° C. and 280 rpm in a New Brunswick Series 25 Incubator Shaker. After 7 to 8 hours of incubation 2.5 or 5.0 ml of the preculture was transferred to 50 or 100 ml of MLBSP medium (Table 5), respectively, with either 20 $\mu$g/ml of kanamycin, or 15 $\mu$g/ml of tetracycline in 500 ml (Bellco) baffled shake flasks for growth and eventual production of the protease. These main shake flask cultures were incubated at 240 rpm and 37° C. for 64 hours before the culture broths were treated to remove intact cells and cellular debris, and to reduce the pH to 5.8 before they were concentrated. The protease production of each culture was monitored by electrophoresis of culture supernatants with reverse polarity on 12.5% homogenous polyacrylamide gels with the Pharmacia PhastSystem.

EXAMPLE 5

Production of Mutant Proteases in Shake Flasks

A hot loop was used to streak each mutant strain from a frozen cryovial culture onto an LB-skim milk agar containing either 20 $\mu$g/ml of kanamycin or 15 $\mu$g/ml of tetracycline. The plates were incubated at 37° C. for 20 to 24 hours. A single, isolated colony producing a good zone of hydrolysis of the skim milk was picked into a 250 ml Erlenmeyer flask containing about 50 ml Luria Broth (LB) which contained either 20 $\mu$g/ml kanamycin or 15 $\mu$g/ml of tetracycline. The broth was incubated in a New Brunswick Series 25 Incubator Shaker at 37° C. with shaking at 280 rpm for 7 to 8 hours. Either 2.5 ml of the turbid preculture was transferred into 50 ml of MLBSP containing either 20 $\mu$g/ml kanamycin or 15 $\mu$g/ml of tetracycline in each of four baffled 500 ml flasks, or 5 ml of preculture was used as an inoculum for 100 ml of MLBSP broth with antibiotic contained in each of two 500 ml baffled flasks (a 5% v/v transfer). All flasks were incubated at 240 rpm and 37° C. for 64 hours. After 64 hours of incubation the set of flasks for each culture was consolidated, transferred to 50 ml centrifuge tubes, and centrifuged at 20,000 $g_{av}$ for 15 minutes at 4° C. The broth was filtered through Miracloth (Calbiochem Corp. #475855) into 400 ml beakers chilled on ice. The broth was slowly stirred on ice for 30 minutes before the broth pH was reduced to 5.8 by the slow addition of glacial acetic acid. More fine debris were removed by centrifugation again at 20,000 $g_{av}$ and the broth was filtered through Miracloth into graduated cylinders to measure the volume. Two sets of 1 ml samples were made for PhastSystem gels and activity assays. The broth was stored on ice until the protease could be purified. The MLBSP media used for the production of BLAP in shake flask cultures is described in Table 5.

TABLE 5

| COMPOSITION OF MLBSP MEDIUM | |
|---|---|
| Component | Quantity (for 1 liter of media) |
| deionized water | 750 ml |
| Difco Casitone | 10 gm |
| Difco Tryptone | 20 gm |
| Difco Yeast Extract | 10 gm |
| NaCl | 5 gm |
| Sodium Succinate | 27 gm |

The media was adjusted to pH of 7.2 by addition of NaOH, the volume adjusted to 815 ml with water and autoclaved 15 minutes at 121° C. at 15 lbs/in$^2$. The media was cooled before adding the sterile stock solutions described in Appendix 1, while stirring.

TABLE 5-continued

COMPOSITION OF MLBSP MEDIUM

APPENDIX 1 (additions to MLBSP broth)

| Component | | Quantity (for 1 L of media) |
|---|---|---|
| MgSO$_4$.7H$_2$O | (100 mg/ml stock, autoclaved) | 1.0 ml |
| CaCl$_2$.2H$_2$O | (30 mg/ml stock, autoclaved) | 2.5 ml |
| FeSO$_4$.7H$_2$O | (1 mM stock, filter sterilized) | 0.5 ml |
| MnCl$_2$.4H$_2$O | (1 mM stock, autoclaved) | 0.5 ml |
| Glucose | (25% (w/v) stock, autoclaved) | 80.0 ml |
| PIPES Buffer[1] | (pH 7.2, 1M stock, autoclaved) | 50.0 ml |
| KPO$_4$ Buffer[2] | (1.5M stock, autoclaved) | 50.0 ml |

[1]Piperazine-N,N'-bis(2-ethane sulfonic acid).
[2]A sufficient amount of 1.5M dibasic phosphate (K$_2$HPO$_4$) was added to 200 ml of 1.5M monobasic phosphate (KH$_2$PO$_4$) to adjust the pH to 6.0 using a Beckman pHI44 pH meter equipped with a Beckman combination electrode (#3952C). The final pH was adjusted to 7.0 with 4M KOH.

Either kanamycin or tetracycline antibiotic stock solutions were added to the media just before use to a final concentration of 20 μg/ml and 15 μg/ml respectively.

EXAMPLE 6

Purification of BLAP

Fermentation broth of transformed *B. subtilis* DB104, while still in the fermenter, was adjusted to pH 5.8 with 4N H$_2$SO$_4$. The broth was collected and cooled to 4° C. If not mentioned otherwise, all subsequent steps were performed on ice or at 4° C. An aliquot of the broth material was clarified by centrifugation at 15,000×$g_{av.}$ for 60 min. Floating lipid material was removed by aspiration, and the supernatant filtered through Miracloth. The dark brown solution was placed in dialysis tubing (Spectrapor; #1, 6 to 8 kilodalton (kDa) molecular-weight-cut-off, 1.7 ml/cm) and dialyzed for 16 hours in 20 mM 2-(N-morpholino)ethanesulfonic acid (MES) containing 1 mM CaCl$_2$, adjusted with NaOH to pH 5.8 ('MES buffer'). The dialysate was clarified by centrifugation (20,000×$g_{av.}$ for 10 min) and the pH of the solution was adjusted to 7.8 with 2N NaOH. The enzyme solution containing approximately 0.9 g of protein in 1.2 liter was loaded at a flow rate of 150 ml/hour onto a column of S-Sepharose Fast Flow (SSFF, Pharmacia; 25 mm diameter, 260 mm long) previously equilibrated with 20 mM N-(2-hydroxyethyl)piperazine-N'-(2-ethanesulfonic acid) [HEPES], containing 1 mM CaCl$_2$, adjusted with NaOH to pH 7.8 ('HEPES buffer'). After the application of the enzyme solution the column was washed with 2 column volumes (250 ml) of HEPES buffer and then developed at a flow rate of 140 ml/hour with a gradient of 0 to 0.25 M NaCl in 600 ml of HEPES buffer. The gradient eluate was fractionated into 5.2-ml aliquots which were collected into tubes containing 2 ml of 100 mM MES/Na+, pH 5.8. The enzyme eluted between 0.12 and 0.15 M NaCl. Fractions containing the enzyme were pooled and protein was precipitated with ammonium sulfate at 52% of saturation. Solid salt (0.33 g per ml of solution) was added slowly with stirring over a period of 15 min, and stirring was continued for another 15 min. The precipitate was collected by centrifugation, the pellet was dissolved in MES buffer and the protein concentration in the solution was adjusted to 5 to 7 mg/ml. Following dialysis for 16 hours in MES buffer the solution was clarified by centrifugation and the pH of the supernatant was adjusted to 7.2. The protease was purified further by a second cation exchange separation on SSFF. All steps of this procedure were the same as above except that the pH of the HEPES buffer was 7.2 and that the NaCl gradient was from 0 to 0.25 M in 600 ml of HEPES buffer. Protein in pooled fractions was precipitated as above the ammonium sulfate and the enzyme was stored as ammonium sulfate precipitate at −70° C. Prior to use the ammonium sulfate precipitate of the enzyme was dissolved in an appropriate buffer, typically MES buffer, at the desired protein concentration, and dialyzed overnight in the buffer of choice.

EXAMPLE 7

Purification of BLAP Mutants

Fermentation broth from shake flasks, on average 180 ml, was collected and clarified by centrifugation at 20,000×$g_{av.}$ for 15 min. The supernatant was placed, with stirring, on ice and after 30 min the pH of the solution was adjusted to 5.8 with glacial acetic acid. If not mentioned otherwise, all subsequent steps were performed on ice or at 4° C. The solution was clarified again by centrifugation (20,000×$g_{av.}$ for 15 min) and was concentrated approximately 4-fold by ultrafiltration (Amicon; YM30 membrane). The dark brown solution was placed in dialysis tubing (Spectrapor; #1, 6 to 8 KDa molecular-weight-cut-off, 1.7 ml/cm) and dialyzed for 16 hours in 20 mM HEPES/Na+, pH 7.8, containing 1 mM CaCl$_2$ ('HEPES buffer'). The dialysate was clarified by centrifugation (20,000×$g_{av.}$ for 10 min) and the pH of the solution, if necessary, was adjusted to 7.8 with 2N NaOH. The enzyme solution was loaded at a flow rate of 60 ml/hour onto a column of SSFF (15 mm diameter, 75 mm long), previously equilibrated with HEPES buffer. When all colored by-products were eluted, the column was washed with 50 ml of HEPES buffer. Then, the enzyme was eluted with 0.25 M NaCl in HEPES buffer. Fractions of 1.2 ml were collected into tubes containing 0.5 ml of 100 mM MES/Na+, pH 5.8. Protein content in fractions was monitored either by a UV detector set at 280 nm or by protein assay as described below. Pooled fractions containing protease protein were placed on ice and protein was precipitated with a 5 to 8-fold volume excess of acetone at −20° C. The protein was allowed to precipitate for 6 min, the mixture was centrifuged for 4 min at 6,600×$g_{av.}$, the supernatant was discarded, the pellet was briefly exposed to vacuum (water aspirator) to remove most of the acetone, and the pellet was dissolved in 20 mM MES/Na+, pH 5.8, to give an approximate protein concentration of 30 mg/ml. Prior to any assays, the solution was centrifuged in an Eppendorf centrifuge for 3 min at full speed (13,000×$g_{max.}$).

EXAMPLE 8

Protein Determination

Protein was determined by a modified biuret method (Gornall, A.G., et al. (1948) J. Biol. Chem. 177:751–766). The protein in a total volume of 500 μl was mixed with 500 μl of biuret reagent and incubated for 10 min at 50° C. The solution was briefly chilled and its absorbance was measured at 540 nm. Typically, a reagent blank and three different protein aliquots in duplicates were measured and the recorded optical densities analyzed by linear regression. Bovine serum albumin (BSA, crystalline; Calbiochem) was used as protein standard. With purified BLAP protein the usefulness of BSA as protein standard in the biuret assay was confirmed. A BLAP sample was exhaustively dialyzed in 1 mM sodium phosphate, pH 5.8, and subsequently lyophilized. A sample of the solid material was weighed, dissolved in 1 mM sodium phosphate, pH 5.8, and used to generate a standard curve for the biuret assay. From the actual difference in phosphate content (Black, M.J., and Jones, M.E. (1983) Anal. Biochem. 135:233–238) of the final protein solution and the nominally 1 mM sodium phosphate solution used to dissolve the protein, the contribution of phosphate to the weight of solid BLAP was estimated and used to correct the standard curve.

EXAMPLE 9

Protease Assays

Two different protease assays were used. With the HPE method protease activity was established at a single concentration of case in (prepared according to Hammarsten; Merck, #2242) as substrate. In the AAPF-pNA assay initial ratesofsuccinyl-L-alanyl-L-alanyl-L-prolyl-L-phenylalanyl-p-nitroanilide (AAPF-pNA; Bachem) supported catalysis were used to determine the kinetic parameters $K_m$, $k_{cat}$, and $k_{cat}/K^m$.

A. HPE Method

Culture supernatants or solutions of purified proteases were diluted with chilled buffer (10 mMMES/Na+, pH 5.8) to give three different solutions with a protein concentration ratio of 1:3:5. The substrate solution contained 9.6 mg/ml case in, 24 mM Tris, and 0.4% (w/v) sodium tripolyphosphate, dissolved in synthetic tap water (STW; 0.029% (w/v) $CaCl_2.2H_2O$, 0.014% (w/v) $MgCl_2.6H_2O$, and 0.021% (w/v) $NaHCO_3$ in deionized water) adjusted to pH 8.5 at 50° C., prepared as follows. With stirring for 10 min, 6 g of case in was dissolved in 350 ml of STW. To this, 50 ml of 0.3 M Tris in STW was added and stirring was continued for another 10 min. This solution was heated to 70° C., then allowed to cool slowly At 50° C., the pH was adjusted to 8.5 with 0.1N NaOH. When the solution reached room temperature, the volume was adjusted to 500 ml with STW, followed by the addition of 125 ml of 2% (w/v) pentasodium tripolyphosphate in STW, pH 8.5 (adjusted with 3N HCl). The protease assay was started by adding 50 μl of protease solution to 750 μl of substrate solution placed in a 2.2 ml Eppendorf container preincubated for 10 min at 50° C. After 15 min, the reaction was terminated by the addition of 600 μl of trichloroacetic reagent (0.44 M trichloroacetic acid, 0.22 M sodium acetate in 3% (v/v) glacial acetic acid). The mixture was placed on ice for 15 min, the precipitated protein removed by centrifugation for 8 min (at $13,000 \times g_{max}$) and a 900 μl aliquot of the supernatant was mixed with 600 μl of 2N NaOH. The absorbance at 290 nm of this solution was recorded. Each dilution was assayed in duplicates and the data points for three different dilutions from one enzyme sample was analyzed by linear regression. A slope of 1 in this assay corresponds to 80 HPE units in the least diluted sample. In case of strongly colored culture supernatants with measurable quantities of UV absorbing material carried over by the diluted protease aliquot into the assay cuvette a control curve was constructed whose slope was subtracted from the slope of the protease assay before final HPE units were calculated.

B. AAPF-pNA Assay

Protease samples were diluted with 50% (v/v) 1,2-propanediol in 100 mM Tris, adjusted with 2N HCl to pH 8.6 at 25° C. ('Tris-propanediol buffer'), in which they were stable for at least 6 h at room temperature. A stock solution of 160 mM AAPF-pNA was prepared in dimethylsulfoxide dried with a molecular sieve (Aldrich; 4 Å, 4–8 mesh) for at least 24 h prior to use. Fixed point assays were performed at 25° C. with 1.6 mM AAPF-pNA in 100 mM Tris, adjusted with 2N HCl to pH 8 6 at 25° C., in a total volume of 1.020 ml. The substrate was added to the assay buffer 1 min prior to the assay initiation and the reaction was started by addition of enzyme at a final concentration of 20 ng to 1.3 μg of protein per ml (0.75 to 48.5 nM enzyme) depending on specific activity. Release of p-nitroanilide was monitored at 410 nm, and a molar extinction coefficient of 8,480 $M^{-1}cm^{-1}$ was used to calculate amount and concentration of product formed (DelMar, E.G., et al. (1979) Anal. Biochem. 99:316–320). Kinetic parameters were calculated from a velocity vs. substrate concentration plot constructed from initial rates measured once each at 12 different AAPF-pNA concentrations ranging from 0.16 to 3.2 mM. Data were fitted to a hyperbolic curve and proportionally weighted using the program ENZFITTER (Leatherbarrow, R.J. (1987) ENZFITTER, Biosoft, Cambridge, UK). A nominal molecular weight of 26.8 kDa was used in all calculations that required the interconversion of protein concentration and molarity of protease enzyme.

EXAMPLE 10

Temperature Stability of Purified Proteases

Stability of protease proteins was evaluated under two different conditions: (a) 100 mM glycine/Na+, pH 10 at 60° C., and (b) 100 mM glycine/Na+, pH 11 at 50° C. At t=0 min, the protein was diluted to approximately 0.25 mg/ml into incubation buffer maintained at the desired temperature. Periodically, an aliquot was removed from this incubation mixture and diluted into Tris-propanediol buffer chilled on ice. Residual protease activity was determined by the AAPF-pNA assay at a fixed AAPF-pNA concentration (1.6 mM). Stability is expressed as half-life ($t_½$) of activity determined from semi-logarithmic plots of residual activity as function of time. Each plot consisted of 6 data points with $t_½$ approximately in the center between experimental points.

EXAMPLE 11

Resistance of Proteases to Sodium Dodecylsulfate (SDS)

SDS was selected as representative of surfactants in general. Resistance of proteases to SDS was evaluated under two different conditions: (a) 100 mM Tris adjusted with 2N HCl to pH 8.6 at 50° C., containing 1% (w/v) SDS, and (b) 50 mM sodium carbonate, pH 10.5 at 50° C., containing 1% (w/v) SDS. Protease proteins were incubated at a final protein concentration of 0.25 mg/ml. Data were collected and evaluated as described above under Example 10.

EXAMPLE 12

Polyacrylamide Gel Electrophoresis

Purity of protease samples was evaluated on 20% nondenaturing PhastSystem gels (Pharmacia) run with reversed polarity. The same system was used to monitor the protease content of crude shake flask and fermentation broths. Buffer strips were prepared as described in Application File No. 300 (Pharmacia).

Molecular weight determinations were performed on 20% SDS PhastSystem gels, using the following markers: bovine serum albumin, 66 kDa; egg albumin, 45 kDa; glyceral-dehydephosphate dehydrogenase, 36 kDa; carbonic anhydrase, 29 kDa; trypsinogen, 24 kDa; trypsin inhibitor, 20.1 kDa; α-lactalbumin, 14.2 kDa (all from Sigma). Prior to SDS-PAGE, a protease sample was denatured with formic acid at a final concentration of 30 to 50% (v/v). Upon dilution of formic acid to 15% (v/v) protein was precipitated with trichloroacetic acid at a final concentration of 10% (v/v). The collected pellet was washed once with water, then dissolved in 2% (w/v) SDS and heated for 2 min in a boiling water-bath. Gels were stained with Coomassie Brilliant Blue R-250 (Kodak).

DEPOSIT OF MICROORGANISMS

Living cultures of the following have been accepted for deposit under the Budapest Treaty on the International Recognition of the Deposit of Microorganisms for the purposes of patent procedure by the American Type Culture Collection, 12301 Parklawn Drive, Rockville, Md. 20852 on May 8, 1991 (the accession number preceeds each deposit description): ATCC 68614—*Bacillus licheniformis* ATCC 53926 strain which contains a tetracycline-resistance plasmid originally derived from Bacillus plasmid pBC16 which carries the ATCC 53926 alkaline protease-BLAP ClaI fusion gene, whose structural gene has the mutations S3T, V4I, A188P, V193M, V199I; ATCC 68615—*E. coli* WK6 which carries phasmid pMc13C, a chloramphenicol-resistant derivative of phasmid pMc-5-8, that contains the ATCC 53926 alkaline protease- BLAP ClaI fusion gene and a 164 bp KpnI fragment carrying the ATCC 53926 alkaline protease gene's transcriptional terminator. The genotype of strain WK6 are Δlac-proAB, galE, strA, mutS::Tn10/F'lacI$^q$, ZΔM15, proA+B+ (Zell, R., and Fritz, H. -J. (1987) EMBO J. 6:1809–1815); ATCC 68616—*E. coli* GM33 which carries plasmid pCB13C, an ampicillin-resistant derivative of Pharmacia plasmid vector pTZ19R (Pharmacia) that contains the ATCC 53926 alkaline protease-ClaI fusion gene. The GM33 strain's genotype is dam3 (dam-methylase minus (Marinus, M.G. and Morris, N.R. (1974) J. Mol. Biol. 85:309–322)); ATCC 68617—*E. coli* WK6 which carries phasmid pMa5-8, an ampicillin-resistant mutagenesis vector described in Stanssens, P. et al. (1989) Nucleic Acids Research 17:4441–4454. The genotype of strain WK6 mutations are Δlac-proAB, galE, StrA, mutS::Tn10/F'lacI$^q$, ZΔM15, proA+B+ (Zell, R., and Fritz, H. -J. (1987) EMBO J. 6:1809–1815); ATCC 68618—an *E. coli* WK6 which carries phasmid pMc5-8, a chloramphenicol-resistant mutagenesis vector described in Stanssens, P., et al. (1989) Nucleic Acids Res. 17:4441–4454. The genotype of strain WK6 are Δlac-prOAB, galE, strA, mutS::Tn10/F'lacI$^q$, ZΔM15, proA+B+(Zell, R., and Fritz, H. -J. (1987) EMBO J. 6:1809–1815).

---

What is claimed is:

1. A substantially pure mutant *Bacillus lentus* DSM 5483 protease derived by replacement of at least one amino acid residue of the mature form of the *Bacillus lentus* DSM 5483 alkaline protease shown in SEQ ID NO: 52 wherein the position for said replacement of at least one amino acid residue is selected from the group consisting of Ser3, Val4, Ala188, Val193, and Val199, and wherein, the amino acid for replacement of Val4 is selected from the group consisting of isoleucine, serine, threonine, glycine, alanine or cysteine;

the amino acid for replacement of Ala188 is selected from the group consisting of proline, threonine, glycine, valine, or isoleucine;

the amino acid for replacement of Val193 is selected from the group consisting of methionine, threonine, glycine, alanine or isoleucine;

the amino acid for replacement of Val199 is selected from the group consisting of isoleucine, threonine, glycine, or alanine.

2. A mutant *Bacillus lentus* DSM 5483 protease of claim 1 wherein the valine residue at position 199 is substituted by isoleucine, the valine residue at position 193 is substituted by methionine, the alanine residue at position 188 is substituted by proline, the valine residue at position 4 is substituted by isoleucine, and the serine residue at position 3 is substituted by threonine.

3. A mutant *Bacillus lentus* DSM 5483 protease of claim 1 wherein the valine residue at position 199 is substituted by isoleucine, the valine residue at position 193 is substituted by methionine, the alanine residue at position 188 is substituted by proline, and the serine residue at position 3 is substituted by threonine.

4. A mutant *Bacillus lentus* DSM 5483 protease of claim 1 wherein the valine residue at position 199 is substituted by isoleucine, the valine residue at position 193 is substituted by methionine, the alanine residue at position 188 is substituted by proline, and the valine residue at position 4 is substituted by isoleucine.

5. A mutant *Bacillus lentus* DSM 5483 protease of claim 1 wherein the valine residue at position 199 is substituted by isoleucine, the valine residue at position 193 is substituted by methionine, the alanine residue at position 188 is substituted by proline, and the serine residue at position 139 is substituted by tyrosine.

6. A mutant *Bacillus lentus* DSM 5483 protease of claim 1 wherein the valine residue at position 199 is substituted by isoleucine, the valine residue at position 193 is substituted by methionine, the alanine residue at position 188 is substituted by proline, the serine residue at position 139 is substituted by tyrosine and the serine residue at position 130 is substituted by threonine.

7. A mutant *Bacillus lentus* DSM 5483 protease of claim 1 wherein the valine residue at position 199 is substituted by isoleucine, the valine residue at position 193 is substituted by methionine, the alanine residue at position 188 is substituted by proline.

8. A mutant *Bacillus lentus* DSM 5483 protease of claim 1 wherein the valine residue at position 193 is substituted by methionine, the alanine residue at position 188 is substituted by proline, and the serine residue at position 3 is substituted by threonine.

9. A mutant *Bacillus lentus* DSM 5483 protease of claim 1 wherein the valine residue at position 193 is substituted by methionine, and the alanine residue at position 188 is substituted by proline.

10. A mutant *Bacillus lentus* DSM 5483 protease of claim 1 wherein the alanine residue at position 188 is substituted by proline.

11. A mutant *Bacillus lentus* DSM 5483 protease of claim 1 wherein the valine residue at position 193 is substituted by methionine, the alanine residue at position 188 is substituted by proline, the valine residue at position 4 is substituted by isoleucine and the serine residue at position 3 is substituted by threonine.

12. A mutant *Bacillus lentus* DSM 5483 protease of claim 1 wherein the valine residue at position 193 is substituted by methionine.

13. A mutant *Bacillus lentus* DSM 5483 protease of claim 1 wherein the valine residue at position 193 is substituted by methionine, and the alanine residue at position 188 is substituted by proline, and the valine residue at position 4 is substituted by isoleucine.

14. A mutant *Bacillus lentus* DSM 5483 protease of claim 1 wherein the valine residue at position 199 is substituted by isoleucine.

15. A mutant *Bacillus lentus* DSM 5483 protease of claim 1 wherein the valine residue at position 4 is substituted by isoleucine.

16. An isolated mutant gene encoding a mutant *Bacillus lentus* DSM 5483 protease, the gene comprising in the direction of transcription a promoter in operable linkage with a downstream coding region, a ribosomal binding site, and the coding region, wherein said coding region comprises an initiation codon and the major portion of the pre region of the *Bacillus licheniformis* ATCC 53926 alkaline protease gene operably linked to a portion of the pre region and all of the pro and mature regions of the *Bacillus lentus* DSM alkaline protease gene, wherein one or more codons of said *Bacillus lentus* DSM 5483 protease gene are altered to encode a mutant protease derived by replacement of at least one amino acid residue of the mature form of the *Bacillus lentus* DSM 5483 alkaline protease shown in SEQ ID NO: 52 wherein the position for said replacement of at least one amino acid residue is selected from the group consisting of Ser3, Val4, Ala188, Val193 and Val199, and wherein, the amino acid for replacement of Ser3 is selected from the group consisting of glycine, valine, alanine or isoleucine;

the amino acid for replacement of Val4 is selected from the group consisting of isoleucine, serine, threonine, glycine, alanine or cysteine;

the amino acid for replacement of Ala188 is selected from the group consisting of proline, threonine, glycine, valine, or isoleucine;

the amino acid for replacement of Val193 is selected from the group consisting of methionine, threonine, glycine, alanine or isoleucine;

the amino acid for replacement of Val199 is selected from the group consisting of isoleucine, threonine, glycine, or alanine.

17. The mutant gene of claim 16 which encodes for said mutant protease wherein the valine residue at position 199 is substituted by isoleucine, the valine residue at position 193 is substituted by methionine, the alanine residue at position 188 is substituted by proline, the valine residue at position 4 is substituted by isoleucine, and the serine residue at position 3 is substituted by threonine.

18. The mutant gene of claim 16 which encodes for said mutant protease wherein the valine residue at position 199 is substituted by isoleucine, the valine residue at position 193 is substituted by methionine, the alanine residue at position 188 is substituted by proline, and the serine residue at position 3 is substituted by threonine.

19. The mutant gene of claim 16 which encodes for said mutant protease wherein the valine residue at position 199 is substituted by isoleucine, the valine residue at position 193 is substituted by methionine, the alanine residue at position 188 is substituted by proline, and the valine residue at position 4 is substituted by isoleucine.

20. The mutant gene of claim 16 which encodes for said mutant protease wherein the valine residue at position 199 is substituted by isoleucine, the valine residue at position 193 is substituted by methionine, the alanine residue at position 188 is substituted by proline, and the serine residue at position 139 is substituted by tyrosine.

21. The mutant gene of claim 16 which encodes for said mutant protease wherein the valine residue at position 199 is substituted by isoleucine, the valine residue at position 193 is substituted by methionine, the alanine residue at position 188 is substituted by proline, the serine residue at position 139 is substituted by tyrosine and the serine residue at position 130 is substituted by threonine.

22. The mutant gene of claim 16 which encodes for said mutant protease wherein the valine residue at position 199 is substituted by isoleucine, the valine residue at position 193 is substituted by methionine, the alanine residue at position 188 is substituted by proline.

23. The mutant gene of claim 16 which encodes for said mutant protease wherein the valine residue at position 193 is substituted by methionine, the alanine residue at position 188 is substituted by proline, and the serine residue at position 3 is substituted by threonine.

24. The mutant gene of claim 16 which encodes for said mutant protease wherein the valine residue at position 193 is substituted by methionine, and the alanine residue at position 188 is substituted by proline.

25. The mutant gene of claim 16 which encodes for said mutant protease wherein the alanine residue at position 188 is substituted by proline.

26. The mutant gene of claim 16 which encodes for said mutant protease wherein the valine residue at position 193 is substituted by methionine, the alanine residue at position 188 is substituted by proline, the valine residue at position 4 is substituted by isoleucine and the serine residue at position 3 is substituted by threonine.

27. The mutant gene of claim 16 which encodes for said mutant protease wherein the valine residue at position 193 is substituted by methionine.

28. The mutant gene of claim 16 which encodes for said mutant protease wherein the valine residue at position 193 is substituted by methionine, and the alanine residue at position 188 is substituted by proline, and the valine residue at position 4 is substituted by isoleucine.

29. The mutant gene of claim 16 which encodes for said mutant protease wherein the valine residue at position 199 is substituted by isoleucine.

30. The mutant gene of claim 16 which encodes for said mutant protease wherein the valine residue at position 4 is substituted by isoleucine.

31. A hybrid plasmid capable of replication in Bacillus, the plasmid comprising a mutant gene encoding a mutant Bacillus lentus DSM 5483 protease wherein the gene is in operable linkage with a 164 bp DNA fragment containing the transcription terminator from the Bacillus licheniformis ATCC 53926 alkaline protease gene, and wherein said gene encoding a mutant Bacillus lentus DSM 5483 protease comprises in the direction of transcription a promoter in operable linkage with a downstream coding region, a ribosomal binding site, and the coding region, wherein the coding region comprises an initiation codon and the major portion of the pre region of the Bacillus licheniformis ATCC 53926 alkaline protease gene operably linked to a portion of the pre region and all of the pro and mature regions of the Bacillus lentus DSM alkaline protease gene, wherein one or more codons of said Bacillus lentus DSM 5483 protease gene are altered to encode a mutant protease derived by replacement of at least one amino acid residue of the mature form of the Bacillus lentus DSM 5483 alkaline protease shown in SEQ ID NO: 52 wherein the position for said replacement of at least one amino acid residue is selected from the group consisting of Ser3, Val4, Ala188, Val193 and Val199, and wherein, the amino acid for replacement of Ser3 is selected from the group consisting of glycine, valine, alanine or isoleucine;

the amino acid for replacement of Val4 is selected from the group consisting of isoleucine, serine, threonine, glycine, alanine or cysteine;

the amino acid for replacement of Ala188 is selected from the group consisting of proline, threonine, glycine, valine, or isoleucine;

the amino acid for replacement of Val193 is selected from the group consisting of methionine, threonine, glycine, alanine or isoleucine;

the amino acid for replacement of Val199 is selected from the group consisting of isoleucine, threonine, glycine, or alanine.

32. The hybrid plasmid of claim 31 wherein said mutant gene encodes for said mutant protease wherein the valine residue at position 199 is substituted by isoleucine, the valine residue at position 193 is substituted by methionine, the alanine residue at position 188 is substituted by proline, the valine residue at position 4 is substituted by isoleucine, and the serine residue at position 3 is substituted by threonine.

33. The hybrid plasmid of claim 31 wherein said mutant gene encodes for said mutant protease wherein the valine residue at position 199 is substituted by isoleucine, the valine residue at position 193 is substituted by methionine, the alanine residue at position 188 is substituted by proline, and the serine residue at position 3 is substituted by threonine.

34. The hybrid plasmid of claim 31 wherein said mutant gene encodes for said mutant protease wherein the valine residue at position 199 is substituted by isoleucine, the valine residue at position 193 is substituted by methionine, the alanine residue at position 188 is substituted by proline, and the valine residue at position 4 is substituted by isoleucine.

35. The hybrid plasmid of claim 31 wherein said mutant gene encodes for said mutant protease wherein the valine residue at position 199 is substituted by isoleucine, the valine residue at position 193 is substituted by methionine, the alanine residue at position 188 is substituted by proline, and the serine residue at position 139 is substituted by tyrosine.

36. The hybrid plasmid of claim 31 wherein said mutant gene encodes for said mutant protease wherein the valine residue at position 199 is substituted by isoleucine, the valine residue at position 193 is substituted by methionine, the alanine residue at position 188 is substituted by proline, the serine residue at position 139 is substituted by tyrosine and the serine residue at position 130 is substituted by threonine.

37. The hybrid plasmid of claim 31 wherein said mutant gene encodes for said mutant protease wherein the valine residue at position 199 is substituted by isoleucine, the valine residue at position 193 is substituted by methionine, the alanine residue at position 188 is substituted by proline.

38. The hybrid plasmid of claim 31 wherein said mutant gene encodes for said mutant protease wherein the valine residue at position 193 is substituted by methionine, the alanine residue at position 188 is substituted by proline, and the serine residue at position 3 is substituted by threonine.

39. The hybrid plasmid of claim 31 wherein said mutant gene encodes for said mutant protease wherein the valine residue at position 193 is substituted by methionine, and the alanine residue at position 188 is substituted by proline.

40. The hybrid plasmid of claim 31 wherein said mutant gene encodes for said mutant protease wherein the alanine residue at position 188 is substituted by proline.

41. The hybrid plasmid of claim 31 wherein said mutant gene encodes for said mutant protease wherein the valine residue at position 193 is substituted by methionine, the alanine residue at position 188 is substituted by proline, the valine residue at position 4 is substituted by isoleucine and the serine residue at position 3 is substituted by threonine.

42. The hybrid plasmid of claim 31 wherein said mutant gene encodes for said mutant protease wherein the valine residue at position 193 is substituted by methionine.

43. The hybrid plasmid of claim 31 wherein said mutant gene encodes for said mutant protease wherein the valine residue at position 193 is substituted by methionine, and the alanine residue at position 188 is substituted by proline, and the valine residue at position 4 is substituted by isoleucine.

44. The hybrid plasmid of claim 31 wherein said mutant gene encodes for said mutant protease wherein the valine residue at position 199 is substituted by isoleucine.

45. The hybrid plasmid of claim 31 wherein said mutant gene encodes for said mutant protease wherein the valine residue at position 4 is substituted by isoleucine.

* * * * *

SEQUENCE LISTING ( 1 ) GENERAL INFORMATION:

( i i i ) NUMBER OF SEQUENCES: 104

( 2 ) INFORMATION FOR SEQ ID NO:1:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: S3T, V4I, A188P, V193M, V199I ( x i ) SEQUENCE DESCRIPTION: SEQ ID NO:1:

```
Ala  Gln  Thr  Ile  Pro  Trp  Gly  Ile  Ser  Arg  Val  Gln  Ala  Pro  Ala  Ala
 1              5                        10                       15

His  Asn  Arg  Gly  Leu  Thr  Gly  Ser  Gly  Val  Lys  Val  Ala  Val  Leu  Asp
               20                       25                      30

Thr  Gly  Ile  Ser  Thr  His  Pro  Asp  Leu  Asn  Ile  Arg  Gly  Gly  Ala  Ser
               35                       40                      45

Phe  Val  Pro  Gly  Glu  Pro  Ser  Thr  Gln  Asp  Gly  Asn  Gly  His  Gly  Thr
          50                      55                      60

His  Val  Ala  Gly  Thr  Ile  Ala  Ala  Leu  Asn  Asn  Ser  Ile  Gly  Val  Leu
 65                  70                       75                           80

Gly  Val  Ala  Pro  Ser  Ala  Glu  Leu  Tyr  Ala  Val  Lys  Val  Leu  Gly  Ala
                    85                       90                           95
```

```
Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

( 2 ) INFORMATION FOR SEQ ID NO:2:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: S3T, A188P, V193M, V199I ( x i ) SEQUENCE DESCRIPTION: SEQ ID NO:2:

```
Ala Gln Thr Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
```

|   | 130 |   |   |   | 135 |   |   |   | 140 |   |   |   |   |
|---|---|---|---|---|---|---|---|---|---|---|---|---|---|

Val Leu Val Val Ala Ala Ser Gly Asn Ser Gly Ala Ser Ser Ile Ser
145                     150                     155                     160

Tyr Pro Ala Arg Tyr Ala Asn Ala Met Ala Val Gly Ala Thr Asp Gln
                165                     170                     175

Asn Asn Asn Arg Ala Ser Phe Ser Gln Tyr Gly Pro Gly Leu Asp Ile
            180                     185                     190

Met Ala Pro Gly Val Asn Ile Gln Ser Thr Tyr Pro Gly Ser Thr Tyr
        195                     200                     205

Ala Ser Leu Asn Gly Thr Ser Met Ala Thr Pro His Val Ala Gly Ala
    210                     215                     220

Ala Ala Leu Val Lys Gln Lys Asn Pro Ser Trp Ser Asn Val Gln Ile
225                     230                     235                     240

Arg Asn His Leu Lys Asn Thr Ala Thr Ser Leu Gly Ser Thr Asn Leu
                245                     250                     255

Tyr Gly Ser Gly Leu Val Asn Ala Glu Ala Ala Thr Arg
            260                     265

( 2 ) INFORMATION FOR SEQ ID NO:3:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: V4I, A188P, V193M, V199I ( x i ) SEQUENCE DESCRIPTION: SEQ ID NO:3:

Ala Gln Ser Ile Pro Trp Gly Ile Ser Arg Val Gln Ala Pro Ala Ala
1               5                       10                      15

His Asn Arg Gly Leu Thr Gly Ser Gly Val Lys Val Ala Val Leu Asp
            20                      25                      30

Thr Gly Ile Ser Thr His Pro Asp Leu Asn Ile Arg Gly Gly Ala Ser
        35                      40                      45

Phe Val Pro Gly Glu Pro Ser Thr Gln Asp Gly Asn Gly His Gly Thr
    50                      55                      60

His Val Ala Gly Thr Ile Ala Ala Leu Asn Asn Ser Ile Gly Val Leu
65                      70                      75                      80

Gly Val Ala Pro Ser Ala Glu Leu Tyr Ala Val Lys Val Leu Gly Ala
                85                      90                      95

Asp Gly Arg Gly Ala Ile Ser Ser Ile Ala Gln Gly Leu Glu Trp Ala
            100                     105                     110

Gly Asn Asn Gly Met His Val Ala Asn Leu Ser Leu Gly Ser Pro Ser
        115                     120                     125

Pro Ser Ala Thr Leu Glu Gln Ala Val Asn Ser Ala Thr Ser Arg Gly
    130                     135                     140

Val Leu Val Val Ala Ala Ser Gly Asn Ser Gly Ala Ser Ser Ile Ser
145                     150                     155                     160

Tyr Pro Ala Arg Tyr Ala Asn Ala Met Ala Val Gly Ala Thr Asp Gln
                165                     170                     175

|     |     |     |     |     |     |     |     |     |     |     |     |     |     |     |
|---|---|---|---|---|---|---|---|---|---|---|---|---|---|---|
| Asn | Asn | Asn | Arg 180 | Ala | Ser | Phe | Ser | Gln 185 | Tyr | Gly | Pro | Gly | Leu 190 | Asp | Ile |
| Met | Ala | Pro 195 | Gly | Val | Asn | Ile | Gln 200 | Ser | Thr | Tyr | Pro | Gly 205 | Ser | Thr | Tyr |
| Ala | Ser | Leu | Asn 210 | Gly | Thr | Ser 215 | Met | Ala | Thr | Pro | His 220 | Val | Ala | Gly | Ala |
| Ala 225 | Ala | Leu | Val | Lys | Gln 230 | Lys | Asn | Pro | Ser | Trp 235 | Ser | Asn | Val | Gln | Ile 240 |
| Arg | Asn | His | Leu | Lys 245 | Asn | Thr | Ala | Thr | Ser 250 | Leu | Gly | Ser | Thr | Asn 255 | Leu |
| Tyr | Gly | Ser | Gly 260 | Leu | Val | Asn | Ala | Glu 265 | Ala | Ala | Thr | Arg |

(2) INFORMATION FOR SEQ ID NO:4:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S139Y, A188P, V193M, V199I (xi) SEQUENCE DESCRIPTION: SEQ ID NO:4:

|     |     |     |     |     |     |     |     |     |     |     |     |     |     |     |     |
|---|---|---|---|---|---|---|---|---|---|---|---|---|---|---|---|
| Ala 1 | Gln | Ser | Val | Pro 5 | Trp | Gly | Ile | Ser | Arg 10 | Val | Gln | Ala | Pro | Ala 15 |
| His | Asn | Arg | Gly 20 | Leu | Thr | Gly | Ser 25 | Gly | Val | Lys | Val | Ala 30 | Val | Leu | Asp |
| Thr | Gly | Ile | Ser 35 | Thr | His | Pro | Asp 40 | Leu | Asn | Ile | Arg | Gly 45 | Gly | Ala | Ser |
| Phe | Val 50 | Pro | Gly | Glu | Pro | Ser 55 | Thr | Gln | Asp | Gly | Asn 60 | Gly | His | Gly | Thr |
| His 65 | Val | Ala | Gly | Thr | Ile 70 | Ala | Ala | Leu | Asn | Asn 75 | Ser | Ile | Gly | Val | Leu 80 |
| Gly | Val | Ala | Pro | Ser 85 | Ala | Glu | Leu | Tyr | Ala 90 | Val | Lys | Val | Leu | Gly 95 | Ala |
| Asp | Gly | Arg | Gly 100 | Ala | Ile | Ser | Ser | Ile 105 | Ala | Gln | Gly | Leu | Glu 110 | Trp | Ala |
| Gly | Asn | Asn | Gly 115 | Met | His | Val | Ala | Asn 120 | Leu | Ser | Leu | Gly 125 | Ser | Pro | Ser |
| Pro | Ser | Ala | Thr 130 | Leu | Glu | Gln | Ala | Val 135 | Asn | Tyr | Ala | Thr 140 | Ser | Arg | Gly |
| Val | Leu 145 | Val | Val | Ala | Ala | Ser 150 | Gly | Asn | Ser | Gly 155 | Ala | Ser | Ser | Ile | Ser 160 |
| Tyr | Pro | Ala | Arg | Tyr 165 | Ala | Asn | Ala | Met | Ala 170 | Val | Gly | Ala | Thr | Asp 175 | Gln |
| Asn | Asn | Asn | Arg 180 | Ala | Ser | Phe | Ser | Gln 185 | Tyr | Gly | Pro | Gly | Leu 190 | Asp | Ile |
| Met | Ala | Pro 195 | Gly | Val | Asn | Ile | Gln 200 | Ser | Thr | Tyr | Pro | Gly 205 | Ser | Thr | Tyr |
| Ala | Ser | Leu | Asn 210 | Gly | Thr | Ser 215 | Met | Ala | Thr | Pro | His 220 | Val | Ala | Gly | Ala |

```
        Ala  Ala  Leu  Val  Lys  Gln  Lys  Asn  Pro  Ser  Trp  Ser  Asn  Val  Gln  Ile
        225                 230                      235                          240

Arg  Asn  His  Leu  Lys  Asn  Thr  Ala  Thr  Ser  Leu  Gly  Ser  Thr  Asn  Leu
                            245                      250                     255

Tyr  Gly  Ser  Gly  Leu  Val  Asn  Ala  Glu  Ala  Ala  Thr  Arg
                       260                      265
```

( 2 ) INFORMATION FOR SEQ ID NO:5:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: S130T, S139Y, A188P, V193M, V199I ( x i ) SEQUENCE DESCRIPTION: SEQ ID NO:5:

```
        Ala  Gln  Ser  Val  Pro  Trp  Gly  Ile  Ser  Arg  Val  Gln  Ala  Pro  Ala  Ala
        1                   5                        10                          15

His  Asn  Arg  Gly  Leu  Thr  Gly  Ser  Gly  Val  Lys  Val  Ala  Val  Leu  Asp
                       20                   25                           30

Thr  Gly  Ile  Ser  Thr  His  Pro  Asp  Leu  Asn  Ile  Arg  Gly  Gly  Ala  Ser
                            35                   40                      45

Phe  Val  Pro  Gly  Glu  Pro  Ser  Thr  Gln  Asp  Gly  Asn  Gly  His  Gly  Thr
             50                      55                           60

His  Val  Ala  Gly  Thr  Ile  Ala  Ala  Leu  Asn  Asn  Ser  Ile  Gly  Val  Leu
        65                       70                       75                           80

Gly  Val  Ala  Pro  Ser  Ala  Glu  Leu  Tyr  Ala  Val  Lys  Val  Leu  Gly  Ala
                            85                   90                           95

Asp  Gly  Arg  Gly  Ala  Ile  Ser  Ser  Ile  Ala  Gln  Gly  Leu  Glu  Trp  Ala
                       100                      105                     110

Gly  Asn  Asn  Gly  Met  His  Val  Ala  Asn  Leu  Ser  Leu  Gly  Ser  Pro  Ser
                       115                      120                     125

Pro  Thr  Ala  Thr  Leu  Glu  Gln  Ala  Val  Asn  Tyr  Ala  Thr  Ser  Arg  Gly
             130                     135                      140

Val  Leu  Val  Val  Ala  Ala  Ser  Gly  Asn  Ser  Gly  Ala  Ser  Ser  Ile  Ser
        145                      150                      155                          160

Tyr  Pro  Ala  Arg  Tyr  Ala  Asn  Ala  Met  Ala  Val  Gly  Ala  Thr  Asp  Gln
                            165                      170                     175

Asn  Asn  Asn  Arg  Ala  Ser  Phe  Ser  Gln  Tyr  Gly  Pro  Gly  Leu  Asp  Ile
                       180                      185                     190

Met  Ala  Pro  Gly  Val  Asn  Ile  Gln  Ser  Thr  Tyr  Pro  Gly  Ser  Thr  Tyr
                  195                     200                      205

Ala  Ser  Leu  Asn  Gly  Thr  Ser  Met  Ala  Thr  Pro  His  Val  Ala  Gly  Ala
             210                     215                           220

Ala  Ala  Leu  Val  Lys  Gln  Lys  Asn  Pro  Ser  Trp  Ser  Asn  Val  Gln  Ile
        225                 230                      235                          240

Arg  Asn  His  Leu  Lys  Asn  Thr  Ala  Thr  Ser  Leu  Gly  Ser  Thr  Asn  Leu
                            245                      250                     255

Tyr  Gly  Ser  Gly  Leu  Val  Asn  Ala  Glu  Ala  Ala  Thr  Arg
```

5,340,735

41

-continued 260        265

(2) INFORMATION FOR SEQ ID NO:6:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: A188P, V193M, V199I (xi) SEQUENCE DESCRIPTION: SEQ ID NO:6:

```
Ala Gln Ser Val Pro Trp Gly Ile Ser Arg Val Gln Ala Pro Ala Ala
 1               5                  10                  15
His Asn Arg Gly Leu Thr Gly Ser Gly Val Lys Val Ala Val Leu Asp
                20                  25                  30
Thr Gly Ile Ser Thr His Pro Asp Leu Asn Ile Arg Gly Gly Ala Ser
                35                  40                  45
Phe Val Pro Gly Glu Pro Ser Thr Gln Asp Gly Asn Gly His Gly Thr
50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Asp Gly Arg Gly Ala Ile Ser Ser Ile Ala Gln Gly Leu Glu Trp Ala
                100                 105                 110
Gly Asn Asn Gly Met His Val Ala Asn Leu Ser Leu Gly Ser Pro Ser
            115                 120                 125
Pro Ser Ala Thr Leu Glu Gln Ala Val Asn Ser Ala Thr Ser Arg Gly
            130                 135                 140
Val Leu Val Val Ala Ala Ser Gly Asn Ser Gly Ala Ser Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Pro Gly Leu Asp Ile
            180                 185                 190
Met Ala Pro Gly Val Asn Ile Gln Ser Thr Tyr Pro Gly Ser Thr Tyr
            195                 200                 205
Ala Ser Leu Asn Gly Thr Ser Met Ala Thr Pro His Val Ala Gly Ala
210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
                260                 265
```

(2) INFORMATION FOR SEQ ID NO:7:

(i) SEQUENCE CHARACTERISTICS:
        (A) LENGTH: 269 amino acids
        (B) TYPE: amino acid ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
    ( A ) ORGANISM: Serine Protease
    ( B ) STRAIN: Bacillus lentus DSM 5843

( v i i ) IMMEDIATE SOURCE:
    ( B ) CLONE: S3T, A188P, V193M ( x i ) SEQUENCE DESCRIPTION: SEQ ID NO:7:

```
Ala Gln Thr Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
             20                  25                  30

Thr Gly Ile Ser Thr His Pro Asp Leu Asn Ile Arg Gly Gly Ala Ser
             35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
             115                 120                 125

Pro Ser Ala Thr Leu Glu Gln Ala Val Asn Ser Ala Thr Ser Arg Gly
 130                 135                 140

Val Leu Val Val Ala Ala Ser Gly Asn Ser Gly Ala Ser Ser Ile Ser
 145                 150                 155                 160

Tyr Pro Ala Arg Tyr Ala Asn Ala Met Ala Val Gly Ala Thr Asp Gln
                 165                 170                 175

Asn Asn Asn Arg Ala Ser Phe Ser Gln Tyr Gly Pro Gly Leu Asp Ile
             180                 185                 190

Met Ala Pro Gly Val Asn Val Gln Ser Thr Tyr Pro Gly Ser Thr Tyr
             195                 200                 205

Ala Ser Leu Asn Gly Thr Ser Met Ala Thr Pro His Val Ala Gly Ala
 210                 215                 220

Ala Ala Leu Val Lys Gln Lys Asn Pro Ser Trp Ser Asn Val Gln Ile
 225                 230                 235                 240

Arg Asn His Leu Lys Asn Thr Ala Thr Ser Leu Gly Ser Thr Asn Leu
             245                 250                 255

Tyr Gly Ser Gly Leu Val Asn Ala Glu Ala Ala Thr Arg
             260                 265
```

( 2 ) INFORMATION FOR SEQ ID NO:8:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO (vi) ORIGINAL SOURCE:
    (A) ORGANISM: Serine Protease
    (B) STRAIN: Bacillus lentus DSM 5843

(vii) IMMEDIATE SOURCE:
    (B) CLONE: S157T (xi) SEQUENCE DESCRIPTION: SEQ ID NO:8:

| | | | | | | | | | | | | | | |
|---|---|---|---|---|---|---|---|---|---|---|---|---|---|---|
| Ala 1 | Gln | Ser | Val | Pro 5 | Trp | Gly | Ile | Ser | Arg 10 | Val | Gln | Ala | Pro | Ala 15 |
| His | Asn | Arg | Gly 20 | Leu | Thr | Gly | Ser | Gly 25 | Val | Lys | Val | Ala | Val 30 | Leu | Asp |
| Thr | Gly | Ile 35 | Ser | Thr | His | Pro | Asp 40 | Leu | Asn | Ile | Arg | Gly 45 | Gly | Ala | Ser |
| Phe | Val 50 | Pro | Gly | Glu | Pro | Ser 55 | Thr | Gln | Asp | Gly | Asn 60 | Gly | His | Gly | Thr |
| His 65 | Val | Ala | Gly | Thr | Ile 70 | Ala | Ala | Leu | Asn | Asn 75 | Ser | Ile | Gly | Val | Leu 80 |
| Gly | Val | Ala | Pro | Ser 85 | Ala | Glu | Leu | Tyr | Ala 90 | Val | Lys | Val | Leu | Gly 95 | Ala |
| Asp | Gly | Arg | Gly 100 | Ala | Ile | Ser | Ser | Ile 105 | Ala | Gln | Gly | Leu | Glu 110 | Trp | Ala |
| Gly | Asn | Asn 115 | Gly | Met | His | Val | Ala 120 | Asn | Leu | Ser | Leu | Gly 125 | Ser | Pro | Ser |
| Pro | Ser 130 | Ala | Thr | Leu | Glu | Gln 135 | Ala | Val | Asn | Ser | Ala 140 | Thr | Ser | Arg | Gly |
| Val 145 | Leu | Val | Val | Ala | Ala 150 | Ser | Gly | Asn | Ser | Gly 155 | Ala | Thr | Ser | Ile | Ser 160 |
| Tyr | Pro | Ala | Arg | Tyr 165 | Ala | Asn | Ala | Met | Ala 170 | Val | Gly | Ala | Thr | Asp 175 | Gln |
| Asn | Asn | Asn | Arg 180 | Ala | Ser | Phe | Ser | Gln 185 | Tyr | Gly | Ala | Gly | Leu 190 | Asp | Ile |
| Val | Ala | Pro | Gly 195 | Val | Asn | Val | Gln 200 | Ser | Thr | Tyr | Pro | Gly 205 | Ser | Thr | Tyr |
| Ala | Ser 210 | Leu | Asn | Gly | Thr | Ser 215 | Met | Ala | Thr | Pro | His 220 | Val | Ala | Gly | Ala |
| Ala 225 | Ala | Leu | Val | Lys | Gln 230 | Lys | Asn | Pro | Ser | Trp 235 | Ser | Asn | Val | Gln | Ile 240 |
| Arg | Asn | His | Leu | Lys 245 | Asn | Thr | Ala | Thr | Ser 250 | Leu | Gly | Ser | Thr | Asn 255 | Leu |
| Tyr | Gly | Ser | Gly 260 | Leu | Val | Asn | Ala | Glu 265 | Ala | Ala | Thr | Arg | | | |

(2) INFORMATION FOR SEQ ID NO:9:

(i) SEQUENCE CHARACTERISTICS:
    (A) LENGTH: 269 amino acids
    (B) TYPE: amino acid
    (D) TOPOLOGY: unknown (ii) MOLECULE TYPE: protein (iii) HYPOTHETICAL: NO (iv) ANTI-SENSE: NO (vi) ORIGINAL SOURCE:
    (A) ORGANISM: Serine Protease
    (B) STRAIN: Bacillus lentus DSM 5843

(vii) IMMEDIATE SOURCE:
    (B) CLONE: A188P, V193M (xi) SEQUENCE DESCRIPTION: SEQ ID NO:9:

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
 65                 70                  75                      80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

( 2 ) INFORMATION FOR SEQ ID NO:10:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: A188P ( x i ) SEQUENCE DESCRIPTION: SEQ ID NO:10:

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
```

|  |  |  | 35 |  |  |  | 40 |  |  |  | 45 |  |  |
|---|---|---|---|---|---|---|---|---|---|---|---|---|---|
| Phe | Val 50 | Pro | Gly | Glu | Pro | Ser 55 | Thr | Gln | Asp | Gly | Asn 60 | Gly | His | Gly | Thr |
| His 65 | Val | Ala | Gly | Thr | Ile 70 | Ala | Ala | Leu | Asn | Asn 75 | Ser | Ile | Gly | Val | Leu 80 |
| Gly | Val | Ala | Pro | Ser 85 | Ala | Glu | Leu | Tyr | Ala 90 | Val | Lys | Val | Leu | Gly 95 | Ala |
| Asp | Gly | Arg | Gly 100 | Ala | Ile | Ser | Ser | Ile 105 | Ala | Gln | Gly | Leu | Glu 110 | Trp | Ala |
| Gly | Asn | Asn 115 | Gly | Met | His | Val | Ala 120 | Asn | Leu | Ser | Leu | Gly 125 | Ser | Pro | Ser |
| Pro | Ser 130 | Ala | Thr | Leu | Glu | Gln 135 | Ala | Val | Asn | Ser | Ala 140 | Thr | Ser | Arg | Gly |
| Val 145 | Leu | Val | Val | Ala | Ala 150 | Ser | Gly | Asn | Ser | Gly 155 | Ala | Ser | Ser | Ile | Ser 160 |
| Tyr | Pro | Ala | Arg | Tyr 165 | Ala | Asn | Ala | Met | Ala 170 | Val | Gly | Ala | Thr | Asp 175 | Gln |
| Asn | Asn | Asn | Arg 180 | Ala | Ser | Phe | Ser | Gln 185 | Tyr | Gly | Pro | Gly | Leu 190 | Asp | Ile |
| Val | Ala | Pro 195 | Gly | Val | Asn | Val | Gln 200 | Ser | Thr | Tyr | Pro | Gly 205 | Ser | Thr | Tyr |
| Ala | Ser 210 | Leu | Asn | Gly | Thr | Ser 215 | Met | Ala | Thr | Pro | His 220 | Val | Ala | Gly | Ala |
| Ala 225 | Ala | Leu | Val | Lys | Gln 230 | Lys | Asn | Pro | Ser | Trp 235 | Ser | Asn | Val | Gln | Ile 240 |
| Arg | Asn | His | Leu | Lys 245 | Asn | Thr | Ala | Thr | Ser 250 | Leu | Gly | Ser | Thr | Asn 255 | Leu |
| Tyr | Gly | Ser | Gly 260 | Leu | Val | Asn | Ala | Glu 265 | Ala | Ala | Thr | Arg |

(2) INFORMATION FOR SEQ ID NO:11:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S3T, V4I, A188P, V193M (xi) SEQUENCE DESCRIPTION: SEQ ID NO:11:

| Ala 1 | Gln | Thr | Ile | Pro 5 | Trp | Gly | Ile | Ser | Arg 10 | Val | Gln | Ala | Pro | Ala 15 | Ala |
|---|---|---|---|---|---|---|---|---|---|---|---|---|---|---|---|
| His | Asn | Arg | Gly 20 | Leu | Thr | Gly | Ser | Gly 25 | Val | Lys | Val | Ala | Val 30 | Leu | Asp |
| Thr | Gly | Ile | Ser | Thr 35 | His | Pro | Asp | Leu | Asn 40 | Ile | Arg | Gly | Gly | Ala 45 | Ser |
| Phe | Val 50 | Pro | Gly | Glu | Pro | Ser 55 | Thr | Gln | Asp | Gly | Asn 60 | Gly | His | Gly | Thr |
| His 65 | Val | Ala | Gly | Thr | Ile 70 | Ala | Ala | Leu | Asn | Asn 75 | Ser | Ile | Gly | Val | Leu 80 |

```
Gly Val Ala Pro Ser Ala Glu Leu Tyr Ala Val Lys Val Leu Gly Ala
                85                  90                  95
Asp Gly Arg Gly Ala Ile Ser Ser Ile Ala Gln Gly Leu Glu Trp Ala
            100                 105                 110
Gly Asn Asn Gly Met His Val Ala Asn Leu Ser Leu Gly Ser Pro Ser
        115                 120                 125
Pro Ser Ala Thr Leu Glu Gln Ala Val Asn Ser Ala Thr Ser Arg Gly
    130                 135                 140
Val Leu Val Val Ala Ala Ser Gly Asn Ser Gly Ala Ser Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Pro Gly Leu Asp Ile
            180                 185                 190
Met Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Ala
210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
                260                 265
```

( 2 ) INFORMATION FOR SEQ ID NO:12:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: V193M ( x i ) SEQUENCE DESCRIPTION: SEQ ID NO:12:

```
Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
                20                  25                  30
Thr Gly Ile Ser Thr His Pro Asp Leu Asn Ile Arg Gly Gly Ala Ser
            35                  40                  45
Phe Val Pro Gly Glu Pro Ser Thr Gln Asp Gly Asn Gly His Gly Thr
        50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Asp Gly Arg Gly Ala Ile Ser Ser Ile Ala Gln Gly Leu Glu Trp Ala
            100                 105                 110
Gly Asn Asn Gly Met His Val Ala Asn Leu Ser Leu Gly Ser Pro Ser
        115                 120                 125
```

```
Pro  Ser  Ala  Thr  Leu  Glu  Gln  Ala  Val  Asn  Ser  Ala  Thr  Ser  Arg  Gly
     130                 135                      140

Val  Leu  Val  Val  Ala  Ala  Ser  Gly  Asn  Ser  Gly  Ala  Ser  Ser  Ile  Ser
145                      150                      155                           160

Tyr  Pro  Ala  Arg  Tyr  Ala  Asn  Ala  Met  Ala  Val  Gly  Ala  Thr  Asp  Gln
               165                      170                      175

Asn  Asn  Asn  Arg  Ala  Ser  Phe  Ser  Gln  Tyr  Gly  Ala  Gly  Leu  Asp  Ile
               180                      185                      190

Met  Ala  Pro  Gly  Val  Asn  Val  Gln  Ser  Thr  Tyr  Pro  Gly  Ser  Thr  Tyr
          195                      200                      205

Ala  Ser  Leu  Asn  Gly  Thr  Ser  Met  Ala  Thr  Pro  His  Val  Ala  Gly  Ala
     210                      215                      220

Ala  Ala  Leu  Val  Lys  Gln  Lys  Asn  Pro  Ser  Trp  Ser  Asn  Val  Gln  Ile
225                      230                      235                           240

Arg  Asn  His  Leu  Lys  Asn  Thr  Ala  Thr  Ser  Leu  Gly  Ser  Thr  Asn  Leu
               245                      250                      255

Tyr  Gly  Ser  Gly  Leu  Val  Asn  Ala  Glu  Ala  Ala  Thr  Arg
               260                      265
```

( 2 ) INFORMATION FOR SEQ ID NO:13:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: S104T ( x i ) SEQUENCE DESCRIPTION: SEQ ID NO:13:

```
Ala  Gln  Ser  Val  Pro  Trp  Gly  Ile  Ser  Arg  Val  Gln  Ala  Pro  Ala  Ala
1                   5                        10                       15

His  Asn  Arg  Gly  Leu  Thr  Gly  Ser  Gly  Val  Lys  Val  Ala  Val  Leu  Asp
               20                       25                       30

Thr  Gly  Ile  Ser  Thr  His  Pro  Asp  Leu  Asn  Ile  Arg  Gly  Gly  Ala  Ser
               35                       40                       45

Phe  Val  Pro  Gly  Glu  Pro  Ser  Thr  Gln  Asp  Gly  Asn  Gly  His  Gly  Thr
     50                       55                       60

His  Val  Ala  Gly  Thr  Ile  Ala  Ala  Leu  Asn  Asn  Ser  Ile  Gly  Val  Leu
65                       70                       75                            80

Gly  Val  Ala  Pro  Ser  Ala  Glu  Leu  Tyr  Ala  Val  Lys  Val  Leu  Gly  Ala
               85                       90                       95

Asp  Gly  Arg  Gly  Ala  Ile  Ser  Thr  Ile  Ala  Gln  Gly  Leu  Glu  Trp  Ala
               100                      105                      110

Gly  Asn  Asn  Gly  Met  His  Val  Ala  Asn  Leu  Ser  Leu  Gly  Ser  Pro  Ser
               115                      120                      125

Pro  Ser  Ala  Thr  Leu  Glu  Gln  Ala  Val  Asn  Ser  Ala  Thr  Ser  Arg  Gly
     130                      135                      140

Val  Leu  Val  Val  Ala  Ala  Ser  Gly  Asn  Ser  Gly  Ala  Ser  Ser  Ile  Ser
145                      150                      155                           160

Tyr  Pro  Ala  Arg  Tyr  Ala  Asn  Ala  Met  Ala  Val  Gly  Ala  Thr  Asp  Gln
```

|   | 165 |   |   |   |   |   | 170 |   |   |   |   | 175 |   |
|---|---|---|---|---|---|---|---|---|---|---|---|---|---|

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225             230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265

( 2 ) INFORMATION FOR SEQ ID NO:14:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: T69V ( x i ) SEQUENCE DESCRIPTION: SEQ ID NO:14:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Val Ile Ala Ala Leu Asn Asn Ser Ile Gly Val Leu
65              70                  75                  80

Gly Val Ala Pro Ser Ala Glu Leu Tyr Ala Val Lys Val Leu Gly Ala
            85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

|  |  |  |  |  |  |  |  |  |  |  |  |  |  |
|--|--|--|--|--|--|--|--|--|--|--|--|--|--|
| Ala | Ser | Leu | Asn | Gly | Thr | Ser | Met | Ala | Thr | Pro | His | Val | Ala | Gly | Ala |
|  210 |  |  |  |  |  215 |  |  |  |  220 |  |  |  |

| Ala | Ala | Leu | Val | Lys | Gln | Lys | Asn | Pro | Ser | Trp | Ser | Asn | Val | Gln | Ile |
|--|--|--|--|--|--|--|--|--|--|--|--|--|--|--|--|
| 225 |  |  |  |  | 230 |  |  |  |  | 235 |  |  |  |  | 240 |

| Arg | Asn | His | Leu | Lys | Asn | Thr | Ala | Thr | Ser | Leu | Gly | Ser | Thr | Asn | Leu |
|--|--|--|--|--|--|--|--|--|--|--|--|--|--|--|--|
|  |  |  |  | 245 |  |  |  |  | 250 |  |  |  |  | 255 |  |

| Tyr | Gly | Ser | Gly | Leu | Val | Asn | Ala | Glu | Ala | Ala | Thr | Arg |
|--|--|--|--|--|--|--|--|--|--|--|--|--|
|  |  |  | 260 |  |  |  |  | 265 |  |  |  |  |

( 2 ) INFORMATION FOR SEQ ID NO:15:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: V4I, A188P, V193M ( x i ) SEQUENCE DESCRIPTION: SEQ ID NO:15:

| Ala | Gln | Ser | Ile | Pro | Trp | Gly | Ile | Ser | Arg | Val | Gln | Ala | Pro | Ala | Ala |
|--|--|--|--|--|--|--|--|--|--|--|--|--|--|--|--|
| 1 |  |  |  | 5 |  |  |  |  | 10 |  |  |  |  | 15 |  |

| His | Asn | Arg | Gly | Leu | Thr | Gly | Ser | Gly | Val | Lys | Val | Ala | Val | Leu | Asp |
|--|--|--|--|--|--|--|--|--|--|--|--|--|--|--|--|
|  |  |  | 20 |  |  |  |  | 25 |  |  |  |  | 30 |  |  |

| Thr | Gly | Ile | Ser | Thr | His | Pro | Asp | Leu | Asn | Ile | Arg | Gly | Gly | Ala | Ser |
|--|--|--|--|--|--|--|--|--|--|--|--|--|--|--|--|
|  |  |  | 35 |  |  |  | 40 |  |  |  |  | 45 |  |  |  |

| Phe | Val | Pro | Gly | Glu | Pro | Ser | Thr | Gln | Asp | Gly | Asn | Gly | His | Gly | Thr |
|--|--|--|--|--|--|--|--|--|--|--|--|--|--|--|--|
|  | 50 |  |  |  |  | 55 |  |  |  |  | 60 |  |  |  |  |

| His | Val | Ala | Gly | Thr | Ile | Ala | Ala | Leu | Asn | Asn | Ser | Ile | Gly | Val | Leu |
|--|--|--|--|--|--|--|--|--|--|--|--|--|--|--|--|
| 65 |  |  |  | 70 |  |  |  |  | 75 |  |  |  |  |  | 80 |

| Gly | Val | Ala | Pro | Ser | Ala | Glu | Leu | Tyr | Ala | Val | Lys | Val | Leu | Gly | Ala |
|--|--|--|--|--|--|--|--|--|--|--|--|--|--|--|--|
|  |  |  |  | 85 |  |  |  |  | 90 |  |  |  |  | 95 |  |

| Asp | Gly | Arg | Gly | Ala | Ile | Ser | Ser | Ile | Ala | Gln | Gly | Leu | Glu | Trp | Ala |
|--|--|--|--|--|--|--|--|--|--|--|--|--|--|--|--|
|  |  |  | 100 |  |  |  |  | 105 |  |  |  |  | 110 |  |  |

| Gly | Asn | Asn | Gly | Met | His | Val | Ala | Asn | Leu | Ser | Leu | Gly | Ser | Pro | Ser |
|--|--|--|--|--|--|--|--|--|--|--|--|--|--|--|--|
|  |  | 115 |  |  |  |  | 120 |  |  |  |  | 125 |  |  |  |

| Pro | Ser | Ala | Thr | Leu | Glu | Gln | Ala | Val | Asn | Ser | Ala | Thr | Ser | Arg | Gly |
|--|--|--|--|--|--|--|--|--|--|--|--|--|--|--|--|
|  | 130 |  |  |  |  | 135 |  |  |  |  | 140 |  |  |  |  |

| Val | Leu | Val | Val | Ala | Ala | Ser | Gly | Asn | Ser | Gly | Ala | Ser | Ser | Ile | Ser |
|--|--|--|--|--|--|--|--|--|--|--|--|--|--|--|--|
| 145 |  |  |  |  | 150 |  |  |  |  | 155 |  |  |  |  | 160 |

| Tyr | Pro | Ala | Arg | Tyr | Ala | Asn | Ala | Met | Ala | Val | Gly | Ala | Thr | Asp | Gln |
|--|--|--|--|--|--|--|--|--|--|--|--|--|--|--|--|
|  |  |  |  | 165 |  |  |  |  | 170 |  |  |  |  | 175 |  |

| Asn | Asn | Asn | Arg | Ala | Ser | Phe | Ser | Gln | Tyr | Gly | Pro | Gly | Leu | Asp | Ile |
|--|--|--|--|--|--|--|--|--|--|--|--|--|--|--|--|
|  |  |  |  | 180 |  |  |  |  | 185 |  |  |  |  | 190 |  |

| Met | Ala | Pro | Gly | Val | Asn | Val | Gln | Ser | Thr | Tyr | Pro | Gly | Ser | Thr | Tyr |
|--|--|--|--|--|--|--|--|--|--|--|--|--|--|--|--|
|  |  | 195 |  |  |  |  | 200 |  |  |  |  | 205 |  |  |  |

| Ala | Ser | Leu | Asn | Gly | Thr | Ser | Met | Ala | Thr | Pro | His | Val | Ala | Gly | Ala |
|--|--|--|--|--|--|--|--|--|--|--|--|--|--|--|--|
|  | 210 |  |  |  |  | 215 |  |  |  |  | 220 |  |  |  |  |

| Ala | Ala | Leu | Val | Lys | Gln | Lys | Asn | Pro | Ser | Trp | Ser | Asn | Val | Gln | Ile |
|--|--|--|--|--|--|--|--|--|--|--|--|--|--|--|--|
| 225 |  |  |  |  | 230 |  |  |  |  | 235 |  |  |  |  | 240 |

| Arg | Asn | His | Leu | Lys | Asn | Thr | Ala | Thr | Ser | Leu | Gly | Ser | Thr | Asn | Leu |
|--|--|--|--|--|--|--|--|--|--|--|--|--|--|--|--|
|  |  |  |  | 245 |  |  |  |  | 250 |  |  |  |  | 255 |  |

```
              Tyr  Gly  Ser  Gly  Leu  Val  Asn  Ala  Glu  Ala  Ala  Thr  Arg
                        260                      265
```

( 2 ) INFORMATION FOR SEQ ID NO:16:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: A224V ( x i ) SEQUENCE DESCRIPTION: SEQ ID NO:16:

```
     Ala  Gln  Ser  Val  Pro  Trp  Gly  Ile  Ser  Arg  Val  Gln  Ala  Pro  Ala  Ala
     1              5                        10                       15

His  Asn  Arg  Gly  Leu  Thr  Gly  Ser  Gly  Val  Lys  Val  Ala  Val  Leu  Asp
                    20                       25                       30

Thr  Gly  Ile  Ser  Thr  His  Pro  Asp  Leu  Asn  Ile  Arg  Gly  Gly  Ala  Ser
                         35                  40                  45

Phe  Val  Pro  Gly  Glu  Pro  Ser  Thr  Gln  Asp  Gly  Asn  Gly  His  Gly  Thr
               50                  55                       60

His  Val  Ala  Gly  Thr  Ile  Ala  Ala  Leu  Asn  Asn  Ser  Ile  Gly  Val  Leu
     65                       70                  75                            80

Gly  Val  Ala  Pro  Ser  Ala  Glu  Leu  Tyr  Ala  Val  Lys  Val  Leu  Gly  Ala
                         85                  90                       95

Asp  Gly  Arg  Gly  Ala  Ile  Ser  Ser  Ile  Ala  Gln  Gly  Leu  Glu  Trp  Ala
                    100                      105                      110

Gly  Asn  Asn  Gly  Met  His  Val  Ala  Asn  Leu  Ser  Leu  Gly  Ser  Pro  Ser
                    115                      120                      125

Pro  Ser  Ala  Thr  Leu  Glu  Gln  Ala  Val  Asn  Ser  Ala  Thr  Ser  Arg  Gly
          130                      135                      140

Val  Leu  Val  Val  Ala  Ala  Ser  Gly  Asn  Ser  Gly  Ala  Ser  Ser  Ile  Ser
     145                           150                      155                 160

Tyr  Pro  Ala  Arg  Tyr  Ala  Asn  Ala  Met  Ala  Val  Gly  Ala  Thr  Asp  Gln
                    165                      170                      175

Asn  Asn  Asn  Arg  Ala  Ser  Phe  Ser  Gln  Tyr  Gly  Ala  Gly  Leu  Asp  Ile
                    180                      185                      190

Val  Ala  Pro  Gly  Val  Asn  Val  Gln  Ser  Thr  Tyr  Pro  Gly  Ser  Thr  Tyr
               195                      200                      205

Ala  Ser  Leu  Asn  Gly  Thr  Ser  Met  Ala  Thr  Pro  His  Val  Ala  Gly  Val
          210                      215                      220

Ala  Ala  Leu  Val  Lys  Gln  Lys  Asn  Pro  Ser  Trp  Ser  Asn  Val  Gln  Ile
     225                      230                      235                      240

Arg  Asn  His  Leu  Lys  Asn  Thr  Ala  Thr  Ser  Leu  Gly  Ser  Thr  Asn  Leu
                         245                      250                      255

Tyr  Gly  Ser  Gly  Leu  Val  Asn  Ala  Glu  Ala  Ala  Thr  Arg
                    260                      265
```

( 2 ) INFORMATION FOR SEQ ID NO:17:

( i ) SEQUENCE CHARACTERISTICS:

(A) LENGTH: 269 amino acids
(B) TYPE: amino acid
(D) TOPOLOGY: unknown (ii) MOLECULE TYPE: protein (iii) HYPOTHETICAL: NO (iv) ANTI-SENSE: NO (vi) ORIGINAL SOURCE:
(A) ORGANISM: Serine Protease
(B) STRAIN: Bacillus lentus DSM 5843

(vii) IMMEDIATE SOURCE:
(B) CLONE: V199I (xi) SEQUENCE DESCRIPTION: SEQ ID NO:17:

```
Ala Gln Ser Val Pro Trp Gly Ile Ser Arg Val Gln Ala Pro Ala Ala
 1               5                  10                  15
His Asn Arg Gly Leu Thr Gly Ser Gly Val Lys Val Ala Val Leu Asp
                20                  25                  30
Thr Gly Ile Ser Thr His Pro Asp Leu Asn Ile Arg Gly Gly Ala Ser
            35                  40                  45
Phe Val Pro Gly Glu Pro Ser Thr Gln Asp Gly Asn Gly His Gly Thr
    50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Asp Gly Arg Gly Ala Ile Ser Ser Ile Ala Gln Gly Leu Glu Trp Ala
               100                 105                 110
Gly Asn Asn Gly Met His Val Ala Asn Leu Ser Leu Gly Ser Pro Ser
               115                 120                 125
Pro Ser Ala Thr Leu Glu Gln Ala Val Asn Ser Ala Thr Ser Arg Gly
           130                 135                 140
Val Leu Val Val Ala Ala Ser Gly Asn Ser Gly Ala Ser Ser Ile Ser
145                 150                 155                 160
Tyr Pro Ala Arg Tyr Ala Asn Ala Met Ala Val Gly Ala Thr Asp Gln
               165                 170                 175
Asn Asn Asn Arg Ala Ser Phe Ser Gln Tyr Gly Ala Gly Leu Asp Ile
               180                 185                 190
Val Ala Pro Gly Val Asn Ile Gln Ser Thr Tyr Pro Gly Ser Thr Tyr
           195                 200                 205
Ala Ser Leu Asn Gly Thr Ser Met Ala Thr Pro His Val Ala Gly Ala
       210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
               245                 250                 255
Tyr Gly Ser Gly Leu Val Asn Ala Glu Ala Ala Thr Arg
           260                 265
```

(2) INFORMATION FOR SEQ ID NO:18:

(i) SEQUENCE CHARACTERISTICS:
(A) LENGTH: 269 amino acids
(B) TYPE: amino acid
(D) TOPOLOGY: unknown (ii) MOLECULE TYPE: protein (iii) HYPOTHETICAL: NO (iv) ANTI-SENSE: NO (vi) ORIGINAL SOURCE:
    (A) ORGANISM: Serine Protease
    (B) STRAIN: Bacillus lentus DSM 5843

(vii) IMMEDIATE SOURCE:
    (B) CLONE: V4I (xi) SEQUENCE DESCRIPTION: SEQ ID NO:18:

| Ala | Gln | Ser | Ile | Pro | Trp | Gly | Ile | Ser | Arg | Val | Gln | Ala | Pro | Ala | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| His | Asn | Arg | Gly | Leu | Thr | Gly | Ser | Gly | Val | Lys | Val | Ala | Val | Leu | Asp |
|     |     |     | 20  |     |     |     |     | 25  |     |     |     |     | 30  |     |     |
| Thr | Gly | Ile | Ser | Thr | His | Pro | Asp | Leu | Asn | Ile | Arg | Gly | Gly | Ala | Ser |
|     |     |     | 35  |     |     |     | 40  |     |     |     |     | 45  |     |     |     |
| Phe | Val | Pro | Gly | Glu | Pro | Ser | Thr | Gln | Asp | Gly | Asn | Gly | His | Gly | Thr |
|     |     | 50  |     |     |     | 55  |     |     |     |     | 60  |     |     |     |     |
| His | Val | Ala | Gly | Thr | Ile | Ala | Ala | Leu | Asn | Asn | Ser | Ile | Gly | Val | Leu |
| 65  |     |     |     |     | 70  |     |     |     |     | 75  |     |     |     |     | 80  |
| Gly | Val | Ala | Pro | Ser | Ala | Glu | Leu | Tyr | Ala | Val | Lys | Val | Leu | Gly | Ala |
|     |     |     |     | 85  |     |     |     |     | 90  |     |     |     |     | 95  |     |
| Asp | Gly | Arg | Gly | Ala | Ile | Ser | Ser | Ile | Ala | Gln | Gly | Leu | Glu | Trp | Ala |
|     |     |     | 100 |     |     |     |     | 105 |     |     |     |     | 110 |     |     |
| Gly | Asn | Asn | Gly | Met | His | Val | Ala | Asn | Leu | Ser | Leu | Gly | Ser | Pro | Ser |
|     |     | 115 |     |     |     |     | 120 |     |     |     |     | 125 |     |     |     |
| Pro | Ser | Ala | Thr | Leu | Glu | Gln | Ala | Val | Asn | Ser | Ala | Thr | Ser | Arg | Gly |
|     | 130 |     |     |     |     | 135 |     |     |     |     | 140 |     |     |     |     |
| Val | Leu | Val | Val | Ala | Ala | Ser | Gly | Asn | Ser | Gly | Ala | Ser | Ser | Ile | Ser |
| 145 |     |     |     |     | 150 |     |     |     |     | 155 |     |     |     |     | 160 |
| Tyr | Pro | Ala | Arg | Tyr | Ala | Asn | Ala | Met | Ala | Val | Gly | Ala | Thr | Asp | Gln |
|     |     |     |     | 165 |     |     |     |     | 170 |     |     |     |     | 175 |     |
| Asn | Asn | Asn | Arg | Ala | Ser | Phe | Ser | Gln | Tyr | Gly | Ala | Gly | Leu | Asp | Ile |
|     |     |     | 180 |     |     |     |     | 185 |     |     |     |     | 190 |     |     |
| Val | Ala | Pro | Gly | Val | Asn | Val | Gln | Ser | Thr | Tyr | Pro | Gly | Ser | Thr | Tyr |
|     |     | 195 |     |     |     |     | 200 |     |     |     |     | 205 |     |     |     |
| Ala | Ser | Leu | Asn | Gly | Thr | Ser | Met | Ala | Thr | Pro | His | Val | Ala | Gly | Ala |
|     | 210 |     |     |     |     | 215 |     |     |     |     | 220 |     |     |     |     |
| Ala | Ala | Leu | Val | Lys | Gln | Lys | Asn | Pro | Ser | Trp | Ser | Asn | Val | Gln | Ile |
| 225 |     |     |     |     | 230 |     |     |     |     | 235 |     |     |     |     | 240 |
| Arg | Asn | His | Leu | Lys | Asn | Thr | Ala | Thr | Ser | Leu | Gly | Ser | Thr | Asn | Leu |
|     |     |     |     | 245 |     |     |     |     | 250 |     |     |     |     | 255 |     |
| Tyr | Gly | Ser | Gly | Leu | Val | Asn | Ala | Glu | Ala | Ala | Thr | Arg |     |     |     |
|     |     |     | 260 |     |     |     |     | 265 |     |     |     |     |     |     |     |

(2) INFORMATION FOR SEQ ID NO:19:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S3T (xi) SEQUENCE DESCRIPTION: SEQ ID NO:19:

| | | | | | | | | | | | | | | | |
|---|---|---|---|---|---|---|---|---|---|---|---|---|---|---|---|
| Ala | Gln | Thr | Val | Pro | Trp | Gly | Ile | Ser | Arg | Val | Gln | Ala | Pro | Ala | Ala |
| 1 | | | | 5 | | | | | 10 | | | | | 15 | |
| His | Asn | Arg | Gly | Leu | Thr | Gly | Ser | Gly | Val | Lys | Val | Ala | Val | Leu | Asp |
| | | | 20 | | | | | 25 | | | | | 30 | | |
| Thr | Gly | Ile | Ser | Thr | His | Pro | Asp | Leu | Asn | Ile | Arg | Gly | Gly | Ala | Ser |
| | | | 35 | | | | 40 | | | | | 45 | | | |
| Phe | Val | Pro | Gly | Glu | Pro | Ser | Thr | Gln | Asp | Gly | Asn | Gly | His | Gly | Thr |
| | 50 | | | | | 55 | | | | | 60 | | | | |
| His | Val | Ala | Gly | Thr | Ile | Ala | Ala | Leu | Asn | Asn | Ser | Ile | Gly | Val | Leu |
| 65 | | | | | 70 | | | | | 75 | | | | | 80 |
| Gly | Val | Ala | Pro | Ser | Ala | Glu | Leu | Tyr | Ala | Val | Lys | Val | Leu | Gly | Ala |
| | | | | 85 | | | | | 90 | | | | | 95 | |
| Asp | Gly | Arg | Gly | Ala | Ile | Ser | Ser | Ile | Ala | Gln | Gly | Leu | Glu | Trp | Ala |
| | | | 100 | | | | | 105 | | | | | 110 | | |
| Gly | Asn | Asn | Gly | Met | His | Val | Ala | Asn | Leu | Ser | Leu | Gly | Ser | Pro | Ser |
| | | 115 | | | | | 120 | | | | | 125 | | | |
| Pro | Ser | Ala | Thr | Leu | Glu | Gln | Ala | Val | Asn | Ser | Ala | Thr | Ser | Arg | Gly |
| | 130 | | | | | 135 | | | | | 140 | | | | |
| Val | Leu | Val | Val | Ala | Ala | Ser | Gly | Asn | Ser | Gly | Ala | Ser | Ser | Ile | Ser |
| 145 | | | | | 150 | | | | | 155 | | | | | 160 |
| Tyr | Pro | Ala | Arg | Tyr | Ala | Asn | Ala | Met | Ala | Val | Gly | Ala | Thr | Asp | Gln |
| | | | | 165 | | | | | 170 | | | | | 175 | |
| Asn | Asn | Asn | Arg | Ala | Ser | Phe | Ser | Gln | Tyr | Gly | Ala | Gly | Leu | Asp | Ile |
| | | | 180 | | | | | 185 | | | | | 190 | | |
| Val | Ala | Pro | Gly | Val | Asn | Val | Gln | Ser | Thr | Tyr | Pro | Gly | Ser | Thr | Tyr |
| | | | 195 | | | | 200 | | | | | 205 | | | |
| Ala | Ser | Leu | Asn | Gly | Thr | Ser | Met | Ala | Thr | Pro | His | Val | Ala | Gly | Ala |
| | 210 | | | | | 215 | | | | | 220 | | | | |
| Ala | Ala | Leu | Val | Lys | Gln | Lys | Asn | Pro | Ser | Trp | Ser | Asn | Val | Gln | Ile |
| 225 | | | | | 230 | | | | | 235 | | | | | 240 |
| Arg | Asn | His | Leu | Lys | Asn | Thr | Ala | Thr | Ser | Leu | Gly | Ser | Thr | Asn | Leu |
| | | | | 245 | | | | | 250 | | | | | 255 | |
| Tyr | Gly | Ser | Gly | Leu | Val | Asn | Ala | Glu | Ala | Ala | Thr | Arg | | | |
| | | | 260 | | | | | 265 | | | | | | | |

(2) INFORMATION FOR SEQ ID NO:20:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S139Y (xi) SEQUENCE DESCRIPTION: SEQ ID NO:20:

| | | | | | | | | | | | | | | | |
|---|---|---|---|---|---|---|---|---|---|---|---|---|---|---|---|
| Ala | Gln | Ser | Val | Pro | Trp | Gly | Ile | Ser | Arg | Val | Gln | Ala | Pro | Ala | Ala |
| 1 | | | | 5 | | | | | 10 | | | | | 15 | |
| His | Asn | Arg | Gly | Leu | Thr | Gly | Ser | Gly | Val | Lys | Val | Ala | Val | Leu | Asp |
| | | | 20 | | | | | 25 | | | | | 30 | | |

```
Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Tyr Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:21:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: N242A (xi) SEQUENCE DESCRIPTION: SEQ ID NO:21:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
```

-continued

```
         65                         70                         75                         80
Gly  Val  Ala  Pro  Ser  Ala  Glu  Leu  Tyr  Ala  Val  Lys  Val  Leu  Gly  Ala
                    85                      90                          95

Asp  Gly  Arg  Gly  Ala  Ile  Ser  Ser  Ile  Ala  Gln  Gly  Leu  Glu  Trp  Ala
                   100                     105                         110

Gly  Asn  Asn  Gly  Met  His  Val  Ala  Asn  Leu  Ser  Leu  Gly  Ser  Pro  Ser
              115                     120                    125

Pro  Ser  Ala  Thr  Leu  Glu  Gln  Ala  Val  Asn  Ser  Ala  Thr  Ser  Arg  Gly
         130                     135                    140

Val  Leu  Val  Val  Ala  Ala  Ser  Gly  Asn  Ser  Gly  Ala  Ser  Ser  Ile  Ser
145                     150                    155                          160

Tyr  Pro  Ala  Arg  Tyr  Ala  Asn  Ala  Met  Ala  Val  Gly  Ala  Thr  Asp  Gln
                   165                     170                         175

Asn  Asn  Asn  Arg  Ala  Ser  Phe  Ser  Gln  Tyr  Gly  Ala  Gly  Leu  Asp  Ile
                   180                     185                    190

Val  Ala  Pro  Gly  Val  Asn  Val  Gln  Ser  Thr  Tyr  Pro  Gly  Ser  Thr  Tyr
              195                     200                    205

Ala  Ser  Leu  Asn  Gly  Thr  Ser  Met  Ala  Thr  Pro  His  Val  Ala  Gly  Ala
         210                     215                    220

Ala  Ala  Leu  Val  Lys  Gln  Lys  Asn  Pro  Ser  Trp  Ser  Asn  Val  Gln  Ile
225                     230                    235                          240

Arg  Ala  His  Leu  Lys  Asn  Thr  Ala  Thr  Ser  Leu  Gly  Ser  Thr  Asn  Leu
                   245                     250                         255

Tyr  Gly  Ser  Gly  Leu  Val  Asn  Ala  Glu  Ala  Ala  Thr  Arg
              260                     265
```

( 2 ) INFORMATION FOR SEQ ID NO:22:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: S236T ( x i ) SEQUENCE DESCRIPTION: SEQ ID NO:22:

```
Ala  Gln  Ser  Val  Pro  Trp  Gly  Ile  Ser  Arg  Val  Gln  Ala  Pro  Ala  Ala
1                    5                      10                          15

His  Asn  Arg  Gly  Leu  Thr  Gly  Ser  Gly  Val  Lys  Val  Ala  Val  Leu  Asp
                    20                      25                          30

Thr  Gly  Ile  Ser  Thr  His  Pro  Asp  Leu  Asn  Ile  Arg  Gly  Gly  Ala  Ser
              35                      40                         45

Phe  Val  Pro  Gly  Glu  Pro  Ser  Thr  Gln  Asp  Gly  Asn  Gly  His  Gly  Thr
         50                      55                    60

His  Val  Ala  Gly  Thr  Ile  Ala  Ala  Leu  Asn  Asn  Ser  Ile  Gly  Val  Leu
65                      70                     75                           80

Gly  Val  Ala  Pro  Ser  Ala  Glu  Leu  Tyr  Ala  Val  Lys  Val  Leu  Gly  Ala
                    85                      90                          95

Asp  Gly  Arg  Gly  Ala  Ile  Ser  Ser  Ile  Ala  Gln  Gly  Leu  Glu  Trp  Ala
                   100                     105                         110
```

| | | | | | | | | | | | | | | | |
|---|---|---|---|---|---|---|---|---|---|---|---|---|---|---|---|
| Gly | Asn | Asn 115 | Gly | Met | His | Val | Ala 120 | Asn | Leu | Ser | Leu | Gly 125 | Ser | Pro | Ser |
| Pro | Ser | Ala 130 | Thr | Leu | Glu | Gln 135 | Ala | Val | Asn | Ser | Ala 140 | Thr | Ser | Arg | Gly |
| Val 145 | Leu | Val | Val | Ala | Ala 150 | Ser | Gly | Asn | Ser | Gly 155 | Ala | Ser | Ser | Ile | Ser 160 |
| Tyr | Pro | Ala | Arg | Tyr 165 | Ala | Asn | Ala | Met | Ala 170 | Val | Gly | Ala | Thr | Asp 175 | Gln |
| Asn | Asn | Asn | Arg 180 | Ala | Ser | Phe | Ser | Gln 185 | Tyr | Gly | Ala | Gly | Leu 190 | Asp | Ile |
| Val | Ala | Pro 195 | Gly | Val | Asn | Val | Gln 200 | Ser | Thr | Tyr | Pro | Gly 205 | Ser | Thr | Tyr |
| Ala | Ser 210 | Leu | Asn | Gly | Thr | Ser 215 | Met | Ala | Thr | Pro | His 220 | Val | Ala | Gly | Ala |
| Ala 225 | Ala | Leu | Val | Lys | Gln 230 | Lys | Asn | Pro | Ser | Trp 235 | Thr | Asn | Val | Gln | Ile 240 |
| Arg | Asn | His | Leu | Lys 245 | Asn | Thr | Ala | Thr | Ser 250 | Leu | Gly | Ser | Thr | Asn 255 | Leu |
| Tyr | Gly | Ser | Gly 260 | Leu | Val | Asn | Ala | Glu 265 | Ala | Ala | Thr | Arg | | | |

(2) INFORMATION FOR SEQ ID NO:23:

(i) SEQUENCE CHARACTERISTICS:
      (A) LENGTH: 269 amino acids
      (B) TYPE: amino acid
      (D) TOPOLOGY: unknown (ii) MOLECULE TYPE: protein (iii) HYPOTHETICAL: NO (iv) ANTI-SENSE: NO (vi) ORIGINAL SOURCE:
      (A) ORGANISM: Serine Protease
      (B) STRAIN: Bacillus lentus DSM 5843

(vii) IMMEDIATE SOURCE:
      (B) CLONE: S36A (xi) SEQUENCE DESCRIPTION: SEQ ID NO:23:

| | | | | | | | | | | | | | | | |
|---|---|---|---|---|---|---|---|---|---|---|---|---|---|---|---|
| Ala 1 | Gln | Ser | Val | Pro 5 | Trp | Gly | Ile | Ser | Arg 10 | Val | Gln | Ala | Pro | Ala 15 | Ala |
| His | Asn | Arg | Gly 20 | Leu | Thr | Gly | Ser | Gly 25 | Val | Lys | Val | Ala | Val 30 | Leu | Asp |
| Thr | Gly | Ile 35 | Ala | Thr | His | Pro | Asp 40 | Leu | Asn | Ile | Arg | Gly 45 | Gly | Ala | Ser |
| Phe | Val 50 | Pro | Gly | Glu | Pro | Ser 55 | Thr | Gln | Asp | Gly | Asn 60 | Gly | His | Gly | Thr |
| His 65 | Val | Ala | Gly | Thr | Ile 70 | Ala | Ala | Leu | Asn | Asn 75 | Ser | Ile | Gly | Val | Leu 80 |
| Gly | Val | Ala | Pro | Ser 85 | Ala | Glu | Leu | Tyr | Ala 90 | Val | Lys | Val | Leu | Gly 95 | Ala |
| Asp | Gly | Arg | Gly 100 | Ala | Ile | Ser | Ser | Ile 105 | Ala | Gln | Gly | Leu | Glu 110 | Trp | Ala |
| Gly | Asn | Asn 115 | Gly | Met | His | Val | Ala 120 | Asn | Leu | Ser | Leu | Gly 125 | Ser | Pro | Ser |
| Pro | Ser | Ala 130 | Thr | Leu | Glu | Gln 135 | Ala | Val | Asn | Ser | Ala 140 | Thr | Ser | Arg | Gly |
| Val 145 | Leu | Val | Val | Ala | Ala 150 | Ser | Gly | Asn | Ser | Gly 155 | Ala | Ser | Ser | Ile | Ser 160 |

```
Tyr Pro Ala Arg Tyr Ala Asn Ala Met Ala Val Gly Ala Thr Asp Gln
            165             170                 175

Asn Asn Asn Arg Ala Ser Phe Ser Gln Tyr Gly Ala Gly Leu Asp Ile
            180             185                 190

Val Ala Pro Gly Val Asn Val Gln Ser Thr Tyr Pro Gly Ser Thr Tyr
            195             200             205

Ala Ser Leu Asn Gly Thr Ser Met Ala Thr Pro His Val Ala Gly Ala
210             215                 220

Ala Ala Leu Val Lys Gln Lys Asn Pro Ser Trp Ser Asn Val Gln Ile
225             230             235                         240

Arg Asn His Leu Lys Asn Thr Ala Thr Ser Leu Gly Ser Thr Asn Leu
            245             250                 255

Tyr Gly Ser Gly Leu Val Asn Ala Glu Ala Ala Thr Arg
            260             265
```

(2) INFORMATION FOR SEQ ID NO:24:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: H243A (xi) SEQUENCE DESCRIPTION: SEQ ID NO:24:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20              25                  30

Thr Gly Ile Ser Thr His Pro Asp Leu Asn Ile Arg Gly Gly Ala Ser
            35              40                  45

Phe Val Pro Gly Glu Pro Ser Thr Gln Asp Gly Asn Gly His Gly Thr
    50              55                  60

His Val Ala Gly Thr Ile Ala Ala Leu Asn Asn Ser Ile Gly Val Leu
65              70                  75                      80

Gly Val Ala Pro Ser Ala Glu Leu Tyr Ala Val Lys Val Leu Gly Ala
            85              90                  95

Asp Gly Arg Gly Ala Ile Ser Ser Ile Ala Gln Gly Leu Glu Trp Ala
            100             105                 110

Gly Asn Asn Gly Met His Val Ala Asn Leu Ser Leu Gly Ser Pro Ser
            115             120                 125

Pro Ser Ala Thr Leu Glu Gln Ala Val Asn Ser Ala Thr Ser Arg Gly
    130             135                 140

Val Leu Val Val Ala Ala Ser Gly Asn Ser Gly Ala Ser Ser Ile Ser
145             150                 155                     160

Tyr Pro Ala Arg Tyr Ala Asn Ala Met Ala Val Gly Ala Thr Asp Gln
            165             170                 175

Asn Asn Asn Arg Ala Ser Phe Ser Gln Tyr Gly Ala Gly Leu Asp Ile
            180             185                 190

Val Ala Pro Gly Val Asn Val Gln Ser Thr Tyr Pro Gly Ser Thr Tyr
```

```
              195                      200                         205
    Ala  Ser  Leu  Asn  Gly  Thr  Ser  Met  Ala  Thr  Pro  His  Val  Ala  Gly  Ala
         210                      215                 220

Ala  Ala  Leu  Val  Lys  Gln  Lys  Asn  Pro  Ser  Trp  Ser  Asn  Val  Gln  Ile
    225                 230                      235                          240

Arg  Asn  Ala  Leu  Lys  Asn  Thr  Ala  Thr  Ser  Leu  Gly  Ser  Thr  Asn  Leu
                        245                 250                          255

Tyr  Gly  Ser  Gly  Leu  Val  Asn  Ala  Glu  Ala  Ala  Thr  Arg
                   260                 265
```

( 2 ) INFORMATION FOR SEQ ID NO:25:

( i ) SEQUENCE CHARACTERISTICS:
    ( A ) LENGTH: 269 amino acids
    ( B ) TYPE: amino acid
    ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
    ( A ) ORGANISM: Serine Protease
    ( B ) STRAIN: Bacillus lentus DSM 5843

( v i i ) IMMEDIATE SOURCE:
    ( B ) CLONE: A101T ( x i ) SEQUENCE DESCRIPTION: SEQ ID NO:25:

```
    Ala  Gln  Ser  Val  Pro  Trp  Gly  Ile  Ser  Arg  Val  Gln  Ala  Pro  Ala  Ala
    1              5                   10                       15

His  Asn  Arg  Gly  Leu  Thr  Gly  Ser  Gly  Val  Lys  Val  Ala  Val  Leu  Asp
                   20                  25                       30

Thr  Gly  Ile  Ser  Thr  His  Pro  Asp  Leu  Asn  Ile  Arg  Gly  Gly  Ala  Ser
                   35                  40                       45

Phe  Val  Pro  Gly  Glu  Pro  Ser  Thr  Gln  Asp  Gly  Asn  Gly  His  Gly  Thr
         50                  55                       60

His  Val  Ala  Gly  Thr  Ile  Ala  Ala  Leu  Asn  Asn  Ser  Ile  Gly  Val  Leu
    65                  70                       75                            80

Gly  Val  Ala  Pro  Ser  Ala  Glu  Leu  Tyr  Ala  Val  Lys  Val  Leu  Gly  Ala
                        85                  90                       95

Asp  Gly  Arg  Gly  Thr  Ile  Ser  Ser  Ile  Ala  Gln  Gly  Leu  Glu  Trp  Ala
                   100                 105                      110

Gly  Asn  Asn  Gly  Met  His  Val  Ala  Asn  Leu  Ser  Leu  Gly  Ser  Pro  Ser
                   115                 120                      125

Pro  Ser  Ala  Thr  Leu  Glu  Gln  Ala  Val  Asn  Ser  Ala  Thr  Ser  Arg  Gly
    130                      135                 140

Val  Leu  Val  Val  Ala  Ala  Ser  Gly  Asn  Ser  Gly  Ala  Ser  Ser  Ile  Ser
    145                 150                 155                          160

Tyr  Pro  Ala  Arg  Tyr  Ala  Asn  Ala  Met  Ala  Val  Gly  Ala  Thr  Asp  Gln
                        165                 170                      175

Asn  Asn  Asn  Arg  Ala  Ser  Phe  Ser  Gln  Tyr  Gly  Ala  Gly  Leu  Asp  Ile
                   180                 185                      190

Val  Ala  Pro  Gly  Val  Asn  Val  Gln  Ser  Thr  Tyr  Pro  Gly  Ser  Thr  Tyr
              195                 200                      205

Ala  Ser  Leu  Asn  Gly  Thr  Ser  Met  Ala  Thr  Pro  His  Val  Ala  Gly  Ala
         210                      215                 220

Ala  Ala  Leu  Val  Lys  Gln  Lys  Asn  Pro  Ser  Trp  Ser  Asn  Val  Gln  Ile
    225                 230                      235                          240
```

```
        Arg  Asn  His  Leu  Lys  Asn  Thr  Ala  Thr  Ser  Leu  Gly  Ser  Thr  Asn  Leu
                            245                      250                      255

Tyr  Gly  Ser  Gly  Leu  Val  Asn  Ala  Glu  Ala  Ala  Thr  Arg
                       260                      265
```

( 2 ) INFORMATION FOR SEQ ID NO:26:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: S236A ( x i ) SEQUENCE DESCRIPTION: SEQ ID NO:26:

```
        Ala  Gln  Ser  Val  Pro  Trp  Gly  Ile  Ser  Arg  Val  Gln  Ala  Pro  Ala  Ala
        1                    5                        10                       15

His  Asn  Arg  Gly  Leu  Thr  Gly  Ser  Gly  Val  Lys  Val  Ala  Val  Leu  Asp
                       20                       25                       30

Thr  Gly  Ile  Ser  Thr  His  Pro  Asp  Leu  Asn  Ile  Arg  Gly  Gly  Ala  Ser
                            35                       40                       45

Phe  Val  Pro  Gly  Glu  Pro  Ser  Thr  Gln  Asp  Gly  Asn  Gly  His  Gly  Thr
             50                            55                       60

His  Val  Ala  Gly  Thr  Ile  Ala  Ala  Leu  Asn  Asn  Ser  Ile  Gly  Val  Leu
        65                            70                       75                       80

Gly  Val  Ala  Pro  Ser  Ala  Glu  Leu  Tyr  Ala  Val  Lys  Val  Leu  Gly  Ala
                            85                       90                       95

Asp  Gly  Arg  Gly  Ala  Ile  Ser  Ser  Ile  Ala  Gln  Gly  Leu  Glu  Trp  Ala
                       100                      105                      110

Gly  Asn  Asn  Gly  Met  His  Val  Ala  Asn  Leu  Ser  Leu  Gly  Ser  Pro  Ser
                       115                      120                      125

Pro  Ser  Ala  Thr  Leu  Glu  Gln  Ala  Val  Asn  Ser  Ala  Thr  Ser  Arg  Gly
             130                      135                      140

Val  Leu  Val  Val  Ala  Ala  Ser  Gly  Asn  Ser  Gly  Ala  Ser  Ser  Ile  Ser
        145                      150                      155                      160

Tyr  Pro  Ala  Arg  Tyr  Ala  Asn  Ala  Met  Ala  Val  Gly  Ala  Thr  Asp  Gln
                       165                      170                      175

Asn  Asn  Asn  Arg  Ala  Ser  Phe  Ser  Gln  Tyr  Gly  Ala  Gly  Leu  Asp  Ile
                       180                      185                      190

Val  Ala  Pro  Gly  Val  Asn  Val  Gln  Ser  Thr  Tyr  Pro  Gly  Ser  Thr  Tyr
                  195                      200                      205

Ala  Ser  Leu  Asn  Gly  Thr  Ser  Met  Ala  Thr  Pro  His  Val  Ala  Gly  Ala
                  210                      215                      220

Ala  Ala  Leu  Val  Lys  Gln  Lys  Asn  Pro  Ser  Trp  Ala  Asn  Val  Gln  Ile
        225                      230                      235                      240

Arg  Asn  His  Leu  Lys  Asn  Thr  Ala  Thr  Ser  Leu  Gly  Ser  Thr  Asn  Leu
                            245                      250                      255

Tyr  Gly  Ser  Gly  Leu  Val  Asn  Ala  Glu  Ala  Ala  Thr  Arg
                       260                      265
```

( 2 ) INFORMATION FOR SEQ ID NO:27:

( i ) SEQUENCE CHARACTERISTICS:
  ( A ) LENGTH: 269 amino acids
  ( B ) TYPE: amino acid
  ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
  ( A ) ORGANISM: Serine Protease
  ( B ) STRAIN: Bacillus lentus DSM 5843

( v i i ) IMMEDIATE SOURCE:
  ( B ) CLONE: E87R ( x i ) SEQUENCE DESCRIPTION: SEQ ID NO:27:

| | | | | | | | | | | | | | | |
|---|---|---|---|---|---|---|---|---|---|---|---|---|---|---|
| Ala | Gln | Ser | Val | Pro | Trp | Gly | Ile | Ser | Arg | Val | Gln | Ala | Pro | Ala |
| 1 | | | | 5 | | | | | 10 | | | | | 15 |
| His | Asn | Arg | Gly | Leu | Thr | Gly | Ser | Gly | Val | Lys | Val | Ala | Val | Leu | Asp |
| | | | 20 | | | | | 25 | | | | | 30 | | |
| Thr | Gly | Ile | Ser | Thr | His | Pro | Asp | Leu | Asn | Ile | Arg | Gly | Gly | Ala | Ser |
| | | | 35 | | | | 40 | | | | | 45 | | | |
| Phe | Val | Pro | Gly | Glu | Pro | Ser | Thr | Gln | Asp | Gly | Asn | Gly | His | Gly | Thr |
| | 50 | | | | | 55 | | | | | 60 | | | | |
| His | Val | Ala | Gly | Thr | Ile | Ala | Ala | Leu | Asn | Asn | Ser | Ile | Gly | Val | Leu |
| 65 | | | | | 70 | | | | | 75 | | | | | 80 |
| Gly | Val | Ala | Pro | Ser | Ala | Arg | Leu | Tyr | Ala | Val | Lys | Val | Leu | Gly | Ala |
| | | | | 85 | | | | | 90 | | | | | 95 | |
| Asp | Gly | Arg | Gly | Ala | Ile | Ser | Ser | Ile | Ala | Gln | Gly | Leu | Glu | Trp | Ala |
| | | | 100 | | | | | 105 | | | | | 110 | | |
| Gly | Asn | Asn | Gly | Met | His | Val | Ala | Asn | Leu | Ser | Leu | Gly | Ser | Pro | Ser |
| | | 115 | | | | | 120 | | | | | 125 | | | |
| Pro | Ser | Ala | Thr | Leu | Glu | Gln | Ala | Val | Asn | Ser | Ala | Thr | Ser | Arg | Gly |
| | 130 | | | | | 135 | | | | | 140 | | | | |
| Val | Leu | Val | Val | Ala | Ala | Ser | Gly | Asn | Ser | Gly | Ala | Ser | Ser | Ile | Ser |
| 145 | | | | | 150 | | | | | 155 | | | | | 160 |
| Tyr | Pro | Ala | Arg | Tyr | Ala | Asn | Ala | Met | Ala | Val | Gly | Ala | Thr | Asp | Gln |
| | | | | 165 | | | | | 170 | | | | | 175 | |
| Asn | Asn | Asn | Arg | Ala | Ser | Phe | Ser | Gln | Tyr | Gly | Ala | Gly | Leu | Asp | Ile |
| | | | 180 | | | | | 185 | | | | | 190 | | |
| Val | Ala | Pro | Gly | Val | Asn | Val | Gln | Ser | Thr | Tyr | Pro | Gly | Ser | Thr | Tyr |
| | | 195 | | | | | 200 | | | | | 205 | | | |
| Ala | Ser | Leu | Asn | Gly | Thr | Ser | Met | Ala | Thr | Pro | His | Val | Ala | Gly | Ala |
| | 210 | | | | | 215 | | | | | 220 | | | | |
| Ala | Ala | Leu | Val | Lys | Gln | Lys | Asn | Pro | Ser | Trp | Ser | Asn | Val | Gln | Ile |
| 225 | | | | | 230 | | | | | 235 | | | | | 240 |
| Arg | Asn | His | Leu | Lys | Asn | Thr | Ala | Thr | Ser | Leu | Gly | Ser | Thr | Asn | Leu |
| | | | | 245 | | | | | 250 | | | | | 255 | |
| Tyr | Gly | Ser | Gly | Leu | Val | Asn | Ala | Glu | Ala | Ala | Thr | Arg | | | |
| | | | 260 | | | | | 265 | | | | | | | |

( 2 ) INFORMATION FOR SEQ ID NO:28:

( i ) SEQUENCE CHARACTERISTICS:
    ( A ) LENGTH: 269 amino acids
    ( B ) TYPE: amino acid
    ( D ) TOPOLOGY: unknown ( i i ) MOLECULE TYPE: protein (i i i) HYPOTHETICAL: NO (i v) ANTI-SENSE: NO (v i) ORIGINAL SOURCE:
    (A) ORGANISM: Serine Protease
    (B) STRAIN: Bacillus lentus DSM 5843

(v i i) IMMEDIATE SOURCE:
    (B) CLONE: N114S (x i) SEQUENCE DESCRIPTION: SEQ ID NO:28:

```
Ala Gln Ser Val Pro Trp Gly Ile Ser Arg Val Gln Ala Pro Ala Ala
 1               5                  10                  15
His Asn Arg Gly Leu Thr Gly Ser Gly Val Lys Val Ala Val Leu Asp
             20                  25                  30
Thr Gly Ile Ser Thr His Pro Asp Leu Asn Ile Arg Gly Gly Ala Ser
             35                  40                  45
Phe Val Pro Gly Glu Pro Ser Thr Gln Asp Gly Asn Gly His Gly Thr
             50                  55                  60
His Val Ala Gly Thr Ile Ala Ala Leu Asn Asn Ser Ile Gly Val Leu
 65                  70                  75                  80
Gly Val Ala Pro Ser Ala Glu Leu Tyr Ala Val Lys Val Leu Gly Ala
             85                  90                  95
Asp Gly Arg Gly Ala Ile Ser Ser Ile Ala Gln Gly Leu Glu Trp Ala
             100                 105                 110
Gly Ser Asn Gly Met His Val Ala Asn Leu Ser Leu Gly Ser Pro Ser
             115                 120                 125
Pro Ser Ala Thr Leu Glu Gln Ala Val Asn Ser Ala Thr Ser Arg Gly
     130                 135                 140
Val Leu Val Val Ala Ala Ser Gly Asn Ser Gly Ala Ser Ser Ile Ser
145                  150                 155                 160
Tyr Pro Ala Arg Tyr Ala Asn Ala Met Ala Val Gly Ala Thr Asp Gln
                 165                 170                 175
Asn Asn Asn Arg Ala Ser Phe Ser Gln Tyr Gly Ala Gly Leu Asp Ile
             180                 185                 190
Val Ala Pro Gly Val Asn Val Gln Ser Thr Tyr Pro Gly Ser Thr Tyr
         195                 200                 205
Ala Ser Leu Asn Gly Thr Ser Met Ala Thr Pro His Val Ala Gly Ala
     210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                 245                 250                 255
Tyr Gly Ser Gly Leu Val Asn Ala Glu Ala Ala Thr Arg
             260                 265
```

(2) INFORMATION FOR SEQ ID NO:29:

(i) SEQUENCE CHARACTERISTICS:
        (A) LENGTH: 269 amino acids
        (B) TYPE: amino acid
        (D) TOPOLOGY: unknown (i i) MOLECULE TYPE: protein (i i i) HYPOTHETICAL: NO (i v) ANTI-SENSE: NO (v i) ORIGINAL SOURCE:
        (A) ORGANISM: Serine Protease
        (B) STRAIN: Bacillus lentus DSM 5843

(v i i) IMMEDIATE SOURCE:
    (B) CLONE: A47W (x i) SEQUENCE DESCRIPTION: SEQ ID NO:29:

```
Ala Gln Ser Val Pro Trp Gly Ile Ser Arg Val Gln Ala Pro Ala Ala
 1               5                  10                 15

His Asn Arg Gly Leu Thr Gly Ser Gly Val Lys Val Ala Val Leu Asp
             20                  25                 30

Thr Gly Ile Ser Thr His Pro Asp Leu Asn Ile Arg Gly Gly Trp Ser
             35              40                  45

Phe Val Pro Gly Glu Pro Ser Thr Gln Asp Gly Asn Gly His Gly Thr
         50              55                  60

His Val Ala Gly Thr Ile Ala Ala Leu Asn Asn Ser Ile Gly Val Leu
 65              70                  75                      80

Gly Val Ala Pro Ser Ala Glu Leu Tyr Ala Val Lys Val Leu Gly Ala
                 85              90                  95

Asp Gly Arg Gly Ala Ile Ser Ser Ile Ala Gln Gly Leu Glu Trp Ala
            100             105                 110

Gly Asn Asn Gly Met His Val Ala Asn Leu Ser Leu Gly Ser Pro Ser
            115             120                 125

Pro Ser Ala Thr Leu Glu Gln Ala Val Asn Ser Ala Thr Ser Arg Gly
    130             135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165             170                 175

Asn Asn Asn Arg Ala Ser Phe Ser Gln Tyr Gly Ala Gly Leu Asp Ile
            180             185                 190

Val Ala Pro Gly Val Asn Val Gln Ser Thr Tyr Pro Gly Ser Thr Tyr
        195             200                 205

Ala Ser Leu Asn Gly Thr Ser Met Ala Thr Pro His Val Ala Gly Ala
    210             215                 220

Ala Ala Leu Val Lys Gln Lys Asn Pro Ser Trp Ser Asn Val Gln Ile
225             230                 235                     240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:30:

(i) SEQUENCE CHARACTERISTICS:
    (A) LENGTH: 269 amino acids
    (B) TYPE: amino acid
    (D) TOPOLOGY: unknown (i i) MOLECULE TYPE: protein (i i i) HYPOTHETICAL: NO (i v) ANTI-SENSE: NO (v i) ORIGINAL SOURCE:
    (A) ORGANISM: Serine Protease
    (B) STRAIN: Bacillus lentus DSM 5843

(v i i) IMMEDIATE SOURCE:
    (B) CLONE: A120S (x i) SEQUENCE DESCRIPTION: SEQ ID NO:30:

```
Ala Gln Ser Val Pro Trp Gly Ile Ser Arg Val Gln Ala Pro Ala Ala
 1               5                  10                 15
```

```
His  Asn  Arg  Gly  Leu  Thr  Gly  Ser  Gly  Val  Lys  Val  Ala  Val  Leu  Asp
               20                      25                      30

Thr  Gly  Ile  Ser  Thr  His  Pro  Asp  Leu  Asn  Ile  Arg  Gly  Gly  Ala  Ser
               35                      40                      45

Phe  Val  Pro  Gly  Glu  Pro  Ser  Thr  Gln  Asp  Gly  Asn  Gly  His  Gly  Thr
     50                      55                      60

His  Val  Ala  Gly  Thr  Ile  Ala  Ala  Leu  Asn  Asn  Ser  Ile  Gly  Val  Leu
65                       70                      75                            80

Gly  Val  Ala  Pro  Ser  Ala  Glu  Leu  Tyr  Ala  Val  Lys  Val  Leu  Gly  Ala
                85                      90                           95

Asp  Gly  Arg  Gly  Ala  Ile  Ser  Ser  Ile  Ala  Gln  Gly  Leu  Glu  Trp  Ala
               100                     105                     110

Gly  Asn  Asn  Gly  Met  His  Val  Ser  Asn  Leu  Ser  Leu  Gly  Ser  Pro  Ser
               115                     120                     125

Pro  Ser  Ala  Thr  Leu  Glu  Gln  Ala  Val  Asn  Ser  Ala  Thr  Ser  Arg  Gly
     130                     135                     140

Val  Leu  Val  Val  Ala  Ala  Ser  Gly  Asn  Ser  Gly  Ala  Ser  Ser  Ile  Ser
145                      150                     155                           160

Tyr  Pro  Ala  Arg  Tyr  Ala  Asn  Ala  Met  Ala  Val  Gly  Ala  Thr  Asp  Gln
               165                     170                     175

Asn  Asn  Asn  Arg  Ala  Ser  Phe  Ser  Gln  Tyr  Gly  Ala  Gly  Leu  Asp  Ile
               180                     185                     190

Val  Ala  Pro  Gly  Val  Asn  Val  Gln  Ser  Thr  Tyr  Pro  Gly  Ser  Thr  Tyr
          195                     200                     205

Ala  Ser  Leu  Asn  Gly  Thr  Ser  Met  Ala  Thr  Pro  His  Val  Ala  Gly  Ala
     210                     215                     220

Ala  Ala  Leu  Val  Lys  Gln  Lys  Asn  Pro  Ser  Trp  Ser  Asn  Val  Gln  Ile
225                      230                     235                           240

Arg  Asn  His  Leu  Lys  Asn  Thr  Ala  Thr  Ser  Leu  Gly  Ser  Thr  Asn  Leu
               245                     250                     255

Tyr  Gly  Ser  Gly  Leu  Val  Asn  Ala  Glu  Ala  Ala  Thr  Arg
               260                     265
```

( 2 ) INFORMATION FOR SEQ ID NO:31:

( i ) SEQUENCE CHARACTERISTICS:
  ( A ) LENGTH: 269 amino acids
  ( B ) TYPE: amino acid
  ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
  ( A ) ORGANISM: Serine Protease
  ( B ) STRAIN: Bacillus lentus DSM 5843

( v i i ) IMMEDIATE SOURCE:
  ( B ) CLONE: T56V ( x i ) SEQUENCE DESCRIPTION: SEQ ID NO:31:

```
Ala  Gln  Ser  Val  Pro  Trp  Gly  Ile  Ser  Arg  Val  Gln  Ala  Pro  Ala  Ala
1              5                       10                      15

His  Asn  Arg  Gly  Leu  Thr  Gly  Ser  Gly  Val  Lys  Val  Ala  Val  Leu  Asp
               20                      25                      30

Thr  Gly  Ile  Ser  Thr  His  Pro  Asp  Leu  Asn  Ile  Arg  Gly  Gly  Ala  Ser
               35                      40                      45

Phe  Val  Pro  Gly  Glu  Pro  Ser  Val  Gln  Asp  Gly  Asn  Gly  His  Gly  Thr
     50                      55                      60
```

| His | Val | Ala | Gly | Thr | Ile | Ala | Ala | Leu | Asn | Asn | Ser | Ile | Gly | Val | Leu |
| 65 | | | | 70 | | | | | 75 | | | | | | 80 |

Gly Val Ala Pro Ser Ala Glu Leu Tyr Ala Val Lys Val Leu Gly Ala
                    85                  90                  95

Asp Gly Arg Gly Ala Ile Ser Ser Ile Ala Gln Gly Leu Glu Trp Ala
              100                 105                 110

Gly Asn Asn Gly Met His Val Ala Asn Leu Ser Leu Gly Ser Pro Ser
              115             120                 125

Pro Ser Ala Thr Leu Glu Gln Ala Val Asn Ser Ala Thr Ser Arg Gly
        130             135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
              165                 170                 175

Asn Asn Asn Arg Ala Ser Phe Ser Gln Tyr Gly Ala Gly Leu Asp Ile
              180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
        210             215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
              245                 250                 255

Tyr Gly Ser Gly Leu Val Asn Ala Glu Ala Ala Thr Arg
              260                 265

( 2 ) INFORMATION FOR SEQ ID NO:32:

( i ) SEQUENCE CHARACTERISTICS:
       ( A ) LENGTH: 269 amino acids
       ( B ) TYPE: amino acid
       ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
       ( A ) ORGANISM: Serine Protease
       ( B ) STRAIN: Bacillus lentus DSM 5843

( v i i ) IMMEDIATE SOURCE:
       ( B ) CLONE: A120V ( x i ) SEQUENCE DESCRIPTION: SEQ ID NO:32:

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
              20                  25                  30

Thr Gly Ile Ser Thr His Pro Asp Leu Asn Ile Arg Gly Gly Ala Ser
          35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                    85                  90                  95

Asp Gly Arg Gly Ala Ile Ser Ser Ile Ala Gln Gly Leu Glu Trp Ala

```
            100                    105                    110

Gly  Asn  Asn  Gly  Met  His  Val  Val  Asn  Leu  Ser  Leu  Gly  Ser  Pro  Ser
               115                      120                     125

Pro  Ser  Ala  Thr  Leu  Glu  Gln  Ala  Val  Asn  Ser  Ala  Thr  Ser  Arg  Gly
          130                      135                     140

Val  Leu  Val  Val  Ala  Ala  Ser  Gly  Asn  Ser  Gly  Ala  Ser  Ser  Ile  Ser
145                      150                     155                          160

Tyr  Pro  Ala  Arg  Tyr  Ala  Asn  Ala  Met  Ala  Val  Gly  Ala  Thr  Asp  Gln
               165                      170                     175

Asn  Asn  Asn  Arg  Ala  Ser  Phe  Ser  Gln  Tyr  Gly  Ala  Gly  Leu  Asp  Ile
               180                      185                     190

Val  Ala  Pro  Gly  Val  Asn  Val  Gln  Ser  Thr  Tyr  Pro  Gly  Ser  Thr  Tyr
          195                      200                     205

Ala  Ser  Leu  Asn  Gly  Thr  Ser  Met  Ala  Thr  Pro  His  Val  Ala  Gly  Ala
          210                      215                     220

Ala  Ala  Leu  Val  Lys  Gln  Lys  Asn  Pro  Ser  Trp  Ser  Asn  Val  Gln  Ile
225                      230                     235                          240

Arg  Asn  His  Leu  Lys  Asn  Thr  Ala  Thr  Ser  Leu  Gly  Ser  Thr  Asn  Leu
               245                      250                     255

Tyr  Gly  Ser  Gly  Leu  Val  Asn  Ala  Glu  Ala  Ala  Thr  Arg
          260                      265
```

( 2 ) INFORMATION FOR SEQ ID NO:33:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: G205V ( x i ) SEQUENCE DESCRIPTION: SEQ ID NO:33:

```
Ala  Gln  Ser  Val  Pro  Trp  Gly  Ile  Ser  Arg  Val  Gln  Ala  Pro  Ala  Ala
1                   5                        10                      15

His  Asn  Arg  Gly  Leu  Thr  Gly  Ser  Gly  Val  Lys  Val  Ala  Val  Leu  Asp
               20                       25                      30

Thr  Gly  Ile  Ser  Thr  His  Pro  Asp  Leu  Asn  Ile  Arg  Gly  Gly  Ala  Ser
          35                       40                      45

Phe  Val  Pro  Gly  Glu  Pro  Ser  Thr  Gln  Asp  Gly  Asn  Gly  His  Gly  Thr
50                       55                      60

His  Val  Ala  Gly  Thr  Ile  Ala  Ala  Leu  Asn  Asn  Ser  Ile  Gly  Val  Leu
65                       70                      75                           80

Gly  Val  Ala  Pro  Ser  Ala  Glu  Leu  Tyr  Ala  Val  Lys  Val  Leu  Gly  Ala
               85                       90                      95

Asp  Gly  Arg  Gly  Ala  Ile  Ser  Ser  Ile  Ala  Gln  Gly  Leu  Glu  Trp  Ala
          100                      105                     110

Gly  Asn  Asn  Gly  Met  His  Val  Ala  Asn  Leu  Ser  Leu  Gly  Ser  Pro  Ser
               115                      120                     125

Pro  Ser  Ala  Thr  Leu  Glu  Gln  Ala  Val  Asn  Ser  Ala  Thr  Ser  Arg  Gly
          130                      135                     140
```

```
Val  Leu  Val  Val  Ala  Ala  Ser  Gly  Asn  Ser  Gly  Ala  Ser  Ser  Ile  Ser
145            150                      155                      160

Tyr  Pro  Ala  Arg  Tyr  Ala  Asn  Ala  Met  Ala  Val  Gly  Ala  Thr  Asp  Gln
                    165                 170                      175

Asn  Asn  Asn  Arg  Ala  Ser  Phe  Ser  Gln  Tyr  Gly  Ala  Gly  Leu  Asp  Ile
               180                      185                      190

Val  Ala  Pro  Gly  Val  Asn  Val  Gln  Ser  Thr  Tyr  Pro  Val  Ser  Thr  Tyr
               195                 200                 205

Ala  Ser  Leu  Asn  Gly  Thr  Ser  Met  Ala  Thr  Pro  His  Val  Ala  Gly  Ala
     210                      215                      220

Ala  Ala  Leu  Val  Lys  Gln  Lys  Asn  Pro  Ser  Trp  Ser  Asn  Val  Gln  Ile
225                      230                      235                      240

Arg  Asn  His  Leu  Lys  Asn  Thr  Ala  Thr  Ser  Leu  Gly  Ser  Thr  Asn  Leu
                    245                      250                      255

Tyr  Gly  Ser  Gly  Leu  Val  Asn  Ala  Glu  Ala  Ala  Thr  Arg
               260                      265
```

(2) INFORMATION FOR SEQ ID NO:34:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: S130A (xi) SEQUENCE DESCRIPTION: SEQ ID NO:34:

```
Ala  Gln  Ser  Val  Pro  Trp  Gly  Ile  Ser  Arg  Val  Gln  Ala  Pro  Ala  Ala
1                   5                   10                       15

His  Asn  Arg  Gly  Leu  Thr  Gly  Ser  Gly  Val  Lys  Val  Ala  Val  Leu  Asp
               20                       25                       30

Thr  Gly  Ile  Ser  Thr  His  Pro  Asp  Leu  Asn  Ile  Arg  Gly  Gly  Ala  Ser
               35                  40                       45

Phe  Val  Pro  Gly  Glu  Pro  Ser  Thr  Gln  Asp  Gly  Asn  Gly  His  Gly  Thr
     50                       55                       60

His  Val  Ala  Gly  Thr  Ile  Ala  Ala  Leu  Asn  Asn  Ser  Ile  Gly  Val  Leu
65                       70                       75                       80

Gly  Val  Ala  Pro  Ser  Ala  Glu  Leu  Tyr  Ala  Val  Lys  Val  Leu  Gly  Ala
               85                       90                       95

Asp  Gly  Arg  Gly  Ala  Ile  Ser  Ser  Ile  Ala  Gln  Gly  Leu  Glu  Trp  Ala
               100                      105                      110

Gly  Asn  Asn  Gly  Met  His  Val  Ala  Asn  Leu  Ser  Leu  Gly  Ser  Pro  Ser
               115                      120                      125

Pro  Ala  Ala  Thr  Leu  Glu  Gln  Ala  Val  Asn  Ser  Ala  Thr  Ser  Arg  Gly
          130                      135                      140

Val  Leu  Val  Val  Ala  Ala  Ser  Gly  Asn  Ser  Gly  Ala  Ser  Ser  Ile  Ser
145                      150                      155                      160

Tyr  Pro  Ala  Arg  Tyr  Ala  Asn  Ala  Met  Ala  Val  Gly  Ala  Thr  Asp  Gln
                    165                 170                      175

Asn  Asn  Asn  Arg  Ala  Ser  Phe  Ser  Gln  Tyr  Gly  Ala  Gly  Leu  Asp  Ile
               180                      185                      190
```

```
Val  Ala  Pro  Gly  Val  Asn  Val  Gln  Ser  Thr  Tyr  Pro  Gly  Ser  Thr  Tyr
          195                      200                          205

Ala  Ser  Leu  Asn  Gly  Thr  Ser  Met  Ala  Thr  Pro  His  Val  Ala  Gly  Ala
     210                      215                     220

Ala  Ala  Leu  Val  Lys  Gln  Lys  Asn  Pro  Ser  Trp  Ser  Asn  Val  Gln  Ile
225                      230                     235                          240

Arg  Asn  His  Leu  Lys  Asn  Thr  Ala  Thr  Ser  Leu  Gly  Ser  Thr  Asn  Leu
               245                     250                          255

Tyr  Gly  Ser  Gly  Leu  Val  Asn  Ala  Glu  Ala  Ala  Thr  Arg
               260                      265
```

( 2 ) INFORMATION FOR SEQ ID NO:35:

( i ) SEQUENCE CHARACTERISTICS:
    ( A ) LENGTH: 269 amino acids
    ( B ) TYPE: amino acid
    ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
    ( A ) ORGANISM: Serine Protease
    ( B ) STRAIN: Bacillus lentus DSM 5843

( v i i ) IMMEDIATE SOURCE:
    ( B ) CLONE: S130T ( x i ) SEQUENCE DESCRIPTION: SEQ ID NO:35:

```
Ala  Gln  Ser  Val  Pro  Trp  Gly  Ile  Ser  Arg  Val  Gln  Ala  Pro  Ala  Ala
1                    5                        10                         15

His  Asn  Arg  Gly  Leu  Thr  Gly  Ser  Gly  Val  Lys  Val  Ala  Val  Leu  Asp
               20                      25                          30

Thr  Gly  Ile  Ser  Thr  His  Pro  Asp  Leu  Asn  Ile  Arg  Gly  Gly  Ala  Ser
               35                      40                          45

Phe  Val  Pro  Gly  Glu  Pro  Ser  Thr  Gln  Asp  Gly  Asn  Gly  His  Gly  Thr
     50                      55                          60

His  Val  Ala  Gly  Thr  Ile  Ala  Ala  Leu  Asn  Asn  Ser  Ile  Gly  Val  Leu
65                       70                      75                           80

Gly  Val  Ala  Pro  Ser  Ala  Glu  Leu  Tyr  Ala  Val  Lys  Val  Leu  Gly  Ala
               85                      90                          95

Asp  Gly  Arg  Gly  Ala  Ile  Ser  Ser  Ile  Ala  Gln  Gly  Leu  Glu  Trp  Ala
               100                     105                         110

Gly  Asn  Asn  Gly  Met  His  Val  Ala  Asn  Leu  Ser  Leu  Gly  Ser  Pro  Ser
               115                     120                         125

Pro  Thr  Ala  Thr  Leu  Glu  Gln  Ala  Val  Asn  Ser  Ala  Thr  Ser  Arg  Gly
     130                     135                          140

Val  Leu  Val  Val  Ala  Ala  Ser  Gly  Asn  Ser  Gly  Ala  Ser  Ser  Ile  Ser
145                      150                     155                          160

Tyr  Pro  Ala  Arg  Tyr  Ala  Asn  Ala  Met  Ala  Val  Gly  Ala  Thr  Asp  Gln
               165                     170                         175

Asn  Asn  Asn  Arg  Ala  Ser  Phe  Ser  Gln  Tyr  Gly  Ala  Gly  Leu  Asp  Ile
               180                     185                         190

Val  Ala  Pro  Gly  Val  Asn  Val  Gln  Ser  Thr  Tyr  Pro  Gly  Ser  Thr  Tyr
          195                      200                          205

Ala  Ser  Leu  Asn  Gly  Thr  Ser  Met  Ala  Thr  Pro  His  Val  Ala  Gly  Ala
     210                      215                     220

Ala  Ala  Leu  Val  Lys  Gln  Lys  Asn  Pro  Ser  Trp  Ser  Asn  Val  Gln  Ile
```

|     | 225 |     |     |     | 230 |     |     |     | 235 |     |     |     | 240 |
| --- | --- | --- | --- | --- | --- | --- | --- | --- | --- | --- | --- | --- | --- |
| Arg | Asn | His | Leu | Lys | Asn | Thr | Ala | Thr | Ser | Leu | Gly | Ser | Thr | Asn | Leu |
|     |     |     |     | 245 |     |     |     |     | 250 |     |     |     | 255 |
| Tyr | Gly | Ser | Gly | Leu | Val | Asn | Ala | Glu | Ala | Ala | Thr | Arg |
|     |     |     | 260 |     |     |     |     | 265 |

( 2 ) INFORMATION FOR SEQ ID NO:36:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: A96I ( x i ) SEQUENCE DESCRIPTION: SEQ ID NO:36:

| Ala | Gln | Ser | Val | Pro | Trp | Gly | Ile | Ser | Arg | Val | Gln | Ala | Pro | Ala | Ala |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| His | Asn | Arg | Gly | Leu | Thr | Gly | Ser | Gly | Val | Lys | Val | Ala | Val | Leu | Asp |
|     |     |     | 20  |     |     |     |     | 25  |     |     |     |     | 30  |
| Thr | Gly | Ile | Ser | Thr | His | Pro | Asp | Leu | Asn | Ile | Arg | Gly | Gly | Ala | Ser |
|     |     |     | 35  |     |     |     |     | 40  |     |     |     |     | 45  |
| Phe | Val | Pro | Gly | Glu | Pro | Ser | Thr | Gln | Asp | Gly | Asn | Gly | His | Gly | Thr |
|     | 50  |     |     |     |     | 55  |     |     |     |     | 60  |
| His | Val | Ala | Gly | Thr | Ile | Ala | Ala | Leu | Asn | Asn | Ser | Ile | Gly | Val | Leu |
| 65  |     |     |     |     | 70  |     |     |     |     | 75  |     |     |     |     | 80  |
| Gly | Val | Ala | Pro | Ser | Ala | Glu | Leu | Tyr | Ala | Val | Lys | Val | Leu | Gly | Ile |
|     |     |     |     | 85  |     |     |     |     | 90  |     |     |     |     | 95  |
| Asp | Gly | Arg | Gly | Ala | Ile | Ser | Ser | Ile | Ala | Gln | Gly | Leu | Glu | Trp | Ala |
|     |     |     | 100 |     |     |     |     | 105 |     |     |     |     | 110 |
| Gly | Asn | Asn | Gly | Met | His | Val | Ala | Asn | Leu | Ser | Leu | Gly | Ser | Pro | Ser |
|     |     |     | 115 |     |     |     |     | 120 |     |     |     |     | 125 |
| Pro | Ser | Ala | Thr | Leu | Glu | Gln | Ala | Val | Asn | Ser | Ala | Thr | Ser | Arg | Gly |
|     | 130 |     |     |     |     | 135 |     |     |     |     | 140 |
| Val | Leu | Val | Val | Ala | Ala | Ser | Gly | Asn | Ser | Gly | Ala | Ser | Ser | Ile | Ser |
| 145 |     |     |     |     | 150 |     |     |     |     | 155 |     |     |     |     | 160 |
| Tyr | Pro | Ala | Arg | Tyr | Ala | Asn | Ala | Met | Ala | Val | Gly | Ala | Thr | Asp | Gln |
|     |     |     |     | 165 |     |     |     |     | 170 |     |     |     |     | 175 |
| Asn | Asn | Asn | Arg | Ala | Ser | Phe | Ser | Gln | Tyr | Gly | Ala | Gly | Leu | Asp | Ile |
|     |     |     | 180 |     |     |     |     | 185 |     |     |     |     | 190 |
| Val | Ala | Pro | Gly | Val | Asn | Val | Gln | Ser | Thr | Tyr | Pro | Gly | Ser | Thr | Tyr |
|     |     |     | 195 |     |     |     |     | 200 |     |     |     |     | 205 |
| Ala | Ser | Leu | Asn | Gly | Thr | Ser | Met | Ala | Thr | Pro | His | Val | Ala | Gly | Ala |
|     | 210 |     |     |     |     | 215 |     |     |     |     | 220 |
| Ala | Ala | Leu | Val | Lys | Gln | Lys | Asn | Pro | Ser | Trp | Ser | Asn | Val | Gln | Ile |
| 225 |     |     |     |     | 230 |     |     |     |     | 235 |     |     |     |     | 240 |
| Arg | Asn | His | Leu | Lys | Asn | Thr | Ala | Thr | Ser | Leu | Gly | Ser | Thr | Asn | Leu |
|     |     |     |     | 245 |     |     |     |     | 250 |     |     |     |     | 255 |
| Tyr | Gly | Ser | Gly | Leu | Val | Asn | Ala | Glu | Ala | Ala | Thr | Arg |
|     |     |     | 260 |     |     |     |     | 265 |

( 2 ) INFORMATION FOR SEQ ID NO:37:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: S104T, S139Y, A224V ( x i ) SEQUENCE DESCRIPTION: SEQ ID NO:37:

```
Ala Gln Ser Val Pro Trp Gly Ile Ser Arg Val Gln Ala Pro Ala Ala
 1               5                  10                  15
His Asn Arg Gly Leu Thr Gly Ser Gly Val Lys Val Ala Val Leu Asp
            20                  25                  30
Thr Gly Ile Ser Thr His Pro Asp Leu Asn Ile Arg Gly Gly Ala Ser
        35                  40                  45
Phe Val Pro Gly Glu Pro Ser Thr Gln Asp Gly Asn Gly His Gly Thr
50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Asp Gly Arg Gly Ala Ile Ser Thr Ile Ala Gln Gly Leu Glu Trp Ala
            100                 105                 110
Gly Asn Asn Gly Met His Val Ala Asn Leu Ser Leu Gly Ser Pro Ser
        115                 120                 125
Pro Ser Ala Thr Leu Glu Gln Ala Val Asn Tyr Ala Thr Ser Arg Gly
130                 135                 140
Val Leu Val Val Ala Ala Ser Gly Asn Ser Gly Ala Ser Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Val
210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265
```

( 2 ) INFORMATION FOR SEQ ID NO:38:

( i ) SEQUENCE CHARACTERISTICS:
        ( A ) LENGTH: 269 amino acids
        ( B ) TYPE: amino acid
        ( D ) TOPOLOGY: unknown (ii) MOLECULE TYPE: protein (iii) HYPOTHETICAL: NO (iv) ANTI-SENSE: NO (vi) ORIGINAL SOURCE:
    (A) ORGANISM: Serine Protease
    (B) STRAIN: Bacillus lentus DSM 5843

(vii) IMMEDIATE SOURCE:
    (B) CLONE: S139A (xi) SEQUENCE DESCRIPTION: SEQ ID NO:38:

| | | | | | | | | | | | | | | |
|---|---|---|---|---|---|---|---|---|---|---|---|---|---|---|
| Ala | Gln | Ser | Val | Pro | Trp | Gly | Ile | Ser | Arg | Val | Gln | Ala | Pro | Ala | Ala |
| 1 | | | | 5 | | | | | 10 | | | | | 15 |
| His | Asn | Arg | Gly | Leu | Thr | Gly | Ser | Gly | Val | Lys | Val | Ala | Val | Leu | Asp |
| | | | 20 | | | | | 25 | | | | | 30 | |
| Thr | Gly | Ile | Ser | Thr | His | Pro | Asp | Leu | Asn | Ile | Arg | Gly | Gly | Ala | Ser |
| | | 35 | | | | | 40 | | | | | 45 | | |
| Phe | Val | Pro | Gly | Glu | Pro | Ser | Thr | Gln | Asp | Gly | Asn | Gly | His | Gly | Thr |
| | 50 | | | | | 55 | | | | | 60 | | | | |
| His | Val | Ala | Gly | Thr | Ile | Ala | Ala | Leu | Asn | Asn | Ser | Ile | Gly | Val | Leu |
| 65 | | | | | 70 | | | | | 75 | | | | | 80 |
| Gly | Val | Ala | Pro | Ser | Ala | Glu | Leu | Tyr | Ala | Val | Lys | Val | Leu | Gly | Ala |
| | | | | 85 | | | | | 90 | | | | | 95 | |
| Asp | Gly | Arg | Gly | Ala | Ile | Ser | Ser | Ile | Ala | Gln | Gly | Leu | Glu | Trp | Ala |
| | | | | 100 | | | | | 105 | | | | | 110 | |
| Gly | Asn | Asn | Gly | Met | His | Val | Ala | Asn | Leu | Ser | Leu | Gly | Ser | Pro | Ser |
| | | | 115 | | | | | 120 | | | | | 125 | | |
| Pro | Ser | Ala | Thr | Leu | Glu | Gln | Ala | Val | Asn | Ala | Ala | Thr | Ser | Arg | Gly |
| | | | 130 | | | | | 135 | | | | | 140 | | |
| Val | Leu | Val | Val | Ala | Ala | Ser | Gly | Asn | Ser | Gly | Ala | Ser | Ser | Ile | Ser |
| 145 | | | | | 150 | | | | | 155 | | | | | 160 |
| Tyr | Pro | Ala | Arg | Tyr | Ala | Asn | Ala | Met | Ala | Val | Gly | Ala | Thr | Asp | Gln |
| | | | | 165 | | | | | 170 | | | | | 175 | |
| Asn | Asn | Asn | Arg | Ala | Ser | Phe | Ser | Gln | Tyr | Gly | Ala | Gly | Leu | Asp | Ile |
| | | | 180 | | | | | 185 | | | | | 190 | | |
| Val | Ala | Pro | Gly | Val | Asn | Val | Gln | Ser | Thr | Tyr | Pro | Gly | Ser | Thr | Tyr |
| | | 195 | | | | | 200 | | | | | 205 | | | |
| Ala | Ser | Leu | Asn | Gly | Thr | Ser | Met | Ala | Thr | Pro | His | Val | Ala | Gly | Ala |
| | 210 | | | | | 215 | | | | | 220 | | | | |
| Ala | Ala | Leu | Val | Lys | Gln | Lys | Asn | Pro | Ser | Trp | Ser | Asn | Val | Gln | Ile |
| 225 | | | | | 230 | | | | | 235 | | | | | 240 |
| Arg | Asn | His | Leu | Lys | Asn | Thr | Ala | Thr | Ser | Leu | Gly | Ser | Thr | Asn | Leu |
| | | | | 245 | | | | | 250 | | | | | 255 | |
| Tyr | Gly | Ser | Gly | Leu | Val | Asn | Ala | Glu | Ala | Ala | Thr | Arg | | | |
| | | | 260 | | | | | 265 | | | | | | | |

(2) INFORMATION FOR SEQ ID NO:39:

(i) SEQUENCE CHARACTERISTICS:
    (A) LENGTH: 269 amino acids
    (B) TYPE: amino acid
    (D) TOPOLOGY: unknown (ii) MOLECULE TYPE: protein (iii) HYPOTHETICAL: NO (iv) ANTI-SENSE: NO (vi) ORIGINAL SOURCE:
    (A) ORGANISM: Serine Protease ( B ) STRAIN: Bacillus lentus DSM 5843

( v i i ) IMMEDIATE SOURCE:
  ( B ) CLONE: S142T ( x i ) SEQUENCE DESCRIPTION: SEQ ID NO:39:

| | | | | | | | | | | | | | | |
|---|---|---|---|---|---|---|---|---|---|---|---|---|---|---|
| Ala 1 | Gln | Ser | Val | Pro 5 | Trp | Gly | Ile | Ser | Arg 10 | Val | Gln | Ala | Pro | Ala 15 |
| His | Asn | Arg | Gly 20 | Leu | Thr | Gly | Ser | Gly 25 | Val | Lys | Val | Ala | Val 30 | Leu | Asp |
| Thr | Gly | Ile 35 | Ser | Thr | His | Pro | Asp 40 | Leu | Asn | Ile | Arg | Gly 45 | Gly | Ala | Ser |
| Phe | Val 50 | Pro | Gly | Glu | Pro | Ser 55 | Thr | Gln | Asp | Gly | Asn 60 | Gly | His | Gly | Thr |
| His 65 | Val | Ala | Gly | Thr | Ile 70 | Ala | Ala | Leu | Asn | Asn 75 | Ser | Ile | Gly | Val | Leu 80 |
| Gly | Val | Ala | Pro | Ser 85 | Ala | Glu | Leu | Tyr | Ala 90 | Val | Lys | Val | Leu | Gly 95 | Ala |
| Asp | Gly | Arg | Gly 100 | Ala | Ile | Ser | Ser | Ile 105 | Ala | Gln | Gly | Leu | Glu 110 | Trp | Ala |
| Gly | Asn | Asn 115 | Gly | Met | His | Val | Ala 120 | Asn | Leu | Ser | Leu | Gly 125 | Ser | Pro | Ser |
| Pro | Ser 130 | Ala | Thr | Leu | Glu | Gln 135 | Ala | Val | Asn | Ser | Ala 140 | Thr | Thr | Arg | Gly |
| Val 145 | Leu | Val | Val | Ala | Ala 150 | Ser | Gly | Asn | Ser | Gly 155 | Ala | Ser | Ser | Ile | Ser 160 |
| Tyr | Pro | Ala | Arg | Tyr 165 | Ala | Asn | Ala | Met | Ala 170 | Val | Gly | Ala | Thr | Asp 175 | Gln |
| Asn | Asn | Asn | Arg 180 | Ala | Ser | Phe | Ser | Gln 185 | Tyr | Gly | Ala | Gly | Leu 190 | Asp | Ile |
| Val | Ala | Pro 195 | Gly | Val | Asn | Val | Gln 200 | Ser | Thr | Tyr | Pro | Gly 205 | Ser | Thr | Tyr |
| Ala | Ser 210 | Leu | Asn | Gly | Thr | Ser 215 | Met | Ala | Thr | Pro | His 220 | Val | Ala | Gly | Ala |
| Ala 225 | Ala | Leu | Val | Lys | Gln 230 | Lys | Asn | Pro | Ser | Trp 235 | Ser | Asn | Val | Gln | Ile 240 |
| Arg | Asn | His | Leu | Lys 245 | Asn | Thr | Ala | Thr | Ser 250 | Leu | Gly | Ser | Thr | Asn 255 | Leu |
| Tyr | Gly | Ser | Gly 260 | Leu | Val | Asn | Ala | Glu 265 | Ala | Ala | Thr | Arg | | | |

( 2 ) INFORMATION FOR SEQ ID NO:40:

( i ) SEQUENCE CHARACTERISTICS:
  ( A ) LENGTH: 269 amino acids
  ( B ) TYPE: amino acid
  ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
  ( A ) ORGANISM: Serine Protease
  ( B ) STRAIN: Bacillus lentus DSM 5843

( v i i ) IMMEDIATE SOURCE:
  ( B ) CLONE: S139T ( x i ) SEQUENCE DESCRIPTION: SEQ ID NO:40:

Ala Gln Ser Val Pro Trp Gly Ile Ser Arg Val Gln Ala Pro Ala Ala

|   | 1 |   |   | 5 |   |   |   |   | 10 |   |   |   |   | 15 |
|---|---|---|---|---|---|---|---|---|---|---|---|---|---|---|
|   | His | Asn | Arg | Gly | Leu | Thr | Gly | Ser | Gly | Val | Lys | Val | Ala | Val | Leu | Asp |
|   |     |     |     | 20  |     |     |     |     | 25  |     |     |     |     | 30  |     |     |
|   | Thr | Gly | Ile | Ser | Thr | His | Pro | Asp | Leu | Asn | Ile | Arg | Gly | Gly | Ala | Ser |
|   |     |     |     | 35  |     |     |     |     | 40  |     |     |     |     | 45  |     |     |
|   | Phe | Val | Pro | Gly | Glu | Pro | Ser | Thr | Gln | Asp | Gly | Asn | Gly | His | Gly | Thr |
|   |     |     |     | 50  |     |     |     |     | 55  |     |     |     |     | 60  |     |     |
|   | His | Val | Ala | Gly | Thr | Ile | Ala | Ala | Leu | Asn | Asn | Ser | Ile | Gly | Val | Leu |
|   | 65  |     |     |     |     | 70  |     |     |     |     | 75  |     |     |     |     | 80  |
|   | Gly | Val | Ala | Pro | Ser | Ala | Glu | Leu | Tyr | Ala | Val | Lys | Val | Leu | Gly | Ala |
|   |     |     |     |     | 85  |     |     |     |     | 90  |     |     |     |     | 95  |     |
|   | Asp | Gly | Arg | Gly | Ala | Ile | Ser | Ser | Ile | Ala | Gln | Gly | Leu | Glu | Trp | Ala |
|   |     |     |     | 100 |     |     |     |     | 105 |     |     |     |     | 110 |     |     |
|   | Gly | Asn | Asn | Gly | Met | His | Val | Ala | Asn | Leu | Ser | Leu | Gly | Ser | Pro | Ser |
|   |     |     |     | 115 |     |     |     |     | 120 |     |     |     |     | 125 |     |     |
|   | Pro | Ser | Ala | Thr | Leu | Glu | Gln | Ala | Val | Asn | Thr | Ala | Thr | Ser | Arg | Gly |
|   |     |     |     | 130 |     |     |     |     | 135 |     |     |     |     | 140 |     |     |
|   | Val | Leu | Val | Val | Ala | Ala | Ser | Gly | Asn | Ser | Gly | Ala | Ser | Ser | Ile | Ser |
|   | 145 |     |     |     |     | 150 |     |     |     |     | 155 |     |     |     |     | 160 |
|   | Tyr | Pro | Ala | Arg | Tyr | Ala | Asn | Ala | Met | Ala | Val | Gly | Ala | Thr | Asp | Gln |
|   |     |     |     |     | 165 |     |     |     |     | 170 |     |     |     |     | 175 |     |
|   | Asn | Asn | Asn | Arg | Ala | Ser | Phe | Ser | Gln | Tyr | Gly | Ala | Gly | Leu | Asp | Ile |
|   |     |     |     |     | 180 |     |     |     |     | 185 |     |     |     |     | 190 |     |
|   | Val | Ala | Pro | Gly | Val | Asn | Val | Gln | Ser | Thr | Tyr | Pro | Gly | Ser | Thr | Tyr |
|   |     |     |     |     | 195 |     |     |     |     | 200 |     |     |     |     | 205 |     |
|   | Ala | Ser | Leu | Asn | Gly | Thr | Ser | Met | Ala | Thr | Pro | His | Val | Ala | Gly | Ala |
|   |     |     |     |     | 210 |     |     |     |     | 215 |     |     |     |     | 220 |     |
|   | Ala | Ala | Leu | Val | Lys | Gln | Lys | Asn | Pro | Ser | Trp | Ser | Asn | Val | Gln | Ile |
|   | 225 |     |     |     |     | 230 |     |     |     |     | 235 |     |     |     |     | 240 |
|   | Arg | Asn | His | Leu | Lys | Asn | Thr | Ala | Thr | Ser | Leu | Gly | Ser | Thr | Asn | Leu |
|   |     |     |     |     | 245 |     |     |     |     | 250 |     |     |     |     | 255 |     |
|   | Tyr | Gly | Ser | Gly | Leu | Val | Asn | Ala | Glu | Ala | Ala | Thr | Arg |     |     |     |
|   |     |     |     | 260 |     |     |     |     | 265 |     |     |     |     |     |     |     |

( 2 ) INFORMATION FOR SEQ ID NO:41:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: I102W ( x i ) SEQUENCE DESCRIPTION: SEQ ID NO:41:

|   | Ala | Gln | Ser | Val | Pro | Trp | Gly | Ile | Ser | Arg | Val | Gln | Ala | Pro | Ala | Ala |
|---|-----|-----|-----|-----|-----|-----|-----|-----|-----|-----|-----|-----|-----|-----|-----|-----|
|   | 1   |     |     |     | 5   |     |     |     |     | 10  |     |     |     |     | 15  |     |
|   | His | Asn | Arg | Gly | Leu | Thr | Gly | Ser | Gly | Val | Lys | Val | Ala | Val | Leu | Asp |
|   |     |     |     | 20  |     |     |     |     | 25  |     |     |     |     | 30  |     |     |
|   | Thr | Gly | Ile | Ser | Thr | His | Pro | Asp | Leu | Asn | Ile | Arg | Gly | Gly | Ala | Ser |
|   |     |     |     | 35  |     |     |     |     | 40  |     |     |     |     | 45  |     |     |

```
Phe  Val  Pro  Gly  Glu  Pro  Ser  Thr  Gln  Asp  Gly  Asn  Gly  His  Gly  Thr
 50                  55                       60

His  Val  Ala  Gly  Thr  Ile  Ala  Ala  Leu  Asn  Asn  Ser  Ile  Gly  Val  Leu
 65                  70                       75                            80

Gly  Val  Ala  Pro  Ser  Ala  Glu  Leu  Tyr  Ala  Val  Lys  Val  Leu  Gly  Ala
                 85                      90                            95

Asp  Gly  Arg  Gly  Ala  Trp  Ser  Ser  Ile  Ala  Gln  Gly  Leu  Glu  Trp  Ala
                100                     105                      110

Gly  Asn  Asn  Gly  Met  His  Val  Ala  Asn  Leu  Ser  Leu  Gly  Ser  Pro  Ser
           115                      120                      125

Pro  Ser  Ala  Thr  Leu  Glu  Gln  Ala  Val  Asn  Ser  Ala  Thr  Ser  Arg  Gly
     130                      135                      140

Val  Leu  Val  Val  Ala  Ala  Ser  Gly  Asn  Ser  Gly  Ala  Ser  Ser  Ile  Ser
 145                      150                      155                      160

Tyr  Pro  Ala  Arg  Tyr  Ala  Asn  Ala  Met  Ala  Val  Gly  Ala  Thr  Asp  Gln
                165                      170                      175

Asn  Asn  Asn  Arg  Ala  Ser  Phe  Ser  Gln  Tyr  Gly  Ala  Gly  Leu  Asp  Ile
                180                      185                      190

Val  Ala  Pro  Gly  Val  Asn  Val  Gln  Ser  Thr  Tyr  Pro  Gly  Ser  Thr  Tyr
                195                      200                      205

Ala  Ser  Leu  Asn  Gly  Thr  Ser  Met  Ala  Thr  Pro  His  Val  Ala  Gly  Ala
     210                      215                      220

Ala  Ala  Leu  Val  Lys  Gln  Lys  Asn  Pro  Ser  Trp  Ser  Asn  Val  Gln  Ile
 225                      230                      235                      240

Arg  Asn  His  Leu  Lys  Asn  Thr  Ala  Thr  Ser  Leu  Gly  Ser  Thr  Asn  Leu
                245                      250                      255

Tyr  Gly  Ser  Gly  Leu  Val  Asn  Ala  Glu  Ala  Ala  Thr  Arg
                260                      265
```

( 2 ) INFORMATION FOR SEQ ID NO:42:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: A96N ( x i ) SEQUENCE DESCRIPTION: SEQ ID NO:42:

```
Ala  Gln  Ser  Val  Pro  Trp  Gly  Ile  Ser  Arg  Val  Gln  Ala  Pro  Ala  Ala
 1                   5                       10                       15

His  Asn  Arg  Gly  Leu  Thr  Gly  Ser  Gly  Val  Lys  Val  Ala  Val  Leu  Asp
            20                       25                       30

Thr  Gly  Ile  Ser  Thr  His  Pro  Asp  Leu  Asn  Ile  Arg  Gly  Gly  Ala  Ser
            35                       40                       45

Phe  Val  Pro  Gly  Glu  Pro  Ser  Thr  Gln  Asp  Gly  Asn  Gly  His  Gly  Thr
 50                  55                       60

His  Val  Ala  Gly  Thr  Ile  Ala  Ala  Leu  Asn  Asn  Ser  Ile  Gly  Val  Leu
 65                  70                       75                            80

Gly  Val  Ala  Pro  Ser  Ala  Glu  Leu  Tyr  Ala  Val  Lys  Val  Leu  Gly  Asn
                 85                      90                            95
```

```
Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
        260                 265
```

( 2 ) INFORMATION FOR SEQ ID NO:43:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: N42F ( x i ) SEQUENCE DESCRIPTION: SEQ ID NO:43:

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Phe Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
            85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140
```

|  |  |  |  |  |  |  |  |  |  |  |  |  |  |  |
|---|---|---|---|---|---|---|---|---|---|---|---|---|---|---|
|  |  | 130 |  |  |  | 135 |  |  |  | 140 |  |  |  |  |
| Val | Leu | Val | Val | Ala | Ala | Ser | Gly | Asn | Ser | Gly | Ala | Ser | Ser | Ile | Ser |
| 145 |  |  |  |  | 150 |  |  |  |  | 155 |  |  |  |  | 160 |
| Tyr | Pro | Ala | Arg | Tyr | Ala | Asn | Ala | Met | Ala | Val | Gly | Ala | Thr | Asp | Gln |
|  |  |  |  | 165 |  |  |  |  | 170 |  |  |  |  | 175 |  |
| Asn | Asn | Asn | Arg | Ala | Ser | Phe | Ser | Gln | Tyr | Gly | Ala | Gly | Leu | Asp | Ile |
|  |  |  | 180 |  |  |  |  | 185 |  |  |  |  | 190 |  |  |
| Val | Ala | Pro | Gly | Val | Asn | Val | Gln | Ser | Thr | Tyr | Pro | Gly | Ser | Thr | Tyr |
|  |  | 195 |  |  |  |  | 200 |  |  |  |  | 205 |  |  |  |
| Ala | Ser | Leu | Asn | Gly | Thr | Ser | Met | Ala | Thr | Pro | His | Val | Ala | Gly | Ala |
|  | 210 |  |  |  |  | 215 |  |  |  |  | 220 |  |  |  |  |
| Ala | Ala | Leu | Val | Lys | Gln | Lys | Asn | Pro | Ser | Trp | Ser | Asn | Val | Gln | Ile |
| 225 |  |  |  |  | 230 |  |  |  |  | 235 |  |  |  |  | 240 |
| Arg | Asn | His | Leu | Lys | Asn | Thr | Ala | Thr | Ser | Leu | Gly | Ser | Thr | Asn | Leu |
|  |  |  |  | 245 |  |  |  |  | 250 |  |  |  |  | 255 |  |
| Tyr | Gly | Ser | Gly | Leu | Val | Asn | Ala | Glu | Ala | Ala | Thr | Arg |  |  |  |
|  |  |  | 260 |  |  |  |  | 265 |  |  |  |  |  |  |  |

( 2 ) INFORMATION FOR SEQ ID NO:44:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: S142A ( x i ) SEQUENCE DESCRIPTION: SEQ ID NO:44:

|  |  |  |  |  |  |  |  |  |  |  |  |  |  |  |  |
|---|---|---|---|---|---|---|---|---|---|---|---|---|---|---|---|
| Ala | Gln | Ser | Val | Pro | Trp | Gly | Ile | Ser | Arg | Val | Gln | Ala | Pro | Ala | Ala |
| 1 |  |  |  | 5 |  |  |  |  | 10 |  |  |  |  | 15 |  |
| His | Asn | Arg | Gly | Leu | Thr | Gly | Ser | Gly | Val | Lys | Val | Ala | Val | Leu | Asp |
|  |  |  | 20 |  |  |  |  | 25 |  |  |  |  | 30 |  |  |
| Thr | Gly | Ile | Ser | Thr | His | Pro | Asp | Leu | Asn | Ile | Arg | Gly | Gly | Ala | Ser |
|  |  |  | 35 |  |  |  | 40 |  |  |  |  | 45 |  |  |  |
| Phe | Val | Pro | Gly | Glu | Pro | Ser | Thr | Gln | Asp | Gly | Asn | Gly | His | Gly | Thr |
|  | 50 |  |  |  |  | 55 |  |  |  |  | 60 |  |  |  |  |
| His | Val | Ala | Gly | Thr | Ile | Ala | Ala | Leu | Asn | Asn | Ser | Ile | Gly | Val | Leu |
| 65 |  |  |  |  | 70 |  |  |  |  | 75 |  |  |  |  | 80 |
| Gly | Val | Ala | Pro | Ser | Ala | Glu | Leu | Tyr | Ala | Val | Lys | Val | Leu | Gly | Ala |
|  |  |  |  | 85 |  |  |  |  | 90 |  |  |  |  | 95 |  |
| Asp | Gly | Arg | Gly | Ala | Ile | Ser | Ser | Ile | Ala | Gln | Gly | Leu | Glu | Trp | Ala |
|  |  |  | 100 |  |  |  |  | 105 |  |  |  |  | 110 |  |  |
| Gly | Asn | Asn | Gly | Met | His | Val | Ala | Asn | Leu | Ser | Leu | Gly | Ser | Pro | Ser |
|  |  |  | 115 |  |  |  |  | 120 |  |  |  |  | 125 |  |  |
| Pro | Ser | Ala | Thr | Leu | Glu | Gln | Ala | Val | Asn | Ser | Ala | Thr | Ala | Arg | Gly |
|  | 130 |  |  |  |  | 135 |  |  |  |  | 140 |  |  |  |  |
| Val | Leu | Val | Val | Ala | Ala | Ser | Gly | Asn | Ser | Gly | Ala | Ser | Ser | Ile | Ser |
| 145 |  |  |  |  | 150 |  |  |  |  | 155 |  |  |  |  | 160 |
| Tyr | Pro | Ala | Arg | Tyr | Ala | Asn | Ala | Met | Ala | Val | Gly | Ala | Thr | Asp | Gln |
|  |  |  |  | 165 |  |  |  |  | 170 |  |  |  |  | 175 |  |

-continued

```
Asn  Asn  Asn  Arg  Ala  Ser  Phe  Ser  Gln  Tyr  Gly  Ala  Gly  Leu  Asp  Ile
              180                      185                      190

Val  Ala  Pro  Gly  Val  Asn  Val  Gln  Ser  Thr  Tyr  Pro  Gly  Ser  Thr  Tyr
         195                      200                     205

Ala  Ser  Leu  Asn  Gly  Thr  Ser  Met  Ala  Thr  Pro  His  Val  Ala  Gly  Ala
    210                        215                     220

Ala  Ala  Leu  Val  Lys  Gln  Lys  Asn  Pro  Ser  Trp  Ser  Asn  Val  Gln  Ile
225                      230                     235                          240

Arg  Asn  His  Leu  Lys  Asn  Thr  Ala  Thr  Ser  Leu  Gly  Ser  Thr  Asn  Leu
              245                      250                      255

Tyr  Gly  Ser  Gly  Leu  Val  Asn  Ala  Glu  Ala  Ala  Thr  Arg
              260                      265
```

(2) INFORMATION FOR SEQ ID NO:45:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (vi) ORIGINAL SOURCE:
        (A) ORGANISM: Serine Protease
        (B) STRAIN: Bacillus lentus DSM 5843

(vii) IMMEDIATE SOURCE:
        (B) CLONE: H118F (xi) SEQUENCE DESCRIPTION: SEQ ID NO:45:

```
Ala  Gln  Ser  Val  Pro  Trp  Gly  Ile  Ser  Arg  Val  Gln  Ala  Pro  Ala  Ala
1                   5                       10                      15

His  Asn  Arg  Gly  Leu  Thr  Gly  Ser  Gly  Val  Lys  Val  Ala  Val  Leu  Asp
              20                      25                      30

Thr  Gly  Ile  Ser  Thr  His  Pro  Asp  Leu  Asn  Ile  Arg  Gly  Gly  Ala  Ser
              35                      40                      45

Phe  Val  Pro  Gly  Glu  Pro  Ser  Thr  Gln  Asp  Gly  Asn  Gly  His  Gly  Thr
    50                       55                      60

His  Val  Ala  Gly  Thr  Ile  Ala  Ala  Leu  Asn  Asn  Ser  Ile  Gly  Val  Leu
65                       70                      75                           80

Gly  Val  Ala  Pro  Ser  Ala  Glu  Leu  Tyr  Ala  Val  Lys  Val  Leu  Gly  Ala
              85                      90                      95

Asp  Gly  Arg  Gly  Ala  Ile  Ser  Ser  Ile  Ala  Gln  Gly  Leu  Glu  Trp  Ala
              100                     105                     110

Gly  Asn  Asn  Gly  Met  Phe  Val  Ala  Asn  Leu  Ser  Leu  Gly  Ser  Pro  Ser
              115                     120                     125

Pro  Ser  Ala  Thr  Leu  Glu  Gln  Ala  Val  Asn  Ser  Ala  Thr  Ser  Arg  Gly
    130                      135                     140

Val  Leu  Val  Val  Ala  Ala  Ser  Gly  Asn  Ser  Gly  Ala  Ser  Ser  Ile  Ser
145                      150                     155                          160

Tyr  Pro  Ala  Arg  Tyr  Ala  Asn  Ala  Met  Ala  Val  Gly  Ala  Thr  Asp  Gln
              165                     170                     175

Asn  Asn  Asn  Arg  Ala  Ser  Phe  Ser  Gln  Tyr  Gly  Ala  Gly  Leu  Asp  Ile
              180                     185                     190

Val  Ala  Pro  Gly  Val  Asn  Val  Gln  Ser  Thr  Tyr  Pro  Gly  Ser  Thr  Tyr
         195                      200                     205

Ala  Ser  Leu  Asn  Gly  Thr  Ser  Met  Ala  Thr  Pro  His  Val  Ala  Gly  Ala
    210                       215                     220
```

```
         Ala   Ala   Leu   Val   Lys   Gln   Lys   Asn   Pro   Ser   Trp   Ser   Asn   Val   Gln   Ile
         225               230                                 235                           240

Arg   Asn   His   Leu   Lys   Asn   Thr   Ala   Thr   Ser   Leu   Gly   Ser   Thr   Asn   Leu
                                 245                     250                           255

Tyr   Gly   Ser   Gly   Leu   Val   Asn   Ala   Glu   Ala   Ala   Thr   Arg
                           260                     265
```

( 2 ) INFORMATION FOR SEQ ID NO:46:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: N237A ( x i ) SEQUENCE DESCRIPTION: SEQ ID NO:46:

```
         Ala   Gln   Ser   Val   Pro   Trp   Gly   Ile   Ser   Arg   Val   Gln   Ala   Pro   Ala   Ala
         1                       5                             10                          15

His   Asn   Arg   Gly   Leu   Thr   Gly   Ser   Gly   Val   Lys   Val   Ala   Val   Leu   Asp
                           20                            25                          30

Thr   Gly   Ile   Ser   Thr   His   Pro   Asp   Leu   Asn   Ile   Arg   Gly   Gly   Ala   Ser
                                 35                      40                          45

Phe   Val   Pro   Gly   Glu   Pro   Ser   Thr   Gln   Asp   Gly   Asn   Gly   His   Gly   Thr
                     50                            55                            60

His   Val   Ala   Gly   Thr   Ile   Ala   Ala   Leu   Asn   Asn   Ser   Ile   Gly   Val   Leu
         65                            70                            75                          80

Gly   Val   Ala   Pro   Ser   Ala   Glu   Leu   Tyr   Ala   Val   Lys   Val   Leu   Gly   Ala
                                 85                            90                          95

Asp   Gly   Arg   Gly   Ala   Ile   Ser   Ser   Ile   Ala   Gln   Gly   Leu   Glu   Trp   Ala
                           100                           105                         110

Gly   Asn   Asn   Gly   Met   His   Val   Ala   Asn   Leu   Ser   Leu   Gly   Ser   Pro   Ser
                           115                           120                         125

Pro   Ser   Ala   Thr   Leu   Glu   Gln   Ala   Val   Asn   Ser   Ala   Thr   Ser   Arg   Gly
                     130                           135                         140

Val   Leu   Val   Val   Ala   Ala   Ser   Gly   Asn   Ser   Gly   Ala   Ser   Ser   Ile   Ser
         145                           150                           155                         160

Tyr   Pro   Ala   Arg   Tyr   Ala   Asn   Ala   Met   Ala   Val   Gly   Ala   Thr   Asp   Gln
                           165                                 170                         175

Asn   Asn   Asn   Arg   Ala   Ser   Phe   Ser   Gln   Tyr   Gly   Ala   Gly   Leu   Asp   Ile
                           180                           185                         190

Val   Ala   Pro   Gly   Val   Asn   Val   Gln   Ser   Thr   Tyr   Pro   Gly   Ser   Thr   Tyr
                     195                           200                         205

Ala   Ser   Leu   Asn   Gly   Thr   Ser   Met   Ala   Thr   Pro   His   Val   Ala   Gly   Ala
                     210                           215                         220

Ala   Ala   Leu   Val   Lys   Gln   Lys   Asn   Pro   Ser   Trp   Ser   Ala   Val   Gln   Ile
         225                           230                           235                         240

Arg   Asn   His   Leu   Lys   Asn   Thr   Ala   Thr   Ser   Leu   Gly   Ser   Thr   Asn   Leu
                                 245                           250                         255

Tyr   Gly   Ser   Gly   Leu   Val   Asn   Ala   Glu   Ala   Ala   Thr   Arg
```

(2) INFORMATION FOR SEQ ID NO:47:

(i) SEQUENCE CHARACTERISTICS:
        (A) LENGTH: 269 amino acids
        (B) TYPE: amino acid
        (D) TOPOLOGY: unknown (ii) MOLECULE TYPE: protein (iii) HYPOTHETICAL: NO (iv) ANTI-SENSE: NO (v) ORIGINAL SOURCE:
        (A) ORGANISM: Serine Protease
        (B) STRAIN: Bacillus lentus DSM 5843

(vii) IMMEDIATE SOURCE:
        (B) CLONE: N255P (xi) SEQUENCE DESCRIPTION: SEQ ID NO:47:

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Pro Leu
                245                 250                 255

Tyr Gly Ser Gly Leu Val Asn Ala Glu Ala Ala Thr Arg
            260                 265
```

(2) INFORMATION FOR SEQ ID NO:48:

(i) SEQUENCE CHARACTERISTICS:
        (A) LENGTH: 269 amino acids
        (B) TYPE: amino acid (D) TOPOLOGY: unknown (ii) MOLECULE TYPE: protein (iii) HYPOTHETICAL: NO (iv) ANTI-SENSE: NO (vi) ORIGINAL SOURCE:
(A) ORGANISM: Serine Protease
(B) STRAIN: Bacillus lentus DSM 5843

(vii) IMMEDIATE SOURCE:
(B) CLONE: T141W, N237A (xi) SEQUENCE DESCRIPTION: SEQ ID NO:48:

```
Ala Gln Ser Val Pro Trp Gly Ile Ser Arg Val Gln Ala Pro Ala Ala
 1               5                  10                  15
His Asn Arg Gly Leu Thr Gly Ser Gly Val Lys Val Ala Val Leu Asp
            20                  25                  30
Thr Gly Ile Ser Thr His Pro Asp Leu Asn Ile Arg Gly Gly Ala Ser
            35                  40                  45
Phe Val Pro Gly Glu Pro Ser Thr Gln Asp Gly Asn Gly His Gly Thr
    50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Asp Gly Arg Gly Ala Ile Ser Ser Ile Ala Gln Gly Leu Glu Trp Ala
            100                 105                 110
Gly Asn Asn Gly Met His Val Ala Asn Leu Ser Leu Gly Ser Pro Ser
            115                 120                 125
Pro Ser Ala Thr Leu Glu Gln Ala Val Asn Ser Ala Trp Ser Arg Gly
    130                 135                 140
Val Leu Val Val Ala Ala Ser Gly Asn Ser Gly Ala Ser Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Ala
    210                 215                 220
Ala Ala Leu Val Lys Gln Lys Asn Pro Ser Trp Ser Ala Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265
```

(2) INFORMATION FOR SEQ ID NO:49:

(i) SEQUENCE CHARACTERISTICS:
(A) LENGTH: 269 amino acids
(B) TYPE: amino acid
(D) TOPOLOGY: unknown (ii) MOLECULE TYPE: protein (iii) HYPOTHETICAL: NO (iv) ANTI-SENSE: NO (vi) ORIGINAL SOURCE:
 (A) ORGANISM: Serine Protease
 (B) STRAIN: Bacillus lentus DSM 5843

(vii) IMMEDIATE SOURCE:
 (B) CLONE: T268V (xi) SEQUENCE DESCRIPTION: SEQ ID NO:49:

| Ala | Gln | Ser | Val | Pro | Trp | Gly | Ile | Ser | Arg | Val | Gln | Ala | Pro | Ala | Ala |
|---|---|---|---|---|---|---|---|---|---|---|---|---|---|---|---|
| 1 | | | | 5 | | | | | 10 | | | | | 15 | |
| His | Asn | Arg | Gly | Leu | Thr | Gly | Ser | Gly | Val | Lys | Val | Ala | Val | Leu | Asp |
| | | | 20 | | | | | 25 | | | | | 30 | | |
| Thr | Gly | Ile | Ser | Thr | His | Pro | Asp | Leu | Asn | Ile | Arg | Gly | Gly | Ala | Ser |
| | | | 35 | | | | 40 | | | | | 45 | | | |
| Phe | Val | Pro | Gly | Glu | Pro | Ser | Thr | Gln | Asp | Gly | Asn | Gly | His | Gly | Thr |
| | 50 | | | | | 55 | | | | | 60 | | | | |
| His | Val | Ala | Gly | Thr | Ile | Ala | Ala | Leu | Asn | Asn | Ser | Ile | Gly | Val | Leu |
| 65 | | | | | 70 | | | | | 75 | | | | | 80 |
| Gly | Val | Ala | Pro | Ser | Ala | Glu | Leu | Tyr | Ala | Val | Lys | Val | Leu | Gly | Ala |
| | | | | 85 | | | | | 90 | | | | | 95 | |
| Asp | Gly | Arg | Gly | Ala | Ile | Ser | Ser | Ile | Ala | Gln | Gly | Leu | Glu | Trp | Ala |
| | | | 100 | | | | | 105 | | | | | 110 | | |
| Gly | Asn | Asn | Gly | Met | His | Val | Ala | Asn | Leu | Ser | Leu | Gly | Ser | Pro | Ser |
| | | | 115 | | | | | 120 | | | | | 125 | | |
| Pro | Ser | Ala | Thr | Leu | Glu | Gln | Ala | Val | Asn | Ser | Ala | Thr | Ser | Arg | Gly |
| | 130 | | | | | 135 | | | | | 140 | | | | |
| Val | Leu | Val | Val | Ala | Ala | Ser | Gly | Asn | Ser | Gly | Ala | Ser | Ser | Ile | Ser |
| 145 | | | | | 150 | | | | | 155 | | | | | 160 |
| Tyr | Pro | Ala | Arg | Tyr | Ala | Asn | Ala | Met | Ala | Val | Gly | Ala | Thr | Asp | Gln |
| | | | | 165 | | | | | 170 | | | | | 175 | |
| Asn | Asn | Asn | Arg | Ala | Ser | Phe | Ser | Gln | Tyr | Gly | Ala | Gly | Leu | Asp | Ile |
| | | | 180 | | | | | 185 | | | | | 190 | | |
| Val | Ala | Pro | Gly | Val | Asn | Val | Gln | Ser | Thr | Tyr | Pro | Gly | Ser | Thr | Tyr |
| | | 195 | | | | | 200 | | | | | 205 | | | |
| Ala | Ser | Leu | Asn | Gly | Thr | Ser | Met | Ala | Thr | Pro | His | Val | Ala | Gly | Ala |
| | 210 | | | | | 215 | | | | | 220 | | | | |
| Ala | Ala | Leu | Val | Lys | Gln | Lys | Asn | Pro | Ser | Trp | Ser | Asn | Val | Gln | Ile |
| 225 | | | | | 230 | | | | | 235 | | | | | 240 |
| Arg | Asn | His | Leu | Lys | Asn | Thr | Ala | Thr | Ser | Leu | Gly | Ser | Thr | Asn | Leu |
| | | | | 245 | | | | | 250 | | | | | 255 | |
| Tyr | Gly | Ser | Gly | Leu | Val | Asn | Ala | Glu | Ala | Ala | Val | Arg | | | |
| | | | 260 | | | | | 265 | | | | | | | |

(2) INFORMATION FOR SEQ ID NO:50:

(i) SEQUENCE CHARACTERISTICS:
 (A) LENGTH: 269 amino acids
 (B) TYPE: amino acid
 (D) TOPOLOGY: unknown (ii) MOLECULE TYPE: protein (iii) HYPOTHETICAL: NO (iv) ANTI-SENSE: NO (vi) ORIGINAL SOURCE:
 (A) ORGANISM: Serine Protease
 (B) STRAIN: Bacillus lentus DSM 5843

(vii) IMMEDIATE SOURCE:
 (B) CLONE: K229W (xi) SEQUENCE DESCRIPTION: SEQ ID NO:50:

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
             20                  25                  30

Thr Gly Ile Ser Thr His Pro Asp Leu Asn Ile Arg Gly Gly Ala Ser
         35                  40                  45

Phe Val Pro Gly Glu Pro Ser Thr Gln Asp Gly Asn Gly His Gly Thr
     50                  55                  60

His Val Ala Gly Thr Ile Ala Ala Leu Asn Asn Ser Ile Gly Val Leu
 65              70                  75                  80

Gly Val Ala Pro Ser Ala Glu Leu Tyr Ala Val Lys Val Leu Gly Ala
                 85                  90                  95

Asp Gly Arg Gly Ala Ile Ser Ser Ile Ala Gln Gly Leu Glu Trp Ala
             100                 105                 110

Gly Asn Asn Gly Met His Val Ala Asn Leu Ser Leu Gly Ser Pro Ser
             115                 120                 125

Pro Ser Ala Thr Leu Glu Gln Ala Val Asn Ser Ala Thr Ser Arg Gly
     130                 135                 140

Val Leu Val Val Ala Ala Ser Gly Asn Ser Gly Ala Ser Ser Ile Ser
 145                 150                 155                 160

Tyr Pro Ala Arg Tyr Ala Asn Ala Met Ala Val Gly Ala Thr Asp Gln
             165                 170                 175

Asn Asn Asn Arg Ala Ser Phe Ser Gln Tyr Gly Ala Gly Leu Asp Ile
             180                 185                 190

Val Ala Pro Gly Val Asn Val Gln Ser Thr Tyr Pro Gly Ser Thr Tyr
         195                 200                 205

Ala Ser Leu Asn Gly Thr Ser Met Ala Thr Pro His Val Ala Gly Ala
     210                 215                 220

Ala Ala Leu Val Trp Gln Lys Asn Pro Ser Trp Ser Asn Val Gln Ile
 225                 230                 235                 240

Arg Asn His Leu Lys Asn Thr Ala Thr Ser Leu Gly Ser Thr Asn Leu
             245                 250                 255

Tyr Gly Ser Gly Leu Val Asn Ala Glu Ala Ala Thr Arg
             260                 265
```

( 2 ) INFORMATION FOR SEQ ID NO:51:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: T141W ( x i ) SEQUENCE DESCRIPTION: SEQ ID NO:51:

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
             20                  25                  30

Thr Gly Ile Ser Thr His Pro Asp Leu Asn Ile Arg Gly Gly Ala Ser
```

```
                35                          40                          45
    Phe Val Pro Gly Glu Pro Ser Thr Gln Asp Gly Asn Gly His Gly Thr
        50                      55                      60
    His Val Ala Gly Thr Ile Ala Ala Leu Asn Asn Ser Ile Gly Val Leu
    65                      70                      75                      80
    Gly Val Ala Pro Ser Ala Glu Leu Tyr Ala Val Lys Val Leu Gly Ala
                        85                      90                      95
    Asp Gly Arg Gly Ala Ile Ser Ser Ile Ala Gln Gly Leu Glu Trp Ala
                    100                     105                     110
    Gly Asn Asn Gly Met His Val Ala Asn Leu Ser Leu Gly Ser Pro Ser
                115                     120                     125
    Pro Ser Ala Thr Leu Glu Gln Ala Val Asn Ser Ala Trp Ser Arg Gly
            130                     135                     140
    Val Leu Val Val Ala Ala Ser Gly Asn Ser Gly Ala Ser Ser Ile Ser
    145                     150                     155                     160
    Tyr Pro Ala Arg Tyr Ala Asn Ala Met Ala Val Gly Ala Thr Asp Gln
                        165                     170                     175
    Asn Asn Asn Arg Ala Ser Phe Ser Gln Tyr Gly Ala Gly Leu Asp Ile
                    180                     185                     190
    Val Ala Pro Gly Val Asn Val Gln Ser Thr Tyr Pro Gly Ser Thr Tyr
                195                     200                     205
    Ala Ser Leu Asn Gly Thr Ser Met Ala Thr Pro His Val Ala Gly Ala
        210                     215                     220
    Ala Ala Leu Val Lys Gln Lys Asn Pro Ser Trp Ser Asn Val Gln Ile
    225                     230                     235                     240
    Arg Asn His Leu Lys Asn Thr Ala Thr Ser Leu Gly Ser Thr Asn Leu
                        245                     250                     255
    Tyr Gly Ser Gly Leu Val Asn Ala Glu Ala Ala Thr Arg
                    260                     265
```

( 2 ) INFORMATION FOR SEQ ID NO:52:

( i ) SEQUENCE CHARACTERISTICS:
        ( A ) LENGTH: 269 amino acids
        ( B ) TYPE: amino acid
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Serine Protease
        ( B ) STRAIN: Bacillus lentus DSM 5843

( v i i ) IMMEDIATE SOURCE:
        ( B ) CLONE: wildtype ( x i ) SEQUENCE DESCRIPTION: SEQ ID NO:52:

```
    Ala Gln Ser Val Pro Trp Gly Ile Ser Arg Val Gln Ala Pro Ala Ala
    1                   5                       10                      15
    His Asn Arg Gly Leu Thr Gly Ser Gly Val Lys Val Ala Val Leu Asp
                        20                      25                      30
    Thr Gly Ile Ser Thr His Pro Asp Leu Asn Ile Arg Gly Gly Ala Ser
                    35                      40                      45
    Phe Val Pro Gly Glu Pro Ser Thr Gln Asp Gly Asn Gly His Gly Thr
        50                      55                      60
    His Val Ala Gly Thr Ile Ala Ala Leu Asn Asn Ser Ile Gly Val Leu
    65                      70                      75                      80
```

|  |  |  |  |  |  |  |  |  |  |  |  |  |  |  |
|---|---|---|---|---|---|---|---|---|---|---|---|---|---|---|
| Gly | Val | Ala | Pro | Ser<br>85 | Ala | Glu | Leu | Tyr | Ala<br>90 | Val | Lys | Val | Leu | Gly Ala<br>95 |
| Asp | Gly | Arg | Gly<br>100 | Ala | Ile | Ser | Ser | Ile<br>105 | Ala | Gln | Gly | Leu | Glu<br>110 | Trp Ala |
| Gly | Asn | Asn<br>115 | Gly | Met | His | Val | Ala<br>120 | Asn | Leu | Ser | Leu | Gly<br>125 | Ser | Pro Ser |
| Pro | Ser<br>130 | Ala | Thr | Leu | Glu | Gln<br>135 | Ala | Val | Asn | Ser | Ala<br>140 | Thr | Ser | Arg Gly |
| Val<br>145 | Leu | Val | Val | Ala | Ala<br>150 | Ser | Gly | Asn | Ser | Gly<br>155 | Ala | Ser | Ser | Ile Ser<br>160 |
| Tyr | Pro | Ala | Arg | Tyr<br>165 | Ala | Asn | Ala | Met | Ala<br>170 | Val | Gly | Ala | Thr | Asp Gln<br>175 |
| Asn | Asn | Asn | Arg<br>180 | Ala | Ser | Phe | Ser | Gln<br>185 | Tyr | Gly | Ala | Gly | Leu<br>190 | Asp Ile |
| Val | Ala | Pro<br>195 | Gly | Val | Asn | Val | Gln<br>200 | Ser | Thr | Tyr | Pro | Gly<br>205 | Ser | Thr Tyr |
| Ala | Ser<br>210 | Leu | Asn | Gly | Thr | Ser<br>215 | Met | Ala | Thr | Pro | His<br>220 | Val | Ala | Gly Ala |
| Ala<br>225 | Ala | Leu | Val | Lys | Gln<br>230 | Lys | Asn | Pro | Ser | Trp<br>235 | Ser | Asn | Val | Gln Ile<br>240 |
| Arg | Asn | His | Leu | Lys<br>245 | Asn | Thr | Ala | Thr | Ser<br>250 | Leu | Gly | Ser | Thr | Asn Leu<br>255 |
| Tyr | Gly | Ser | Gly<br>260 | Leu | Val | Asn | Ala | Glu<br>265 | Ala | Ala | Thr | Arg |  |  |

( 2 ) INFORMATION FOR SEQ ID NO:53:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
       -continued

| | | | | | |
|---|---|---|---|---|---|
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:54:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: S3T, A188P, V193M, V199I ( x i ) SEQUENCE DESCRIPTION: SEQ ID NO:54:

| | | | | | |
|---|---|---|---|---|---|
| GCGCAAACAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CCCAGGGCTT | GACATTATGG | CACCAGGGGT | AAACATTCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:55:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: V4I, A188P, V193M, V199I ( x i ) SEQUENCE DESCRIPTION: SEQ ID NO:55:

| | | | | | |
|---|---|---|---|---|---|
| GCGCAATCAA | TCCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |

```
TTAAATATTC GTGGTGGCGC TAGCTTTGTA CCAGGGGAAC CATCCACTCA AGATGGGAAT    180

GGGCATGGCA CGCATGTGGC CGGGACGATT GCTGCTTTAA ACAATTCGAT TGGCGTTCTT    240

GGCGTAGCGC CTAGTGCGGA ACTATACGCT GTTAAAGTTT TAGGAGCCGA CGGTAGAGGT    300

GCAATCAGCT CGATTGCCCA AGGGTTGGAA TGGGCAGGGA ACAATGGCAT GCACGTTGCT    360

AATTTGAGTT TAGGAAGCCC TTCGCCAAGT GCCACACTTG AGCAAGCTGT TAATAGCGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CCCAGGGCTT GACATTATGG CACCAGGGGT AAACATTCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AAGAACCCAT CTTGGTCCAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                       807
```

( 2 ) INFORMATION FOR SEQ ID NO:56:

( i ) SEQUENCE CHARACTERISTICS:
( A ) LENGTH: 807 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( B ) STRAIN: Bacillus lentus DSM 5483

( v i i ) IMMEDIATE SOURCE:
( B ) CLONE: S139Y, A188P, V193M, V199I ( x i ) SEQUENCE DESCRIPTION: SEQ ID NO:56:

```
GCGCAATCAG TGCCATGGGG AATTAGCCGT GTGCAAGCCC CGGCTGCCCA TAACCGTGGA     60

TTGACAGGTT CTGGTGTAAA AGTTGCTGTC CTCGATACAG GTATTTCCAC TCATCCAGAC    120

TTAAATATTC GTGGTGGCGC TAGCTTTGTA CCAGGGGAAC CATCCACTCA AGATGGGAAT    180

GGGCATGGCA CGCATGTGGC CGGGACGATT GCTGCTTTAA ACAATTCGAT TGGCGTTCTT    240

GGCGTAGCGC CTAGTGCGGA ACTATACGCT GTTAAAGTTT TAGGAGCCGA CGGTAGAGGT    300

GCAATCAGCT CGATTGCCCA AGGGTTGGAA TGGGCAGGGA ACAATGGCAT GCACGTTGCT    360

AATTTGAGTT TAGGAAGCCC TTCGCCAAGT GCCACACTTG AGCAAGCTGT TAATTATGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CCCAGGGCTT GACATTATGG CACCAGGGGT AAACATTCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AAGAACCCAT CTTGGTCCAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                       807
```

( 2 ) INFORMATION FOR SEQ ID NO:57:

( i ) SEQUENCE CHARACTERISTICS:
( A ) LENGTH: 807 base pairs
( B ) TYPE: nucleic acid (C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(B) STRAIN: Bacillus lentus DSM 5483

(vii) IMMEDIATE SOURCE:
(B) CLONE: S130T, S139Y, A188P, V193M, V199I (xi) SEQUENCE DESCRIPTION: SEQ ID NO:57:

| | | | | | |
|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAACA | GCCACACTTG | AGCAAGCTGT | TAATTATGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CCCAGGGCTT | GACATTATGG | CACCAGGGGT | AAACATTCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

(2) INFORMATION FOR SEQ ID NO:58:

(i) SEQUENCE CHARACTERISTICS:
(A) LENGTH: 807 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(B) STRAIN: Bacillus lentus DSM 5483

(vii) IMMEDIATE SOURCE:
(B) CLONE: A188P, V193M, V199I (xi) SEQUENCE DESCRIPTION: SEQ ID NO:58:

| | | | | | |
|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |

-continued

```
ACTTCTAGAG GCGTTCTTGT TGTAGCGGCA TCTGGGAATT CAGGTGCAAG CTCAATCAGC      480
TATCCGGCCC GTTATGCGAA CGCAATGGCA GTCGGAGCTA CTGACCAAAA CAACAACCGC      540
GCCAGCTTTT CACAGTATGG CCCAGGGCTT GACATTATGG CACCAGGGGT AAACATTCAG      600
AGCACATACC CAGGTTCAAC GTATGCCAGC TTAAACGGTA CATCGATGGC TACTCCTCAT      660
GTTGCAGGTG CAGCAGCCCT TGTTAAACAA AGAACCCAT CTTGGTCCAA TGTACAAATC       720
CGCAACCATC TAAAGAATAC GGCAACGAGC TTAGGAAGCA CGAACTTGTA TGGAAGCGGA      780
CTTGTCAATG CAGAAGCGGC AACACGC                                         807
```

(2) INFORMATION FOR SEQ ID NO:59:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: S3T, A188P, V193M (xi) SEQUENCE DESCRIPTION: SEQ ID NO:59:

```
GCGCAAACAG TGCCATGGGG AATTAGCCGT GTGCAAGCCC CGGCTGCCCA TAACCGTGGA       60
TTGACAGGTT CTGGTGTAAA AGTTGCTGTC CTCGATACAG GTATTTCCAC TCATCCAGAC      120
TTAAATATTC GTGGTGGCGC TAGCTTTGTA CCAGGGGAAC CATCCACTCA AGATGGGAAT      180
GGGCATGGCA CGCATGTGGC CGGGACGATT GCTGCTTTAA CAATTCGAT TGGCGTTCTT       240
GGCGTAGCGC CTAGTGCGGA ACTATACGCT GTTAAAGTTT TAGGAGCCGA CGGTAGAGGT      300
GCAATCAGCT CGATTGCCCA AGGGTTGGAA TGGGCAGGGA ACAATGGCAT GCACGTTGCT      360
AATTTGAGTT TAGGAAGCCC TTCGCCAAGT GCCACACTTG AGCAAGCTGT TAATAGCGCG      420
ACTTCTAGAG GCGTTCTTGT TGTAGCGGCA TCTGGGAATT CAGGTGCAAG CTCAATCAGC      480
TATCCGGCCC GTTATGCGAA CGCAATGGCA GTCGGAGCTA CTGACCAAAA CAACAACCGC      540
GCCAGCTTTT CACAGTATGG CCCAGGGCTT GACATTATGG CACCAGGGGT AAACGTGCAG      600
AGCACATACC CAGGTTCAAC GTATGCCAGC TTAAACGGTA CATCGATGGC TACTCCTCAT      660
GTTGCAGGTG CAGCAGCCCT TGTTAAACAA AGAACCCAT CTTGGTCCAA TGTACAAATC       720
CGCAACCATC TAAAGAATAC GGCAACGAGC TTAGGAAGCA CGAACTTGTA TGGAAGCGGA      780
CTTGTCAATG CAGAAGCGGC AACACGC                                         807
```

(2) INFORMATION FOR SEQ ID NO:60:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(v i i) IMMEDIATE SOURCE:
    (B) CLONE: S157T (x i) SEQUENCE DESCRIPTION: SEQ ID NO:60:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTGCT     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATT CAGGTGCAAC ATCAATCAGC     480
TATCCGGCCC GTTATGCGAA CGCAATGGCA GTCGGAGCTA CTGACCAAAA CAACAACCGC     540
GCCAGCTTTT CACAGTATGG CGCAGGGCTT GACATTGTCG CACCAGGGGT AAACGTGCAG     600
AGCACATACC CAGGTTCAAC GTATGCCAGC TTAAACGGTA CATCGATGGC TACTCCTCAT     660
GTTGCAGGTG CAGCAGCCCT TGTTAAACAA AAGAACCCAT CTTGGTCCAA TGTACAAATC     720
CGCAACCATC TAAAGAATAC GGCAACGAGC TTAGGAAGCA CGAACTTGTA TGGAAGCGGA     780
CTTGTCAATG CAGAAGCGGC AACACGC                                         807
```

(2) INFORMATION FOR SEQ ID NO:61:

(i) SEQUENCE CHARACTERISTICS:
      (A) LENGTH: 807 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (B) STRAIN: Bacillus lentus DSM 5483

(vii) IMMEDIATE SOURCE:
        (B) CLONE: A188P, V193M (xi) SEQUENCE DESCRIPTION: SEQ ID NO:61:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTGCT     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CCCAGGGCTT GACATTATGG CACCAGGGGT AAACGTGCAG     600
AGCACATACC CAGGTTCAAC GTATGCCAGC TTAAACGGTA CATCGATGGC TACTCCTCAT     660
GTTGCAGGTG CAGCAGCCCT TGTTAAACAA AAGAACCCAT CTTGGTCCAA TGTACAAATC     720
CGCAACCATC TAAAGAATAC GGCAACGAGC TTAGGAAGCA CGAACTTGTA TGGAAGCGGA     780
```

CTTGTCAATG CAGAAGCGGC AACACGC      807

(2) INFORMATION FOR SEQ ID NO:62:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: A188P (xi) SEQUENCE DESCRIPTION: SEQ ID NO:62:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT AGGAGCCGA CGGTAGAGGT      300
GCAATCAGCT CGATTGCCCA AGGGTTGGAA TGGGCAGGGA ACAATGGCAT GCACGTTGCT     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CCCAGGGCTT GACATTGTCG CACCAGGGGT AAACGTGCAG     600
AGCACATACC CAGGTTCAAC GTATGCCAGC TTAAACGGTA CATCGATGGC TACTCCTCAT     660
GTTGCAGGTG CAGCAGCCCT TGTTAAACAA AAGAACCCAT CTTGGTCCAA TGTACAAATC     720
CGCAACCATC TAAAGAATAC GGCAACGAGC TTAGGAAGCA CGAACTTGTA TGGAAGCGGA     780
CTTGTCAATG CAGAAGCGGC AACACGC                                          807
```

(2) INFORMATION FOR SEQ ID NO:63:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: S3T, V4I, A188P, V193M (xi) SEQUENCE DESCRIPTION: SEQ ID NO:63:

```
GCGCAAACAA TCCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
```

| | | | | | | |
|---|---|---|---|---|---|---|
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CCCAGGGCTT | GACATTATGG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:64:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: V193M ( x i ) SEQUENCE DESCRIPTION: SEQ ID NO:64:

| | | | | | | |
|---|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTATGG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:65:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear (ii) MOLECULE TYPE: DNA (genomic)

(iii) HYPOTHETICAL: NO (iv) ANTI-SENSE: NO (vi) ORIGINAL SOURCE:
    (B) STRAIN: Bacillus lentus DSM 5483

(vii) IMMEDIATE SOURCE:
    (B) CLONE: S104T (xi) SEQUENCE DESCRIPTION: SEQ ID NO:65:

| | | | | | | |
|---|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCA | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

(2) INFORMATION FOR SEQ ID NO:66:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: T69V (xi) SEQUENCE DESCRIPTION: SEQ ID NO:66:

| | | | | | | |
|---|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGGTTATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |

| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:67:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: V4I, A188P, V193M ( x i ) SEQUENCE DESCRIPTION: SEQ ID NO:67:

| GCGCAATCAA | TCCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | CAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CCCAGGGCTT | GACATTATGG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:68:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:

(B) CLONE: A224V (xi) SEQUENCE DESCRIPTION: SEQ ID NO:68:

```
GCGCAATCAG TGCCATGGGG AATTAGCCGT GTGCAAGCCC CGGCTGCCCA TAACCGTGGA        60
TTGACAGGTT CTGGTGTAAA AGTTGCTGTC CTCGATACAG GTATTTCCAC TCATCCAGAC       120
TTAAATATTC GTGGTGGCGC TAGCTTTGTA CCAGGGGAAC CATCCACTCA AGATGGGAAT       180
GGGCATGGCA CGCATGTGGC CGGGACGATT GCTGCTTTAA ACAATTCGAT TGGCGTTCTT       240
GGCGTAGCGC CTAGTGCGGA ACTATACGCT GTTAAAGTTT TAGGAGCCGA CGGTAGAGGT       300
GCAATCAGCT CGATTGCCCA AGGGTTGGAA TGGGCAGGGA ACAATGGCAT GCACGTTGCT       360
AATTTGAGTT TAGGAAGCCC TTCGCCAAGT GCCACACTTG AGCAAGCTGT TAATAGCGCG       420
ACTTCTAGAG GCGTTCTTGT TGTAGCGGCA TCTGGGAATT CAGGTGCAAG CTCAATCAGC       480
TATCCGGCCC GTTATGCGAA CGCAATGGCA GTCGGAGCTA CTGACCAAAA CAACAACCGC       540
GCCAGCTTTT CACAGTATGG CGCAGGGCTT GACATTGTCG CACCAGGGGT AAACGTGCAG       600
AGCACATACC CAGGTTCAAC GTATGCCAGC TTAAACGGTA CATCGATGGC TACTCCTCAT       660
GTTGCAGGTG TTGCAGCCCT TGTTAAACAA AAGAACCCAT CTTGGTCCAA TGTACAAATC       720
CGCAACCATC TAAAGAATAC GGCAACGAGC TTAGGAAGCA CGAACTTGTA TGGAAGCGGA       780
CTTGTCAATG CAGAAGCGGC AACACGC                                          807
```

(2) INFORMATION FOR SEQ ID NO:69:

(i) SEQUENCE CHARACTERISTICS:
(A) LENGTH: 807 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(B) STRAIN: Bacillus lentus DSM 5483

(vii) IMMEDIATE SOURCE:
(B) CLONE: V199I (xi) SEQUENCE DESCRIPTION: SEQ ID NO:69:

```
GCGCAATCAG TGCCATGGGG AATTAGCCGT GTGCAAGCCC CGGCTGCCCA TAACCGTGGA        60
TTGACAGGTT CTGGTGTAAA AGTTGCTGTC CTCGATACAG GTATTTCCAC TCATCCAGAC       120
TTAAATATTC GTGGTGGCGC TAGCTTTGTA CCAGGGGAAC CATCCACTCA AGATGGGAAT       180
GGGCATGGCA CGCATGTGGC CGGGACGATT GCTGCTTTAA ACAATTCGAT TGGCGTTCTT       240
GGCGTAGCGC CTAGTGCGGA ACTATACGCT GTTAAAGTTT TAGGAGCCGA CGGTAGAGGT       300
GCAATCAGCT CGATTGCCCA AGGGTTGGAA TGGGCAGGGA ACAATGGCAT GCACGTTGCT       360
AATTTGAGTT TAGGAAGCCC TTCGCCAAGT GCCACACTTG AGCAAGCTGT TAATAGCGCG       420
ACTTCTAGAG GCGTTCTTGT TGTAGCGGCA TCTGGGAATT CAGGTGCAAG CTCAATCAGC       480
TATCCGGCCC GTTATGCGAA CGCAATGGCA GTCGGAGCTA CTGACCAAAA CAACAACCGC       540
GCCAGCTTTT CACAGTATGG CGCAGGGCTT GACATTGTCG CACCAGGGGT AAACATTCAG       600
AGCACATACC CAGGTTCAAC GTATGCCAGC TTAAACGGTA CATCGATGGC TACTCCTCAT       660
GTTGCAGGTG CAGCAGCCCT TGTTAAACAA AAGAACCCAT CTTGGTCCAA TGTACAAATC       720
CGCAACCATC TAAAGAATAC GGCAACGAGC TTAGGAAGCA CGAACTTGTA TGGAAGCGGA       780
CTTGTCAATG CAGAAGCGGC AACACGC                                          807
```

( 2 ) INFORMATION FOR SEQ ID NO:70:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: V4I ( x i ) SEQUENCE DESCRIPTION: SEQ ID NO:70:

| | | | | | |
|---|---|---|---|---|---|
| GCGCAATCAA | TCCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:71:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: S3T ( x i ) SEQUENCE DESCRIPTION: SEQ ID NO:71:

| | | | | | |
|---|---|---|---|---|---|
| GCGCAAACAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |

| | | | | | | |
|---|---|---|---|---|---|---|
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:72:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: S139Y ( x i ) SEQUENCE DESCRIPTION: SEQ ID NO:72:

| | | | | | | |
|---|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATTATGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:73:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
(B) STRAIN: Bacillus lentus DSM 5483

( v i i ) IMMEDIATE SOURCE:
(B) CLONE: N242A ( x i ) SEQUENCE DESCRIPTION: SEQ ID NO:73:

| | | | | | | |
|---|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | AGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCGCACATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:74:

( i ) SEQUENCE CHARACTERISTICS:
(A) LENGTH: 807 base pairs
(B) TYPE: nucleic acid
(C) STRANDEDNESS: double
(D) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
(B) STRAIN: Bacillus lentus DSM 5483

( v i i ) IMMEDIATE SOURCE:
(B) CLONE: S236T ( x i ) SEQUENCE DESCRIPTION: SEQ ID NO:74:

| | | | | | | |
|---|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | AGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |

| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AGAACCCAT | CTTGGACAAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:75:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: S36A ( x i ) SEQUENCE DESCRIPTION: SEQ ID NO:75:

| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTGCAAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:76:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: H243A ( x i ) SEQUENCE DESCRIPTION: SEQ ID NO:76:

| | | | | | |
|---|---|---|---|---|---|
| GCGCAATCAG | TGCCATGGGG | AATTAGCCGT | GTGCAAGCCC | CGGCTGCCCA | TAACCGTGGA | 60
| TTGACAGGTT | CTGGTGTAAA | AGTTGCTGTC | CTCGATACAG | GTATTTCCAC | TCATCCAGAC | 120
| TTAAATATTC | GTGGTGGCGC | TAGCTTTGTA | CCAGGGGAAC | CATCCACTCA | AGATGGGAAT | 180
| GGGCATGGCA | CGCATGTGGC | CGGGACGATT | GCTGCTTTAA | ACAATTCGAT | TGGCGTTCTT | 240
| GGCGTAGCGC | CTAGTGCGGA | ACTATACGCT | GTTAAAGTTT | TAGGAGCCGA | CGGTAGAGGT | 300
| GCAATCAGCT | CGATTGCCCA | AGGGTTGGAA | TGGGCAGGGA | ACAATGGCAT | GCACGTTGCT | 360
| AATTTGAGTT | TAGGAAGCCC | TTCGCCAAGT | GCCACACTTG | AGCAAGCTGT | TAATAGCGCG | 420
| ACTTCTAGAG | GCGTTCTTGT | TGTAGCGGCA | TCTGGGAATT | CAGGTGCAAG | CTCAATCAGC | 480
| TATCCGGCCC | GTTATGCGAA | CGCAATGGCA | GTCGGAGCTA | CTGACCAAAA | CAACAACCGC | 540
| GCCAGCTTTT | CACAGTATGG | CGCAGGGCTT | GACATTGTCG | CACCAGGGGT | AAACGTGCAG | 600
| AGCACATACC | CAGGTTCAAC | GTATGCCAGC | TTAAACGGTA | CATCGATGGC | TACTCCTCAT | 660
| GTTGCAGGTG | CAGCAGCCCT | TGTTAAACAA | AAGAACCCAT | CTTGGTCCAA | TGTACAAATC | 720
| CGCAACGCAC | TAAAGAATAC | GGCAACGAGC | TTAGGAAGCA | CGAACTTGTA | TGGAAGCGGA | 780
| CTTGTCAATG | CAGAAGCGGC | AACACGC | | | | 807

( 2 ) INFORMATION FOR SEQ ID NO:77:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: A101T ( x i ) SEQUENCE DESCRIPTION: SEQ ID NO:77:

| | | | | | |
|---|---|---|---|---|---|
| GCGCAATCAG | TGCCATGGGG | AATTAGCCGT | GTGCAAGCCC | CGGCTGCCCA | TAACCGTGGA | 60
| TTGACAGGTT | CTGGTGTAAA | AGTTGCTGTC | CTCGATACAG | GTATTTCCAC | TCATCCAGAC | 120
| TTAAATATTC | GTGGTGGCGC | TAGCTTTGTA | CCAGGGGAAC | CATCCACTCA | AGATGGGAAT | 180
| GGGCATGGCA | CGCATGTGGC | CGGGACGATT | GCTGCTTTAA | ACAATTCGAT | TGGCGTTCTT | 240
| GGCGTAGCGC | CTAGTGCGGA | ACTATACGCT | GTTAAAGTTT | TAGGAGCCGA | CGGTAGAGGT | 300
| ACAATCAGCT | CGATTGCCCA | AGGGTTGGAA | TGGGCAGGGA | ACAATGGCAT | GCACGTTGCT | 360
| AATTTGAGTT | TAGGAAGCCC | TTCGCCAAGT | GCCACACTTG | AGCAAGCTGT | TAATAGCGCG | 420
| ACTTCTAGAG | GCGTTCTTGT | TGTAGCGGCA | TCTGGGAATT | CAGGTGCAAG | CTCAATCAGC | 480
| TATCCGGCCC | GTTATGCGAA | CGCAATGGCA | GTCGGAGCTA | CTGACCAAAA | CAACAACCGC | 540
| GCCAGCTTTT | CACAGTATGG | CGCAGGGCTT | GACATTGTCG | CACCAGGGGT | AAACGTGCAG | 600
| AGCACATACC | CAGGTTCAAC | GTATGCCAGC | TTAAACGGTA | CATCGATGGC | TACTCCTCAT | 660
| GTTGCAGGTG | CAGCAGCCCT | TGTTAAACAA | AAGAACCCAT | CTTGGTCCAA | TGTACAAATC | 720
| CGCAACCATC | TAAAGAATAC | GGCAACGAGC | TTAGGAAGCA | CGAACTTGTA | TGGAAGCGGA | 780
| CTTGTCAATG | CAGAAGCGGC | AACACGC | | | | 807

5,340,735

157                                 158

-continued ( 2 ) INFORMATION FOR SEQ ID NO:78:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: S236A ( x i ) SEQUENCE DESCRIPTION: SEQ ID NO:78:

```
GCGCAATCAG TGCCATGGGG AATTAGCCGT GTGCAAGCCC CGGCTGCCCA TAACCGTGGA    60
TTGACAGGTT CTGGTGTAAA AGTTGCTGTC CTCGATACAG GTATTTCCAC TCATCCAGAC   120
TTAAATATTC GTGGTGGCGC TAGCTTTGTA CCAGGGGAAC CATCCACTCA AGATGGGAAT   180
GGGCATGGCA CGCATGTGGC CGGGACGATT GCTGCTTTAA ACAATTCGAT TGGCGTTCTT   240
GGCGTAGCGC CTAGTGCGGA ACTATACGCT GTTAAAGTTT TAGGAGCCGA CGGTAGAGGT   300
GCAATCAGCT CGATTGCCCA AGGGTTGGAA TGGGCAGGGA ACAATGGCAT GCACGTTGCT   360
AATTTGAGTT TAGGAAGCCC TTCGCCAAGT GCCACACTTG AGCAAGCTGT TAATAGCGCG   420
ACTTCTAGAG GCGTTCTTGT TGTAGCGGCA TCTGGGAATT CAGGTGCAAG CTCAATCAGC   480
TATCCGGCCC GTTATGCGAA CGCAATGGCA GTCGGAGCTA CTGACCAAAA CAACAACCGC   540
GCCAGCTTTT CACAGTATGG CGCAGGGCTT GACATTGTCG CACCAGGGGT AAACGTGCAG   600
AGCACATACC CAGGTTCAAC GTATGCCAGC TTAAACGGTA CATCGATGGC TACTCCTCAT   660
GTTGCAGGTG CAGCAGCCCT TGTTAAACAA AAGAACCCAT CTTGGGCAAA TGTACAAATC   720
CGCAACCATC TAAAGAATAC GGCAACGAGC TTAGGAAGCA CGAACTTGTA TGGAAGCGGA   780
CTTGTCAATG CAGAAGCGGC AACACGC                                      807
```

( 2 ) INFORMATION FOR SEQ ID NO:79:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: E87R ( x i ) SEQUENCE DESCRIPTION: SEQ ID NO:79:

```
GCGCAATCAG TGCCATGGGG AATTAGCCGT GTGCAAGCCC CGGCTGCCCA TAACCGTGGA    60
TTGACAGGTT CTGGTGTAAA AGTTGCTGTC CTCGATACAG GTATTTCCAC TCATCCAGAC   120
TTAAATATTC GTGGTGGCGC TAGCTTTGTA CCAGGGGAAC CATCCACTCA AGATGGGAAT   180
GGGCATGGCA CGCATGTGGC CGGGACGATT GCTGCTTTAA ACAATTCGAT TGGCGTTCTT   240
GGCGTAGCGC CTAGTGCGCG TCTATACGCT GTTAAAGTTT TAGGAGCCGA CGGTAGAGGT   300
```

```
GCAATCAGCT CGATTGCCCA AGGGTTGGAA TGGGCAGGGA ACAATGGCAT GCACGTTGCT    360

AATTTGAGTT TAGGAAGCCC TTCGCCAAGT GCCACACTTG AGCAAGCTGT TAATAGCGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CGCAGGGCTT GACATTGTCG CACCAGGGGT AAACGTGCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AGAACCCAT CTTGGTCCAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                       807
```

( 2 ) INFORMATION FOR SEQ ID NO:80:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: N114S ( x i ) SEQUENCE DESCRIPTION: SEQ ID NO:80:

```
GCGCAATCAG TGCCATGGGG AATTAGCCGT GTGCAAGCCC CGGCTGCCCA TAACCGTGGA     60

TTGACAGGTT CTGGTGTAAA AGTTGCTGTC CTCGATACAG GTATTTCCAC TCATCCAGAC    120

TTAAATATTC GTGGTGGCGC TAGCTTTGTA CCAGGGGAAC CATCCACTCA AGATGGGAAT    180

GGGCATGGCA CGCATGTGGC CGGGACGATT GCTGCTTTAA ACAATTCGAT TGGCGTTCTT    240

GGCGTAGCGC CTAGTGCGGA ACTATACGCT GTTAAAGTTT TAGGAGCCGA CGGTAGAGGT    300

GCAATCAGCT CGATTGCCCA AGGGTTGGAA TGGGCAGGGA GCAATGGCAT GCACGTTGCT    360

AATTTGAGTT TAGGAAGCCC TTCGCCAAGT GCCACACTTG AGCAAGCTGT TAATAGCGCG    420

ACTTCTAGAG GCGTTCTTGT TGTAGCGGCA TCTGGGAATT CAGGTGCAAG CTCAATCAGC    480

TATCCGGCCC GTTATGCGAA CGCAATGGCA GTCGGAGCTA CTGACCAAAA CAACAACCGC    540

GCCAGCTTTT CACAGTATGG CGCAGGGCTT GACATTGTCG CACCAGGGGT AAACGTGCAG    600

AGCACATACC CAGGTTCAAC GTATGCCAGC TTAAACGGTA CATCGATGGC TACTCCTCAT    660

GTTGCAGGTG CAGCAGCCCT TGTTAAACAA AGAACCCAT CTTGGTCCAA TGTACAAATC    720

CGCAACCATC TAAAGAATAC GGCAACGAGC TTAGGAAGCA CGAACTTGTA TGGAAGCGGA    780

CTTGTCAATG CAGAAGCGGC AACACGC                                       807
```

( 2 ) INFORMATION FOR SEQ ID NO:81:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO (iv) ANTI-SENSE: NO (vi) ORIGINAL SOURCE:
  (B) STRAIN: Bacillus lentus DSM 5483

(vii) IMMEDIATE SOURCE:
  (B) CLONE: A47W (xi) SEQUENCE DESCRIPTION: SEQ ID NO:81:

| | | | | | | |
|---|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCTG | GAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

(2) INFORMATION FOR SEQ ID NO:82:

(i) SEQUENCE CHARACTERISTICS:
    (A) LENGTH: 807 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (B) STRAIN: Bacillus lentus DSM 5483

(vii) IMMEDIATE SOURCE:
    (B) CLONE: A120S (xi) SEQUENCE DESCRIPTION: SEQ ID NO:82:

| | | | | | | |
|---|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTAGC | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |

| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:83:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: T56V ( x i ) SEQUENCE DESCRIPTION: SEQ ID NO:83:

| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCGTTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:84:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: A120V ( x i ) SEQUENCE DESCRIPTION: SEQ ID NO:84:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTGTT     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CGCAGGGCTT GACATTGTCG CACCAGGGGT AAACGTGCAG     600
AGCACATACC CAGGTTCAAC GTATGCCAGC TTAAACGGTA CATCGATGGC TACTCCTCAT     660
GTTGCAGGTG CAGCAGCCCT TGTTAAACAA AGAACCCAT  CTTGGTCCAA TGTACAAATC     720
CGCAACCATC TAAAGAATAC GGCAACGAGC TTAGGAAGCA CGAACTTGTA TGGAAGCGGA     780
CTTGTCAATG CAGAAGCGGC AACACGC                                        807
```

(2) INFORMATION FOR SEQ ID NO:85:

(i) SEQUENCE CHARACTERISTICS:
  (A) LENGTH: 807 base pairs
  (B) TYPE: nucleic acid
  (C) STRANDEDNESS: double
  (D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (B) STRAIN: Bacillus lentus DSM 5483

(vii) IMMEDIATE SOURCE:
  (B) CLONE: G205V (xi) SEQUENCE DESCRIPTION: SEQ ID NO:85:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTGCT     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CGCAGGGCTT GACATTGTCG CACCAGGGGT AAACGTGCAG     600
AGCACATACC CAGTTTCAAC GTATGCCAGC TTAAACGGTA CATCGATGGC TACTCCTCAT     660
GTTGCAGGTG CAGCAGCCCT TGTTAAACAA AGAACCCAT  CTTGGTCCAA TGTACAAATC     720
CGCAACCATC TAAAGAATAC GGCAACGAGC TTAGGAAGCA CGAACTTGTA TGGAAGCGGA     780
CTTGTCAATG CAGAAGCGGC AACACGC                                        807
```

(2) INFORMATION FOR SEQ ID NO:86:

( i ) SEQUENCE CHARACTERISTICS:
    ( A ) LENGTH: 807 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( B ) STRAIN: Bacillus lentus DSM 5483

( v i i ) IMMEDIATE SOURCE:
    ( B ) CLONE: S130A ( x i ) SEQUENCE DESCRIPTION: SEQ ID NO:86:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA CAATTCGAT TGGCGTTCTT      240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTGCT     360
AATTTGAGTT TAGGAAGCCC TTCGCCAGCA GCCACACTTG AGCAAGCTGT TAATAGCGCG     420
ACTTCTAGAG GCGTTCTTGT TGTAGCGGCA TCTGGGAATT CAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CGCAGGGCTT GACATTGTCG CACCAGGGGT AAACGTGCAG     600
AGCACATACC CAGGTTCAAC GTATGCCAGC TTAAACGGTA CATCGATGGC TACTCCTCAT     660
GTTGCAGGTG CAGCAGCCCT TGTTAAACAA AAGAACCCAT CTTGGTCCAA TGTACAAATC     720
CGCAACCATC TAAAGAATAC GGCAACGAGC TTAGGAAGCA CGAACTTGTA TGGAAGCGGA     780
CTTGTCAATG CAGAAGCGGC AACACGC                                        807
```

( 2 ) INFORMATION FOR SEQ ID NO:87:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: S130T ( x i ) SEQUENCE DESCRIPTION: SEQ ID NO:87:

```
GCGCAATCAG TGCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA CAATTCGAT TGGCGTTCTT      240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTGCT     360
```

| | | | | | |
|---|---|---|---|---|---|
| AATTTGAGTT | TAGGAAGCCC | TTCGCCAACA | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:88:

( i ) SEQUENCE CHARACTERISTICS:
   ( A ) LENGTH: 807 base pairs
   ( B ) TYPE: nucleic acid
   ( C ) STRANDEDNESS: double
   ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
   ( B ) STRAIN: Bacillus lentus DSM 5483

( v i i ) IMMEDIATE SOURCE:
   ( B ) CLONE: A96I ( x i ) SEQUENCE DESCRIPTION: SEQ ID NO:88:

| | | | | | |
|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAATTGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:89:

( i ) SEQUENCE CHARACTERISTICS:
   ( A ) LENGTH: 807 base pairs
   ( B ) TYPE: nucleic acid
   ( C ) STRANDEDNESS: double
   ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( B ) STRAIN: Bacillus lentus DSM 5483

( v i i ) IMMEDIATE SOURCE:
    ( B ) CLONE: S104T, S139Y, A224V ( x i ) SEQUENCE DESCRIPTION: SEQ ID NO:89:

```
GCGCAATCAG TGCCATGGGG AATTAGCCGT GTGCAAGCCC CGGCTGCCCA TAACCGTGGA     60
TTGACAGGTT CTGGTGTAAA AGTTGCTGTC CTCGATACAG GTATTTCCAC TCATCCAGAC    120
TTAAATATTC GTGGTGGCGC TAGCTTTGTA CCAGGGGAAC CATCCACTCA AGATGGGAAT    180
GGGCATGGCA CGCATGTGGC CGGGACGATT GCTGCTTTAA ACAATTCGAT TGGCGTTCTT    240
GGCGTAGCGC CTAGTGCGGA ACTATACGCT GTTAAAGTTT TAGGAGCCGA CGGTAGAGGT    300
GCAATCAGCA CGATTGCCCA AGGGTTGGAA TGGGCAGGGA ACAATGGCAT GCACGTTGCT    360
AATTTGAGTT TAGGAAGCCC TTCGCCAAGT GCCACACTTG AGCAAGCTGT TAATTATGCG    420
ACTTCTAGAG GCGTTCTTGT TGTAGCGGCA TCTGGGAATT CAGGTGCAAG CTCAATCAGC    480
TATCCGGCCC GTTATGCGAA CGCAATGGCA GTCGGAGCTA CTGACCAAAA CAACAACCGC    540
GCCAGCTTTT CACAGTATGG CGCAGGGCTT GACATTGTCG CACCAGGGGT AAACGTGCAG    600
AGCACATACC CAGGTTCAAC GTATGCCAGC TTAAACGGTA CATCGATGGC TACTCCTCAT    660
GTTGCAGGTG TTGCAGCCCT TGTTAAACAA AAGAACCCAT CTTGGTCCAA TGTACAAATC    720
CGCAACCATC TAAAGAATAC GGCAACGAGC TTAGGAAGCA CGAACTTGTA TGGAAGCGGA    780
CTTGTCAATG CAGAAGCGGC AACACGC                                        807
```

( 2 ) INFORMATION FOR SEQ ID NO:90:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: S139A ( x i ) SEQUENCE DESCRIPTION: SEQ ID NO:90:

```
GCGCAATCAG TGCCATGGGG AATTAGCCGT GTGCAAGCCC CGGCTGCCCA TAACCGTGGA     60
TTGACAGGTT CTGGTGTAAA AGTTGCTGTC CTCGATACAG GTATTTCCAC TCATCCAGAC    120
TTAAATATTC GTGGTGGCGC TAGCTTTGTA CCAGGGGAAC CATCCACTCA AGATGGGAAT    180
GGGCATGGCA CGCATGTGGC CGGGACGATT GCTGCTTTAA ACAATTCGAT TGGCGTTCTT    240
GGCGTAGCGC CTAGTGCGGA ACTATACGCT GTTAAAGTTT TAGGAGCCGA CGGTAGAGGT    300
GCAATCAGCT CGATTGCCCA AGGGTTGGAA TGGGCAGGGA ACAATGGCAT GCACGTTGCT    360
AATTTGAGTT TAGGAAGCCC TTCGCCAAGT GCCACACTTG AGCAAGCTGT TAATGCAGCG    420
ACTTCTAGAG GCGTTCTTGT TGTAGCGGCA TCTGGGAATT CAGGTGCAAG CTCAATCAGC    480
TATCCGGCCC GTTATGCGAA CGCAATGGCA GTCGGAGCTA CTGACCAAAA CAACAACCGC    540
GCCAGCTTTT CACAGTATGG CGCAGGGCTT GACATTGTCG CACCAGGGGT AAACGTGCAG    600
AGCACATACC CAGGTTCAAC GTATGCCAGC TTAAACGGTA CATCGATGGC TACTCCTCAT    660
```

-continued

| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:91:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: S142T ( x i ) SEQUENCE DESCRIPTION: SEQ ID NO:91:

| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTACAAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:92:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: S139T ( x i ) SEQUENCE DESCRIPTION: SEQ ID NO:92:

| GCGCAATCAG | TGCCATGGGG | AATTAGCCGT | GTGCAAGCCC | CGGCTGCCCA | TAACCGTGGA | 60 |

| | | | | | |
|---|---|---|---|---|---|
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATACAGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:93:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: I102W ( x i ) SEQUENCE DESCRIPTION: SEQ ID NO:93:

| | | | | | |
|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCATGGAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:94:

( i ) SEQUENCE CHARACTERISTICS:
        ( A ) LENGTH: 807 base pairs ( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( B ) STRAIN: Bacillus lentus DSM 5483

( v i i ) IMMEDIATE SOURCE:
( B ) CLONE: A96N ( x i ) SEQUENCE DESCRIPTION: SEQ ID NO:94:

| | | | | | |
|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAAACGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:95:

( i ) SEQUENCE CHARACTERISTICS:
( A ) LENGTH: 807 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( B ) STRAIN: Bacillus lentus DSM 5483

( v i i ) IMMEDIATE SOURCE:
( B ) CLONE: N42F ( x i ) SEQUENCE DESCRIPTION: SEQ ID NO:95:

| | | | | | |
|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTATTTATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |

```
ACTTCTAGAG  GCGTTCTTGT  TGTAGCGGCA  TCTGGGAATT  CAGGTGCAAG  CTCAATCAGC    480
TATCCGGCCC  GTTATGCGAA  CGCAATGGCA  GTCGGAGCTA  CTGACCAAAA  CAACAACCGC    540
GCCAGCTTTT  CACAGTATGG  CGCAGGGCTT  GACATTGTCG  CACCAGGGGT  AAACGTGCAG    600
AGCACATACC  CAGGTTCAAC  GTATGCCAGC  TTAAACGGTA  CATCGATGGC  TACTCCTCAT    660
GTTGCAGGTG  CAGCAGCCCT  TGTTAAACAA  AAGAACCCAT  CTTGGTCCAA  TGTACAAATC    720
CGCAACCATC  TAAAGAATAC  GGCAACGAGC  TTAGGAAGCA  CGAACTTGTA  TGGAAGCGGA    780
CTTGTCAATG  CAGAAGCGGC  AACACGC                                           807
```

(2) INFORMATION FOR SEQ ID NO:96:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: Bacillus lentus DSM 5483

(vii) IMMEDIATE SOURCE:
        (B) CLONE: S142A (xi) SEQUENCE DESCRIPTION: SEQ ID NO:96:

```
GCGCAATCAG  TGCCATGGGG  AATTAGCCGT  GTGCAAGCCC  CGGCTGCCCA  TAACCGTGGA     60
TTGACAGGTT  CTGGTGTAAA  AGTTGCTGTC  CTCGATACAG  GTATTTCCAC  TCATCCAGAC    120
TTAAATATTC  GTGGTGGCGC  TAGCTTTGTA  CCAGGGGAAC  CATCCACTCA  AGATGGGAAT    180
GGGCATGGCA  CGCATGTGGC  CGGGACGATT  GCTGCTTTAA  CAATTCGAT   TGGCGTTCTT    240
GGCGTAGCGC  CTAGTGCGGA  ACTATACGCT  GTTAAAGTTT  TAGGAGCCGA  CGGTAGAGGT    300
GCAATCAGCT  CGATTGCCCA  AGGGTTGGAA  TGGGCAGGGA  ACAATGGCAT  GCACGTTGCT    360
AATTTGAGTT  TAGGAAGCCC  TTCGCCAAGT  GCCACACTTG  AGCAAGCTGT  TAATAGCGCG    420
ACTGCAAGAG  GCGTTCTTGT  TGTAGCGGCA  TCTGGGAATT  CAGGTGCAAG  CTCAATCAGC    480
TATCCGGCCC  GTTATGCGAA  CGCAATGGCA  GTCGGAGCTA  CTGACCAAAA  CAACAACCGC    540
GCCAGCTTTT  CACAGTATGG  CGCAGGGCTT  GACATTGTCG  CACCAGGGGT  AAACGTGCAG    600
AGCACATACC  CAGGTTCAAC  GTATGCCAGC  TTAAACGGTA  CATCGATGGC  TACTCCTCAT    660
GTTGCAGGTG  CAGCAGCCCT  TGTTAAACAA  AAGAACCCAT  CTTGGTCCAA  TGTACAAATC    720
CGCAACCATC  TAAAGAATAC  GGCAACGAGC  TTAGGAAGCA  CGAACTTGTA  TGGAAGCGGA    780
CTTGTCAATG  CAGAAGCGGC  AACACGC                                           807
```

(2) INFORMATION FOR SEQ ID NO:97:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:

(B) STRAIN: Bacillus lentus DSM 5483

(vii) IMMEDIATE SOURCE:
    (B) CLONE: H118F (xi) SEQUENCE DESCRIPTION: SEQ ID NO:97:

| | | | | | | |
|---|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GTTTGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

(2) INFORMATION FOR SEQ ID NO:98:

(i) SEQUENCE CHARACTERISTICS:
      (A) LENGTH: 807 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (B) STRAIN: Bacillus lentus DSM 5483

(vii) IMMEDIATE SOURCE:
      (B) CLONE: N237A (xi) SEQUENCE DESCRIPTION: SEQ ID NO:98:

| | | | | | | |
|---|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCGC | TGTACAAATC | 720 |

| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:99:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: N255P ( x i ) SEQUENCE DESCRIPTION: SEQ ID NO:99:

| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | CAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGCCATTGTA | TGGAAGCGGA | 780 |
| CTTGTCAATG | CAGAAGCGGC | AACACGC | | | | 807 |

( 2 ) INFORMATION FOR SEQ ID NO:100:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: T141W, N237A ( x i ) SEQUENCE DESCRIPTION: SEQ ID NO:100:

| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |

```
TTAAATATTC GTGGTGGCGC TAGCTTTGTA CCAGGGGAAC CATCCACTCA AGATGGGAAT      180

GGGCATGGCA CGCATGTGGC CGGGACGATT GCTGCTTTAA ACAATTCGAT TGGCGTTCTT      240

GGCGTAGCGC CTAGTGCGGA ACTATACGCT GTTAAAGTTT AGGAGCCGA CGGTAGAGGT       300

GCAATCAGCT CGATTGCCCA AGGGTTGGAA TGGGCAGGGA ACAATGGCAT GCACGTTGCT      360

AATTTGAGTT TAGGAAGCCC TTCGCCAAGT GCCACACTTG AGCAAGCTGT TAATAGCGCG      420

TGGTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTGTCG CACCAGGGGT AAACGTGCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AGAACCCAT CTTGGTCCGC TGTACAAATC       720

CGCAACCATC TAAAGAATAC GGCAACGAGC TTAGGAAGCA CGAACTTGTA TGGAAGCGGA      780

CTTGTCAATG CAGAAGCGGC AACACGC                                         807
```

( 2 ) INFORMATION FOR SEQ ID NO:101:

( i ) SEQUENCE CHARACTERISTICS:
        ( A ) LENGTH: 807 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: Bacillus lentus DSM 5483

( v i i ) IMMEDIATE SOURCE:
        ( B ) CLONE: T268V ( x i ) SEQUENCE DESCRIPTION: SEQ ID NO:101:

```
GCGCAATCAG TGCCATGGGG AATTAGCCGT GTGCAAGCCC CGGCTGCCCA TAACCGTGGA       60

TTGACAGGTT CTGGTGTAAA AGTTGCTGTC CTCGATACAG GTATTTCCAC TCATCCAGAC      120

TTAAATATTC GTGGTGGCGC TAGCTTTGTA CCAGGGGAAC CATCCACTCA AGATGGGAAT      180

GGGCATGGCA CGCATGTGGC CGGGACGATT GCTGCTTTAA ACAATTCGAT TGGCGTTCTT      240

GGCGTAGCGC CTAGTGCGGA ACTATACGCT GTTAAAGTTT AGGAGCCGA CGGTAGAGGT       300

GCAATCAGCT CGATTGCCCA AGGGTTGGAA TGGGCAGGGA ACAATGGCAT GCACGTTGCT      360

AATTTGAGTT TAGGAAGCCC TTCGCCAAGT GCCACACTTG AGCAAGCTGT TAATAGCGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CGCAGGGCTT GACATTGTCG CACCAGGGGT AAACGTGCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AGAACCCAT CTTGGTCCAA TGTACAAATC       720

CGCAACCATC TAAAGAATAC GGCAACGAGC TTAGGAAGCA CGAACTTGTA TGGAAGCGGA      780

CTTGTCAATG CAGAAGCGGC AGTTCGC                                         807
```

( 2 ) INFORMATION FOR SEQ ID NO:102:

( i ) SEQUENCE CHARACTERISTICS:
        ( A ) LENGTH: 807 base pairs
        ( B ) TYPE: nucleic acid
        ( C ) STRANDEDNESS: double ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
 ( B ) STRAIN: Bacillus lentus DSM 5483

( v i i ) IMMEDIATE SOURCE:
 ( B ) CLONE: K229W ( x i ) SEQUENCE DESCRIPTION: SEQ ID NO:102:

| | | | | | |
|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTTGGCAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:103:

( i ) SEQUENCE CHARACTERISTICS:
 ( A ) LENGTH: 807 base pairs
 ( B ) TYPE: nucleic acid
 ( C ) STRANDEDNESS: double
 ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
 ( B ) STRAIN: Bacillus lentus DSM 5483

( v i i ) IMMEDIATE SOURCE:
 ( B ) CLONE: T141W ( x i ) SEQUENCE DESCRIPTION: SEQ ID NO:103:

| | | | | | |
|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| TGGTCTAGAG | GCGTTCTTGT | TGTAGCGGCA | TCTGGGAATT | CAGGTGCAAG | CTCAATCAGC | 480 |

| | | | | | | |
|---|---|---|---|---|---|---|
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |

( 2 ) INFORMATION FOR SEQ ID NO:104:

( i ) SEQUENCE CHARACTERISTICS:
  ( A ) LENGTH: 807 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Bacillus lentus
  ( B ) STRAIN: DSM 5483

( v i i ) IMMEDIATE SOURCE:
  ( B ) CLONE: wild type ( x i ) SEQUENCE DESCRIPTION: SEQ ID NO:104:

| | | | | | | |
|---|---|---|---|---|---|---|
| GCGCAATCAG | TGCCATGGGG | AATTAGCCGT | GTGCAAGCCC | CGGCTGCCCA | TAACCGTGGA | 60 |
| TTGACAGGTT | CTGGTGTAAA | AGTTGCTGTC | CTCGATACAG | GTATTTCCAC | TCATCCAGAC | 120 |
| TTAAATATTC | GTGGTGGCGC | TAGCTTTGTA | CCAGGGGAAC | CATCCACTCA | AGATGGGAAT | 180 |
| GGGCATGGCA | CGCATGTGGC | CGGGACGATT | GCTGCTTTAA | ACAATTCGAT | TGGCGTTCTT | 240 |
| GGCGTAGCGC | CTAGTGCGGA | ACTATACGCT | GTTAAAGTTT | TAGGAGCCGA | CGGTAGAGGT | 300 |
| GCAATCAGCT | CGATTGCCCA | AGGGTTGGAA | TGGGCAGGGA | ACAATGGCAT | GCACGTTGCT | 360 |
| AATTTGAGTT | TAGGAAGCCC | TTCGCCAAGT | GCCACACTTG | AGCAAGCTGT | TAATAGCGCG | 420 |
| ACTTCTAGAG | GCGTTCTTGT | TGTAGCGGCA | TCTGGGAATT | CAGGTGCAAG | CTCAATCAGC | 480 |
| TATCCGGCCC | GTTATGCGAA | CGCAATGGCA | GTCGGAGCTA | CTGACCAAAA | CAACAACCGC | 540 |
| GCCAGCTTTT | CACAGTATGG | CGCAGGGCTT | GACATTGTCG | CACCAGGGGT | AAACGTGCAG | 600 |
| AGCACATACC | CAGGTTCAAC | GTATGCCAGC | TTAAACGGTA | CATCGATGGC | TACTCCTCAT | 660 |
| GTTGCAGGTG | CAGCAGCCCT | TGTTAAACAA | AAGAACCCAT | CTTGGTCCAA | TGTACAAATC | 720 |
| CGCAACCATC | TAAAGAATAC | GGCAACGAGC | TTAGGAAGCA | CGAACTTGTA | TGGAAGCGGA | 780 |
| CTTGTCAATG | CAGAAGCGGC | AACACGC | | | | 807 |